(12) United States Patent
Belvin et al.

(10) Patent No.: US 8,604,014 B2
(45) Date of Patent: Dec. 10, 2013

(54) COMBINATIONS OF PHOSPHOINOSITIDE 3-KINASE INHIBITOR COMPOUNDS CHEMOTHERAPEUTIC AGENTS, AND METHODS OF USE

(75) Inventors: Marcia Belvin, South San Francisco, CA (US); Lori Friedman, South San Francisco, CA (US); Klaus Hoeflich, South San Francisco, CA (US); Deepak Sampath, South San Francisco, CA (US); Ulka Vijapurkar, South San Francisco, CA (US); Jeffrey Wallin, South San Francisco, CA (US); Leisa Johnson, South San Francisco, CA (US); Mallika Singh, South San Francisco, CA (US); Sonal Patel, Basel (GB)

(73) Assignees: Genentech, Inc., South San Francisco, CA (US); F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 13/109,670

(22) Filed: May 17, 2011

(65) Prior Publication Data

US 2011/0223619 A1    Sep. 15, 2011

Related U.S. Application Data

(62) Division of application No. 12/208,227, filed on Sep. 10, 2008, now Pat. No. 8,247,397.

(60) Provisional application No. 60/971,773, filed on Sep. 12, 2007.

(51) Int. Cl.
*A61K 31/33* (2006.01)
*G01N 33/00* (2006.01)

(52) U.S. Cl.
USPC .............................. 514/183; 436/91

(58) Field of Classification Search
USPC ............................. 514/183; 436/91
See application file for complete search history.

(56) References Cited

U.S. PATENT DOCUMENTS

| | | | |
|---|---|---|---|
| 6,608,053 | B2 | 8/2003 | Hayakawa et al. |
| 2006/0030536 | A1 | 2/2006 | Yu et al. |
| 2006/0063824 | A1 | 3/2006 | Kirkpatrick et al. |
| 2008/0039459 | A1 | 2/2008 | Folkes et al. |
| 2008/0076758 | A1 | 3/2008 | Folkes et al. |
| 2008/0076768 | A1 | 3/2008 | Chuckowree et al. |
| 2008/0207609 | A1 | 8/2008 | Shuttleworth et al. |
| 2008/0207611 | A1 | 8/2008 | Shuttleworth et al. |
| 2008/0242665 | A1 | 10/2008 | Bayliss et al. |
| 2008/0269210 | A1 | 10/2008 | Castanedo et al. |

FOREIGN PATENT DOCUMENTS

| | | |
|---|---|---|
| WO | WO 2004/065391 | 8/2004 |
| WO | WO 2005/094358 | 10/2005 |
| WO | WO 2006/046031 A1 * | 5/2006 ........ C07D 495/04 |
| WO | WO 2006/046035 | 5/2006 |
| WO | WO 2007/122410 | 11/2007 |
| WO | WO 2007/127175 | 11/2007 |
| WO | WO 2007/132171 | 11/2007 |
| WO | WO 2008/152387 | 12/2008 |
| WO | WO 2008/152390 | 12/2008 |
| WO | WO 2008/152394 | 12/2008 |

OTHER PUBLICATIONS

Nagata et al 'PTEN activation contributes to tumor inhibition by trastuzumab, and loss of PTEN predicts trastuzumab resistance in patient' Cancer Cell, vol. 6, p. 117-127, 2004.*
Bernhard, E.J., et al., "Inhibiting Ras prenylation increases the radiosensitivity of human tumor cell lines with activating mutations of *ras* oncogenes", *Cancer Research*, 58(8), 1754-1761 (1998).
Bianco, R., et al., "Loss of PTEN/MMAC1/TEP in EGF receptor-expressing tumor cells counteracts the antitumor action of EGFR tyrosine kinase inhibitors", *Oncogene*, 22, 2812-2822 (2003).
Briel, D., et al., "Selective nucleophilic replacement of the benzylsulfanyl group in 2,4-disulfanyl-substituted thieno[2,3-d]pyrimidin-6-carboxylic acid derivatives by secondary amines", *Journal of Heterocyclic Chemistry*, 42(5), 841-846 (2005).
"CellTiter-Glo® Luminescent Cell Viability Assay: instructions for use of products G7570, G7571, G7572 and G7573", *Promega Technical Bulletin TB288*, Internet URL: www.promega.com, retrieved Sep. 18, 2009, 13 pages.

(Continued)

*Primary Examiner* — Brandon Fetterolf
*Assistant Examiner* — Christopher R Stone
(74) *Attorney, Agent, or Firm* — Viksnins Harris & Padys PLLP

(57) ABSTRACT

Combinations of PI3K inhibitor compounds having Formulas I and II and chemotherapeutic agents, including stereoisomers, geometric isomers, tautomers, metabolites and pharmaceutically acceptable salts thereof, are useful for treating hyperproliferative disorders such as cancer. Methods of using such combinations for in vitro, in situ, and in vivo diagnosis, prevention or treatment of such disorders in mammalian cells, or associated pathological conditions, are disclosed.

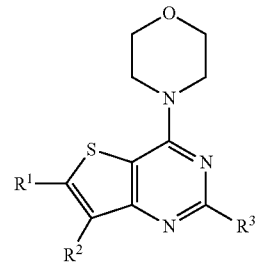

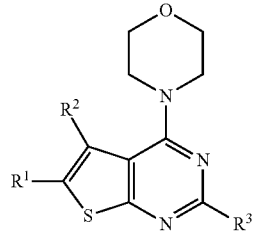

15 Claims, 57 Drawing Sheets

(56) References Cited

OTHER PUBLICATIONS

Chou, T-C et al., "Quantitative Analysis of Dose-Effect Relationships: The Combined Effects of Multiple Drugs or Enzyme Inhibitors", Adv. Enzyme Regul. (1984) 22:27-55.
Edwards et al., "Combined inhibition of the phosphatidylinositol 3-kinase/Akt and Ras/mitogen-activated protein kinase pathways results in synergistic effects in glioblastoma cells", Molecular Cancer Therapeutics, (2006), 5(3), 645-654.
Fludzinski et al., "Indazoles as Indole Bioisosteres: Synthesis and Evaluation of the Tropanyl Ester and Amide of Indazole-3-carboxylate as Antagonists at the Serotonin 5HT3 Receptor", *Journal of Medicinal Chemistry*, 30(9), p. 1535, 1987.
Folkes et al., "The Identification of 2-(1H-indazol-4-yl)-6-(4-methanesulfonyl-piperazin-1-ylmethyl)-4-morpholin-4-yl-thieno[3,2-d]pyrimidine (GDC-0941) as a Potent, Selective, Orally Bioavailable Inhibitor of Class I PI3 Kinase for the Treatment of Cancer", Journal of Medicinal Chemistry, (2008), 51(18), 5522-5532.
Friedman et al., "Preclinical analysis of combined PI3K and MEK inhibition as a strategy for the treatment for cancer", American Association for Cancer Research Annual Meeting, 2008, 99th:Apr. 14, Abstract LB-110.
Friedman et al., "Anti-angiogenic effects of PI3K/Akt/mTOR pathway inhibitors", EORTC, Oct. 2008, Poster 227.
Hayakawa M., et al., "Synthesis and biological evaluation of pyrido[3',2':4,5]furo[3,2-*d*]pyrimidine derivatives as novel PI3 kinase p110alpha inhibitors", *Bioorganic & Medicinal Chemistry Letters*, 17(9), 2438-2442 (2007).
Heffron et al., "Evolution of Potent and Efficacious PI3 Kinase Inhibitors", Abstracts of Papers, 237th ACS National Meeting, Salt Lake City, UT, United States, Mar. 22-26, (2009), MEDI-220.
Ihle et al., "The phosphatidylinositol-3-kinase inhibitor PX-866 overcomes resistance to the epidermal growth facor inhibitor gefitinib in A-549 human non-small cell lung cancer xenografts", *Molecular Cancer Therapy*, vol. 4, pp. 1349-1357, 2005.
Kesari et al., "Targeted Molecular Therapy of Malignant Gliomas", Current Oncology Reports, (2006), 8(1), 58-70.
Lee-Hoeflich et al., "A Central Role for HER3 in HER2-Amplified Breast Cancer: Implications for Targeted Therapy", Cancer Res., (2008), 68(14), 5878-87.
Li, T., et al., "Schedule-dependent cytotoxic synergism of pemetrexed and erlotinib in human non-small cell lung cancer cells", *Cancer Therapy: Preclinical*, 13(11), 3413-3422 (2007).
Loprevite, M., et al., "In vitro study of farnesyltransferase inhibitor SCH 66336, in combination with chemotherapy and radiation, in non-small cell lung cancer cell lines", *Oncology Reports*, 11, 407-414 (2004).
Mendoza, N., et al., "Inhibition of ligand-mediated HER2 activation in androgen-independent prostate cancer", *Cancer Research*, 62(19), 5485-5488 (2002).

Morgensztern et al., "PI3K/Akt/mTOR pathway as a target for cancer therapy", Anti-Cancer Drugs, (2005), 16(8), 797-803.
Nielsen, L., et al., "Combination therapy with the farnesyl protein transferase inhibitor SCH66336 and SCH58500 (p53 Adenovirus) in preclinical cancer models", *Cancer Research*, 59(23), 5896-5901 (1999).
Ohta et al., "Inhibition of Phosphatidylinositol 3-Kinase Increases Efficacy of Cisplatin in in Vivo Ovarian Cancer Models", Endocrinology (2006), 147(4), 1761-1769.
Pao et al., "KRAS Mutations and Primary Resistance of Lung Adenomacarcinomas to Gefitinib or Erlotinib", *PLoS Medicine*, 2(1), pp. 57-61, 2005.
Premkumar et al., "Synergistic Interaction Between 17-AAG and Phosphatidylinositol 3-Kinase Inhibition in Human Malignant Glioma Cells", Molecular Carcinogenesis, (2006), 45(1), 47-59.
Sampath et al., "Combination of class 1 PI3K inhibitor, GDC-0941, with standard of care therapeutics results in enhanced antitumour responses in human cancer models in vitro and in vivo", EORTC, Oct. 2008, Poster 220.
Samuels et al., "Inhibiting Phosphoinositide 3-Kinases", Cancer Biology & Therapy (2005), 4(5), 546-547.
Tumkevicius, S., et al., "First example of synthesis of thieno-[2,3-*d*]pyrimidine-6-carbaldehydes by oxidation of thieno[2,3-*d*]pyrimidin-6-yl methanols with molecular iodine", *Chemistry of Hetrocyclic Compounds*, 41(6), 800-801 (2005).
Wendel et al., "Determinants of Sensitivity and Resistance to Rapamycin-Chemotherapy Drug Combinations in vivo", Cancer Research (2006), 66(15), 7639-7646.
Yu et al., "PWT-458, A Novel Pegylated-17-Hydroxywortmannin, Inhibits Phosphatidylinositol 3-Kinase Signaling and Suppresses Growth of Solid Tumors", Cancer Biology & Therapy, (2005), 4(5), 538-545.
Yu, D. et al., "Role of *erb*B2 in breast cancer chemosensitivity", *BioEssays*, 22(7), 673-680 (2000).
Zhou, H., et al., "Effects of the EGFR/HER2 kinase inhibitor GW572016 on EGFR- and HER2-Overexpressing breast cancer cell line proliferation, radiosensitization, and resistance", *Int. J. Radiation Oncology Biol. Phys.*, 58(2), 344-352, (2004).
Ikezoe et al., "Longitudinal inhibition of PI3K/Akt/mTOR signaling by LY294002 and rapamycin induces growth arrest of adult T-cell leukemia cells", Leuk. Res., vol. 31, 673-682 (2007).
Janmaat et al., "Enhanced cytotoxicity induced by gefitinib and specific inhibitors of the Ras or phosphatidyl inositiol-3 kinase pathways in non-small cell lung cancer cells", Int. J. Cancer, vol. 118, 209-214 (2006).
Shingu et al., "Synergistic Augmentation of Antimicrotubule Agent-induced Cytotoxicity by a Phosphoinositide 3- Kinase Inhibitor in Human Malignant Glioma Cells", Cancer Research 63, 4044-4047 (2003).

\* cited by examiner

*in vitro* Cell Proliferation Assays of Combinations of
Formula Ia Compound (GDC-0941) and Various Chemotherapeutic Agents

| Expt. | Cell Line | Tumor Type | Gene Mutation | Chemotherapeutic | Chemo. EC50 | Compound Ia EC50 | Combination Index (CI) | Synergy |
|---|---|---|---|---|---|---|---|---|
| 1 | MDA-MB-361 | Breast | PI3K E545K | 5-FU | >40 | 0.48 | 0.048 | +++++ |
| 2 | MT3 | Breast | K-ras G12D PI3K H1047R | 5-FU | >40 | 0.58 | 0.954 | +/- |
| 3 | MDA-MB-436 | Breast | PTEN neg | 5-FU | >40 | 0.82 | 0.757 | ++ |
| 4 | MDA-MB-468 | Breast | PTEN neg | 5-FU | 20 | 0.87 | 0.674 | +++ |
| 5 | ZR75-1 | Breast | PTEN neg | 5-FU | 20 | 0.3 | 0.682 | +++ |
| 6 | Cal-120 | Breast | | 5-FU | 1.33 | 1.38 | 1.33 | - |
| 7 | HCC-1569 | Breast | PTEN neg | carboplatin | >40 | 0.322 | 1.1 | - |
| 8 | HCC-1569 | Breast | PTEN neg | docetaxel | 0.0004 | 0.322 | 0.737 | ++ |
| 9 | MDA-MB-361 | Breast | PI3K E545K | docetaxel | 0.0016 | 0.48 | 0.11 | ++++ |
| 10 | MDA-MB-468 | Breast | PTEN neg | docetaxel | 0.005 | 0.87 | 0.136 | ++++ |
| 11 | ZR75-1 | Breast | PTEN neg | docetaxel | 0.0025 | 0.3 | 0.901 | +/- |
| 12 | MT3 | Breast | K-ras G12D PI3K H1047R | docetaxel | 0.001 | 0.58 | 0.278 | ++++ |
| 13 | MCF7 | Breast | PI3K E545K | docetaxel | 0.005 | 0.17 | 0.866 | + |
| 14 | MDA-MB-436 | Breast | PTEN neg | docetaxel | 0.005 | 0.82 | 0.346 | +++ |
| 15 | Cal-120 | Breast | | docetaxel | 0.85 | 1.38 | 0.85 | + |
| 16 | MDA-MB-231 | Breast | K-ras G13G | docetaxel | 0.0001 | 6.5 | 0.96 | - |
| 17 | MDA-MB-361 | Breast | PI3K E545K | doxorubicin | 0.148 | 0.48 | 0.137 | ++++ |
| 18 | Cal-51 | Breast | PI3K E542K, PTEN neg | gemcitabine | 0.002 | 0.76 | 0.189 | ++++ |
| 19 | Cal-120 | Breast | | gemcitabine | 0.4 | 1.38 | 0.4 | +++ |
| 20 | MDA-MB-361 | Breast | PI3K E545K | gemcitabine | 0.006 | 0.48 | 0.421 | +++ |

Figure 1A-1 in vitro Cell Proliferation Assays of Combinations of Formula Ia Compound (GDC-0941) and Various Chemotherapeutic Agents

| | | | | | | | |
|---|---|---|---|---|---|---|---|
| 21 | MT3 | Breast | K-ras G12D PI3K H1047R | gemcitabine | 0.002 | 0.58 | 0.863 | + |
| 22 | MCF7 | Breast | PI3K E545K | gemcitabine | 0.005 | 0.17 | 0.651 | +++ |
| 23 | MDA-MB-436 | Breast | PTEN neg | gemcitabine | 0.001 | 0.82 | 0.959 | +/- |
| 24 | MDA-MB-468 | Breast | PTEN neg | gemcitabine | 0.0025 | 0.87 | 0.722 | ++ |
| 25 | ZR75-1 | Breast | PTEN neg | gemcitabine | 0.01 | 0.3 | 0.655 | +++ |
| 26 | BT474 | Breast | PI3K K111N | lapatinib | 0.1 | 0.52 | 0.22 | ++++ |
| 27 | EFM192A | Breast | PI3K C420R | lapatinib | 0.31 | 0.41 | 0.24 | ++++ |
| 28 | MDA-MB-231 | Breast | K-ras G13G | paclitaxel | 0.0017 | 6.5 | 1.1 | - |
| 29 | Cal-51 | Breast | PI3K E542K, PTEN neg | PD-0325901 | 0.37 | 0.76 | 0.109 | ++++ |
| 30 | MDA-MB-361 | Breast | PI3K E545K | PD-0325901 | >2 | 0.48 | 0.275 | ++++ |
| 31 | MCF7 | Breast | PI3K E545K | PD-0325901 | >20 | 0.17 | 0.95 | +/- |
| 32 | MT3 | Breast | K-ras G12D PI3K H1047R | PD-0325901 | 0.023 | 0.58 | 0.01 | +++++ |
| 33 | MDA-MB-436 | Breast | PTEN neg | PD-0325901 | 2 | 0.82 | 0.092 | +++++ |
| 34 | ZR75-1 | Breast | PTEN neg | PD-0325901 | 0.36 | 0.3 | 0.779 | ++ |
| 35 | MDA-MB-468 | Breast | PTEN neg | PD-0325901 | 0.27 | 0.87 | 0.114 | ++++ |
| 36 | MCF7 | Breast | PI3K E545K | tamoxifen | >10 | 0.17 | 0.353 | +++ |
| 37 | MDA-MB-361 | Breast | PI3K E545K | rapamycin | 0.01 | 0.55 | 0.29 | ++++ |
| 38 | MDA-MB-361 | Breast | PI3K E545K | Akti-1/2 | 3.73 | 0.55 | 0.57 | +++ |
| 39 | MDA-MB-453 | Breast | PI3K H1047R | rapamycin | 0.01 | 0.40 | 0.37 | +++ |
| 40 | MDA-MB-453 | Breast | PI3K H1047R | Akti-1/2 | 1.90 | 0.40 | 0.42 | +++ |
| 41 | T47D | Breast | PI3K H1047R | rapamycin | 0.01 | 0.17 | 0.39 | +++ |
| 42 | T47D | Breast | PI3K H1047R | Akti-1/2 | 0.28 | 0.17 | 0.97 | +/- |
| 43 | ZR75-1 | Breast | PTEN neg | rapamycin | 0.01 | 0.33 | 0.47 | +++ |

Figure 1A-2

*in vitro* Cell Proliferation Assays of Combinations of
Formula Ia Compound (GDC-0941) and Various Chemotherapeutic Agents

| | | | | | | | |
|---|---|---|---|---|---|---|---|
| 44 | ZR75-1 | Breast | PTEN neg | Akti-1/2 | 6.05 | 0.33 | 0.67 | ++ |
| 45 | MDA-MB-468 | Breast | PTEN neg | rapamycin | 0.01 | 1.73 | 0.24 | ++++ |
| 46 | MDA-MB-468 | Breast | PTEN neg | Akti-1/2 | 17.62 | 1.73 | 0.60 | +++ |
| 47 | BT549 | Breast | PTEN neg | rapamycin | 0.01 | 0.28 | 0.23 | ++++ |
| 48 | BT549 | Breast | PTEN neg | Akti-1/2 | 16.81 | 0.28 | 0.58 | +++ |
| 49 | MDA-MB-436 | Breast | PTEN neg | rapamycin | 0.01 | 0.82 | 0.37 | +++ |
| 50 | MDA-MB-436 | Breast | PTEN neg | Akti-1/2 | 17.38 | 0.82 | 0.90 | + |
| 51 | HCC1937 | Breast | PTEN neg | rapamycin | 0.01 | 0.70 | 0.35 | +++ |
| 52 | HCC1937 | Breast | PTEN neg | Akti-1/2 | 10.19 | 0.70 | 0.69 | ++ |
| 53 | SKBR3 | Breast | p53 mut | rapamycin | 0.01 | 0.26 | 0.30 | ++++ |
| 54 | SKBR3 | Breast | p53 mut | Akti-1/2 | 2.21 | 0.26 | 0.71 | ++ |
| 55 | SKBR3 | Breast | p53 mut | lapatinib | 0.07 | 0.33 | 0.66 | ++ |
| 56 | MDA-MB-175 | Breast | p53 mut | rapamycin | 0.01 | 0.42 | 0.32 | +++ |
| 57 | MDA-MB-175 | Breast | p53 mut | Akti-1/2 | 1.43 | 0.42 | 0.67 | ++ |
| 58 | Hs587T | Breast | p53 mut | rapamycin | 0.01 | 0.68 | 0.37 | +++ |
| 59 | Hs587T | Breast | p53 mut | Akti-1/2 | 20 | 0.86 | 0.82 | ++ |
| 60 | HDQ-P1 | Breast | | rapamycin | 0.01 | 0.49 | 0.52 | +++ |
| 61 | HDQ-P1 | Breast | | Akti-1/2 | 4.69 | 0.49 | 0.98 | +/- |
| 62 | C-33A | Cervical | PTEN neg | 5-FU | 3.84 | 1.2 | 0.77 | ++ |
| 63 | ME-180 | Cervical | PI3K E545K | 5-FU | 4 | 0.32 | 0.88 | + |
| 64 | SiHa | Cervical | | 5-FU | 47 | 2.5 | 1.23 | - |
| 65 | C-33A | Cervical | PTEN neg | docetaxel | 0.001 | 1.2 | 0.53 | ++ |
| 66 | ME-180 | Cervical | PI3K E545K | docetaxel | 0.0017 | 0.32 | 0.66 | ++ |
| 67 | SiHa | Cervical | | docetaxel | 0.0025 | 2.5 | 0.85 | + |

Figure 1A-3

*in vitro* Cell Proliferation Assays of Combinations of
Formula Ia Compound (GDC-0941) and Various Chemotherapeutic Agents

| | | | | | | | |
|---|---|---|---|---|---|---|---|
| 68 | C-33A | Cervical | PTEN neg | gemcitabine | 0.0025 | 1.2 | 0.72 | ++ |
| 69 | ME-180 | Cervical | PI3K E545K | gemcitabine | 0.035 | 0.32 | 0.55 | +++ |
| 70 | SiHa | Cervical | | gemcitabine | 0.0025 | 2.5 | 0.6 | ++ |
| 71 | SW620 | Colon | K-ras G12V, p53 mut | erlotinib | >10 | 1.25 | 0.115 | ++++ |
| 72 | KM12 | Colon | PTEN neg | erlotinib | >10 | 3.46 | 1.094 | +/- |
| 73 | WiDR | Colon | K-ras G12V, p53 mut | erlotinib | >10 | 0.27 | 1.1 | - |
| 74 | SW620 | Colon | K-ras G12V | PD-0325901 | 0.01 | 1.25 | 0.37 | +++ |
| 75 | HT-55 | Colon | | PD-0325901 | 0.05 | 0.41 | 0.091 | +++++ |
| 76 | KM12 | Colon | PTEN neg | PD-0325901 | >2 | 3.46 | 0.061 | +++++ |
| 77 | WiDR | Colon | | PD-0325901 | 0.05 | 0.27 | 0.093 | +++++ |
| 78 | HCT-116 | Colon | K-ras G12V | PD-0325901 | 0.13 | 1.16 | 0.03 | +++++ |
| 79 | DLD-1 | Colon | K-ras G12V, PI3K E545K | PD-0325901 | 0.70 | 1.21 | 0.07 | +++++ |
| 80 | RKO | Colon | B-raf V600E, PI3K H1047K | PD-0325901 | 0.07 | 1.66 | 0.08 | +++++ |
| 81 | Colo205 | Colon | B-raf V600E, PI3K H1047K | PD-0325901 | 0.006 | 2.14 | 0.10 | ++++ |
| 82 | HT-29 | Colon | | PD-0325901 | 0.03 | 0.45 | 0.20 | ++++ |
| 83 | LoVo | Colon | K-ras G13D | PD-0325901 | 0.009 | 0.45 | 0.20 | ++++ |
| 84 | HCT116 | Colon | PI3K H1047K, K-ras G13D | rapamycin | 0.01 | 2.5 | 0.75 | ++ |
| 85 | KM12 | Colon | PTEN neg | rapamycin | 0.01 | 3.46 | 0.28 | +++ |
| 86 | LoVo | Colon | K-ras G13D | rapamycin | 0.01 | 2.44 | 0.42 | +++ |
| 87 | MDST8 | Colon | B-raf V600X | rapamycin | 0.01 | 2.44 | 0.2 | +++ |
| 88 | WiDR | Colon | | rapamycin | 0.01 | 0.27 | 0.2 | +++ |

Figure 1A-4

*in vitro* Cell Proliferation Assays of Combinations of
Formula Ia Compound (GDC-0941) and Various Chemotherapeutic Agents

| | | | | | | | |
|---|---|---|---|---|---|---|---|
| 89 | ECC-1 | Endometrial | PTEN neg | 5-FU | 2 | 1.4 | 0.64 | ++ |
| 90 | ECC-1 | Endometrial | PTEN neg | docetaxel | 0.0009 | 1.4 | 0.64 | ++ |
| 91 | ECC-1 | Endometrial | PTEN neg | gemcitabine | 0.0113 | 1.4 | 0.83 | + |
| 92 | HEC-1-A | Endometrial | | 5-FU | 2.5 | 0.9 | 0.8 | + |
| 93 | HEC-1-A | Endometrial | | docetaxel | 0.0012 | 0.9 | 0.56 | +++ |
| 94 | HEC-1-A | Endometrial | | gemcitabine | 0.05 | 0.9 | 0.82 | + |
| 95 | SK-UT-1B | Endometrial | PTEN neg | 5-FU | 1.3 | 0.3 | 0.54 | +++ |
| 96 | SK-UT-1B | Endometrial | PTEN neg | docetaxel | 0.0005 | 0.3 | 0.52 | +++ |
| 97 | SK-UT-1B | Endometrial | PTEN neg | gemcitabine | 0.0019 | 0.3 | 0.79 | + |
| 98 | U87 | Glioma | PTEN neg | temozolomide | 11.7 | 0.27 | 0.004 | +++++ |
| 99 | G111 | Glioma | | temozolomide | 12 | 0.42 | 0.62 | ++ |
| 100 | G402 | Glioma | | 5-FU | | | 0.8 | |
| 101 | G402 | Glioma | | docetaxel | | | 0.49 | |
| 102 | G402 | Glioma | | gemcitabine | | | 0.62 | |
| 103 | G140 | Glioma | PTEN neg | rapamycin | 0.01 | 0.41 | 0.22 | ++++ |
| 104 | G140 | Glioma | PI3K E545K | temozolomide | >16.25 | 0.41 | 0.83 | + |
| 105 | G59 | Glioma | PI3K E545K | temozolomide | >16.25 | 0.24 | 0.76 | ++ |
| 106 | G61 | Glioma | PTEN neg | rapamycin | 0.01 | 1.28 | 0.14 | ++++ |
| 107 | G63 | Glioma | PTEN neg | temozolomide | >16.25 | 0.31 | 1.65 | - |
| 108 | LN229 | Glioma | PI3K E545K | rapamycin | 0.01 | 4.95 | 0.18 | ++++ |
| 109 | LN229 | Glioma | PI3K E545K | temozolomide | >16.25 | 2.5 | 1.1 | - |
| 110 | U87 | Glioma | PTEN neg | temozolomide | 11.7 | 0.27 | 0.48 | +++ |
| 111 | U87 | Glioma | PTEN neg | rapamycin | 0.01 | 0.19 | 0.31 | +++ |
| 112 | H2122 | Lung | K-ras G12C, p53 | carboplatin | >10 | 1.1 | 0.53 | +++ |

Figure 1A-5 in vitro Cell Proliferation Assays of Combinations of Formula Ia Compound (GDC-0941) and Various Chemotherapeutic Agents

| | | | | | | | |
|---|---|---|---|---|---|---|---|
| 113 | LKR10 (mouse) | Lung | K-ras G12C | cisplatin | 0.5 | 1.38 | 0.316 | +++ |
| 114 | LKR13 (mouse) | Lung | K-ras G12C | cisplatin | 1 | 0.815 | 0.403 | +++ |
| 115 | H2122 | Lung | K-ras G12C | cisplatin | 5 | 0.538 | 0.085 | +++++ |
| 116 | H1651 | Lung | mut | cisplatin | 0.75 | 7.71 | 1.142 | - |
| 117 | H2122 | Lung | K-ras G12C, p53 mut | docetaxel | 0.0015 | 0.538 | 0.58 | +++ |
| 118 | LKR10 (mouse) | Lung | K-ras G12C | paclitaxel | 0.0075 | 1.38 | 0.084 | +++++ |
| 119 | LKR13 (mouse) | Lung | K-ras G12C | paclitaxel | 0.005 | 0.815 | 0.064 | +++++ |
| 120 | H2122 | Lung | K-ras G12C, p53 mut | paclitaxel | 0.0015 | 1.1 | 0.77 | ++ |
| 121 | H1651 | Lung | | paclitaxel | 0.0015 | 7.71 | 1.08 | +/- |
| 122 | H2122 | Lung | K-ras G12C, p53 mut | gemcitabine | 0.0036 | 1.1 | 0.87 | + |
| 123 | A549 | Lung | K-ras G12S | gemcitabine | 0.01 | 0.49 | 0.749 | ++ |
| 124 | H1703 | Lung | p53 mut | PD-0325901 | >2 | 0.675 | 0.501 | +++ |
| 125 | A549 | Lung | K-ras G12S | PD-0325901 | 0.06 | 0.485 | 0.076 | +++++ |
| 126 | LKR10 (mouse) | Lung | K-ras G12C | PD-0325901 | 0.03 | 1.38 | 0.124 | ++++ |
| 127 | LKR13 (mouse) | Lung | K-ras G12C | PD-0325901 | 0.02 | 0.815 | 0.156 | ++++ |
| 128 | H322T | Lung | EGFR | PD-0325901 | 0.05 | 1.46 | 0.088 | +++++ |
| 129 | Calu-6 | Lung | K-ras Q61K | PD-0325901 | 0.053 | 3.64 | 0.061 | ++++ |
| 130 | H2126 | Lung | | PD-0325901 | 1.5 | 0.467 | 1.07 | +/- |
| 131 | H2122 | Lung | K-ras G12C, p53 mut | PD-0325901 | 0.002 | 0.538 | 0.036 | +++++ |
| 132 | H1781 | Lung | p53 mut | PD-0325901 | >2 | 0.2 | 0.372 | +++ |
| 133 | H1435 | Lung | p53 mut | PD-0325901 | >2 | 1.25 | 0.341 | +++ |

Figure 1A-6

*in vitro* Cell Proliferation Assays of Combinations of
Formula Ia Compound (GDC-0941) and Various Chemotherapeutic Agents

| | | | | | | | |
|---|---|---|---|---|---|---|---|
| 134 | H661 | Lung | p53 mut | PD-0325901 | >2 | 1.43 | 1.213 | - |
| 135 | H1299 | Lung | p53 mut | PD-0325901 | 2.5 | 0.414 | 0.024 | +++++ |
| 136 | A549 | Lung | K-ras G12S | PD-0325901 | 0.06 | 0.49 | 0.076 | +++++ |
| 137 | H23 | Lung | K-ras G12C | PD-0325901 | 0.01 | 0.82 | 0.154 | ++++ |
| 138 | H838 | Lung | EGFR | PD-0325901 | >2 | 0.578 | 0.949 | +/- |
| 139 | LKR13 (mouse) | Lung | K-ras, p53 mut | PD-0325901 | >2 | 0.578 | 0.949 | +/- |
| 140 | LKR10 (mouse) | Lung | K-ras, p53 mut | erlotinib | 6 | 1.38 | 0.042 | +++++ |
| 141 | LKR13 (mouse) | Lung | K-ras, p53 mut | erlotinib | >10 | 0.815 | 0.109 | +++++ |
| 142 | Calu-6 | Lung | K-ras Q61K | erlotinib | 7 | 3.64 | 0.056 | +++++ |
| 143 | H1299 | Lung | N-ras Q61K | erlotinib | >10 | 0.414 | 0.058 | +++++ |
| 144 | H2126 | Lung | p53 mut | erlotinib | 9 | 0.467 | 0.293 | ++++ |
| 145 | H661 | Lung | p53 mut | erlotinib | 7 | 1.43 | 0.532 | +++ |
| 146 | H1435 | Lung | p53 mut | erlotinib | 2.5 | 1.25 | 0.034 | +++++ |
| 147 | H2122 | Lung | K-ras G12C, p53 mut | erlotinib | 6 | 0.538 | 0.095 | +++++ |
| 148 | H1781 | Lung | p53 mut | erlotinib | >10 | 0.2 | 0.383 | ++++ |
| 149 | A549 | Lung | K-ras G12S | erlotinib | 13.1 | 0.49 | 0.167 | ++++ |
| 150 | H1703 | Lung | p53 mut | erlotinib | 6 | 0.675 | 0.781 | ++ |
| 151 | H1781 | Lung | p53 mut | erlotinib | >10 | 0.2 | 0.383 | ++++ |
| 152 | H838 | Lung | EGFR | erlotinib | 6 | 0.578 | 0.808 | + |
| 153 | H23 | Lung | K-ras G12C | erlotinib | >20 | 0.82 | 0.282 | ++++ |
| 154 | H322T | Lung | EGFR | erlotinib | 0.16 | 1.46 | 0.29 | ++++ |
| 155 | H1651 | Lung | | erlotinib | >10 | 7.71 | 0.739 | ++ |
| 156 | H838 | Lung | EGFR | erlotinib | 6 | 0.578 | 0.808 | ++ |
| 157 | A427 | Lung | K-ras G12D | erlotinib | >10 | 0.458 | 0.038 | +++++ |

Figure 1A-7

*in vitro* Cell Proliferation Assays of Combinations of
Formula Ia Compound (GDC-0941) and Various Chemotherapeutic Agents

| | | | | | | | |
|---|---|---|---|---|---|---|---|
| 158 | H1155 | Lung | K-ras Q61H | erlotinib | 8.62 | 1.456 | 0.415 | +++ |
| 159 | H1299 | Lung | p53 mut | erlotinib | >10 | 0.41 | 0.2 | ++++ |
| 160 | H1975 | Lung | | erlotinib | 5.51 | 0.836 | 0.811 | + |
| 161 | H2009 | Lung | K-ras Q61H | erlotinib | 7.1 | 0.595 | 0.446 | +++ |
| 162 | H2030 | Lung | K-ras G12C | erlotinib | 5.82 | 1.874 | 0.41 | +++ |
| 163 | H292 | Lung | K-ras N85K | erlotinib | 2.1 | 0.391 | 0.446 | +++ |
| 164 | H358 | Lung | K-ras G12C | erlotinib | 0.66 | 2.474 | 0.273 | ++++ |
| 165 | H441 | Lung | K-ras G12V | erlotinib | 4.89 | 4.195 | 0.27 | ++++ |
| 166 | H460 | Lung | K-ras G61H | erlotinib | >10 | 0.24 | 0.314 | +++ |
| 167 | H647 | Lung | K-ras G13D | erlotinib | >2 | 1.43 | 1.213 | - |
| 168 | H650 | Lung | K-ras Q61L | erlotinib | >10 | 14.34 | 0.245 | +++++ |
| 169 | 537MEL | Melanoma | PTEN neg | 5-FU | >50 | 0.49 | 0.65 | ++ |
| 170 | 537MEL | Melanoma | PTEN neg | docetaxel | 0.0125 | 0.49 | 0.29 | ++++ |
| 171 | 537MEL | Melanoma | PTEN neg | gemcitabine | 0.0045 | 0.49 | 0.85 | + |
| 172 | A375 | Melanoma | B-raf V600E | temozolomide | >10 | 2.06 | 0.007 | +++++ |
| 173 | Malme-3M | Melanoma | | temozolomide | >20 | 0.35 | 0.18 | ++++ |
| 174 | 537MEL | Melanoma | PTEN neg | temozolomide | >16.25 | 0.49 | 1.2 | - |
| 175 | 537 Mel | Melanoma | PTEN neg | PD-0325901 | 0.009 | 0.49 | 0.16 | ++++ |
| 176 | A375 | Melanoma | B-raf V600E | PD-0325901 | 0.004 | 2.06 | 0.19 | ++++ |
| 177 | Hs294T | Melanoma | | PD-0325901 | 0.022 | 0.50 | 0.2 | ++++ |
| 178 | Malme-3M | Melanoma | | PD-0325901 | 0.35 | 0.004 | 0.6 | +++ |
| 179 | MeWo | Melanoma | | PD-0325901 | 0.14 | 0.67 | 0.06 | +++++ |
| 180 | A2058 | Melanoma | | PD-0325901 | 0.04 | 0.45 | 0.29 | ++++ |
| 181 | C32 | Melanoma | | PD-0325901 | 0.02 | 0.51 | 0.66 | +++ |

Figure 1A-8

*In vitro* Cell Proliferation Assays of Combinations of Formula Ia Compound (GDC-0941) and Various Chemotherapeutic Agents

| | | | | | | |
|---|---|---|---|---|---|---|
| 182 | LOX | Melanoma | | PD-0325901 | 0.22 | 0.91 | 0.001 | +++++ |
| 183 | RPMI-7951 | Melanoma | | PD-0325901 | 0.01 | 0.32 | 0.60 | +++ |
| 184 | SK-MEL-28 | Melanoma | | PD-0325901 | 0.009 | 0.57 | 0.34 | +++ |
| 185 | 624 Mel | Melanoma | | HPPD | 0.17 | 0.66 | 0.44 | +++ |
| 186 | 888 Mel | Melanoma | | HPPD | 0.48 | 0.73 | 0.31 | +++ |
| 187 | 928 Mel | Melanoma | | HPPD | 0.45 | 0.58 | 0.61 | +++ |
| 188 | 537 Mel | Melanoma | PTEN neg B-raf V600E, PTEN neg | HPPD | 0.26 | 0.49 | 0.39 | +++ |
| 189 | A2058 | Melanoma | B-raf V600E | HPPD | 20.0 | 0.45 | 0.44 | +++ |
| 190 | A375 | Melanoma | | HPPD | 0.16 | 2.06 | 0.73 | ++ |
| 191 | C32 | Melanoma | | HPPD | 0.36 | 0.51 | 0.56 | +++ |
| 192 | Colo829 | Melanoma | | HPPD | 1.52 | 1.11 | 0.30 | +++ |
| 193 | G361 | Melanoma | | HPPD | 0.54 | 0.54 | 0.53 | +++ |
| 194 | Hs 294T | Melanoma | | HPPD | 2.20 | 0.50 | 0.80 | ++ |
| 195 | Hs 695T | Melanoma | | HPPD | 1.80 | 0.24 | 0.83 | ++ |
| 196 | LOX | Melanoma | | HPPD | 20.0 | 0.91 | 0.13 | ++++ |
| 197 | Malme-3M | Melanoma | | HPPD | 0.28 | 0.35 | 0.49 | +++ |
| 198 | MeWo | Melanoma | | HPPD | 20.0 | 0.67 | 2.39 | --- |
| 199 | RPMI-7951 | Melanoma | | HPPD | 2.40 | 0.32 | 0.63 | +++ |
| 200 | SK23 | Melanoma | | HPPD | 1.12 | 0.49 | 1.13 | - |
| 201 | SK-MEL-28 | Melanoma | | HPPD | 0.22 | 0.57 | 0.60 | +++ |
| 202 | TOV21G | Ovarian | K-ras G13C | 5-FU | 1 | 0.48 | 1.019 | +/- |
| 203 | FU-OV1 | Ovarian | | 5-FU | 10 | 0.146 | 0.896 | + |
| 204 | TOV112D | Ovarian | | 5-FU | 5 | 0.294 | 0.899 | + |

Figure 1A-9

*in vitro* Cell Proliferation Assays of Combinations of
Formula Ia Compound (GDC-0941) and Various Chemotherapeutic Agents

| 205 | EFO21 | Ovarian | | 5-FU | 5 | 0.77 | 0.967 | +/- |
|---|---|---|---|---|---|---|---|---|
| 206 | SKOV3 | Ovarian | | 5-FU | >40 | 0.66 | 1.94 | - |
| 207 | OVCAR3 | Ovarian | | 5-FU | 5 | 0.34 | 0.915 | +/- |
| 208 | TOV112D | Ovarian | | carboplatin | 30.7 | 1.53 | 1.06 | +/- |
| 209 | TOV21G | Ovarian | K-ras G13C | carboplatin | 11 | 1.03 | 0.487 | +++ |
| 210 | FU-OV1 | Ovarian | | docetaxel | >0.02 | 0.146 | 0.733 | ++ |
| 211 | TOV112D | Ovarian | | docetaxel | 0.0002 | 1.53 | 0.969 | +/- |
| 212 | TOV112D | Ovarian | | docetaxel | 0.02 | 0.294 | 1.05 | +/- |
| 213 | SKOV3 | Ovarian | | docetaxel | 0.01 | 0.66 | 0.177 | ++++ |
| 214 | OVCAR3 | Ovarian | | docetaxel | 0.001 | 0.34 | 0.709 | ++ |
| 215 | EFO21 | Ovarian | | docetaxel | 0.01 | 0.77 | 0.937 | +/- |
| 216 | TOV21G | Ovarian | K-ras G13C | docetaxel | 0.005 | 0.48 | 0.962 | +/- |
| 217 | EFO21 | Ovarian | | doxorubicin | 0.02 | 0.77 | 0.921 | +/- |
| 218 | SKOV3 | Ovarian | | doxorubicin | 0.3 | 0.66 | 0.39 | +++ |
| 219 | FU-OV1 | Ovarian | | gemcitabine | >0.02 | 0.146 | 0.686 | +++ |
| 220 | EFO21 | Ovarian | | gemcitabine | 0.01 | 0.77 | 0.579 | +++ |
| 221 | SKOV3 | Ovarian | | gemcitabine | 0.0018 | 0.66 | 1.177 | - |
| 222 | OVCAR3 | Ovarian | | gemcitabine | 0.001 | 0.34 | 1.022 | +/- |
| 223 | TOV21G | Ovarian | K-ras G13C | gemcitabine | 0.005 | 0.48 | 0.536 | +++ |
| 224 | EFO21 | Ovarian | | PD-0325901 | 0.01 | 0.77 | 0.196 | ++++ |
| 225 | OVCAR3 | Ovarian | | PD-0325901 | >2 | 0.34 | 0.912 | +/- |
| 226 | SKOV3 | Ovarian | | PD-0325901 | >2 | 0.66 | 0.144 | ++++ |
| 227 | OVCAR3 | Ovarian | | tamoxifen | >20 | 0.34 | 0.875 | + |
| 228 | SKOV3 | Ovarian | | tamoxifen | >20 | 0.66 | 0.821 | ++ |

Figure 1A-10

*in vitro* Cell Proliferation Assays of Combinations of
Formula Ia Compound (GDC-0941) and Various Chemotherapeutic Agents

| | | | | | | | |
|---|---|---|---|---|---|---|---|
| 229 | ASPC-1 | Pancreatic | K-ras G12D | gemcitabine | 0.021 | 3.36 | 0.236 | ++++ |
| 230 | MiaCaPa1 | Pancreatic | K-ras G12C | erlotinib | >10 | 0.78 | 1.13 | - |
| 231 | ASPC-1 | Pancreatic | K-ras G12D | erlotinib | 4.28 | 3.36 | 0.794 | ++ |
| 232 | HPAF-II | Pancreatic | K-ras G12D | PD-0325901 | 0.14 | 1.19 | 0.07 | +++++ |
| 233 | AsPC-1 | Pancreatic | K-ras G12D | PD-0325901 | 0.02 | 0.81 | 0.3 | ++++ |
| 234 | SW1990 | Pancreatic | K-ras G12D | PD-0325901 | 0.03 | 5.43 | 0.3 | ++++ |
| 235 | BxPC3 | Pancreatic | | PD-0325901 | 0.05 | 0.55 | 0.4 | +++ |
| 236 | Panc 05.04 | Pancreatic | K-ras G12D | PD-0325901 | 0.008 | 0.23 | 0.5 | +++ |
| 237 | KP4 | Pancreatic | K-ras G12D | HPPD | 20.0 | 1.73 | 0.86 | + |
| 238 | PATU8988T | Pancreatic | K-ras G12V | HPPD | 20.0 | 0.59 | 1.06 | +/- |
| 239 | SU86.86 | Pancreatic | K-ras G12D | HPPD | 20.0 | 7.90 | 0.39 | +++ |
| 240 | PC-3 | Prostate | | 5-FU | 5 | 0.27 | 0.711 | ++ |
| 241 | DU1145 | Prostate | | docetaxel | 8.2 | 0.865 | 0.918 | +/- |
| 242 | PC-3 | Prostate | | docetaxel | 0.0025 | 0.27 | 0.364 | +++ |
| 243 | 22rv1 | Prostate | | docetaxel | 0.005 | 0.25 | 0.511 | +++ |
| 244 | PC-3 | Prostate | | doxorubicin | 0.002 | 0.27 | 1.248 | - |
| 245 | PC-3 | Prostate | | gemcitabine | 0.01 | 0.27 | 0.972 | +/- |
| 246 | DU1145 | Prostate | | paclitaxel | 0.032 | 0.865 | 0.79 | ++ |
| 247 | 22rv1 | Prostate | | PD-0325901 | >10 | 0.25 | 0.308 | +++ |
| 248 | PC-3 | Prostate | | PD-0325901 | 0.013 | 0.27 | 1.07 | +/- |

Figure 1A-11

*in vitro* Cell Proliferation Assays of Combinations of
Formula IIa Compound and Various Chemotherapeutic Agents

| Expt | Cell Line | Tumor Type | Ras Mutation | Chemotherapeutic | Chemo EC50 | Compound IIa EC50 | Combination Index (CI) | Synergy |
|---|---|---|---|---|---|---|---|---|
| 1 | MDA-MB-361 | Breast | PI3K E545K | 5-FU | >40 | 0.61 | 0.336 | +++ |
| 2 | MDA-MB-468 | Breast | PI3K E545K | 5-FU | 20 | 7.14 | 1.24 | - |
| 3 | MT3 | Breast | K-ras G12D | 5-FU | >40 | 0.77 | 1.11 | - |
| 4 | ZR75-1 | Breast | PTEN neg | 5-FU | 20 | 0.78 | 0.468 | +++ |
| 5 | Cal-120 | Breast | | 5-FU | 1.33 | 2.26 | 1.13 | - |
| 6 | MDA-MB-361 | Breast | PI3K E545K | docetaxel | 0.0016 | 0.61 | 0.092 | +++++ |
| 7 | MDA-MB-468 | Breast | PTEN neg | docetaxel | 0.005 | 7.14 | 0.872 | + |
| 8 | MT3 | Breast | K-ras G12D | docetaxel | 0.001 | 0.77 | 0.691 | +++ |
| 9 | Cal-120 | Breast | | docetaxel | 0.85 | 2.26 | 1.21 | - |
| 10 | ZR75-1 | Breast | PTEN neg | docetaxel | 0.0025 | 0.78 | 0.459 | +++ |
| 11 | MDA-MB-361 | Breast | PI3K E545K | gemcitabine | 0.006 | 0.61 | 0.501 | +++ |
| 12 | MDA-MB-468 | Breast | | gemcitabine | 0.0025 | 7.14 | 1.26 | - |
| 13 | MT3 | Breast | K-ras G12D | gemcitabine | 0.002 | 0.77 | 0.99 | - |
| 14 | Cal-120 | Breast | | gemcitabine | 0.4 | 2.26 | 0.47 | +++ |
| 15 | ZR75-1 | Breast | PTEN neg | 5-FU | 0.01 | 0.78 | 1.06 | +/- |
| 16 | C-33A | Cervical | | 5-FU | 3.84 | 2.5 | 1.27 | - |
| 17 | ME-180 | Cervical | PI3K E545K | 5-FU | 4 | 0.6 | 0.87 | + |
| 18 | SiHa | Cervical | | 5-FU | 47 | 2.5 | 1.25 | - |
| 19 | C-33A | Cervical | PTEN neg | docetaxel | 0.001 | 2.5 | 0.84 | + |
| 20 | ME-180 | Cervical | PI3K E545K | docetaxel | 0.0017 | 0.6 | 0.67 | ++ |
| 21 | SiHa | Cervical | | docetaxel | 0.0025 | 2.5 | 0.98 | - |

Figure 1B-1

*in vitro* Cell Proliferation Assays of Combinations of
Formula IIa Compound and Various Chemotherapeutic Agents

| | | | | | | | |
|---|---|---|---|---|---|---|---|
| 22 | ME-180 | Cervical | PI3K E545K | gemcitabine | 0.035 | 0.6 | 0.54 | +++ |
| 23 | C-33A | Cervical | PTEN neg | gemcitabine | 0.0025 | 2.5 | 1.09 | - |
| 24 | SiHa | Cervical | | gemcitabine | 0.0025 | 2.5 | 0.59 | +++ |
| 25 | ECC-1 | Endometrial | PTEN neg | 5-FU | 2 | 2.5 | 0.75 | ++ |
| 26 | ECC-1 | Endometrial | PTEN neg | docetaxel | 0.0009 | 2.5 | 0.66 | ++ |
| 27 | ECC-1 | Endometrial | PTEN neg | gemcitabine | 0.0113 | 2.5 | 1.17 | - |
| 28 | HEC-1-A | Endometrial | | 5-FU | 2.5 | 1.25 | 0.8 | + |
| 29 | HEC-1-A | Endometrial | | docetaxel | 0.0012 | 1.25 | 0.66 | ++ |
| 30 | HEC-1-A | Endometrial | | gemcitabine | 0.05 | 1.25 | 0.81 | + |
| 31 | SK-UT-1B | Endometrial | PTEN neg | 5-FU | 1.3 | 0.48 | 0.54 | +++ |
| 32 | SK-UT-1B | Endometrial | PTEN neg | docetaxel | 0.0005 | 0.48 | 0.46 | +++ |
| 33 | SK-UT-1B | Endometrial | PTEN neg | gemcitabine | 0.0019 | 0.48 | 0.76 | ++ |
| 34 | U87 | Glioma | PTEN neg | temozolomide | 11.7 | 0.9 | 0.672 | ++ |
| 35 | G402 | Glioma | | 5-FU | | | 0.74 | ++ |
| 36 | G402 | Glioma | | docetaxel | | | 0.47 | +++ |
| 37 | G402 | Glioma | | gemcitabine | | | 0.54 | +++ |
| 38 | 537MEL | Melanoma | PTEN neg | 5-FU | >50 | 2.5 | 1.25 | - |
| 39 | 537MEL | Melanoma | PTEN neg | docetaxel | 0.0125 | 2.5 | 0.51 | +++ |
| 40 | 537MEL | Melanoma | PTEN neg | gemcitabine | 0.0045 | 2.5 | 0.96 | - |
| 41 | PC-3 | Prostate | | gemcitabine | 0.01 | 1.53 | 0.703 | ++ |

Figure 1B-2

*in vitro* Cell Proliferation Assays of Combinations of
Formula Ib Compound and Various Chemotherapeutic Agents

| Expt. | Cell Line | Tumor Type | Ras Mutation | Chemotherapeutic | Chemo EC50 | Compound Ib EC50 | Combination Index (CI) | Synergy |
|---|---|---|---|---|---|---|---|---|
| 1 | MDA-MB-361 | Breast | PI3K E545K | docetaxel | 0.0016 | 0.232 | 0.32 | +++ |
| 2 | MDA-MB-361 | Breast | PI3K E545K | gemcitabine | 0.148 | 0.232 | 0.54 | ++ |
| 3 | C-33A | Cervical | PTEN neg | 5-FU | 3.84 | 1.36 | 0.9 | + |
| 4 | ME-180 | Cervical | PI3K E545K | 5-FU | 4 | 0.6 | 0.87 | + |
| 5 | SiHa | Cervical | | 5-FU | 47 | 0.62 | 1.15 | - |
| 6 | ME-180 | Cervical | PI3K E545K | docetaxel | 0.0017 | 0.14 | 0.74 | + |
| 7 | C-33A | Cervical | PTEN neg | docetaxel | 0.001 | 1.36 | 0.73 | + |
| 8 | SiHa | Cervical | | docetaxel | 0.0026 | 0.62 | 0.93 | + |
| 9 | SiHa | Cervical | | gemcitabine | 0.0025 | 0.62 | 0.47 | ++ |
| 10 | ME-180 | Cervical | PI3K E545K | gemcitabine | 0.035 | 0.6 | 0.54 | ++ |
| 11 | C-33A | Cervical | PTEN neg | gemcitabine | 0.0025 | 1.36 | 0.65 | ++ |
| 12 | ECC-1 | Endometrial | PTEN neg | 5-FU | 2 | 0.34 | 0.66 | ++ |
| 13 | ECC-1 | Endometrial | PTEN neg | docetaxel | 0.0009 | 0.34 | 0.8 | + |
| 14 | ECC-1 | Endometrial | PTEN neg | gemcitabine | 0.0113 | 0.34 | 0.83 | + |
| 15 | HEC-1-A | Endometrial | | 5-FU | 2.5 | 0.3 | 0.94 | + |
| 16 | HEC-1-A | Endometrial | | docetaxel | 0.0012 | 0.3 | 0.77 | + |
| 17 | HEC-1-A | Endometrial | | gemcitabine | 0.05 | 0.3 | 0.7 | + |
| 18 | SK-UT-1B | Endometrial | PTEN neg | 5-FU | 1.3 | 0.11 | 0.87 | + |
| 19 | SK-UT-1B | Endometrial | PTEN neg | docetaxel | 0.0005 | 0.11 | 0.59 | ++ |
| 20 | SK-UT-1B | Endometrial | PTEN neg | gemcitabine | 0.0019 | 0.11 | 0.51 | ++ |
| 21 | G402 | Glioma | | 5-FU | | | 1.05 | - |
| 22 | G402 | Glioma | | docetaxel | | | 0.67 | ++ |

Figure 1C-1

*In vitro* Cell Proliferation Assays of Combinations of
Formula Ib Compound and Various Chemotherapeutic Agents

| | | | | | | |
|---|---|---|---|---|---|---|
| 23 | G402 | Glioma | | gemcitabine | | 0.86 | + |
| 24 | G111 | Glioma | | temozolomide | >16.25 | 0.33 | 0.71 | ++ |
| 25 | G140 | Glioma | PTEN neg | temozolomide | >16.25 | 0.35 | 1.03 | - |
| 26 | G59 | Glioma | PTEN neg | temozolomide | >16.25 | 0.47 | 0.92 | + |
| 27 | G63 | Glioma | PTEN neg | temozolomide | >16.25 | 0.6 | 0.85 | + |
| 28 | LN229 | Glioma | PI3K E545K | temozolomide | >16.25 | 0.7 | 0.99 | - |
| 29 | U87 | Glioma | PTEN neg | temozolomide | 11.7 | 0.266 | 0.66 | ++ |
| 30 | 537MEL | Melanoma | PTEN neg | 5-FU | >16.25 | 0.32 | 1.01 | - |
| 31 | 537MEL | Melanoma | PTEN neg | 5-FU | >50 | 0.625 | 0.67 | ++ |
| 32 | 537MEL | Melanoma | PTEN neg | docetaxel | 0.0125 | 0.625 | 0.33 | +++ |
| 33 | 537MEL | Melanoma | PTEN neg | gemcitabine | 0.0045 | 0.625 | 0.45 | +++ |

Figure 1C-2

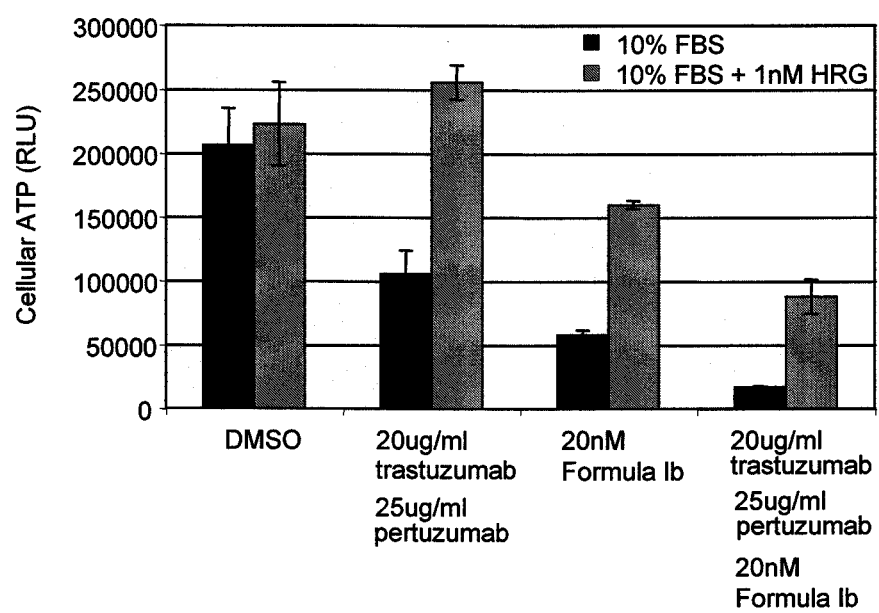
Figure 21-A

COMBINATIONS OF PHOSPHOINOSITIDE 3-KINASE INHIBITOR COMPOUNDS CHEMOTHERAPEUTIC AGENTS, AND METHODS OF USE

CROSS REFERENCE TO RELATED APPLICATIONS

This application is a divisional of U.S. Ser. No. 12/208,227, filed 10 Sep. 2008, which claims the benefit under 35 USC §119(e) of U.S. Provisional Application Ser. No. 60/971,773 filed on 12 Sep. 2007, each of which are incorporated by reference in entirety.

FIELD OF THE INVENTION

The invention relates generally to pharmaceutical combinations of compounds with activity against hyperproliferative disorders such as cancer and which include compounds that inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol is one of a number of phospholipids found in cell membranes, and which participate in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem. 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60). Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and PDK1, phosphoinositide-dependent kinase-1 (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI. The main PI3-kinase isoform in cancer is the Class I PI3-kinase, p110α. (U.S. Pat. No. 5,824,492; U.S. Pat. No. 5,846,824; U.S. Pat. No. 6,274,327). Other isoforms are implicated in cardiovascular and immune-inflammatory disease (Workman P (2004) Biochem Soc Trans 32:393-396; Patel et al (2004) Proc. Am. Assoc. of Cancer Res. (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press), and oncogene mutations in PI3 kinase (Samuels et al (2004) Science 304:554). Oncogenic mutations of p110 alpha have been found at a significant frequency in colon, breast, brain, liver, ovarian, gastric, lung, and head and neck solid tumors. PTEN abnormalities are found in glioblastoma, melanoma, prostate, endometrial, ovarian, breast, lung, head and neck, hepatocellular, and thyroid cancers.

The initial purification and molecular cloning of PI3 kinase revealed that it was a heterodimer consisting of p85 and p110 subunits (Otsu et al (1991) Cell 65:91-104; Hiles et al (1992) Cell 70:419-29). Since then, four distinct Class I PI3Ks have been identified, designated PI3K α (alpha), β (beta), δ (delta), and ω (gamma), each consisting of a distinct 110 kDa catalytic subunit and a regulatory subunit. More specifically, three of the catalytic subunits, i.e., p110 alpha, p110 beta and p110 delta, each interact with the same regulatory subunit, p85; whereas p110 gamma interacts with a distinct regulatory subunit, p101. The patterns of expression of each of these PI3Ks in human cells and tissues are also distinct. In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30; Volinia et al (1992) Oncogene, 7:789-93).

The PI3 kinase/Akt/PTEN pathway is an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. Nos. 7,173,029; 7,037,915; 6,608,056; 6,608,053; 6,838,457; 6,770,641; 6,653,320; 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070). Wortmannin analogs have PI3 kinase activity in mammals (U.S. Pat. No. 6,703,414; WO 97/15658).

Thienopyrimidine compounds of Formulas I and II have p110 alpha binding, PI3 kinase inhibitory activity and inhibit the growth of cancer cells (WO 2006/046031; US 2008/0039459; US 2008/0076768; US 2008/0076758; WO 2008/070740; WO 2008/073785.

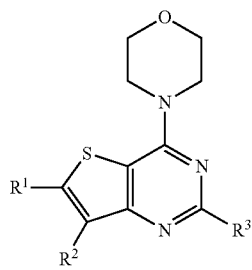

I

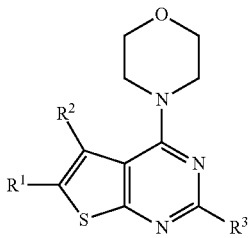

II

Formula I compound, GDC-0941 (Genentech Inc.), is a selective, orally bioavailable inhibitor of PI3K with promising pharmacokinetic and pharmaceutical properties (Belvin et al, American Association for Cancer Research Annual Meeting 2008, 99th: April 15, Abstract 4004; Folkes et al, American Association for Cancer Research Annual Meeting 2008, 99th: April 14, Abstract LB-146; Friedman et al, American Association for Cancer Research Annual Meeting 2008, 99th: April 14, Abstract LB-110).

Combinations of anti-cancer pharmaceutical therapeutics administered simultaneously or sequentially in a dosing regimen are now common in cancer treatment. Successful combination therapy provides improved and even synergistic effect over mono-therapy, i.e. pharmaceutical treatment limited to one drug. Combination therapy for the treatment of hyperproliferative disorders such as cancer has been studied, including antitumor activity of erlotinib in combination with capecitabine in human tumor xenograft models (Ouchi et al (2006) Cancer Chemother. Pharmacol. 57:693-702), and erlotinib in combination gemcitabine and cisplatin in non-small cell lung cancer (NSCLC) tumor xenograft models (Higgins et al (2004) Anti-Cancer Drugs 15:503-512). Preclinical research has been the basis for prediction of clinical stage synergy of anti-cancer pharmaceutical therapeutic combinations including capecitabine and taxanes for the treatment of breast cancer (Sawada et al (1998) Clin. Cancer Res. 4:1013-1019). Certain doses and schedules of combination therapy of capecitabine and taxane can improve safety without compromising efficacy (O'Shaughnessy et al (2006) Clin. Breast Cancer April 7(1):42-50). Synergistic effects of antifungal combinations in vitro have been correlated with clinical stage synergy (Steinbach et al (2003) Clin. Inf. Dis. October 1; 37 Suppl 3:S188-224).

SUMMARY OF THE INVENTION

The invention relates generally to thienopyrimidine compounds of Formulas I and II with anti-cancer activity, and more specifically with PI3 kinase inhibitory activity, administered in combination with chemotherapeutic agents to inhibit the growth of cancer cells. Certain combinations of Formula I and II compounds with chemotherapeutic agents show synergistic effects in inhibiting the growth of cancer cells in vitro and in vivo. The combinations and methods of the invention may be useful in the treatment of hyperproliferative disorders such as cancer. The compositions may inhibit tumor growth in mammals and may be useful for treating human cancer patients.

In one aspect, the invention includes a method for the treatment of a hyperproliferative disorder comprising administering a therapeutic combination as a combined formulation or alternation to a mammal, wherein the therapeutic combination comprises a therapeutically effective amount of a compound having Formula I or II, and a therapeutically effective amount of a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib.

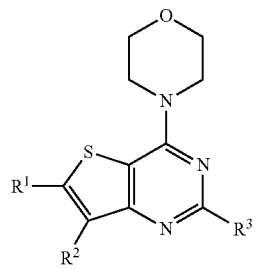

I

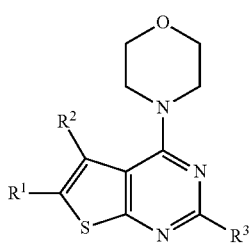

II

The invention also relates to methods of using the compositions for in vitro, in situ, and in vivo diagnosis or treatment of mammalian cells, organisms, or associated pathological conditions.

An aspect of the invention provides therapeutic combinations comprising 4-(2-(1H-indazol-4-yl)-6-((4-(methylsulfonyl)piperazin-1-yl)methyl)thieno[3,2-d]pyrimidin-4-yl)morpholine (US 2008/0076768; WO 2006/046031), also known as GDC-0941 (Genentech, Inc.) and having Formula Ia and a therapeutically effective amount of a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib.

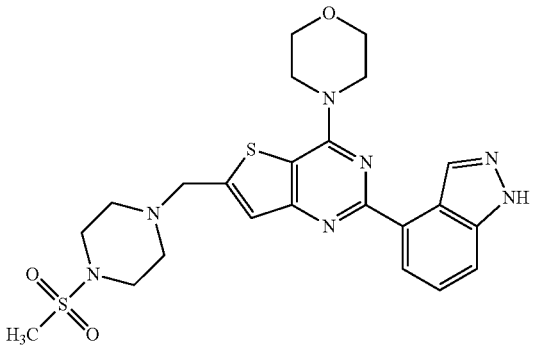

Ia

An aspect of the invention provides therapeutic combinations comprising (S)-1-(4-42-(2-aminopyrimidin-5-yl)-7-methyl-4-morpholinothieno[3,2-d]pyrimidin-6-yl)methyl)piperazin-1-yl)-2-hydroxypropan-1-one (WO 2008/070740) having Formula Ib and a therapeutically effective amount of a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib.

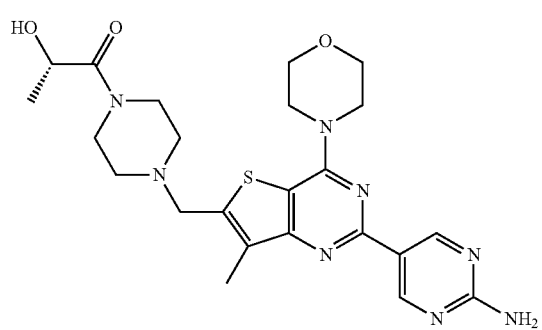

Ib

An aspect of the invention provides therapeutic combinations comprising 4-(2-(1H-indazol-4-yl)-6-((4-(methylsulfonyl)piperazin-1-yl)methyl)thieno[2,3-d]pyrimidin-4-yl)morpholine (US 2008/0076758; WO 2006/046031) having Formula IIa and a therapeutically effective amount of a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib.

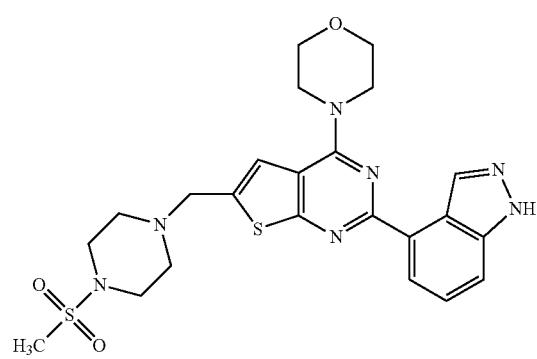

IIa

Formula Ia, Ib, and IIa compounds are orally bioavailable and have single agent anti-tumor activity in multiple human cancer models.

Formula I and II compounds include all stereoisomers, geometric isomers, tautomers, metabolites, and pharmaceutically acceptable salts thereof. Certain Formula I and II compounds are potent inhibitors of PI3K with drug-like physicochemical and pharmacokinetic properties. Certain Formula I and II compounds exhibit selectivity for class Ia PI3Ks over class Ib, in particular for the P110 alpha subtype.

Pharmaceutical compositions and therapeutic combinations of the invention comprise a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib.

Pharmaceutical compositions of the invention may further comprise a pharmaceutically acceptable carrier.

Another aspect of the invention provides methods of treating a hyperproliferative disease or disorder modulated by PI3 kinases, comprising administering to a mammal in need of such treatment effective amounts of a Formula I or II compound and a chemotherapeutic agent. The Formula I or II compound and the chemotherapeutic agent may be co-formulated for administration in a combination as a pharmaceutical composition or they may be administered separately in alternation (sequentially) as a therapeutic combination.

Another aspect of the invention provides methods of treating a hyperproliferative disorder, comprising administering to a mammal in need of such treatment effective amounts of the Formula I or II compound and a chemotherapeutic agent.

In a further aspect the present invention provides a method of using a pharmaceutical composition of the invention to treat a disease or condition modulated by PI3 kinase in a mammal.

An additional aspect of the invention is the use of a pharmaceutical composition of the invention in the preparation of a medicament for the treatment of a disease or condition modulated by PI3 kinase in a mammal.

Another aspect of the invention includes articles of manufacture or kits comprising a Formula I or II compound, a chemotherapeutic agent, a container, and optionally a package insert or label indicating a treatment.

Another aspect of the invention is a product comprising a compound having Formula I or II, and a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib; as a combined preparation for separate, simultaneous or sequential use in the treatment of a hyperproliferative disorder.

Another aspect of the invention includes a method for determining compounds to be used in combination for the treatment of cancer comprising: a) administering a therapeutic combination of a compound having Formula I or II, and a chemotherapeutic agent to HER2-amplified breast cancer cells in laminin-rich, reconstituted basement membrane media, wherein the chemotherapeutic agent targets, binds to, or modulates a HER2 receptor, and b) measuring inhibition of cellular proliferation wherein nonmalignant and malignant mammary cells are discriminated by one or more phenotypic difference selected from cell viability and acinar morphogenesis.

Another aspect of the invention includes a method for determining compounds to be used in combination for the treatment of cancer comprising: a) administering a therapeutic combination of claim 1 to an in vitro tumor cell line with a K-ras mutation, and b) measuring a synergistic or non-synergistic effect.

BRIEF DESCRIPTION OF THE DRAWINGS

FIG. 1-A shows a summary of in vitro cell proliferation assays of combinations of Formula Ia compound and various chemotherapeutic agents, dosed simultaneously. The cell lines are characterized by tumor type and presence of known mutation. The individual measured EC50 values of the chemotherapeutic agent and the Formula Ia compound (GDC-0941) are compared to the combination EC50 value and a combination index score is calculated by the Chou and Talalay method (Chou, T. and Talalay, P. (1984) Adv. Enzyme Regul. 22:27-55). The strength of synergy is scored using the ranking system and is listed in the last column.

FIG. 1-B shows a summary of in vitro cell proliferation assays of combinations of Formula IIa compound and various chemotherapeutic agents. The cell lines are characterized by tumor type and presence of Ras mutation. The individual measured EC50 values of the chemotherapeutic agent and the Formula IIa compound are compared to the combination EC50 value and a combination index score is calculated by the Chou and Talalay method (Chou, T. and Talalay, P. (1984) Adv. Enzyme Regul. 22:27-55). The strength of synergy is scored using the ranking system from Chou and Talalay.

FIG. 1-C shows a summary of in vitro cell proliferation assays of combinations of Formula Ib compound and various chemotherapeutic agents. The cell lines are characterized by tumor type and presence of Ras mutation. The individual measured EC50 values of the chemotherapeutic agent and the Formula Ib compound are compared to the combination EC50 value and a combination index score is calculated by the Chou and Talalay method (Chou, T. and Talalay, P. (1984) Adv. Enzyme Regul. 22:27-55). The strength of synergy is scored using the ranking system from Chou and Talalay.

FIG. 21-A shows treatment of BT474M1 cells in three dimensional (3D) culture. Acini growth and morphogenesis is correlated with cellular ATP production in relative light units (RLU) in 10% FBS medium with and without 1 nM heregulin1 by treatment with (left to right): DMSO, combination of 20 gg/m1trastuzumab and 25 μg/ml pertuzumab, 20 nM Formula Ib compound, and the combination of 20 Wall trastuzumab, 25 μg/ml pertuzumab, and 20 nM Formula Ib compound.

FIG. 52 shows the mean tumor volume change over time with Harlan female nude mice with NCI-H2122 (K-ras) NSCLC tumor cell xenografts dosed on day 0 with:

Figure 2:
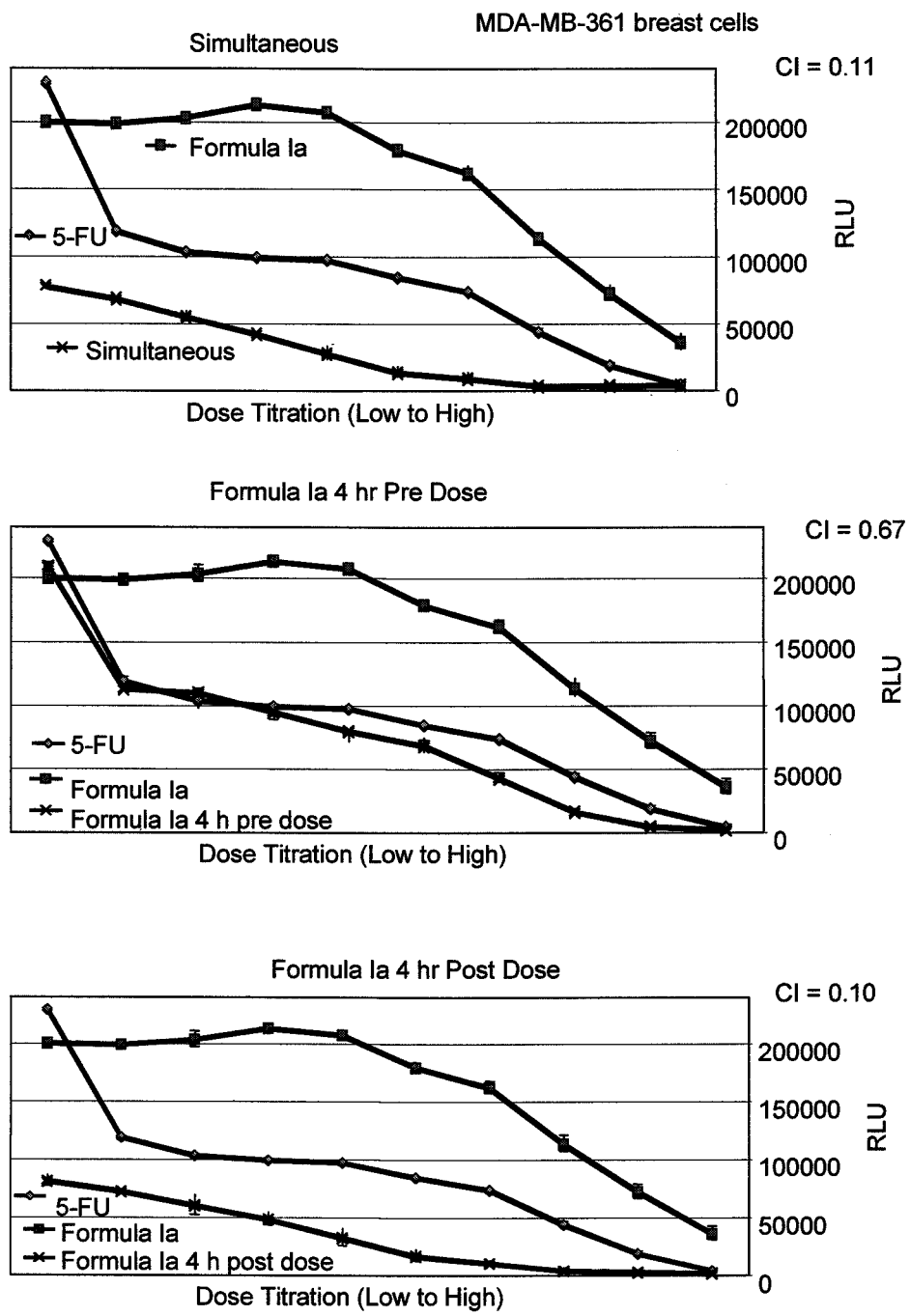
FIG. 2 shows results of in vitro cell proliferation assays (Cell-Titer Glo, Promega) measuring viable cells over varying concentrations (starting at 4× EC50) right to left of 5-FU, Formula Ia compound (GDC-0941), and the combination of 5-FU and Formula Ia. The MDA-MB-361 (breast tumor type) cells are treated simultaneously (top), pre-dosed with Formula Ia 4 hours before dosing with 5-FU (middle), and post-dosed with Formula Ia 4 hours after dosing with 5-FU (bottom).

PD-0325901 6.3 mg/kg orally daily for 21 days, Formula Ia (GDC-0941) at 100 mg/kg orally daily for 21 days, and the combination of: PD-0325901 6.3 mg/kg orally daily for 21 days and Formula Ia at 100 mg/kg orally daily for 21 days, along with mice receiving no drug (Vehicle group).

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$) CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH (CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH (CH$_3$)CH$_2$CH$_2$CH$_2$CH$_3$), 3-hexyl (—CH(CH$_2$CH$_3$) (CH$_2$CH$_2$CH$_3$)), 2-methyl-2-pentyl (—C(CH$_3$)$_2$ CH$_2$CH$_2$CH$_3$), 3-methyl-2-pentyl (—CH(CH$_3$)CH(CH$_3$) CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C (CH$_3$)$_2$CH(CH$_3$)$_2$), 3,3-dimemthyl-2-butyl (—CH(CH$_3$)C (CH$_3$)$_3$, 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, biphenyl, indenyl, indanyl, 1,2-dihydronapthalene, 1,2,3,4-tetrahydronapthyl, and the like. Aryl groups are optionally substituted independently with one or more substituents described herein.

The terms "heterocycle," "hetercyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W.A. Benjamin, N.Y., 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), nitrogen (nitrogen-linked) or oxygen (oxygen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Carbon linked monocyclic heteroaryl" refers to a five- or six-membered, unsubstituted or substituted, monocyclic heteroaryl radical which contains 1, 2, 3 or 4 ring heteroatoms independently selected from N, O and S. The carbon linked monocyclic heteroaryl is attached to the C-2 position of the pyrimidine ring according to Formulas I and II at any carbon atom of the monocyclic heteroaryl $R^3$ group. Carbon linked monocyclic heteroaryl radicals include, but are not limited to: 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl. Carbon linked monocyclic heteroaryls are optionally substituted independently with one or more substituents described herein.

"Carbon linked fused bicyclic $C_3$-$C_{20}$ heterocyclyl" and "carbon linked fused bicyclic $C_1$-$C_{20}$ heteroaryl" containing one or more heteroatoms independently selected from nitrogen, oxygen, and sulfur, differ only by their aromatic character, and have two rings fused together, i.e. share a common bond. Carbon linked fused bicyclic heterocyclyl and heteroaryl radicals are attached to the C-2 position of the pyrimidine ring according to Formulas I and II at any carbon atom of the fused bicyclic $C_3$-$C_{20}$ heterocyclyl or fused bicyclic $C_1$-$C_{20}$ heteroaryl group $R^3$ group. Carbon linked fused bicyclic heterocyclyl and heteroaryl radicals include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine. Fused bicyclic heterocycles and fused bicyclic heteroaryls are optionally substituted independently with one or more substituents described herein.

The substituent groups that alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with include F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R^{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_t-NR^{12}C(=O)(CR^{14}R^{15})_nNR^{10}R^{11}$, and $(CR^4R^5)_t-NR^{10}R^{11}$ The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small- cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a biological (large molecule) or chemical (small molecule) compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, proteins, antibodies, photosensitizers, and kinase inhibitors. Chemotherapeutic agents include compounds used in "targeted therapy" and non-targeted conventional chemotherapy.

Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), bevacizumab (AVASTIN®, Genentech), trastuzumab (HERCEPTIN®, Genentech), pertuzumab (OMNITARG®, rhuMab 2C4, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUBAL®, VALODEX®), doxorubicin (ADRIAMYCIN®), Akti-1/2, HPPD, rapamycin, and lapatinib (TYKERB®, Glaxo SmithKline).

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (MEK inhibitor, Exelixis, WO 2007/044515), ARRY-886 (MEK inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEX®, AstraZeneca), leucovorin (folinic acid), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), capecitabine (XELODA®, Roche), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaI1, calicheamicin omegaI1, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the PI3K inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

The term "mammal" includes, but is not limited to, humans, mice, rats, guinea pigs, monkeys, dogs, cats, horses, cows, pigs, and sheep, and poultry.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate))salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to a physical association or complex of one or more solvent molecules and a compound of the invention. The compounds of the invention may exist in unsolvated as well as solvated forms. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water. This physical association involves varying degrees of ionic and covalent bonding, including hydrogen bonding. In certain instances the solvate will be capable of isolation, for example when one or more solvent molecules are incorporated in the crystal lattice of the crystalline solid. Preparation of solvates is generally known, for example, M. Caira et al, J. Pharmaceutical Sci., 93(3), 601 611 (2004). Similar preparations of solvates, hemisolvate, hydrates and the like are described by E. C. van Tonder et al, AAPS PharmSciTech., 5(1), article 12 (2004); and A. L. Bingham et al, Chem. Commun., 603 604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I.R. spectroscopy, show the presence of the solvent (or water) in the crystals as a solvate (or hydrate).

The term "synergistic" as used herein refers to a therapeutic combination which is more effective than the additive effects of the two or more single agents. A determination of a synergistic interaction between a Formula I or II compound, and one or more chemotherapeutic agent may be based on the results obtained from the assays described herein. The results of these assays are analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided by this invention have been evaluated in several assay systems, and the data can be analyzed utilizing a standard program for quantifying synergism, additivism, and antagonism among anticancer agents. The program preferably utilized is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

Formula I and II Compounds

The present invention includes therapeutic combinations including Formula I and II compounds which have the structures:

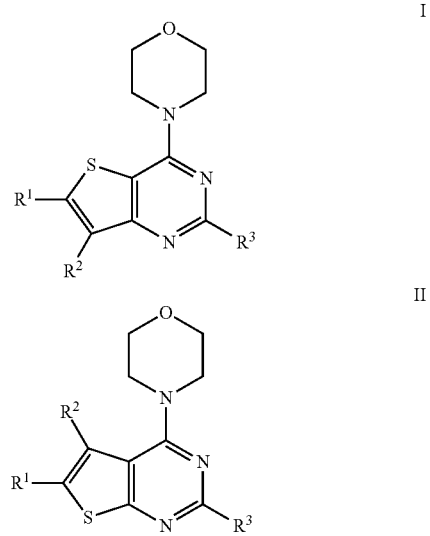

or stereoisomers, geometric isomers, tautomers, or pharmaceutically acceptable salts thereof, where:

$R^1$ is selected from H, F, Cl, Br, I, CN, —$(CR^{14}R^{15})_m$$NR^{10}R^{11}$, —$C(R^{14}R^{15})_nNR^{12}C(=Y)R^{10}$, —$(CR^{14}R^{15})_n$$NR^{12}S(O)_2R^{10}$, —$(CR^{14}R^{15})_mOR^{10}$, —$(CR^{14}R^{15})_nS(O)_2$$R^{10}$, —$(CR^{14}R^{15})_nS(O)_2NR^{10}R^{11}$, —$C(OR^{10})R^{11}R^{14}$, —C(=Y)R$^{10}$, —C(=Y)OR$^{10}$, —C(=Y)NR$^{10}$R$^{11}$, —C(=Y)NR$^{12}$OR$^{10}$, —C(=O)NR$^{12}$S(O)$_2$R$^{10}$, —C(=O)NR$^{12}$(CR$^{14}$R$^{15}$)$_m$NR$^{10}$R$^{11}$, —NO$_2$, —NR$^{12}$C(=Y)R$^{11}$, —NR$^{12}$C(=Y)OR$^{11}$, —NR$^{12}$C(=Y)NR$^{10}$R$^{11}$, —NR$^{12}$S(O)$_2$R$^{10}$, —NR$^{12}$SO$_2$NR$^{10}$R$^{11}$, —SR$^{10}$, —S(O)$_2$R$^{10}$, —S(O)$_2$NR$^{10}$R$^{11}$, —SC(=Y)R$^{10}$, —SC(=Y)OR$^{10}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —(CR$^{14}$R$^{15}$)$_t$NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR10(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is a carbon linked monocyclic heteroaryl, a carbon linked fused bicyclic C$_3$-C$_{20}$ heterocyclyl, or a carbon linked fused bicyclic C$_1$-C$_{20}$ heteroaryl, where the monocyclic heteroaryl, fused bicyclic C$_3$-C$_{20}$ heterocyclyl, and fused bicyclic C$_1$-C$_{20}$ heteroaryl are optionally substituted with one or more groups selected from F, Cl, Br, I, —CN, —NR$^{10}$R$^{11}$, —OR$^{10}$, —C(O)R$^{10}$, —NR$^{10}$C(O)R$^{11}$, —N(C(O)R$^{11}$)$_2$, —NR$^{10}$C(O)NR$^{10}$R$^{11}$, —NR$^{12}$S(O)$_2$R$^{10}$, —C(=O)OR$^{10}$, —C(=O)NR$^{10}$R$^{11}$, C$_1$-C$_{12}$ alkyl and (C$_1$-C$_{12}$ alkyl)-OR$^{10}$;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached form a C$_2$-C$_{20}$ heterocyclic ring optionally substituted with one or more groups independently selected from oxo, (CH$_2$)$_m$OR$^{12}$, NR$^{12}$R$^{12}$, CF$_3$, F, Cl, Br, I, SO$_2$R$^{12}$, C(=O)R$^{12}$, NR$^{12}$C(=Y)R$^{12}$, NR$^{12}$S(O)$_2$R$^{12}$, C(=Y)NR$^{12}$R$^{12}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring;

where said alkyl, alkenyl, alkynyl, carbocyclyl, heterocyclyl, aryl, and heteroaryl, are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)OR$^{11}$, —NR$^{12}$C(=Y)NR$^{10}$R$^{11}$, —(CR$^{14}$R$^{15}$)$_m$NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$(OR$^{11}$), —OP(OR$^{10}$)(OR$^{11}$), —SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

Y is O, S, or NR$^{12}$;

m is 0, 1, 2, 3, 4, 5 or 6; and n is 1, 2, 3, 4, 5 or 6.

Exemplary embodiments of Formula I and II compounds include wherein R$^1$ is —(CR$^{14}$R$^{15}$)$_m$NR$^{10}$R$^{11}$ where m is 1, and R$^{10}$ and R$^{11}$ together with the nitrogen to which they are attached form an optionally substituted C$_3$-C$_{20}$ heterocyclic ring. The C$_3$-C$_{20}$ heterocyclic ring may be piperazinyl, optionally substituted with one or more groups selected from NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, and C$_1$-C$_{12}$ alkyl.

Exemplary embodiments of Formula I and II compounds include wherein R$^1$ is not H.

Exemplary embodiments of Formula I and II compounds include wherein R$^2$ is H, CH$_3$, C$_3$-C$_{12}$ carbocyclyl, C$_2$-C$_{20}$ heterocyclyl, C$_6$-C$_{20}$ aryl, or C$_1$-C$_{20}$ heteroaryl. The C$_1$-C$_{20}$ heteroaryl may be a monocyclic heteroaryl group selected from 2-pyridyl, 3-pyridyl, 4-pyridyl, 3-isoxazolyl, 4-isoxazolyl, 5-isoxazolyl, 2-imidazolyl, 4-imidazolyl, 3-pyrazolyl, 4-pyrazolyl, 2-pyrrolyl, 3-pyrrolyl, 2-thiazolyl, 4-thiazolyl, 5-thiazolyl, 3-pyridazinyl, 4-pyridazinyl, 5-pyridazinyl, 2-pyrimidinyl, 5-pyrimidinyl, 6-pyrimidinyl, 2-pyrazinyl, 2-oxazolyl, 4-oxazolyl, 5-oxazolyl, 2-furanyl, 3-furanyl, 2-thienyl, 3-thienyl, 3-triazolyl, 1-triazolyl, 5-tetrazolyl, 1-tetrazolyl, and 2-tetrazolyl.

Exemplary embodiments of Formula I and II compounds include wherein R$^3$ is 2-aminopyrimidin-5-yl.

Exemplary embodiments of Formula I and II compounds include wherein R$^3$ is a bicyclic heteroaryl group selected from 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine.

Exemplary embodiments of Formula I and II compounds include wherein R$^3$ is 1H-indazol-4-yl.

An exemplary Formula I compound is 4-(2-(1H-indazol-4-yl)-6-((4-(methylsulfonyl)piperazin-1-yl)methyl)thieno[3,2-d]pyrimidin-4-yl)morpholine having Formula Ia:

Ia

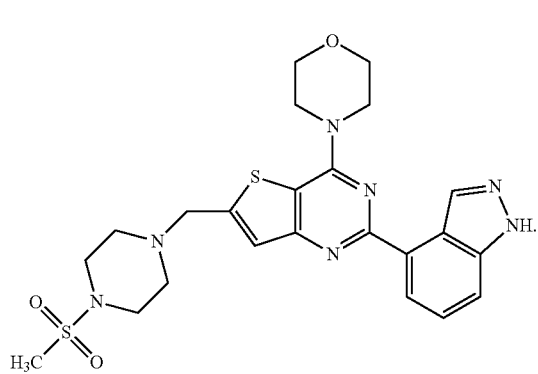

Another exemplary Formula I compound is (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one having Formula Ib:

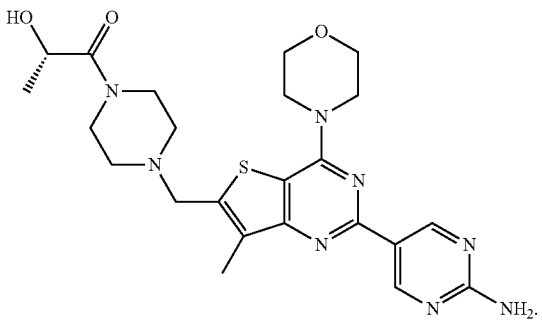

An exemplary Formula II compound is 4-(2-(1H-indazol-4-yl)-6-((4-(methylsulfonyl)piperazin-1-yl)methyl)thieno[2,3-d]pyrimidin-4-yl)morpholine having Formula IIa:

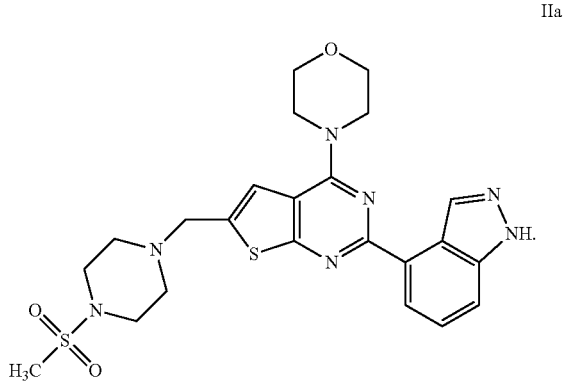

Preparation of Formula I and II Compounds

The Formula I and II compounds may be synthesized by synthetic routes that include processes analogous to those well-known in the chemical arts, and including WO 2006/046031. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4, Aufl. ed. Springer-Verlag, Berlin, including supplements (also available via the Beilstein online database).

Formula I and II compound may be prepared using procedures to prepare other thiophenes and pyrimidines (U.S. Pat. Nos. 6,608,053; 6,492,383; 6,232,320; 6,187,777; 3,763,156; 3,661,908; 3,475,429; 5,075,305; US 2003/220365; GB 1393161; WO 93/13664;); and other heterocycles, which are described in: Comprehensive Heterocyclic Chemistry, Editors Katritzky and Rees, Pergamon Press, 1984.

Formula I and II compounds may be converted into a pharmaceutically acceptable salt, and a salt may be converted into the free base compound, by conventional methods. Formula I and II compounds may be therapeutically effective as a free base or as a pharmaceutically acceptable salt, depending on the desired properties such as solubility, dissolution, hygroscopic nature, and pharmacokinetics. Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid. The salt may be a mesylate, a hydrochloride, a phosphate, a benzenesulfonate or a sulfate. Salts may be mono-salts or bis-salts. For example, the mesylate salt may be the mono-mesylate or the bis-mesylate.

Formula I and II compounds and salts may also exist as hydrates or solvates.

Protection of functional groups (e.g., primary or secondary amine) of intermediates may be necessary in preparing Formula I and II compounds. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

For illustrative purposes, Schemes 1-7 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

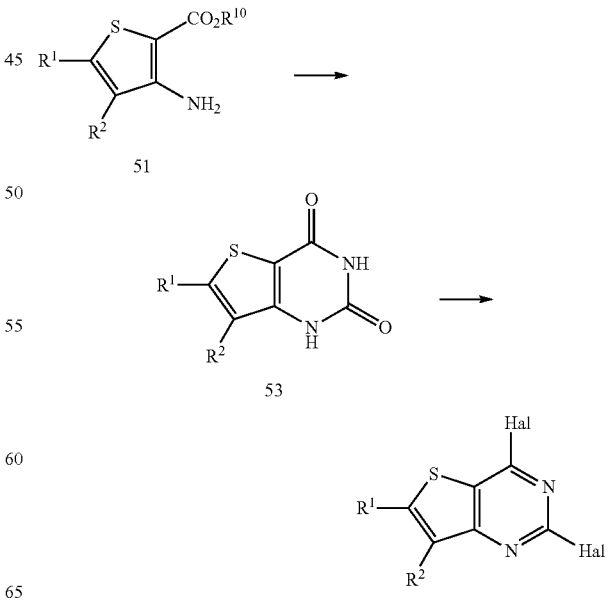

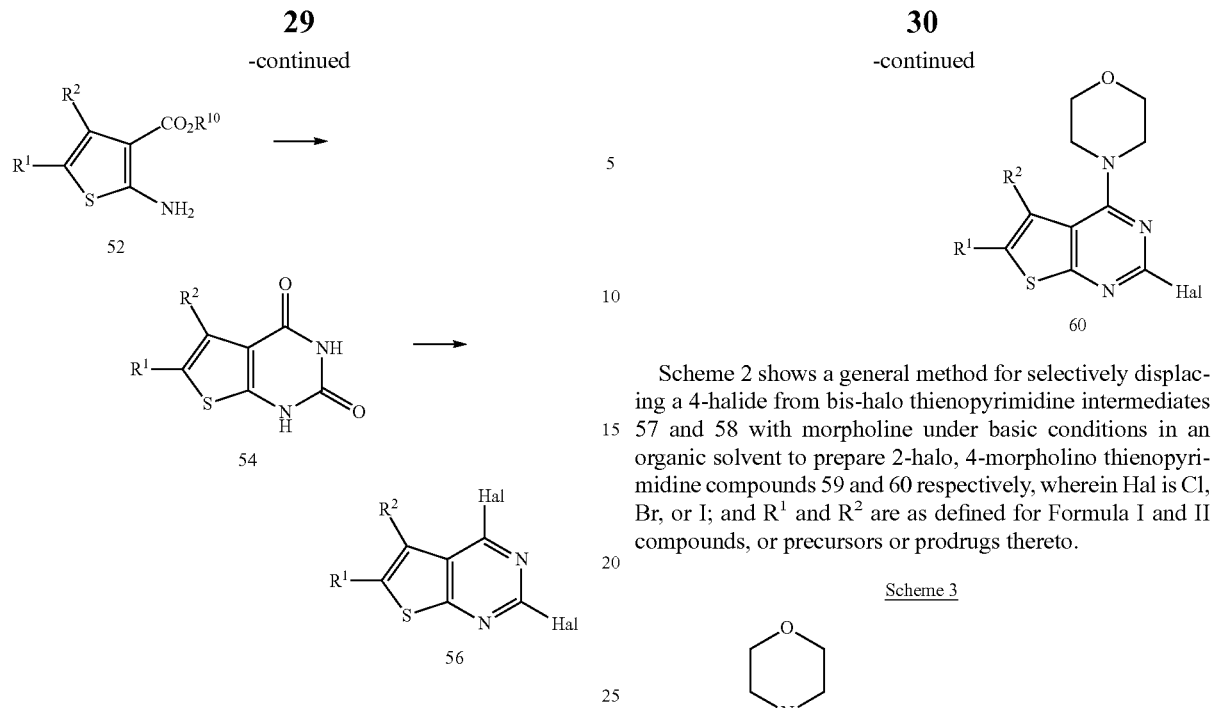

Scheme 1 shows a general method for preparation of the thienopyrimidine intermediates 55 and 56 from 2-carboxyester, 3-amino thiophene, and 2-amino, 3-carboxy ester thiophene reagents, respectively 51 and 52, wherein Hal is Cl, Br, or I; and $R^1$, $R^2$, and $R^{10}$ are as defined for Formula I and II compounds, or precursors or prodrugs thereto.

Scheme 2 shows a general method for selectively displacing a 4-halide from bis-halo thienopyrimidine intermediates 57 and 58 with morpholine under basic conditions in an organic solvent to prepare 2-halo, 4-morpholino thienopyrimidine compounds 59 and 60 respectively, wherein Hal is Cl, Br, or I; and $R^1$ and $R^2$ are as defined for Formula I and II compounds, or precursors or prodrugs thereto.

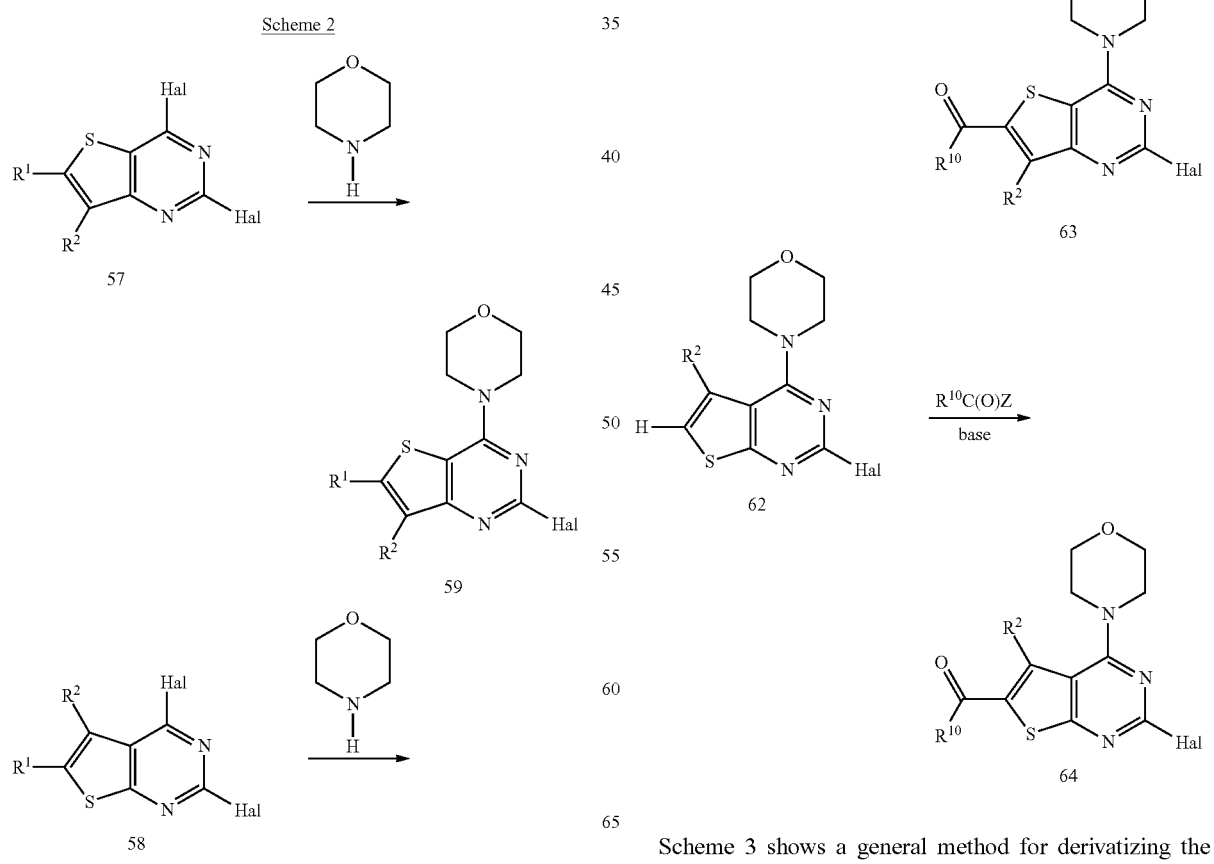

Scheme 3 shows a general method for derivatizing the 6-position of 2-halo, 4-morpholino, 6-hydrogen thienopyrimidine compounds 61 and 62 where $R^1$ is H. Treating 61 or 62 with a lithiating reagent to remove the 6 position proton, followed by adding an acylating reagent $R^{10}C(O)Z$ where Z is a leaving group, such as halide, NHS ester, carboxylate, or dialkylamino, gives 2-halo, 4-morpholino, 6-acyl thienopyrimidine compounds 63 and 64, wherein Hal is Cl, Br, or I; and $R^2$ and $R^{10}$ are as defined for Formula I and II compounds, or precursors or prodrugs thereto. An example of $R^{10}C(O)Z$ to prepare 6-formyl compounds ($R^{10}=H$) is N,N'-dimethylformamide (DMF).

prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, Del. (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2(dppf)$-DCM, $Pd_2(dba)_3$/Pt-$Bu)_3$ (Owens et al (2003) Bioorganic & Med. Chem. Letters 13:4143-4145; Molander et al (2002) Organic Letters 4(11): 1867-1870; U.S. Pat. No. 6,448,433).

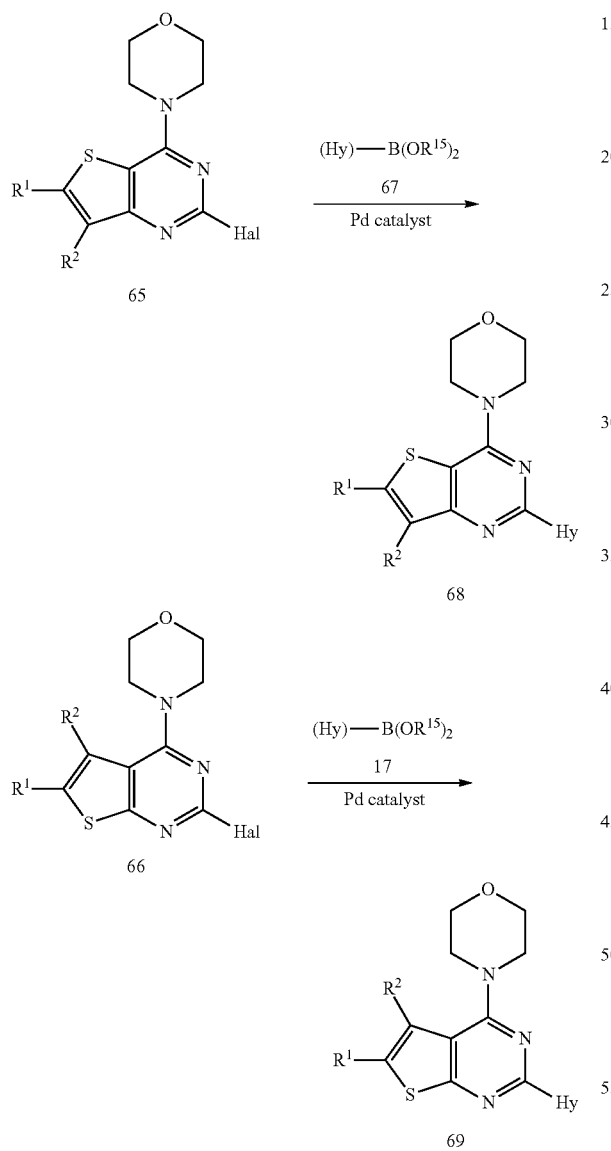

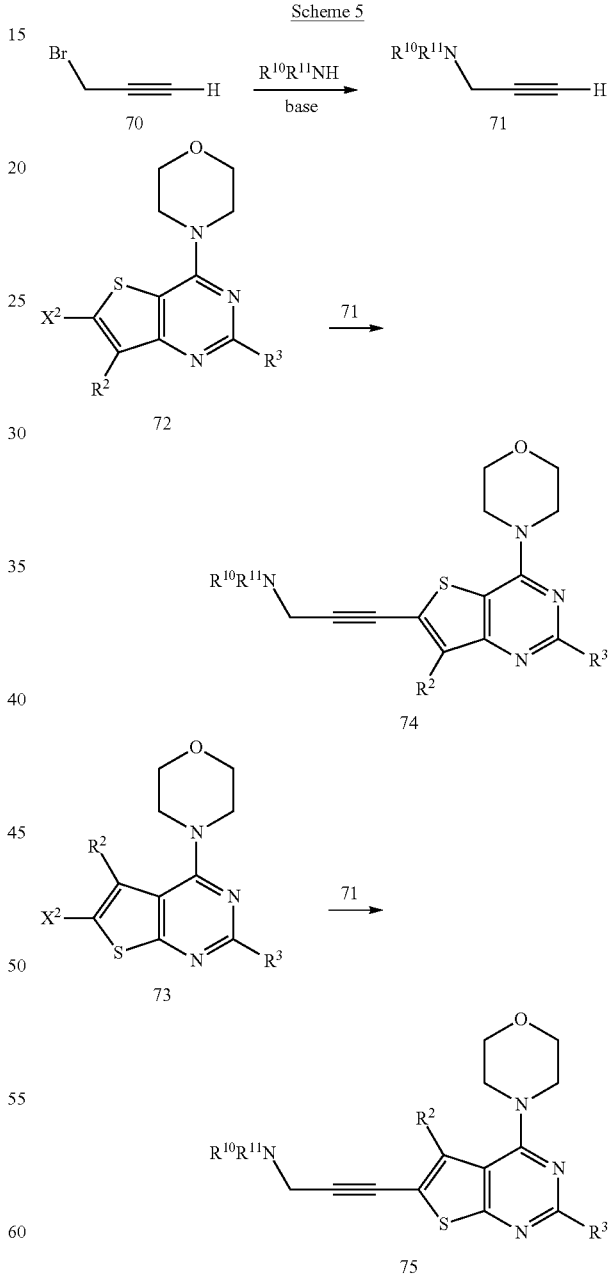

Scheme 4 shows a general method for Suzuki-type coupling of a 2-halo pyrimidine intermediate (65 and 66) with a monocyclic heteroaryl, fused bicyclic heterocyclyl or fused bicyclic heteroaryl boronate acid ($R^{15}=H$) or ester ($R^{15}=$alkyl) reagent 67 to prepare the 2-substituted (Hy), 4-morpholino thienopyrimidine compounds (68 and 69) of Formulas I and II wherein Hal is Cl, Br, or I; and $R^1$ and $R^2$ are as defined for Formula I and II compounds, or precursors or Scheme 5 shows a general method for the synthesis of alkynes 71, which can be used to prepare alkynylated derivatives of compounds 72 and 73. Propargylic amines 71 may be prepared by reaction of propargyl bromide 70 with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* (1995), 2:1039-1074; and Viehe, H. G., (1967) Angew. Chem., Int. Ed. Eng., 6(9):767-778. Alkynes 71 may subsequently be reacted with intermediates 72 ($X^2$=bromo or iodo) or 73 (via Sonogashira coupling), to provide compounds 74 and 75, respectively, wherein $R^2$ and $R^3$ are as defined for Formula I and II compounds, or precursors or prodrugs thereto.

Scheme 6 shows a general method for the synthesis of alkynes 77, which can be used to prepare alkynylated derivatives of compounds 72 and 73. Gem-dialkyl propargylic amines 77 may be prepared using methods described by Zaragoza et al (2004) J. Med. Chem., 47:2833. According to Scheme 6, gem-dialkyl chloride 76 ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the alkyne 77. Alkyne 77 can be reacted with intermediates 72 or 73 (via Sonogashira coupling) to provide compounds 78 and 79, respectively, wherein $R^2$ and $R^3$ are as defined for Formula I and II compounds, or precursors or prodrugs thereto.

Scheme 6

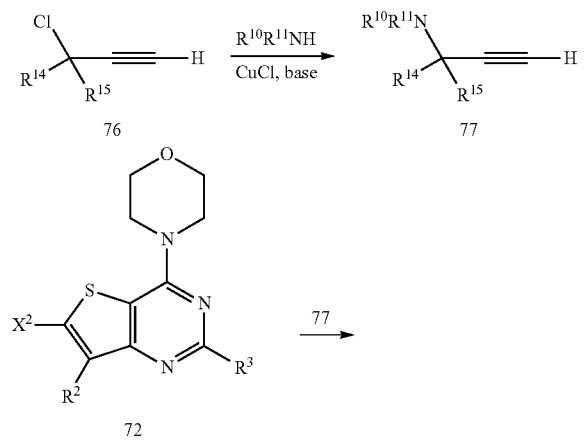

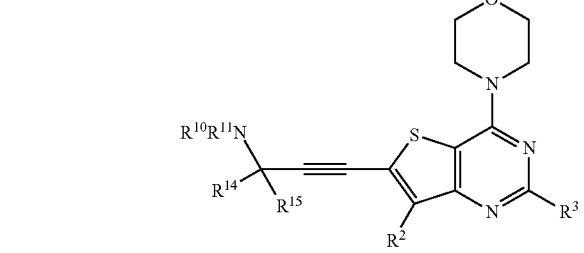

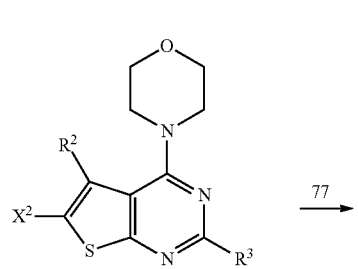

Scheme 7

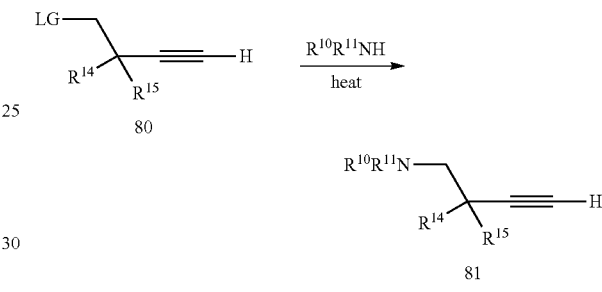

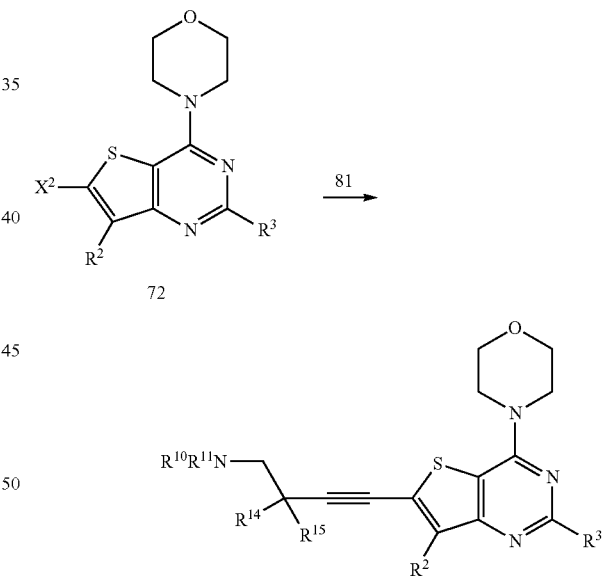

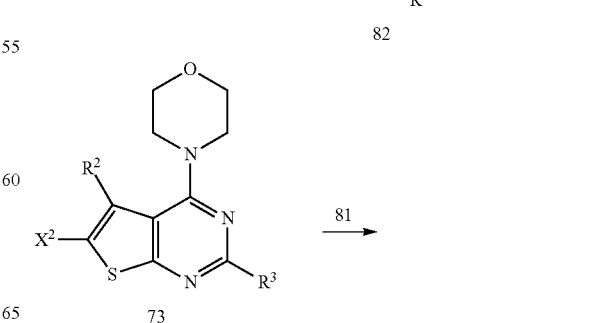

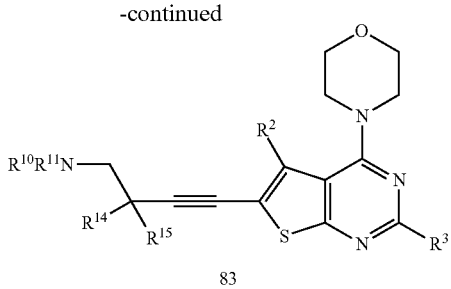

Scheme 7 shows a general scheme for the synthesis of alkynes 81, which can be used to prepare alkynylated derivatives of compounds 72 and 73. But-3-yn-1-amines 81 (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes 80 (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki M. et al (1960) Ann. Chim. 5:845. Alkynes 81 can subsequently be reacted with intermediates 72 or 73 (via Sonogashira coupling), according to the descriptions provided for Schemes 5 and 6 to provide compounds 82 and 83, respectively, wherein $R^2$ and $R^3$ are as defined for Formula I and II compounds, or precursors or prodrugs thereto.

A pharmaceutically acceptable salt of a thienopyrimidine compound of Formula I or II may be prepared using conventional techniques. Typically the process comprises treating the thienopyrimidine of Formula I as defined above with a suitable acid in a suitable solvent.

In the process of the invention as defined above, both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, such as $NaBH(OAc)_3$, $NaBH_4$ or $NaCNBH_4$.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisqmer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenyl-ethylamine(amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the ¹H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Chemotherapeutic Agents

Certain chemotherapeutic agents have demonstrated surprising and unexpected properties in combination with Formula I or II compounds in inhibiting cellular proliferation in vitro and in vivo. Such chemotherapeutic agents include: erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, and rapamycin.

Erlotinib (TARCEVA®, OSI-774, Genentech) is used to treat non-small cell lung cancer (NSCLC), lung cancer, pancreatic cancer and several other types of cancer by specifically targeting the epidermal growth factor receptor (EGFR) tyrosine kinase (U.S. Pat. No. 5,747,498; U.S. Pat. No. 6,900,221; Moyer et al (1997) Cancer Res. 57:4838; Pollack et al (1999) J. Pharmcol. Exp. Ther. 291:739; Perez-Soler et al (2004) J. Clin. Oncol. 22:3238; Kim et al (2002) Curr. Opin. Invest. Drugs 3:1385-1395; Blackhall et al (2005) Expert Opin. Pharmacother. 6:995-1002). Erlotinib is named as N-(3-ethynylphenyl)-6,7-bis(methoxymethoxy)quinazolin-4-amine (CAS Reg. No. 183321-74-6) and has the structure:

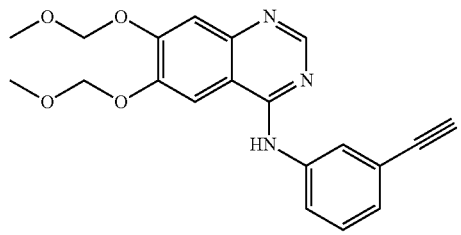 [SMILES: C#Cc1cccc(Nc2ncnc3cc(OCOC)c(OCOC)cc23)c1]

Docetaxel (TAXOTERE®, Sanofi-Aventis) is used to treat breast, ovarian, and NSCLC cancers (U.S. Pat. No. 4,814,470; U.S. Pat. No. 5,438,072; U.S. Pat. No. 5,698,582; U.S. Pat. No. 5,714,512; U.S. Pat. No. 5,750,561; Mangatal et al (1989) Tetrahedron 45:4177; Ringel et al (1991) J. Natl. Cancer Inst. 83:288; Bissery et al (1991) Cancer Res. 51:4845; Herbst et al (2003) Cancer Treat. Rev. 29:407-415; Davies et al (2003) Expert. Opin. Pharmacother. 4:553-565). Docetaxel is named as (2R,3S)-N-carboxy-3-phenylisoserine, N-tert-butyl ester, 13-ester with 5, 20-epoxy-1,2,4,7,10,13-hexahydroxytax-11-en-9-one 4-acetate 2-benzoate, trihydrate (U.S. Pat. No. 4,814,470; EP 253738; CAS Reg. No. 114977-28-5) and has the structure:

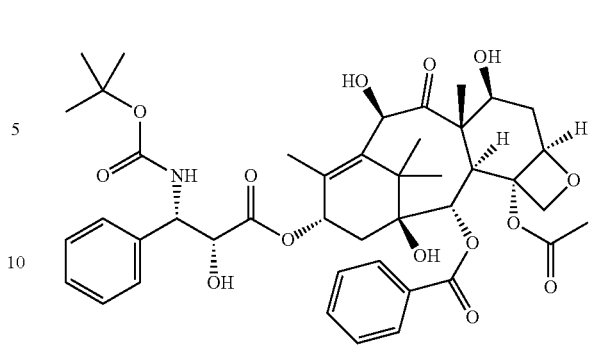

5-FU (fluorouracil, 5-fluorouracil, CAS Reg. No. 51-21-8) is a thymidylate synthase inhibitor and has been used for decades in the treatment of cancer, including colorectal and pancreatic cancer (U.S. Pat. No. 2,802,005; U.S. Pat. No. 2,885,396; Duschinsky et al (1957) J. Am. chem. Soc. 79:4559; Hansen, R. M. (1991) Cancer Invest. 9:637-642). 5-FU is named as 5-fluoro-1H-pyrimidine-2,4-dione, and has the structure:

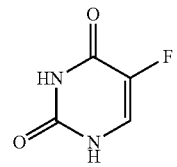

Gemcitabine (GEMZAR®, Lilly, CAS Reg. No. 95058-81-4) is a nucleoside analog which blocks DNA replication, is used to treat various carcinomas including pancreatic, breast, NSCLC, and lymphomas (U.S. Pat. No. 4,808,614; U.S. Pat. No. 5,464,826; Hertel et al (1988) J. Org. Chem. 53:2406; Hertel et al (1990) Cancer Res. 50:4417; Lund et al (1993) Cancer Treat. Rev. 19:45-55). Gemcitabine is named as 4-amino-1-[3,3-difluoro-4-hydroxy-5-(hydroxymethyl)tetrahydrofuran-2-yl]-1H-pyrimidin-2-one, and has the structure:

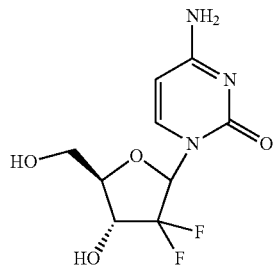 [SMILES: Nc1ccn(C2O[C@H](CO)[C@@H](O)C2(F)F)c(=O)n1]

PD-0325901 (CAS RN 391210-10-9, Pfizer) is a second-generation, non-ATP competitive, allosteric MEK inhibitor for the potential oral tablet treatment of cancer (U.S. Pat. Nos. 6,960,614; 6,972,298; US 2004/147478; US 2005/085550). Phase II clinical trials have been conducted for the potential treatment of breast tumors, colon tumors, and melanoma. PD-0325901 is named as (R)—N-(2,3-dihydroxypropoxy)-3,4-difluoro-2-(2-fluoro-4-iodophenylamino)benzamide, and has the structure:

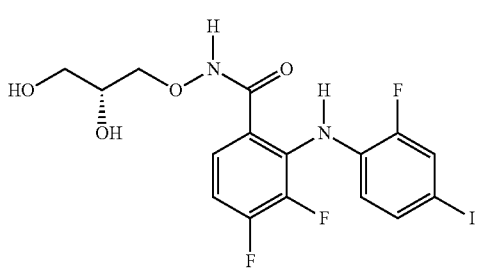 [SMILES: O=C(NOC[C@H](O)CO)c1ccc(F)c(F)c1Nc1ccc(I)cc1F]

Cisplatin (cis-diamine, dichloroplatinum(II), CAS Reg. No. 15663-27-1), is a platinum-based chemotherapy drug used to treat various types of cancers, including sarcomas, some carcinomas (e.g. small cell lung cancer and ovarian cancer), lymphomas and germ cell tumors (Ochs et al (1978) Cancer Treat. Rep. 62:239; Pinedo et al (1978) Eur. J. Cancer 14:1149; "Cisplatin, Current Status and New Developments", A. W. Prestayko et al., Eds., Academic Press, New York, 1980). Cisplatin (CDDP) was the first member of its class, which now also includes carboplatin and oxaliplatin.

Carboplatin (CAS Reg. No. 41575-94-4) is a chemotherapeutic drug used against ovarian carcinoma, lung, head and neck cancers (U.S. Pat. No. 4,140,707; Calvert et al (1982) Cancer Chemother. Pharmacol. 9:140; Harland et al (1984) Cancer Res. 44:1693). Carboplatin is named as azanide; cyclobutane-1,1-dicarboxylic acid; platinum, and has the structure:

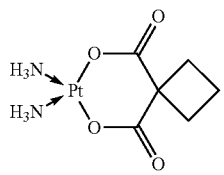

Paclitaxel (TAXOL®, Bristol-Myers Squibb Oncology, Princeton N.J., CAS Reg. No. 33069-62-4) is isolated the compound from the bark of the Pacific yew tree, *Taxus brevifolia*, and used to treat lung, ovarian, breast cancer, and advanced forms of Kaposi's sarcoma (Wani et al (1971) J. Am. Chem. Soc. 93:2325; Mekhail et al (2002) Expert. Opin. Pharmacother. 3:755-766). Paclitaxel is named as β-(benzoylamino)-α-hydroxy-,6,12b-bis(acetyloxy)-12-(benzoyloxy)-2a,3,4,4a,5,6,9,10,11,12,12a,12b-dodecahydro-4,11-dihydroxy-4a,8,13,13-tetramethyl-5-oxo-7,11-methano-1H-cyclodeca(3,4)benz(1,2-b)oxet-9-ylester,(2aR-(2a-α,4-β,4a-β,6-β,9-α(α-R*,β-s*),11-α,12-α,12a-α,2b-α))-benzenepropanoic acid, and has the structure:

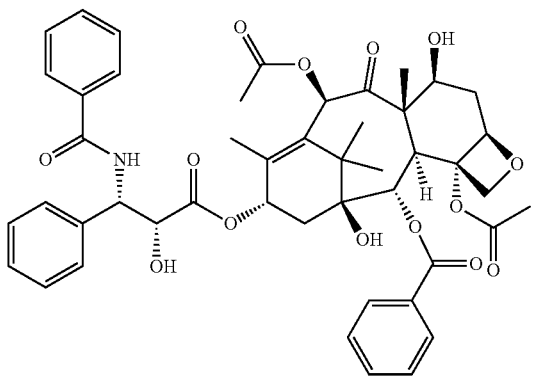 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Bevacizumab (AVASTIN®, Genentech) is a recombinant humanized monoclonal antibody against VEGF, vascular endothelial growth factor (U.S. Pat. No. 6,054,297; Presta et al (1997) Cancer Res. 57:4593-4599). It is used in the treatment of cancer, where it inhibits tumor growth by blocking the formation of new blood vessels. Bevacizumab was the first clinically available angiogenesis inhibitor in the United States, approved by the FDA in 2004 for use in combination with standard chemotherapy in the treatment of metastatic colon cancer and most forms of metastatic non-small cell lung cancer. Several late-stage clinical studies are underway to determine its safety and effectiveness for patients with: adjuvant/non-metastatic colon cancer, metastatic breast cancer, metastatic renal cell carcinoma, metastatic glioblastoma multiforme, metastatic ovarian cancer, metastatic hormone-refractory prostate cancer, and metastatic or unresectable locally advanced pancreatic cancer (Ferrara et al (2004) Nat. Rev. Drug Disc. 3:391-400).

Bevacizumab includes mutated human IgG1 framework regions and antigen-binding complementarity-determining regions from the murine anti-hVEGF monoclonal antibody A.4.6.1 that blocks binding of human VEGF to its receptors. Bevacizumab has a molecular mass of about 149,000 daltons and is glycosylated. Bevacizumab and other humanized anti-VEGF antibodies are further described in U.S. Pat. No. 6,884,879. Additional anti-VEGF antibodies include the G6 or B20 series antibodies, e.g., G6-31, B20-4.1, (WO 2005/012359; WO 2005/044853; U.S. Pat. Nos. 7,060,269; 6,582,959; 6,703,020 ; 6,054,297; WO 98/45332; WO 96/30046; WO 94/10202; EP 0666868B1; US 2006/009360; US 2005/0186208; US 2003/0206899; US 2003/0190317; US 2003/0203409; 20050112126; Popkov et al (2004) Journal of Immunological Methods 288:149-164. A "B20 series antibody" is an anti-VEGF antibody that is derived from a sequence of the B20 antibody or a B20-derived antibody according to any one of FIGS. 27-29 of WO 2005/012359, the entire disclosure of which is expressly incorporated herein by reference. In one embodiment, the B20 series antibody binds to a functional epitope on human VEGF comprising residues F17, M18, D19, Y21, Y25, Q89, 191, K101, E103, and C104. Other anti-VEGF antibodies include those that bind to a functional epitope on human VEGF comprising residues F17, M18, D19, Y21, Y25, Q89, 191, K101, E103, and C104 or, alternatively, comprising residues F17, Y21, Q22, Y25, D63, 183 and Q89.

Trastuzumab (HERCEPTIN®, huMAb4D5-8, rhuMAb HER2, Genentech) is a recombinant DNA-derived humanized, IgG1 kappa, monoclonal antibody version of the murine HER2 antibody which selectively binds with high affinity in a cell-based assay (Kd=5 nM) to the extracellular domain of the human epidermal growth factor receptor2 protein, HER2 (ErbB2) (U.S. Pat. Nos. 5,821,337; 6,054,297; 6,407,213; 6,639,055; Coussens L, et al (1985) Science 230:1132-9; Slamon D J, et al (1989) Science 244:707-12). Trastuzumab contains human framework regions with the complementarity-determining regions of a murine antibody (4D5) that binds to HER2. Trastuzumab binds to the HER2 antigen and thus inhibits the growth of cancerous cells. Trastuzumab has been shown, in both in vitro assays and in animals, to inhibit the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). Trastuzumab is a mediator of antibody-dependent cellular cytotoxicity, ADCC (Hotaling T E, et al (1996) [abstract]. Proc. Annual Meeting Am Assoc Cancer Res; 37:471; Pegram M D, et al (1997) [abstract]. Proc Am Assoc Cancer Res; 38:602;

Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137). HERCEPTIN® was approved in 1998 for the treatment of patients with ErbB2-overexpressing metastatic breast cancers (Baselga et al, (1996) J. Clin. Oncol. 14:737-744). The FDA approved HERCEPTIN® in 2006 as part of a treatment regimen containing doxorubicin, cyclophosphamide and paclitaxel for the adjuvant treatment of patients with HER2-positive, node-positive breast cancer. There is a significant clinical need for developing further HER2-directed cancer therapies for those patients with HER2-overexpressing tumors or other diseases associated with HER2 expression that do not respond, or respond poorly, to HERCEPTIN® treatment.

Pertuzumab (OMNITARG™, rhuMab 2C4, Genentech) is a clinical stage, humanized antibody and the first in a new class of agents known as HER dimerization inhibitors (HDIs) which block the ability of the HER2 receptor to collaborate with other HER receptor family members, i.e. HER1/EGFR, HER3, and HER4 (U.S. Pat. No. 6,949,245; Agus et al (2002) Cancer Cell 2:127-37; Jackson et al (2004) Cancer Res 64:2601-9; Takai et al (2005) Cancer 104:2701-8). In cancer cells, interfering with HER2's ability to collaborate with other HER family receptors blocks cell signaling and may ultimately lead to cancer cell growth inhibition and death of the cancer cell. HDIs, because of their unique mode of action, have the potential to work in a wide variety of tumors, including those that do not overexpress HER2 (Mullen et al (2007) Molecular Cancer Therapeutics 6:93-100).

Temozolomide, (CAS Reg. No. 85622-93-1, TEMODAR®, TEMODAL®, Schering Plough) is a oral chemotherapy drug approved by the FDA for the treatment of anaplastic astrocytoma, and has been studied for other brain tumor types such as glioblastoma multiforme (U.S. Pat. No. 5,260,291; Stevens et al (1984) J. Med. Chem. 27:196; Newlands et al (1997) Cancer Treat. Rev. 23:35-61; Danson et al (2001) Expert Rev. Anticancer Ther. 1:13-19). Temozolomide is named as (4-methyl-5-oxo-2,3,4,6,8-pentazabicyclo [4.3.0]nona-2,7,9-triene-9-carboxamide or 3,4-dihydro-3-methyl-4-oxoimidazo [5,1-d]-as-tetrazine-8-carboxamide (U.S. Pat. No. 5,260,291, CAS No. 85622-93-1), and has the structure:

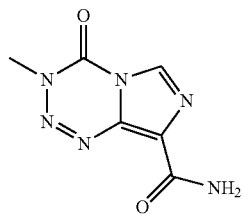

Tamoxifen (NOLVADEX®, ISTUBAL®, VALODEX®) is an orally active, selective estrogen receptor modulator (SERM) which is used in the treatment of breast cancer and is currently the world's largest selling drug for this indication. Tamoxifen (Nolvadex®) was first approved by the FDA (ICI Pharmaceuticals, now AstraZeneca) in 1977 for treatment of metastatic breast cancer (Jordan V C (2006) Br J Pharmacol 147 (Suppl 1): S269-76). Tamoxifen is currently used for the treatment of both early and advanced estrogen receptor (ER) positive breast cancer in pre- and post-menopausal women (Jordan V C (1993) Br J Pharmacol 110 (2): 507-17). It is also approved by the FDA for the prevention of breast cancer in women at high risk of developing the disease and for the reduction of contralateral (in the opposite breast) breast cancer. Tamoxifen is named as (Z)-2-[4-(1,2-diphenylbut-1-enyl)phenoxy]-N,N-dimethyl-ethanamine, (CAS Reg. No. 10540-29-1) and has the structure:

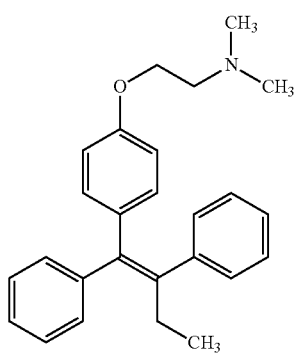 [SMILES: CC/C(=C(\c1ccccc1)c1ccc(OCCN(C)C)cc1)c1ccccc1]

Doxorubicin (ADRIAMYCINID, hydroxyldaunorubicin) is a DNA-interacting drug widely used in chemotherapy since the 1960s. It is an anthracycline antibiotic and structurally related to daunomycin, which also intercalates DNA. Doxorubicin is commonly used in the treatment of a wide range of cancers. Doxorubicin is named as (8S,10S-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione, (CAS Reg. No. 23214-92-8) and has the structure:

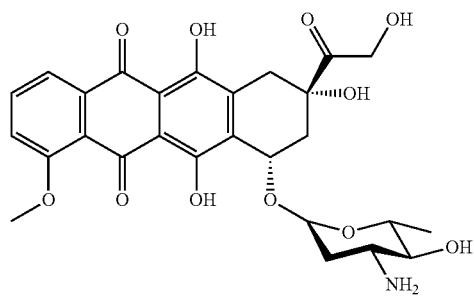

Akti-1/2 is a cell-permeable quinoxaline compound that potently and selectively inhibits Akt1/Akt2 activity: $IC_{50}$=58 nM, 210 nM, and 2.12 µM for Akt1, Akt2, and Akt3, respectively, in in vitro kinase assays (Barnett et al. (2005) Biochem. J. 385,:399; DeFeo-Jones, et al (2005) Mol. Cancer Ther. 4:271; Zhao et al (2005) Bioorg. Med. Chem. Lett. 15:905; Lindsley et al (2005) Bioorg. Med. Chem. Lett. 15:761; US 2006/142178; US 2005/159422; US 2004/102360). The inhibition appears to be pleckstrin homology (PH) domain-dependent. It does not exhibit any inhibitory effect against PH domain-lacking Akts, or other closely related AGC family kinases, PKA, PKC, and SGK, even at concentrations as high as 50 µM. Akti-1/2 overcomes Akt1/Akt2-mediated resistance to chemotherapeutics in tumor cells and is shown to block basal and stimulated phosphorylation/activation of Akt1/Akt2 both in cultured cells in vitro and in mice in vivo. Akti-1/2 (EMD Biosciences Product No. 124018) is named as 1,3-dihydro-1-(1-((4-(6-phenyl-1H-imidazo[4,5-g]quinoxalin-7-yl)phenyl)methyl)-4-piperidinyl)-2H-benzimidazol-2-one, and has the structure:

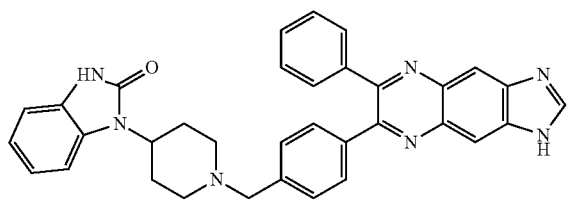 [SMILES: O=c1[nH]c2ccccc2n1C1CCN(Cc2ccc(-c3nc4cc5[nH]cnc5cc4nc3-c3ccccc3)cc2)CC1]

HPPD is a selective B-Raf inhibitor (B-Raf IC50<2 nM, pERK IC50 87 nM) under preclinical investigations (US 2006/0189627). HPPD is named as 5-(1-(2-hydroxyethyl)-3-(pyridin-4-yl)-1H-pyrazol-4-yl)-2,3-dihydro-1H-inden-1-one oxime, and has the structure:

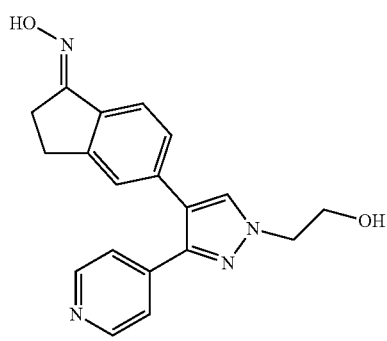 [SMILES: OCCn1cc(-c2ccc3c(c2)CC/C3=N\O)c(-c2ccncc2)n1]

Rapamycin (sirolimus, RAPAMUNE®) is an immunosuppressant drug used to prevent rejection in organ transplantation, and is especially useful in kidney transplants. Rapamycin is a macrolide antibiotic ("-mycin") first discovered as a product of the bacterium *Streptomyces hygroscopicus* in a soil sample from an island called Rapa Nui, better known as Easter Island (Pritchard D I (2005). Drug Discovery Today 10 (10): 688-691). Rapamycin inhibits the response to interleukin-2 (IL-2) and thereby blocks activation of T- and B-cells. The mode of action of rapamycin is to bind the cytosolic protein FK-binding protein 12 (FKBP12). The rapamycin-FKBP12 complex inhibits the mammalian target of rapamycin (mTOR) pathway through directly binding the mTOR Complex1 (mTORC1). mTOR is also called FRAP (FKBP-rapamycin associated protein) or RAFT (rapamycin and FKBP target). Rapamycin is named as (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone (CAS Reg. No. 53123-88-9), and has the structure:

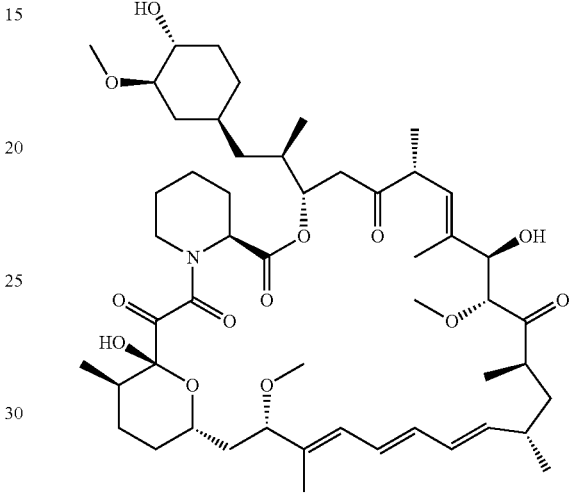

Lapatinib (TYKERB®, GW572016, Glaxo SmithKline) has been approved for use in combination with capecitabine (XELODA®, Roche) for the treatment of patients with advanced or metastatic breast cancer whose tumors overexpress HER2 (ErbB2) and who have received prior therapy including an anthracycline, a taxane and trastuzumab. Lapatinib is an ATP-competitive epidermal growth factor (EGFR) and HER2/neu (ErbB-2) dual tyrosine kinase inhibitor (U.S. Pat. Nos. 6,727,256; 6,713,485; 7,109,333; 6,933,299; 7,084,147; 7,157,466; 7,141,576) which inhibits receptor autophosphorylation and activation by binding to the ATP-binding pocket of the EGFR/HER2 protein kinase domain. Lapatinib is named as N-(3-chloro-4-(3-fluorobenzyloxy)phenyl)-6-(5-((2-(methylsulfonyl)ethylamino)methyl)furan-2-yl)quinazolin-4-amine, and has the structure:

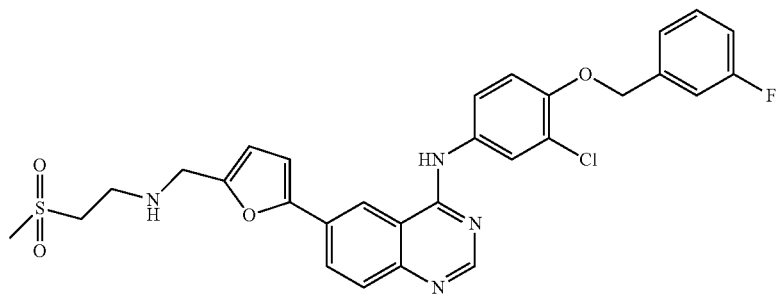 [SMILES: CS(=O)(=O)CCNCc1ccc(-c2ccc3ncnc(Nc4ccc(OCc5cccc(F)c5)c(Cl)c4)c3c2)o1]

Biological Evaluation

Certain Formula I and II compounds bind specifically to PI3 kinase isoforms and inhibit the proliferation of tumor cells (WO 2006/046031; US 2008/0039459; US 2008/0076768; US 2008/0076758; WO 2008/070740; WO 2008/073785).

Certain Formula Ia and IIa compounds bind the p110α isoform at IC50 less than 1 micromole and show single-agent in vivo tumor growth inhibition in mouse xenograft models. Accordingly, Formula I and II compounds may be used to treat a disease or disorder arising from abnormal cell growth, function or behavior as single agents or in combination therapy with one or more chemotherapeutic agents.

Certain exemplary Formula I and II compounds described herein were prepared, characterized, and assayed for their PI3K binding activity (Example 13) and in vitro activity against tumor cells (Example 14). The range of PI3K binding activities (IC50) was less than 1 nM (one nanomolar) to about 10 μM (ten micromolar). Certain exemplary Formula I and II compounds have PI3K binding activity $IC_{50}$ values less than 10 nM. Certain Formula I and II compounds have tumor cell-based activity $EC_{50}$ values less than 100 nM.

The cytotoxic or cytostatic activity of Formula I and II exemplary compounds was measured by: establishing a proliferating mammalian tumor cell line in a cell culture medium, adding a Formula I or II compound, culturing the cells for a period from about 6 hours to about 5 days; and measuring cell viability (Example 14). Cell-based in vitro assays were used to measure viability, i.e. proliferation ($IC_{50}$), cytotoxicity ($EC_{50}$), and induction of apoptosis (caspase activation). Pharmacodynamic and pharmacokinetic properties of absorption, distribution, metabolism, and excretion (ADME) were measured for certain exemplary compounds by assays including: Caco-2 Permeability, Hepatocyte Clearance, Cytochrome P450 Inhibition, Cytochrome P450 Induction, Plasma Protein Binding, and hERG channel blockage.

In Vitro Cell Proliferation Assays

The in vitro potency of the combinations of Formula I or II compounds with chemotherapeutic agents was measured by the cell proliferation assay of Example 14; the CellTiter-Glo® Luminescent Cell Viability Assay, commercially available from Promega Corp., Madison, Wis. This homogeneous assay method is based on the recombinant expression of *Coleoptera* luciferase (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of Formula I and II exemplary compounds and combinations with chemotherapeutic agents were measured by the CellTiter-Glo® Assay (Example 14) against the tumor cell lines in FIGS. 1-A, 1-B and 1-C. $EC_{50}$ values were established for the tested compounds and combinations. The range of in vitro cell potency activities was about 100 nM to about 10 μM.

FIG. 1-A shows a summary of in vitro cell proliferation assays of combinations of Formula Ia compound and various chemotherapeutic agents. FIG. 1-B shows a summary of in vitro cell proliferation assays of combinations of Formula IIa compound and various chemotherapeutic agents. FIG. 1-C shows a summary of in vitro cell proliferation assays of combinations of Formula Ib compound and various chemotherapeutic agents. The cancer cell lines are characterized by tumor type and presence of gene mutation.

The individual measured EC50 values against the particular cell of the Formula Ia, Ib, and IIa compounds and of the chemotherapeutic agent are compared to the combination EC50 value. The combination index (CI) score is calculated by the Chou and Talalay method (Chou, T. and Talalay, P. (1984) Adv. Enzyme Regul. 22:27-55). A CI less than 0.8 indicates synergy. A CI between 0.8 and 1.2 indicates additivity. A CI greater than 1.2 indicates antagonism. The CI values in FIGS. 1-A, 1-B and 1-C are from the EC50 concentrations (third point from the right). The strength of synergy is assessed according to Chou and Talalay and listed in the last column of the tables. Certain combinations in FIGS. 1-A, 1-B and 1-C show the surprising and unexpected property of synergy in the in vitro cell proliferation assays with tumor type cell lines including breast, cervical, colon, endometrial, glioma, lung, melanoma, ovarian, pancreatic, and prostate. Other combinations in FIGS. 1-A, 1-B and 1-C show no synergy; and only show mere additivity or antagonism. Certain combinations are synergistic with one or more tumor types, but not others. The synergy demonstrated in the in vitro cell proliferation assays provides a basis to expect a corresponding synergy in treating cancers including, but not limited to, breast, cervical, colon, endometrial, glioma, lung, melanoma, ovarian, pancreatic, and prostate in human patients.

FIG. 2 shows results of in vitro cell proliferation assays (Cell-Titer Glo, Promega) measuring viable cells over varying concentrations (starting at 4x EC50) right to left of 5-FU, Formula Ia compound, and the combination of 5-FU and Formula Ia. The MDA-MB-361 (breast tumor type) cells are treated simultaneously (top), pre-dosed with Formula Ia 4 hours before dosing with 5-FU (middle), and post-dosed with Formula Ia 4 hours after dosing with 5-FU (bottom). Strong synergy is observed with simultaneous dosing (CI=0.11) and post-dosing with Formula Ia (CI=0.10). A strong dosing order (sequence) effect is observed. Pre-dosing with Formula showed less synergy (CI=0.67).

Figure 3:
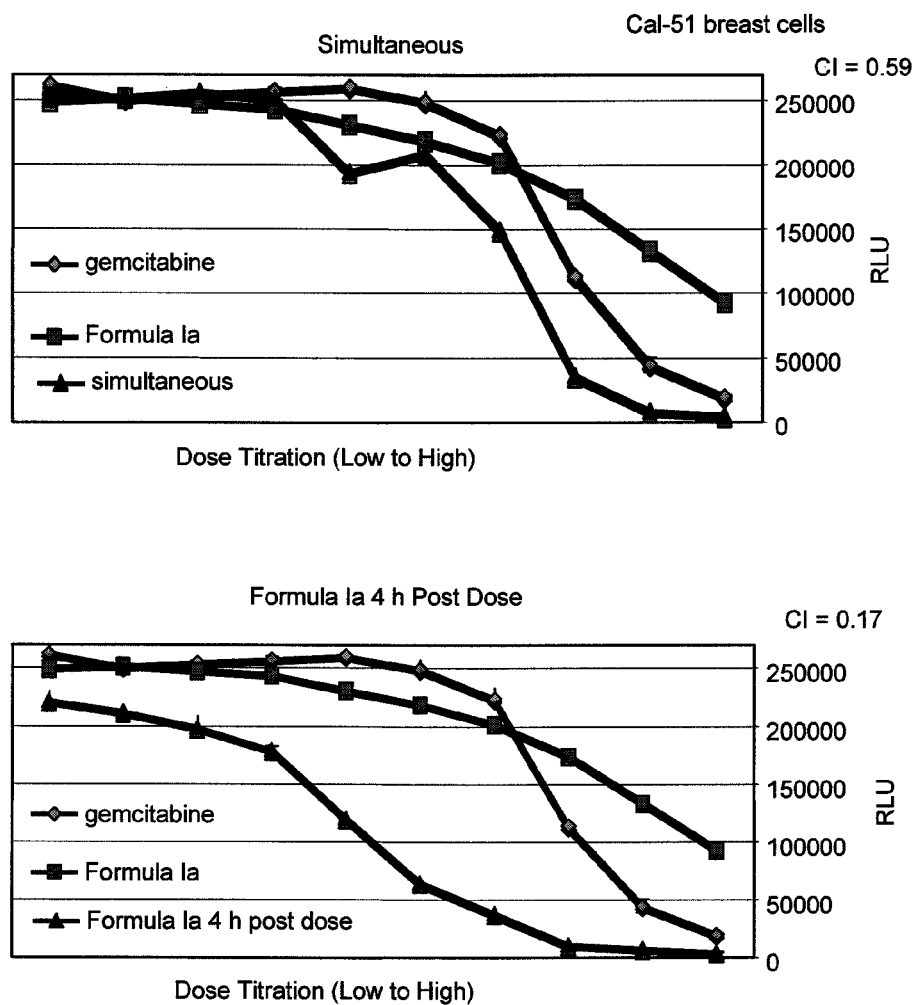
FIG. 3 shows results of in vitro cell proliferation assays (Cell-Titer Glo, Promega) measuring viable cells over varying concentrations (starting at 4× EC50) right to left of gemcitabine, Formula Ia compound (GDC-0941), and the combination of gemcitabine and Formula Ia. The Cal-51 (breast tumor type) cells are treated simultaneously (top), and post-dosed with Formula Ia 4 hours after dosing with gemcitabine (bottom).

FIG. 3 shows results of in vitro cell proliferation assays (Cell-Titer Glo, Promega) measuring viable cells over varying concentrations (starting at 4x EC50) right to left of gemcitabine, Formula Ia compound, and the combination of gemcitabine and Formula Ia. The Cal-51 (breast tumor type) cells are treated simultaneously (top), and post-dosed with Formula Ia 4 hours after dosing with gemcitabine (bottom). Synergy is observed with simultaneous dosing (CI=0.59) and strong synergy with post-dosing with Formula Ia (CI=0.17).

Figure 4:
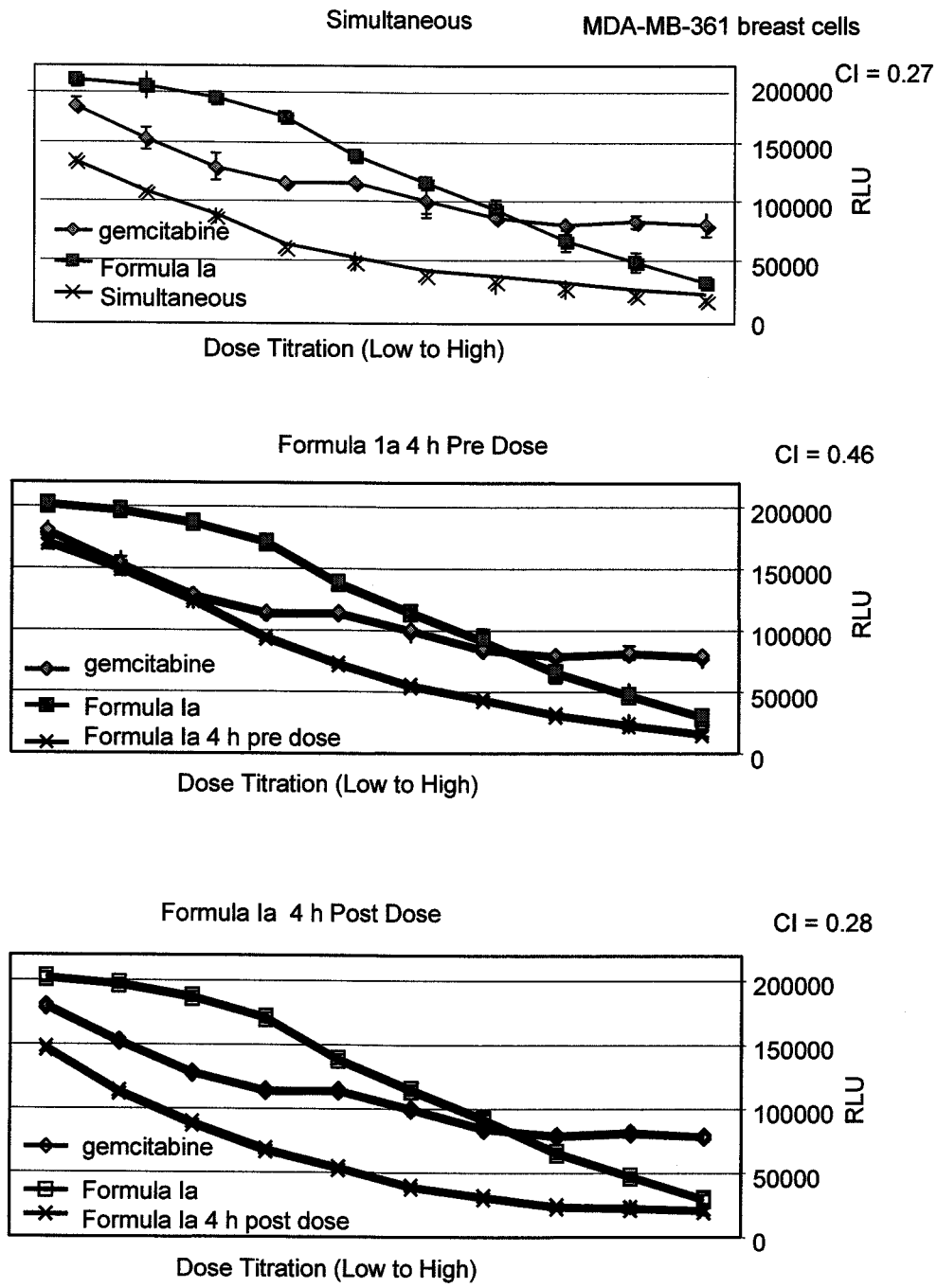
FIG. 4 shows results of in vitro cell proliferation assays (Cell-Titer Glo, Promega) measuring viable cells over varying concentrations (starting at 4× EC50) right to left of gemcitabine, Formula Ia compound (GDC-0941), and the combination of gemcitabine and Formula Ia. The MDA-MB-361 (breast tumor type) cells are treated simultaneously (top), pre-dosed with Formula Ia 4 hours before dosing with gemcitabine (middle), and post-dosed with Formula Ia 4 hours after dosing with gemcitabine (bottom).

FIG. 4 shows results of in vitro cell proliferation assays (Cell-Titer Glo, Promega) measuring viable cells over varying concentrations (starting at 4× EC50) right to left of gemcitabine, Formula Ia compound, and the combination of gemcitabine and Formula Ia. The MDA-MB-361 (breast tumor type) cells are treated simultaneously (top), pre-dosed with Formula Ia 4 hours before dosing with gemcitabine (middle), and post-dosed with Formula Ia 4 hours after dosing with gemcitabine (bottom). Synergy is observed with simultaneous dosing (CI=0.27), pre-dosing with Formula Ia (CI=0.46), and post-dosing with Formula Ia (CI=0.28).

Figure 5:
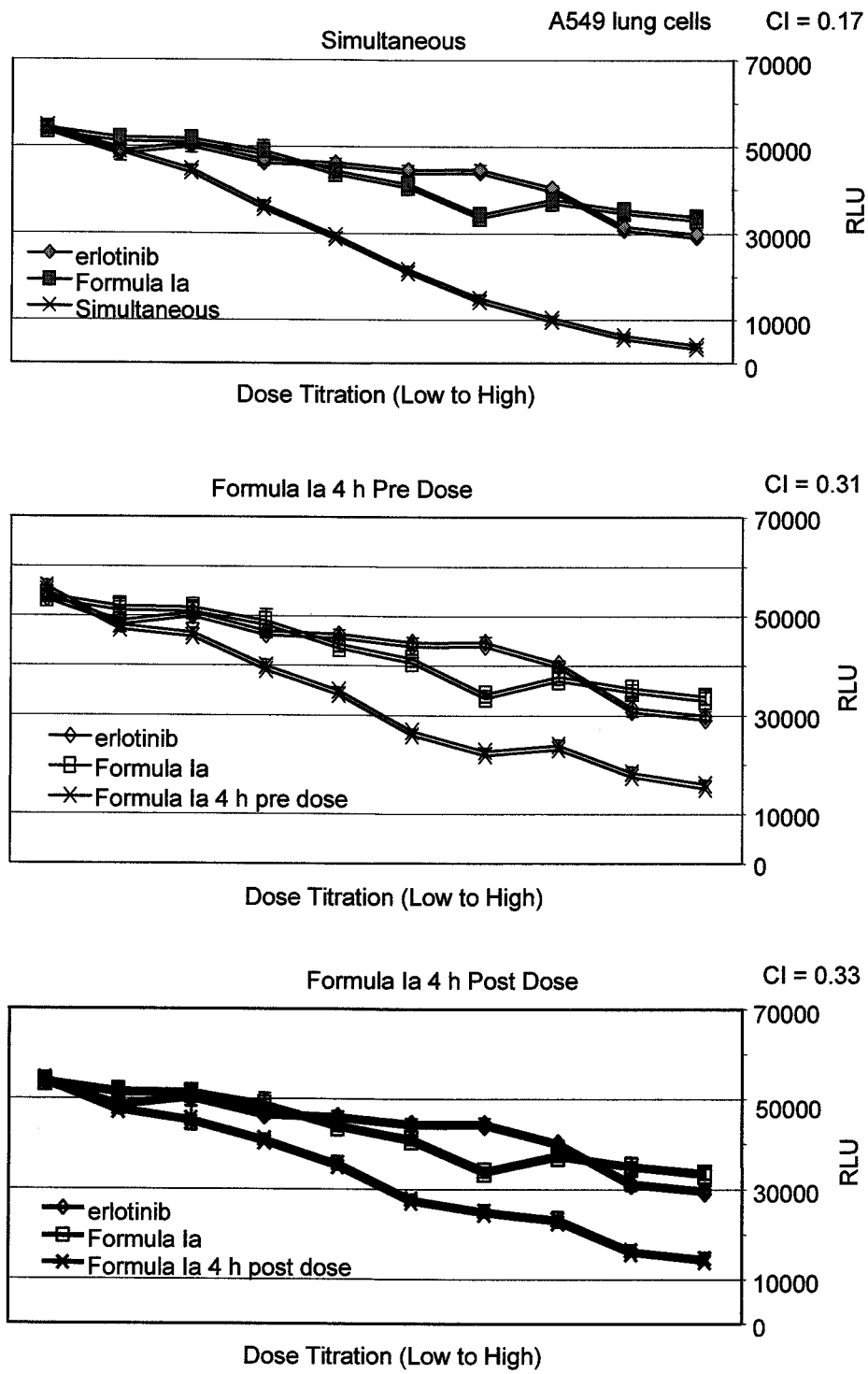
FIG. 5 shows results of in vitro cell proliferation assays (Cell-Titer Glo, Promega) measuring viable cells over varying concentrations (starting at 4× EC50) right to left of erlotinib, Formula Ia compound (GDC-0941), and the combination of erlotinib and Formula Ia. The A549 (lung tumor type with K-ras G12C) cells are treated simultaneously (top), pre-dosed with Formula Ia 4 hours before dosing with erlotinib (middle), and post-dosed with Formula Ia 4 hours after dosing with erlotinib (bottom).

FIG. 5 shows results of in vitro cell proliferation assays (Cell-Titer Glo, Promega) measuring viable cells over varying concentrations (starting at 4× EC50) right to left of erlotinib, Formula Ia compound, and the combination of erlotinib and Formula Ia. The A549 (lung tumor type, with K-ras G12C) cells are treated simultaneously (top), pre-dosed with Formula Ia 4 hours before dosing with erlotinib (middle), and post-dosed with Formula Ia 4 hours after dosing with erlotinib (bottom). Synergy is observed with simultaneous dosing (CI=0.17), pre-dosing with Formula Ia (CI=0.31), and post-dosing with Formula Ia (CI=0.33).

Figure 6:
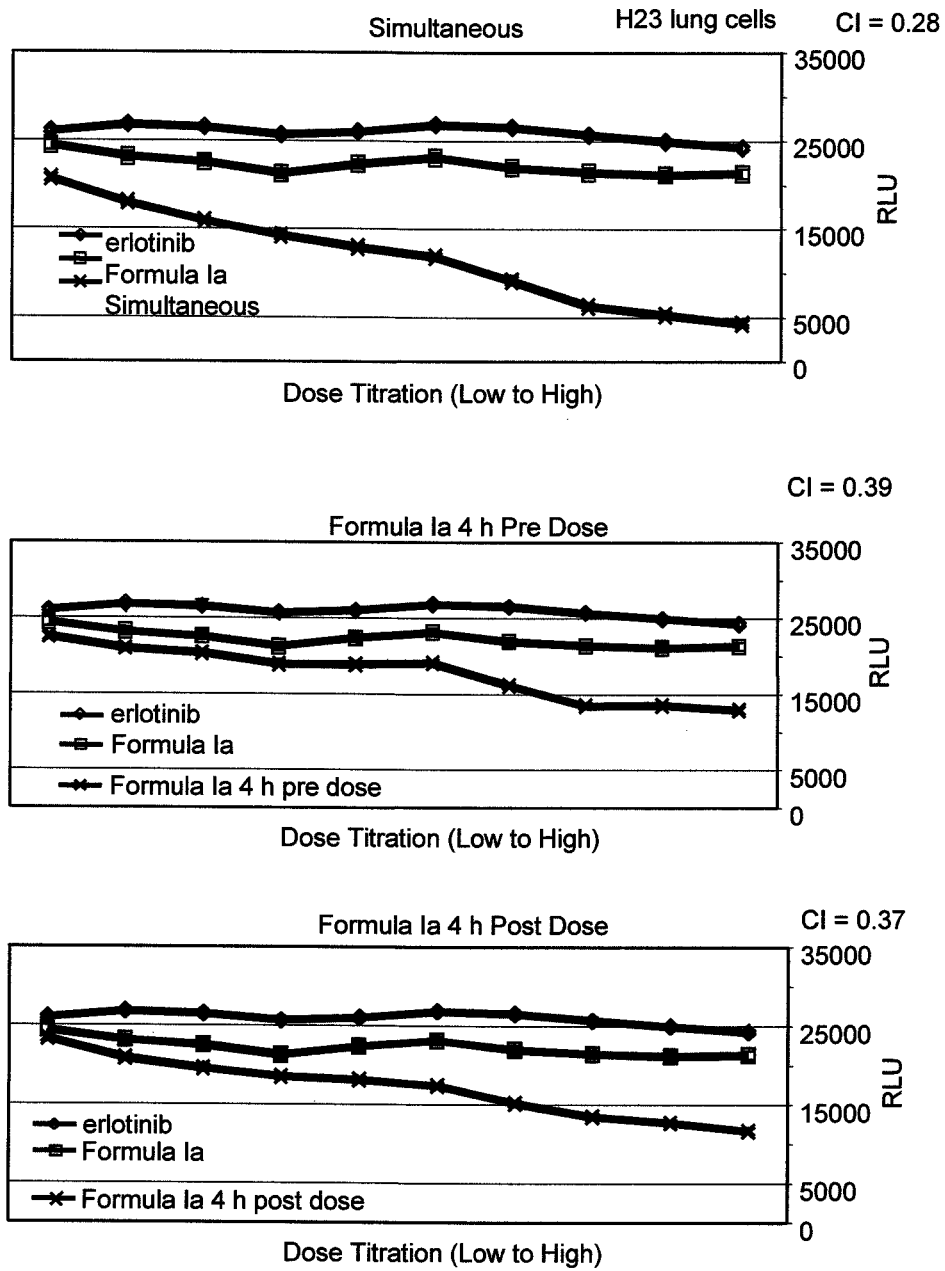
FIG. 6 shows results of in vitro cell proliferation assays (Cell-Titer Glo, Promega) measuring viable cells over varying concentrations (starting at 4× EC50) right to left of erlotinib, Formula Ia compound (GDC-0941), and the combination of erlotinib and Formula Ia. The H23 (lung tumor type, with K-ras G12C mutation) cells are treated simultaneously (top), pre-dosed with Formula Ia 4 hours before dosing with erlotinib (middle), and post-dosed with Formula Ia 4 hours after dosing with erlotinib (bottom).

FIG. 6 shows results of in vitro cell proliferation assays (Cell-Titer Glo, Promega) measuring viable cells over varying concentrations (starting at 4× EC50) right to left of erlotinib, Formula Ia compound, and the combination of erlotinib and Formula Ia. The H23 (lung tumor type, with K-ras G12C mutation) cells are treated simultaneously (top), pre-dosed with Formula Ia 4 hours before dosing with erlotinib (middle), and post-dosed with Formula Ia 4 hours after dosing with erlotinib (bottom). Synergy is observed with simultaneous dosing (CI=0.28), pre-dosing with Formula Ia (CI=0.39), and post-dosing with Formula Ia (CI=0.37).

Figure 7:
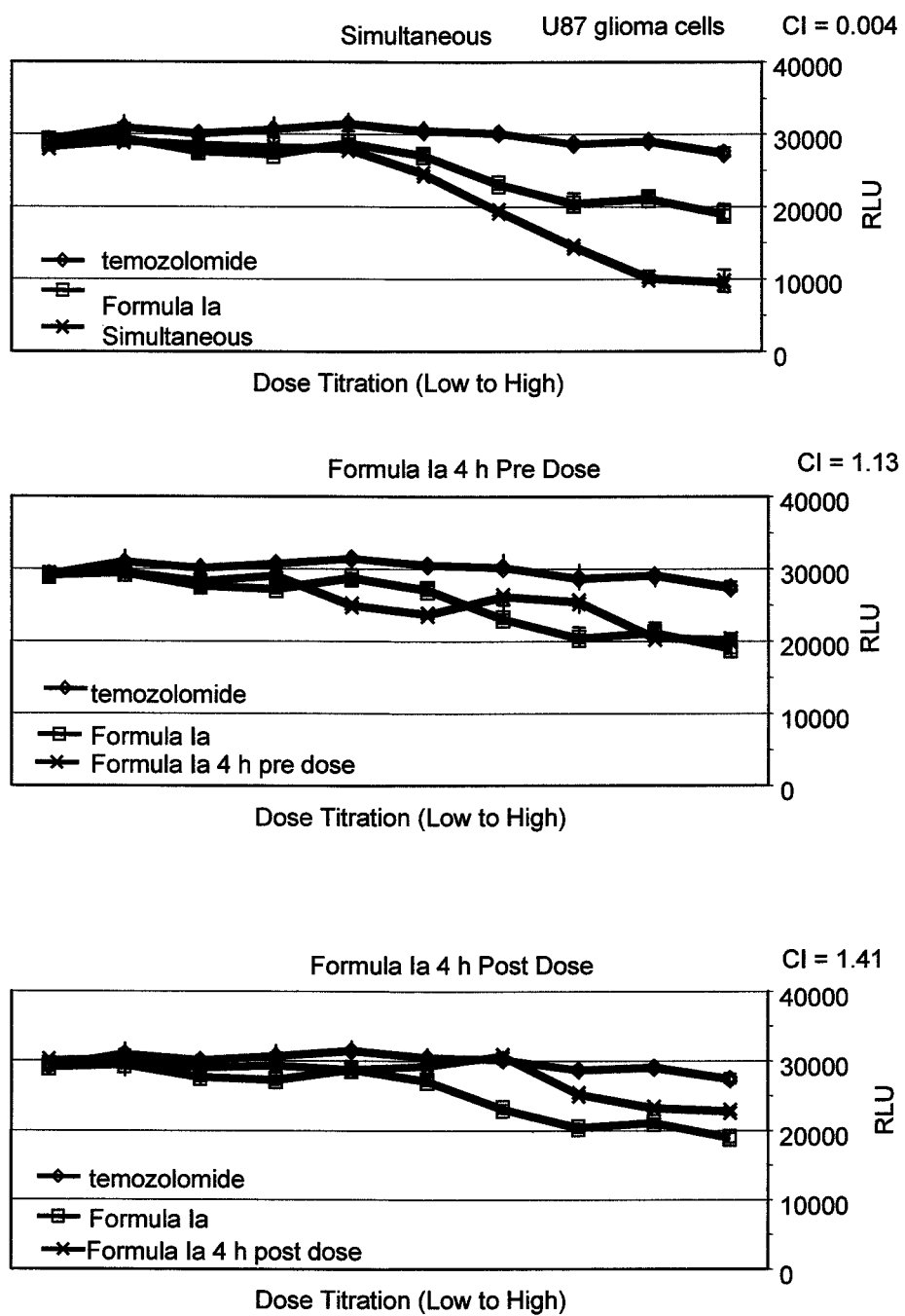
FIG. 7 shows results of in vitro cell proliferation assays (Cell-Titer Glo, Promega) measuring viable cells over varying concentrations (starting at 4× EC50) right to left of temozolomide, Formula Ia compound (GDC-0941), and the combination of temozolomide and Formula Ia. The U87 (glioma tumor type) cells are treated simultaneously (top), pre-dosed with Formula Ia 4 hours before dosing with temozolomide (middle), and post-dosed with Formula Ia 4 hours after dosing with temozolomide (bottom).

FIG. 7 shows results of in vitro cell proliferation assays (Cell-Titer Glo, Promega) measuring viable cells over varying concentrations (starting at 4× EC50) right to left of temozolomide, Formula Ia compound, and the combination of temozolomide and Formula Ia. The U87 (glioma tumor type) cells are treated simultaneously (top), pre-dosed with Formula Ia 4 hours before dosing with temozolomide (middle), and post-dosed with Formula Ia 4 hours after dosing with temozolomide (bottom). Synergy is observed with simultaneous dosing (CI=0.004), but not with pre-dosing with Formula Ia (CI=1.13), and post-dosing with Formula Ia (CI=1.41).

Figure 8:
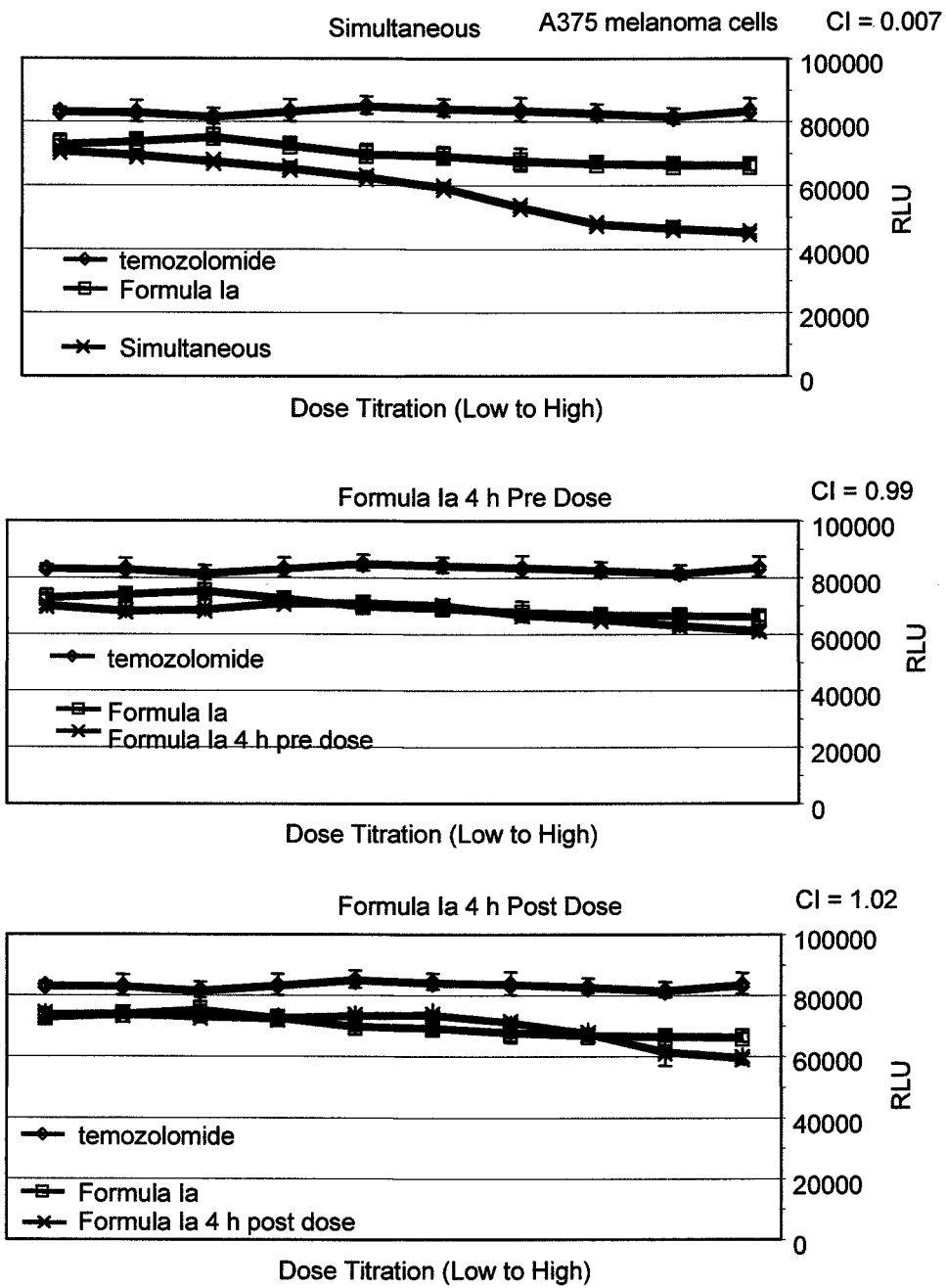
FIG. 8 shows results of in vitro cell proliferation assays (Cell-Titer Glo, Promega) measuring viable cells over varying concentrations (starting at 4× EC50) right to left of temozolomide, Formula Ia compound (GDC-0941), and the combination of temozolomide and Formula Ia. The A375 (melanoma tumor type) cells are treated simultaneously (top), pre-dosed with Formula Ia 4 hours before dosing with temozolomide (middle), and post-dosed with Formula Ia 4 hours after dosing with temozolomide (bottom).

FIG. 8 shows results of in vitro cell proliferation assays (Cell-Titer Glo, Promega) measuring viable cells over varying concentrations (starting at 4× EC50) right to left of temozolomide, Formula Ia compound, and the combination of temozolomide and Formula Ia. The A375 (melanoma tumor type) cells are treated simultaneously (top), pre-dosed with Formula Ia 4 hours before dosing with temozolomide (middle), and post-dosed with Formula Ia 4 hours after dosing with temozolomide (bottom). Synergy is observed with simultaneous dosing (CI=0.007), but not with pre-dosing with Formula Ia (CI=0.99), and post-dosing with Formula Ia (CI=1.02).

Figure 9:
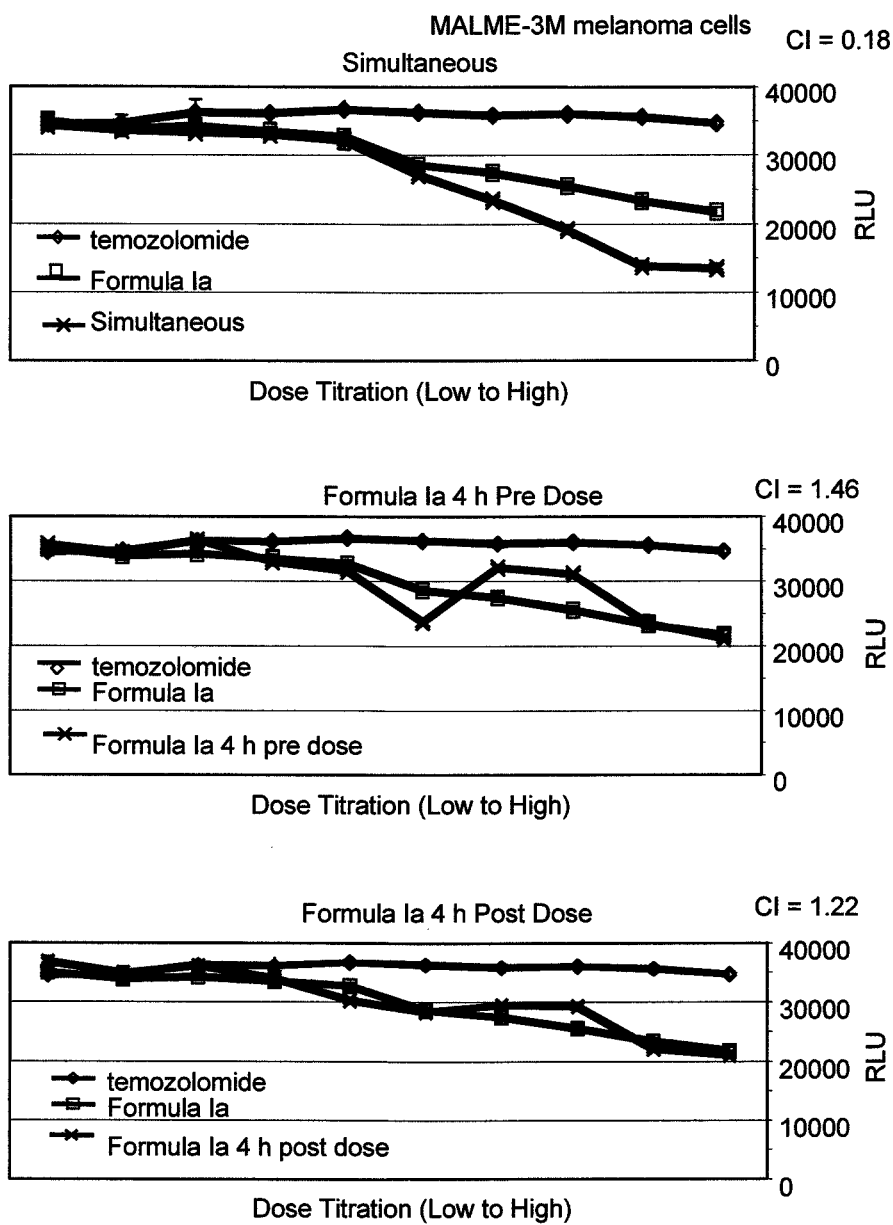
FIG. 9 shows results of in vitro cell proliferation assays (Cell-Titer Glo, Promega) measuring viable cells over varying concentrations (starting at 4× EC50) right to left of temozolomide, Formula Ia compound (GDC-0941), and the combination of temozolomide and Formula Ia. The MALME-3M (melanoma tumor type) cells are treated simultaneously (top), pre-dosed with Formula Ia 4 hours before dosing with temozolomide (middle), and post-dosed with Formula Ia 4 hours after dosing with temozolomide (bottom).

FIG. 9 shows results of in vitro cell proliferation assays (Cell-Titer Glo, Promega) measuring viable cells over varying concentrations (starting at 4× EC50) right to left of temozolomide, Formula Ia compound, and the combination of temozolomide and Formula Ia. The MALME-3M (melanoma tumor type) cells are treated simultaneously (top), pre-dosed with Formula Ia 4 hours before dosing with temozolomide (middle), and post-dosed with Formula Ia 4 hours after dosing with temozolomide (bottom). Synergy is observed with simultaneous dosing (CI=0.18), but not with pre-dosing with Formula Ia (CI=1.46), and post-dosing with Formula Ia (CI=1.22).

Figure 10:
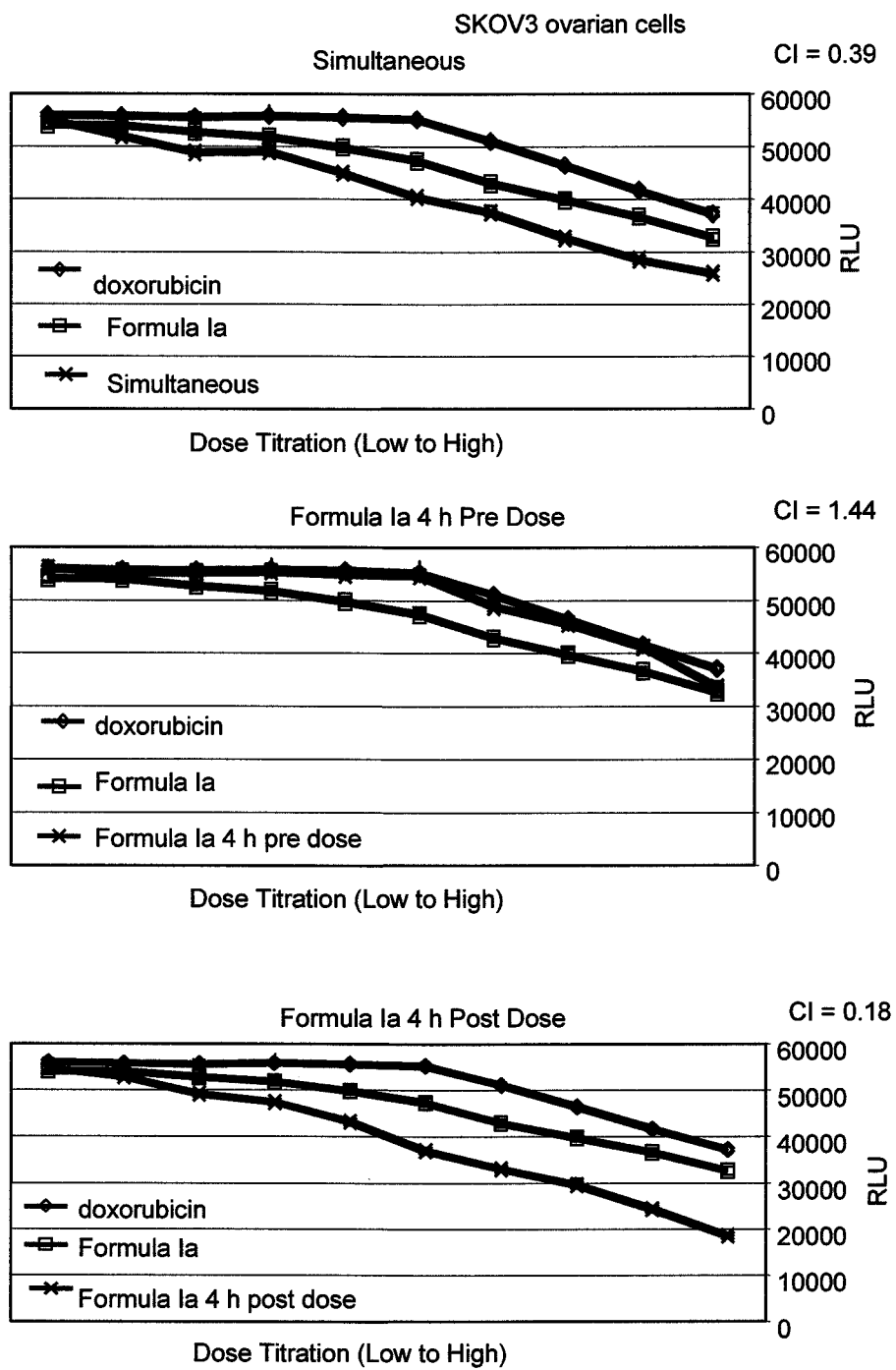
FIG. 10 shows results of in vitro cell proliferation assays (Cell-Titer Glo, Promega) measuring viable cells over varying concentrations (starting at 4× EC50) right to left of doxorubicin, Formula Ia compound (GDC-0941), and the combination of doxorubicin and Formula Ia. The SKOV3 (ovarian tumor type) cells are treated simultaneously (top), pre-dosed with Formula Ia 4 hours before dosing with doxorubicin (middle), and post-dosed with Formula Ia 4 hours after dosing with doxorubicin (bottom).

FIG. 10 shows results of in vitro cell proliferation assays (Cell-Titer Glo, Promega) measuring viable cells over varying concentrations (starting at 4× EC50) right to left of doxorubicin, Formula Ia compound, and the combination of doxorubicin and Formula Ia. The SKOV3 (ovarian tumor type) cells are treated simultaneously (top), pre-dosed with Formula Ia 4 hours before dosing with doxorubicin (middle), and post-dosed with Formula Ia 4 hours after dosing with doxorubicin (bottom). Synergy is observed with simultaneous dosing (CI=0.39), and post-dosing with Formula Ia (CI=0.18), but not with pre-dosing with Formula Ia (CI=1.44).

Figure 11:
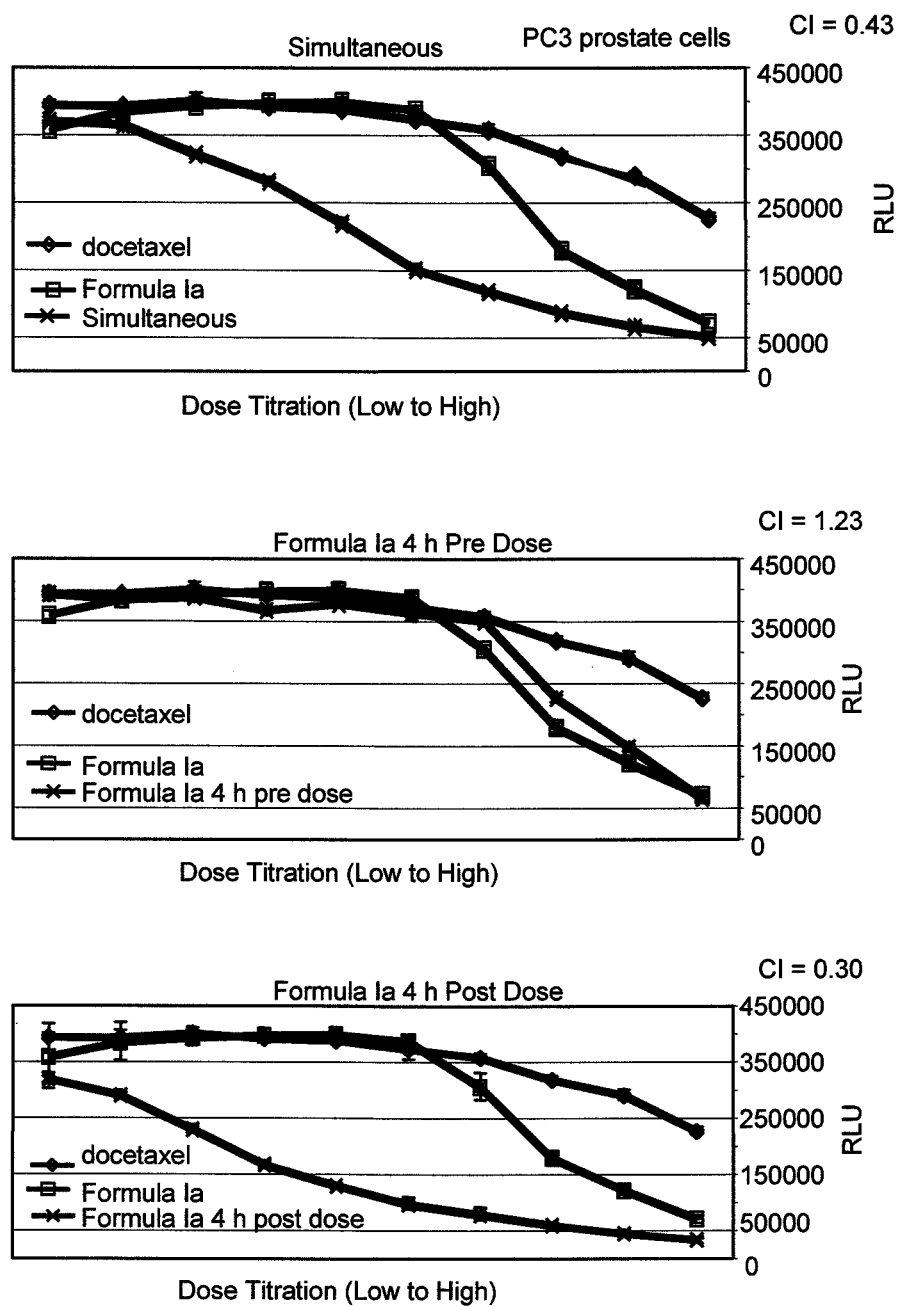
FIG. 11 shows results of in vitro cell proliferation assays (Cell-Titer Glo, Promega) measuring viable cells over varying concentrations (starting at 4× EC50) right to left of docetaxel, Formula Ia compound (GDC-0941), and the combination of docetaxel and Formula Ia. The PC3 (prostate tumor type) cells are treated simultaneously (top), pre-dosed with Formula Ia 4 hours before dosing with docetaxel (middle), and post-dosed with Formula Ia 4 hours after dosing with docetaxel (bottom).

FIG. 11 shows results of in vitro cell proliferation assays (Cell-Titer Glo, Promega) measuring viable cells over varying concentrations (starting at 4× EC50) right to left of docetaxel, Formula Ia compound, and the combination of docetaxel and Formula Ia. The PC3 (prostate tumor type) cells are treated simultaneously (top), pre-dosed with Formula Ia 4 hours before dosing with docetaxel (middle), and post-dosed with Formula Ia 4 hours after dosing with docetaxel (bottom). Synergy is observed with simultaneous dosing (CI=0.43), and post-dosing with Formula Ia (CI=0.30), but not with pre-dosing with Formula Ia (CI=1.23).

Figure 12:
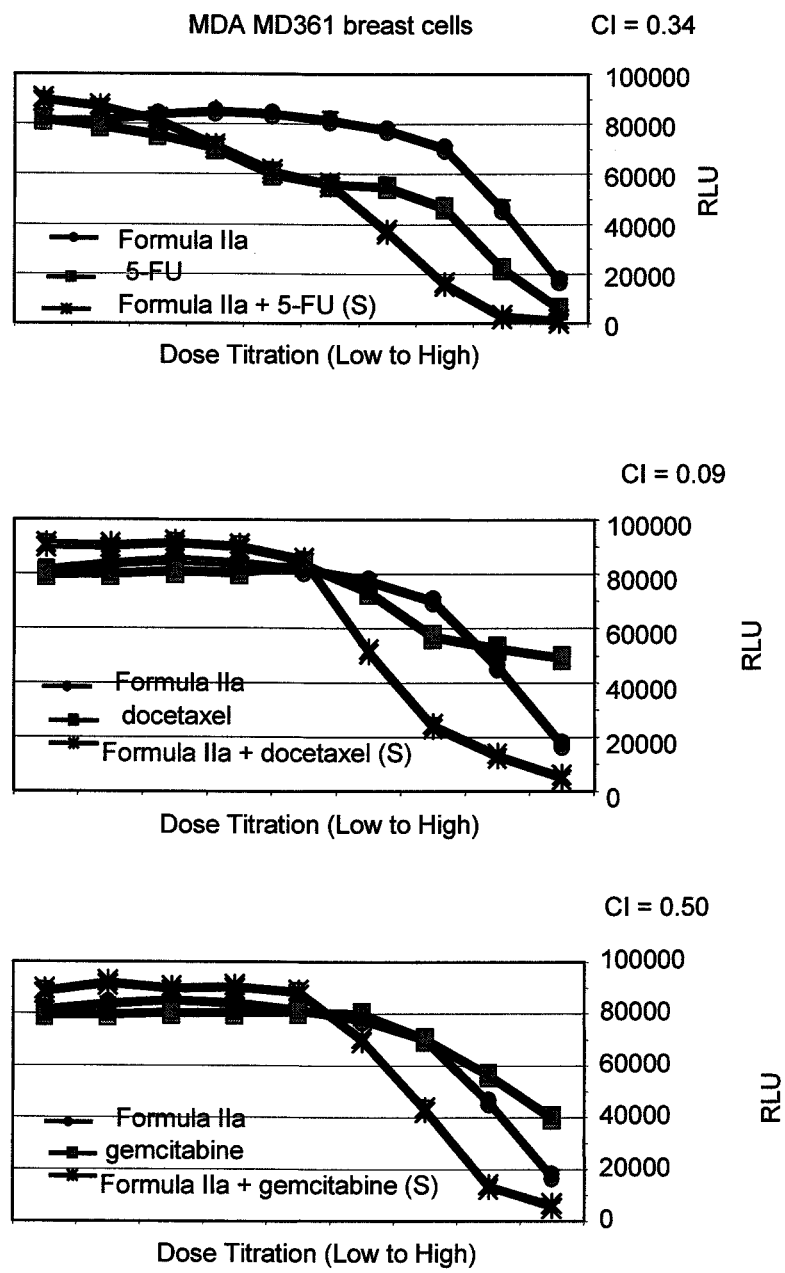
FIG. 12 shows results of in vitro cell proliferation assays (Cell-Titer Glo, Promega) measuring viable MDA-MB 361 (breast tumor type) cells over varying concentrations (starting at 4× EC50) right to left of: (top) 5-FU, Formula IIa compound, and the simultaneous combination of 5-FU and Formula IIa); (middle) docetaxel, Formula IIa compound, and the simultaneous combination of docetaxel and Formula IIa; and (bottom) gemcitabine, Formula IIa compound, and the simultaneous combination of gemcitabine and Formula IIa.

FIG. 12 shows results of in vitro cell proliferation assays (Cell-Titer Glo, Promega) measuring viable MDA MD 361 (breast tumor type) cells over varying concentrations (starting at 4× EC50) right to left of: (top) 5-FU, Formula IIa compound, and the simultaneous combination of 5-FU and Formula IIa; (middle) docetaxel, Formula IIa compound, and the simultaneous combination of docetaxel and Formula IIa; and (bottom) gemcitabine, Formula IIa compound, and the simultaneous combination of gemcitabine and Formula IIa. Synergy is observed with simultaneous dosing of 5-FU and Formula IIa (CI=0.34), docetaxel and Formula IIa (CI=0.09), and gemcitabine and Formula IIa (CI=0.50).

Figure 13:
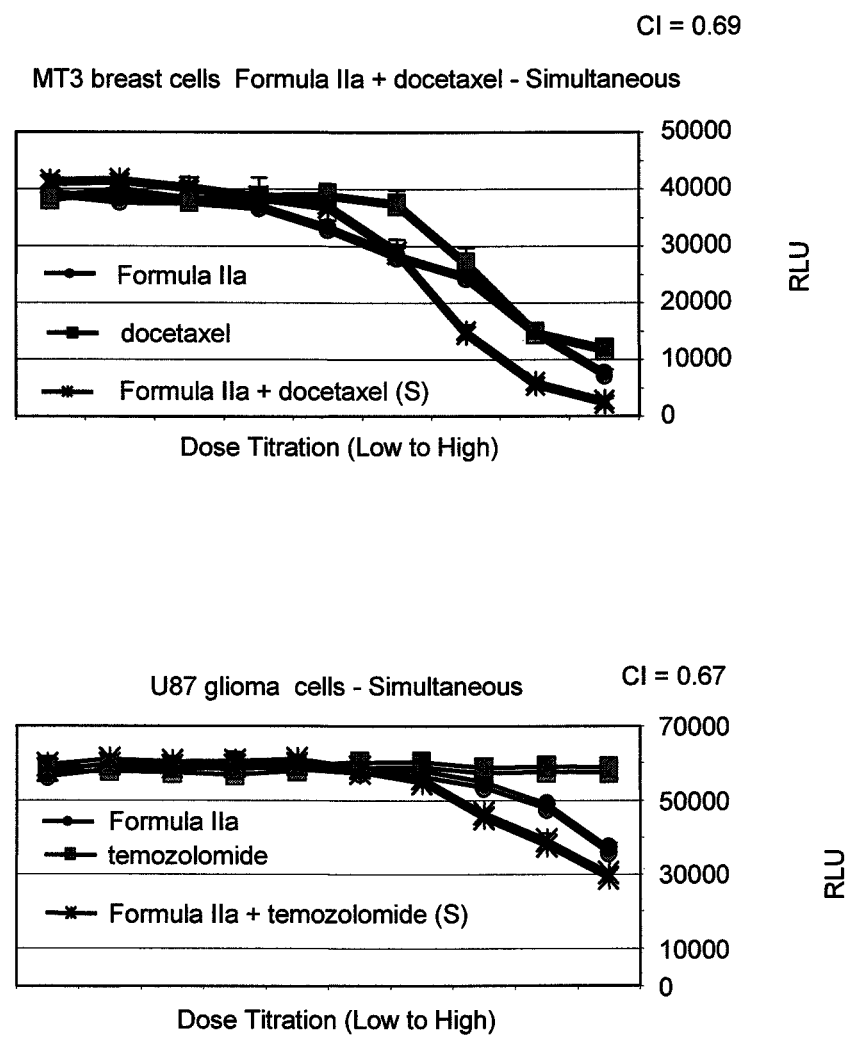
FIG. 13 shows results of in vitro cell proliferation assays (Cell-Titer Glo, Promega) measuring: (top) viable MT3 (breast tumor type) cells over varying concentrations (starting at 4× EC50) right to left of docetaxel, Formula IIa compound, and the simultaneous combination of docetaxel and Formula IIa; and (bottom) viable U87 (glioma tumor type) cells over varying concentrations (starting at 4× EC50) right to left of temozolomide, Formula IIa compound, and the simultaneous combination of temozolomide and Formula IIa.

FIG. 13 shows results of in vitro cell proliferation assays (Cell-Titer Glo, Promega) measuring: (top) viable MT3 (breast tumor type) cells over varying concentrations (starting at 4× EC50) right to left of docetaxel, Formula IIa compound, and the simultaneous combination of docetaxel and Formula IIa; and (bottom) viable U87 (glioma tumor type, PTEN neg mutation) cells over varying concentrations (starting at 4× EC50) right to left of temozolomide, Formula IIa compound, and the simultaneous combination of temozolomide and Formula IIa. Synergy is observed with simultaneous dosing in MT3 cells with docetaxel and Formula IIa (CI=0.69), and in U87 cells with temozolomide and Formula IIa (CI=0.67).

Figure 14:
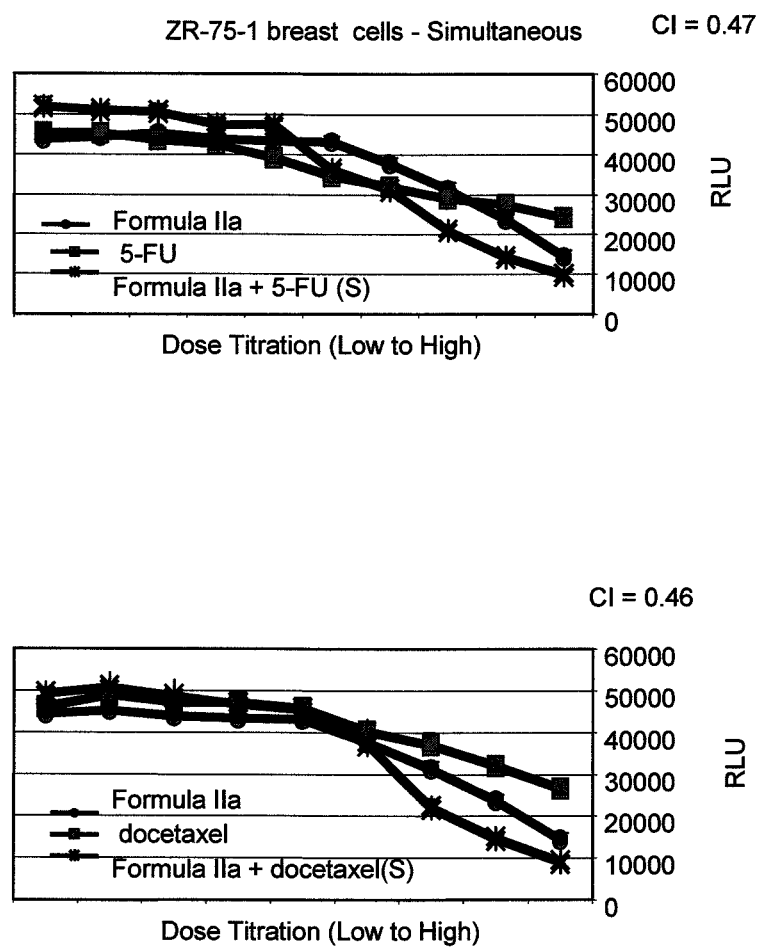
FIG. 14 shows results of in vitro cell proliferation assays (Cell-Titer Glo, Promega) measuring viable ZR75-1 (breast tumor type) cells over varying concentrations (starting at 4× EC50) right to left of: (top) 5-FU, Formula IIa compound, and the simultaneous combination of 5-FU and Formula IIa; and (bottom) docetaxel, Formula IIa compound, and the simultaneous combination of docetaxel and Formula IIa.

FIG. 14 shows results of in vitro cell proliferation assays (Cell-Titer Glo, Promega) measuring viable ZR75-1 (breast tumor type) cells over varying concentrations (starting at 4× EC50) right to left of: (top) 5-FU, Formula IIa compound, and the simultaneous combination of 5-FU and Formula IIa; and (bottom) docetaxel, Formula IIa compound, and the simultaneous combination of docetaxel and Formula IIa. Synergy is observed with simultaneous dosing in ZR75-1 cells with 5-FU and Formula IIa (CI=0.47), and in ZR75-1cells with docetaxel and Formula IIa (CI=0.46).

Figure 15:
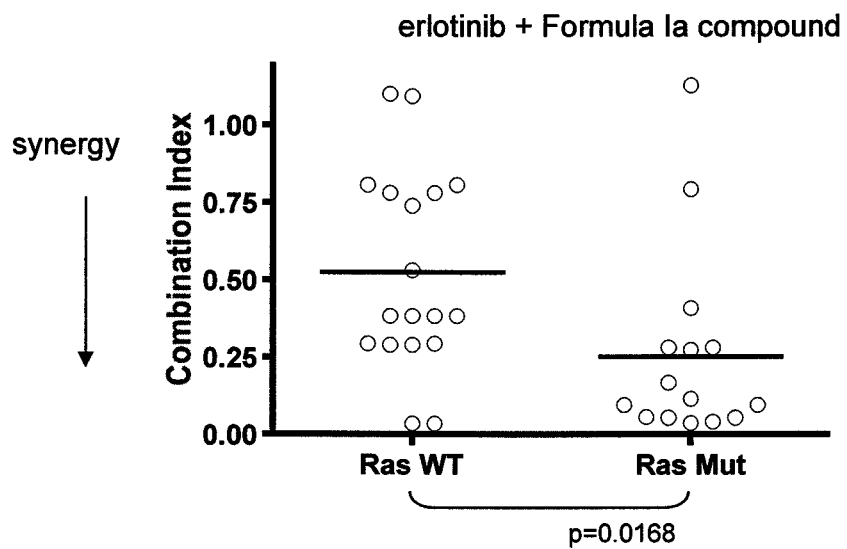
FIG. 15 shows a dot plot of synergy (Combination Index) of erlotinib and Formula Ia compound (GDC-0941) experiments from FIG. 1-A against tumor cell lines without Ras mutations (Ras WT, Expts. 41, 42, 73-75, 77, 79-81, 83, 84, 86) and with Ras mutations (Ras Mut, Expts. 40, 69-72, 76, 78, 82, 144, 145).
Figure 16:
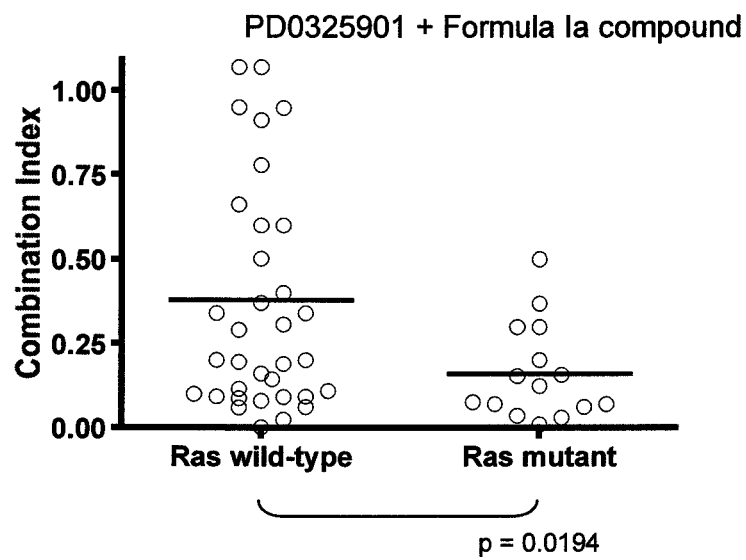
FIG. 16 shows a dot plot of synergy (Combination Index) of PD-0325901 and Formula Ia compound (GDC-0941) experiments from FIG. 1-A against tumor cell lines without Ras mutations (Ras WT, Expts. 22-24, 26-28, 31-33, 36-38, 55, 59, 61, 63-66, 85, 89-98, 149, 161, 162) and with Ras mutations (Ras Mut, Expts. 25, 30, 34, 35, 39, 56-58, 60, 62, 67, 68, 146-148, 150).

The correlation between Ras mutations and the in vitro synergy effects listed in FIG. 1A (Expts. 1-248) due to combinations of Formula Ia compound and chemotherapeutic agents can be displayed by dot plots. Each dot in FIGS. 15 and 16 is an experiment from FIG. 1A. The experiments are grouped as Ras wild-type (Ras WT) or Ras mutant (Ras Mut) with the specific mutations noted in FIG. 1A, plotted against the synergy effect (Combination Index, CI), where synergy increases with decreasing CI as calculated by the Chou and Talalay method (Chou, T. and Talalay, P. (1984) Adv. Enzyme Regul. 22:27-55).

FIG. 15 shows a dot plot of synergy (Combination Index) of erlotinib and Formula Ia compound experiments from FIG. 1A against tumor cell lines with and without Ras mutations (Expts. 71-73, 140-168, 230-231). The ras mutant cell lines show stronger synergy between erlotinib and Formula Ia compound than ras wild-type cell lines.

FIG. 16 shows a dot plot of synergy (Combination Index) of PD-0325901 and Formula Ia compound experiments from FIG. 1A against tumor cell lines with and without Ras mutations (Expts. 29-35, 74-83, 124-139, 175-184, 224-226, 232-236, 247, 248). The ras mutant cell lines show stronger synergy between PD-0325901 and Formula Ia compound than ras wild-type cell lines.

Figure 17:
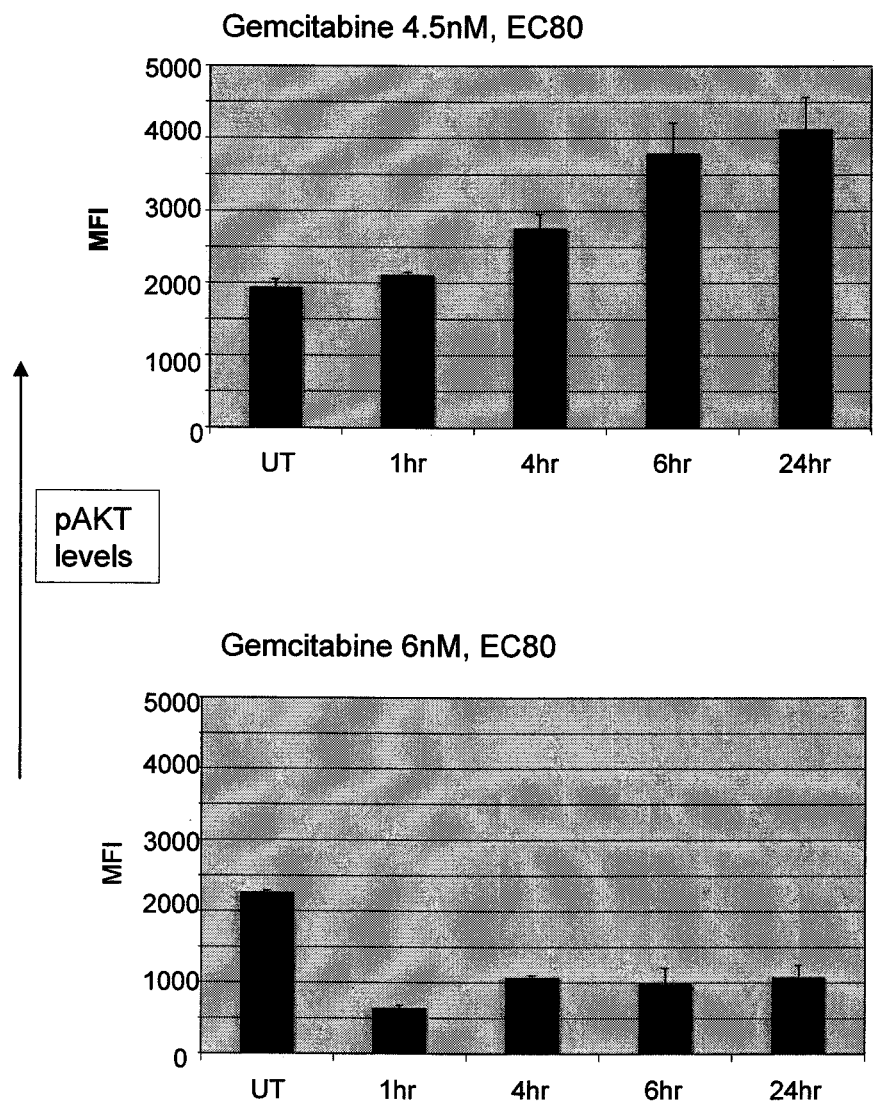
FIG. 17 shows time-course results of treatment of a synergistic tumor cell line MDA-MB-361 and a non-synergistic tumor cell line MT-3 with gemcitabine at EC80 dosing levels. pAKT levels were measured at T=0 (untreated, UT), 1 hr, 4 hr, 6 hr, and 24 hr.

FIG. 17 shows time-course results of treatment of a synergistic tumor cell line MDA-MB-361 and a non-synergistic tumor cell line MT-3 with gemcitabine at EC80 dosing levels. pAkt levels were measured at T=0 (untreated, UT), 1 hr, 4 hr, 6 hr, and 24 hr. Constitutive and inducible Akt activity is known to promote resistance to chemotherapy, trastuzumab, or tamoxifen in breast cancer cells (Clark et al (2002) Mol Cancer Ther. 1(9):707-17). Phospho Akt (pAkt) levels can be measured by the method described in Example 18. Low CI correlates with the effect of the chemotherapeutic to induce an increase in pAkt. Levels of pAkt (Ser473) were determined using bead kits from Biosource (Carlsbad, Calif.) and the Luminex Bio-Plex system (Bio-Rad, Hercules, Calif.). Gemcitabine treatment leads to increased pAkt levels in the synergistic cell line (MDA-MB-361) but not in the non-synergistic cell line (MT-3), demonstrating that an increase in pAkt levels in response to chemotherapy is correlated and predictive of synergy by a Formula I or II compound and a chemotherapeutic agent in treatment of cancer.

Figure 18:
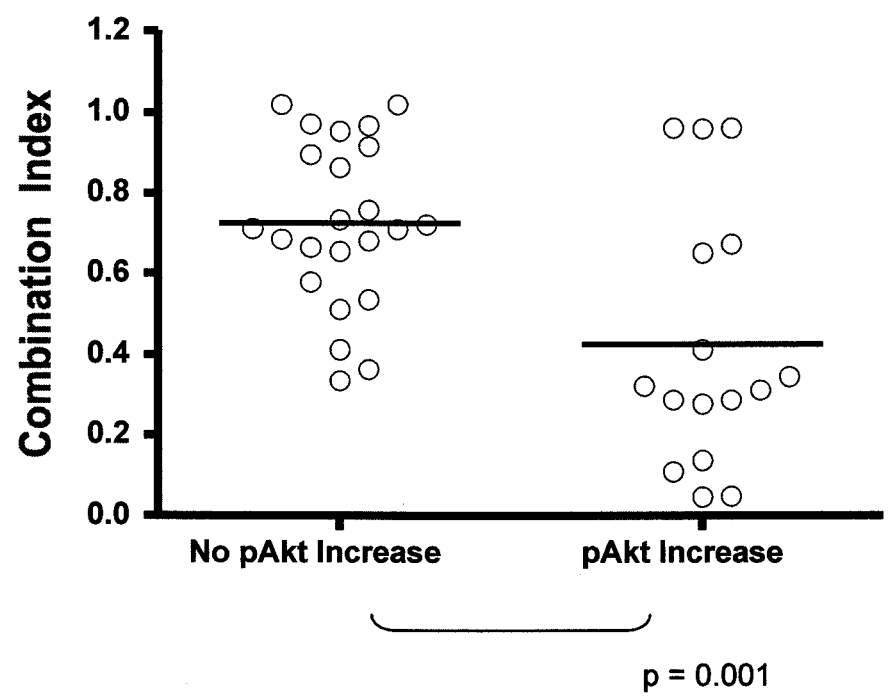
FIG. 18 shows a dot plot of synergy (Combination Index) of docetaxel, 5-FU, or gemcitabine and Formula Ia compound (GDC-0941) experiments from FIG. 1-A against tumor cell lines that show a pAkt increase or no pAkt increase.

FIG. 18 shows a dot plot of synergy (Combination Index) of docetaxel, 5-FU, or gemcitabine and Formula Ia compound experiments from FIG. 1A against tumor cell lines that show a pAkt increase or no pAkt increase in response to the chemotherapeutic agent alone. Cell lines that show an increase in pAkt after treatment with docetaxel, 5-FU, or gemcitabine show stronger synergy with Formula Ia compound than cell lines without a pAkt response.

The invention includes a method for determining compounds to be used in combination for the treatment of cancer comprising: a) administering a therapeutic combination of a compound having Formula I or II, and a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib to an in vitro tumor cell line with a K-ras mutation, and b) measuring a synergistic or non-synergistic effect.

Although other mechanisms of action may be operative in the combinations exemplified in FIGS. 1A, 1B, 1C, and FIGS. 2-14, the results are consistent with PI3K inhibitors exerting a G1 phase specific effect on the inhibition of tumor cell proliferation, 5FU exerting an S phase specific disruption of DNA synthesis, gemcitabine exerting an S phase specific disruption of DNA synthesis, and docetaxel exerting an M phase specific depolarization of microtubules.

Flow Cytometry Facs

Flow cytometry was conducted to measure the effects of combination therapy of Formula Ia compound and several chemotherapeutic agents on MB3 breast tumor and PC3 prostate tumor cells. The Annexin V/PI assay detects early and late apoptotic events (Example 15). Cells that are Annexin V positive are in the early stages of apoptosis and those that are both Annexin V and PI positive are noted as "dead" on the bar graph charts of FIG. 19. The remaining cells make up the "live" population.

Figure 19:
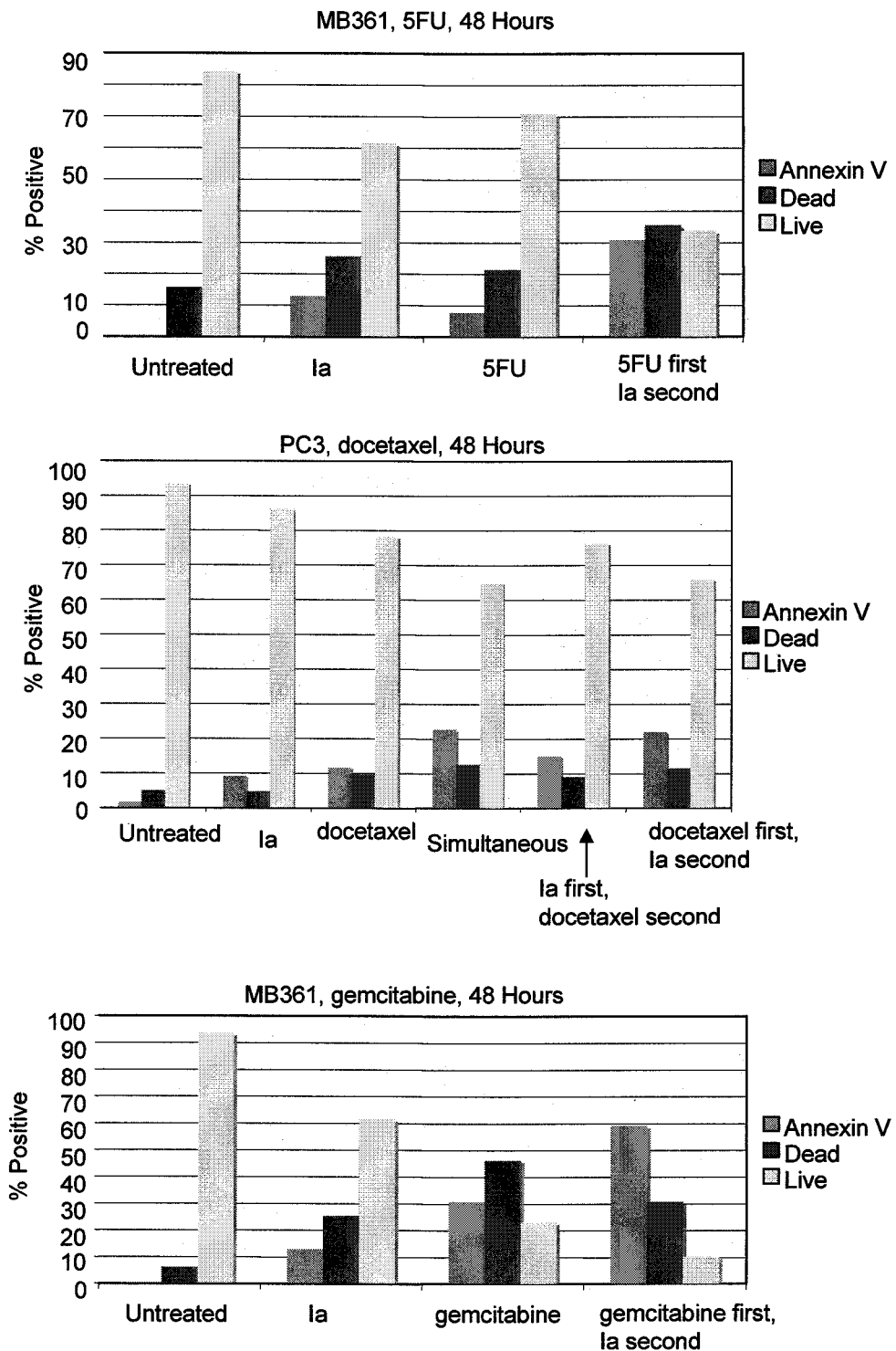
FIG. 19 shows results of flow cytometry FACS (Fluorescence Activated Cell Sorter): (top) MB361 cells are (left to right) untreated, treated with Formula Ia, 5FU, and first with 5FU then Formula Ia compound (GDC-0941); (middle) PC3 cells are (left to right) untreated, treated with Formula Ia, docetaxel, simultaneous with Formula Ia compound and docetaxel, first with Formula Ia then with docetaxel, and first with docetaxel, then with Formula Ia; and (bottom) MB361 cells are (left to right) untreated, treated Formula Ia, gemcitabine, and first with gemcitabine then with Formula Ia.

FIG. 19 shows results of flow cytometry FACS (Fluorescence Activated Cell Sorter): (top) MB361 cells are (left to right) untreated, treated with Formula Ia, 5FU, and first with 5FU then Formula Ia compound; (middle) PC3 cells are (left to right) untreated, treated with Formula Ia, docetaxel, simultaneous with Formula Ia compound and docetaxel, first with Formula Ia then with docetaxel, and first with docetaxel, then with Formula Ia; and (bottom) MB361 cells are (left to right) untreated, treated Formula Ia, gemcitabine, and first with gemcitabine then with Formula Ia.

Formula Ia compound and a genotoxic, chemotherapeutic agent were dosed at EC80 for 24, 48, 72 hours. FACS (Fixed for cell cycle (PI), live cells for Annexin V and PI) Compounds were added either simultaneously, or separated by 4 hours, pre-dosing and post-dosing with Formula Ia compound (Example 19). A wash out effect was noted where maximum synergy was attained after one hour. The combinations remained synergistic with both drugs washed out one hour after dosing. There are increases in early and late apoptosis in all three combinations (FIG. 19) when Formula Ia is combined with the chemotherapeutic drug. A low Chou and Talalay CI value suggests that a significant benefit in tumor inhibition is likely when these drugs are combined in vivo.

Three Dimensional Combination Assay

In glandular tissues such as the breast, the epithelium interacts with a specialized form of extracellular matrix, known as basement membrane. The extracellular matrix regulates normal mammary gland biology and pathogenesis. Adaptation of a reconstituted, laminin-rich basement membrane (1rBM) to standard cell culture can recapitulate the basic acinar architecture of the mammary gland and is considered to be an improved in vitro model to simulate the dynamic microenvironment of a tumor (Debnath J, Brugge J S. (2005) Nat Rev Cancer. 5:675-88). Using broad specificity inhibitors, PI3K signaling has been implicated in acini development of HMT-3522 T4-2 human breast tumor cells grown in 1rBM, whereby PI3K inhibition was sufficient to restore apical-basal polarity and induce growth arrest (Liu H, Radisky D C, Wang F, Bissell M J. (2004) J Cell Biol.; 164:603-12). Given the proposed contribution of PI3K to the initiation and development of breast cancer, 3D culture systems provide a novel and comprehensive means of assessing the efficacy of small-molecule PI3K inhibitors such as Formula Ia compound.

The receptor tyrosine kinase HER2 (Neu/ErbB2) is amplified and over-expressed in approximately 20% of human breast cancer and plays a causal role in mammary carcinogenesis (Yarden Y, Sliwkowski M X. (2001) Nat Rev Mol Cell Biol. 2:127-37). That HER2 over-expression plays a role in human breast cancer is demonstrated by the therapeutic efficacy of the anti-HER2 monoclonal antibody, trastuzumab (HERCEPTIN®, Genentech). In addition to homodimerization, HER2 can also function as a co-receptor for other HER family members. The monoclonal antibody pertuzumab targets the HER2 dimerization arm (extracellular subdomain II) and disrupts the recruitment of HER2 into HER receptor-ligand complexes (Franklin et al (2004) Cancer Cell. 5:317-28). The efficacy of PI3K inhibition was determined using Formula Ia and IIa compounds combined with inhibition of HER family signaling using the therapeutic antibodies, trastuzumab and pertuzumab.

The invention includes a method for determining compounds to be used in combination for the treatment of cancer comprising: a) administering a therapeutic combination of claim 1 to HER2-amplified breast cancer cells in laminin-rich, reconstituted basement membrane media, wherein the chemotherapeutic agent targets, binds to, or modulates a HER2 receptor, and b) measuring inhibition of cellular proliferation wherein nonmalignant and malignant mammary cells are discriminated by one or more phenotypic difference selected from cell viability and acinar morphogenesis.

Combinations of Formula I and II compounds and therapeutic antibodies were evaluated in HER2-amplified BT474M1 cells (Example 16). Cells were cultured in a 3-dimensional (3D) laminin-rich, reconstituted basement membrane to account for the role of extracellular matrix molecules in oncogene signaling and biology. The ability of 3D culture to recapitulate the oncogenic microenvironment connotes that it may be a more reliable predictor of in vivo efficacy (as compared to two-dimensional (2D) cultures of cells on plastic) and can be useful for the characterization of inhibitors and target genes. 3D culture was used to assess HER family signaling and measure the synergistic efficacy of inhibitors. Cell viability and acinar phenotypes (morphogenesis) were used as markers of drug efficacy (Example 16).

HER2-amplified BT474M1 cells were used to detect HER family signaling using novel 3D cell culture phenotypes, and measure synergistic efficacy based on acinar morphogenesis (Example 16). One embodiment of the laminin-rich, reconstituted basement membrane media is Engelbreth-Holm-Swarm extracellular matrix extract, commercially available as BD Matrigel™ (BD Biosciences). Another exemplary embodiment of an extracellular matrix (ECM) for 3D culture is Madin-Darby canine kidney epithelial cells. An exemplary phenotypic difference is the acinar architecture of invasive (malignant) and non-invasive (non-malignant) cells.

Acinar morphogenesis can be scored as an additional assay for drug efficacy. Each inhibitor is titrated to examine pathway pharmacodynamic (PD) markers, cell viability and acinar phenotype. The lowest inhibitor drug concentration was established that effectively inhibits the target. The suitable concentration of a Formula I and II compound for 3D culture assays was determined by administering increasing doses with consideration for overall cell viability, pharmacodynamics of corresponding downstream pathway markers (such as phosphorylated AKT1), and changes in acinar phenotype. The lowest drug concentration that effectively inhibited the target was chosen for the assays. A concentration of 250 nM Formula Ia and IIa compound was selected as the final working concentration for 3D culture assays.

Direct inhibitors of HER2 such as trastuzumab and pertuzumab have been shown to interfere with downstream activation of several key effector pathways, including the PI3K-AKT axis. Combined inhibition of PI3K and HER family signaling in HER2-amplified breast cancer cells may result in potent tumor cell inhibition.

By immunoblot detection of phosphorylated AKT1 (pAkt), 250 nM Formula Ia compound was confirmed to potently inhibit PI3K downstream signaling (Example 16). Therapeutic antibodies were used at saturating concentrations of 20 µg/ml and 25 µg/ml for pertuzumab and trastuzumab, respectively. Combination of Formula Ia and trastuzumab resulted in an additive suppression of the 3D growth of BT474M1 acini cultured in Matrigel devoid of HRG ligand. To detect ligand-dependent HER2-HER3 heterodimer signaling, as has been suggested to be transforming in multiple cell lines, 1 nM HRG was added in these assays. Formula Ia and trastuzumab had no effect on HRG-induced proliferation. By comparison, co-treatment with Formula Ia and pertuzumab resulted in an additive reduction of HRG-induced acini growth and morphogenesis. This effect was shown to be statistically significant upon multiple replicates. In the absence of ligand the reduction of 3D acini growth was greater following treatment with Formula Ia and trastuzumab as compared to Formula Ia and pertuzumab. The combination of trastuzumab and Formula Ia compound inhibit cell proliferation and attenuate heregulin-induced morphogenesis. The combination of trastuzumab and Formula Ia compound have potent and additive effects on 3D growth in normal serum, but no additivity was observed with the combination on acini growth or morphogenesis in heregulin-treated media. The combination of pertuzumab and Formula Ia compound combination potently, but additively, inhibits BT474M1 acini growth and morphogenesis. The triple combination of trastuzumab, pertuzumab, and Formula Ia compound synergistically inhibits BT474M1 acini bud growth and morphogenesis (FIG. 20) in both HRG-supplemented and standard media.

Each inhibitor was titrated to examine relevant pathway pharmacodynamic (PD) markers, cell viability, and acinar phenotype. The lowest inhibitor drug concentration that effectively inhibited the target was established and utilized in all 3D assays.

Figure 20:
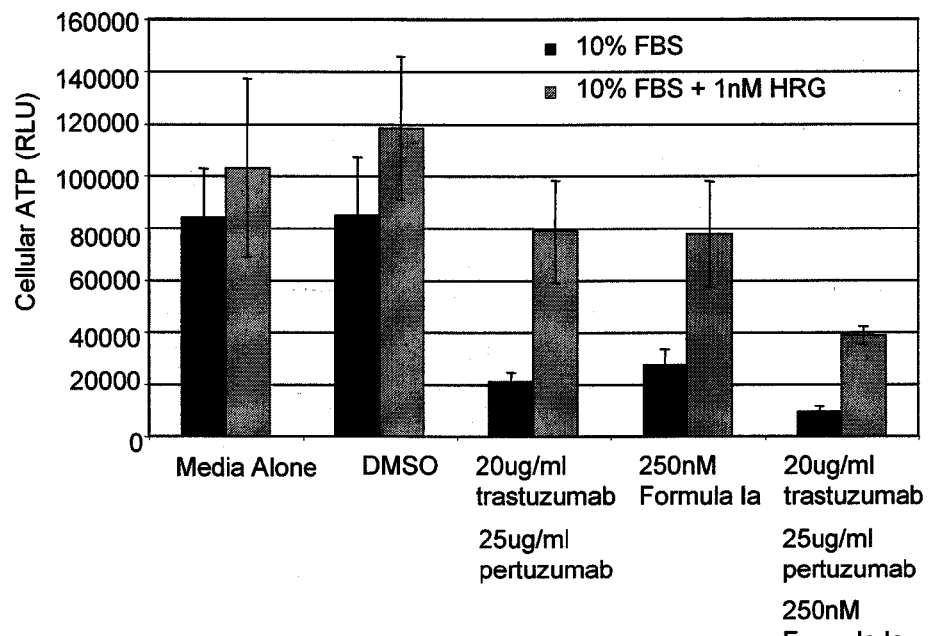
FIG. 20 shows treatment of BT474M1 cells in three dimensional (3D) culture. Acini growth and morphogenesis is correlated with cellular ATP production in relative light units (RLU) in 10% FBS medium with and without 1 nM heregulin1 by treatment with (left to right): media, DMSO, combination of 20 μg/ml trastuzumab and 25 μg/ml pertuzumab, 250 nM Formula Ia compound (GDC-0941), and the combination of 20 μg/ml trastuzumab, 25 μg/ml pertuzumab, and 250 nM Formula Ia compound.

FIG. 20 shows the quantification of BT474 growth in three-dimensional (3D) culture. Cell viability was determined by measuring cellular ATP levels. BT474M1 cells were cultured in either 10% serum or 10% serum with 1 nM heregulin and subject to inhibitor combinations as indicated (left to right): media, DMSO, combination of 20 µg/ml trastuzumab and 25 µg/ml pertuzumab, 250 nM Formula Ia compound, and the combination of 20 µg/ml trastuzumab, 25 µg/ml pertuzumab, and 250 nM Formula Ia compound. Acini growth and morphogenesis is correlated with cellular ATP production in relative light units (RLU) in 10% FBS medium with and without 1 nM heregulin.

In standard media (without heregulin), cell activity is comparatively lower in the presence of trastuzumab, pertuzumab or Formula Ia compound individually, but not in HRG-treated media. The combination of trastuzumab and Formula Ia compound inhibited cell proliferation and attenuated heregulin-induced morphogenesis in normal serum, but no additivity was observed on acini growth or morphogenesis in heregulin-treated media. The combination of pertuzumab and Formula Ia compound potently, and additively, inhibited BT474M1 acini growth and morphogenesis in both standard and heregulin-supplemented media. The triple combination of trastuzumab, pertuzumab, and Formula Ia compound synergistically inhibited BT474M1 cell proliferation and heregulin-induced morphogenesis (FIG. 20) in both standard and HRG-supplemented media. The combination of all three agents synergistically decreases cell viability in both standard and HRG-supplemented media. Heregulin-induced morphogenesis of BT474M1 cells was also abolished by the triple combination as determined through microscopic inspection. These data suggest that the Formula Ia, trastuzumab and pertuzumab triple combination may provide improved efficacy for treating HER2-amplified breast cancer in human patients.

Trastuzumab or Formula Ia significantly reduce acinar size in normal media, but have limited effect on HRG-induced morphogenesis. As a combined treatment, trastuzumab and Formula Ia can minimize acinar size and morphogenesis. By Cell Titer-Glo analysis of cell viability, additivity between trastuzumab and Formula Ia results in decreased cell growth in normal media, but no difference is seen with the addition of HRG.

Pertuzumab completely inhibits HRG-induced morphogenesis, whereas Formula Ia only partially reduces the phenotype. Together, pertuzumab and Formula Ia abates cell growth and morphogenesis in both normal and HRG-supplemented media. By evaluation of cell viability as measured by Cell Titer-Glo. a decrease in cellular activity is observed in the presence of pertuzumab and Formula Ia as either single agents or combined therapy in normal media. HRG-treated acini also show a similar trend, but to a lesser extent. By evaluation of Dunnett's T-test comparison of Cell Titer-Glo replicates (n=8), the combination of pertuzumab and Formula Ia significantly inhibits cellular activity (p=0.0054).

Figure 21:
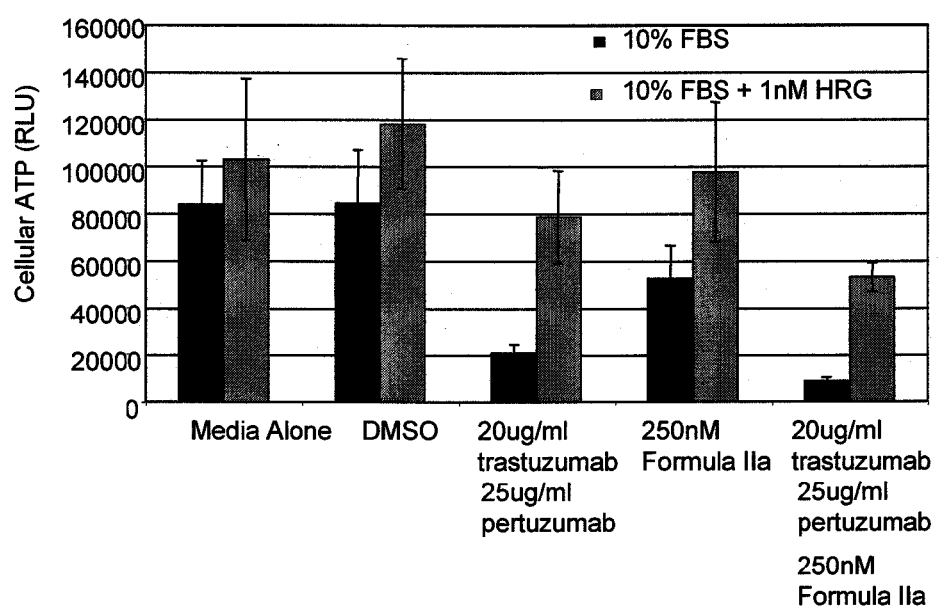
FIG. 21 shows treatment of BT474M1 cells in three dimensional (3D) culture. Acini growth and morphogenesis is correlated with cellular ATP production in relative light units (RLU) in 10% FBS medium with and without 1 nM heregulin1 by treatment with (left to right): media, DMSO, combination of 20 μg/ml trastuzumab and 25 μg/ml pertuzumab, 250 nM Formula IIa compound, and the combination of 20 μg/ml trastuzumab, 25 μg/ml pertuzumab, and 250 nM Formula IIa compound.

FIG. 21 shows a similar effect with the addition of Formula IIa to dual trastuzumab and pertuzumab treatment. FIG. 21 shows BT474 growth in 3D cell culture upon treatment of 20 μg/ml trastuzumab, 25 μg/ml pertuzumab or 250 nM Formula IIa compound, as indicated. Formula IIa significantly reduced acinar size in normal media, but as a single agent had limited effect on HRG-induced morphogenesis. As a combined treatment, Formula IIa, trastuzumab and pertuzumab significantly reduced acinar size and morphogenesis, as determined by measurement of cell viability using Cell Titer Glo. In comparison with Formula Ia compound, Formula IIa compound is slightly less efficacious at 250 nM both as a single agent (p=0.0001, Dunnett's T-test) and in combination with trastuzumab and pertuzumab (p<0.0001, Dunnett's T-test).

FIG. 21-A shows a similar effect with the addition of Formula Ib to dual trastuzumab and pertuzumab treatment. BT474 growth in 3D cell culture was measured upon treatment of 20 μg/ml trastuzumab, 25 μg/ml pertuzumab or 20 nM Formula Ib compound, as indicated. Formula Ib monotherapy reduced acinar size in normal and HRG-supplemented media. The most significant reduction in acinar size and morphogenesis, as determined by measurement of cell viability using Cell Titer Glo, resulted from combined treatment of Formula Ib, trastuzumab and pertuzumab.

In Vivo Tumor Xenograft Efficacy

The efficacy of the combinations of the invention may be measured in vivo by implanting allografts or xenografts of cancer cells in rodents and treating the tumor-bearing animals with the combinations. Variable results are to be expected depending on the cell line, the presence or absence of certain mutations in the tumor cells, the sequence of administration of Formula I or II compound and chemotherapeutic agent, dosing regimen, and other factors. Subject mice were treated with drug(s) or control (Vehicle) and monitored over several weeks or more to measure the time to tumor doubling, log cell kill, and tumor inhibition (Example 17).

Figure 22:
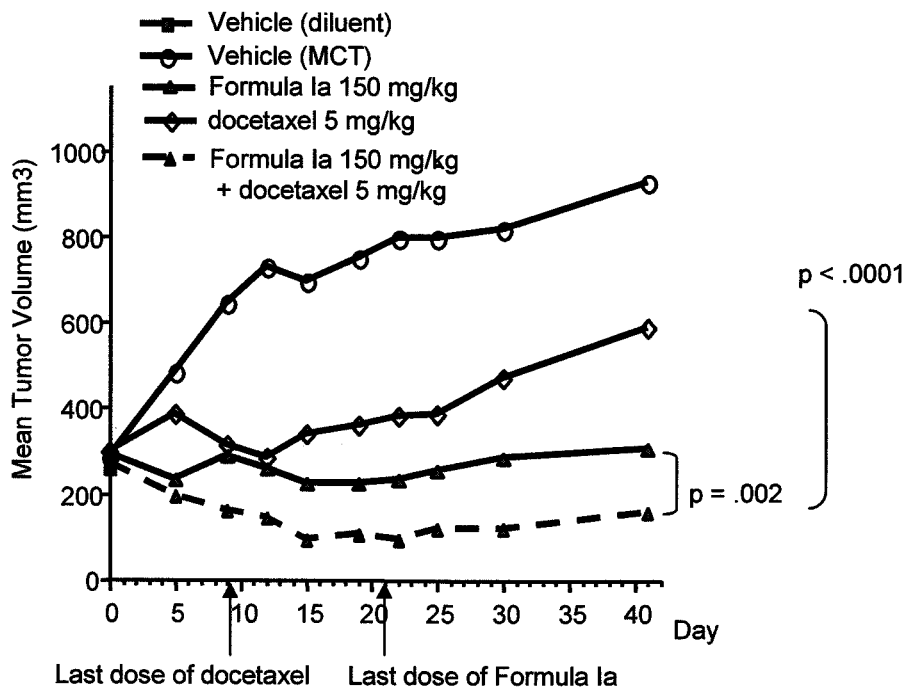
FIG. 22 shows the mean tumor volume change over time in CD-1 nude mice (Charles River Labs) with MDA-MB-361.1 breast tumor cell xenografts dosed on day 0 with: MCT Vehicle (0.5% methylcellulose/0.2% Tween 80), 150 mg/kg Formula Ia (GDC-0941), 5 mg/kg docetaxel, and the combination of Formula Ia 150 mg/kg and docetaxel 5 mg/kg. Mice were dosed with docetaxel on day 1, 5 and 9 (q4d×3) intravenously while Formula Ia was dosed daily for 21 days by oral gavage.

FIG. 22 shows the mean tumor volume change over time in CD-1 nude mice (Charles River Labs) with MDA-MB-361.1 breast tumor cell xenografts dosed on day 0 with: MCT Vehicle (0.5% methylcellulose/0.2% Tween 80), 150 mg/kg Formula Ia, 5 mg/kg docetaxel, and the combination of Formula Ia 150 mg/kg and docetaxel 5 mg/kg. Mice were dosed with docetaxel on day 1, 5 and 9 (q4d×3) intravenously while Formula 1a was dosed daily for 21 days by oral gavage. When administered on the same day, Formula 1a was dosed 1 hour after docetaxel. The combination of 150 mg/kg of formula Ia with 5 mg/kg of docetaxel synergized to inhibit MDA-MB-361.1 breast tumor growth in vivo greater than each single agent alone.

The group of 11 animals dosed with Formula Ia 150 mg/kg showed 75% inhibition after 21 days, and 3 partial regressions and 66% inhibition after 41 days. The group of 10 animals dosed with docetaxel 5 mg/kg showed 78% inhibition after 21 days, and 2 partial regressions and 26% inhibition after 41 days. The group of 9 animals dosed with the combination of Formula Ia 150 mg/kg and docetaxel 5 mg/kg showed 90% inhibition after 21 days, and 7 partial regressions and 83% inhibition after 41 days. The combination showed better efficacy in tumor inhibition and was statistically significant when compared to each single drug (p=0.0001 vs docetaxel and p=0.02 vs Formula Ia).

Figure 23:
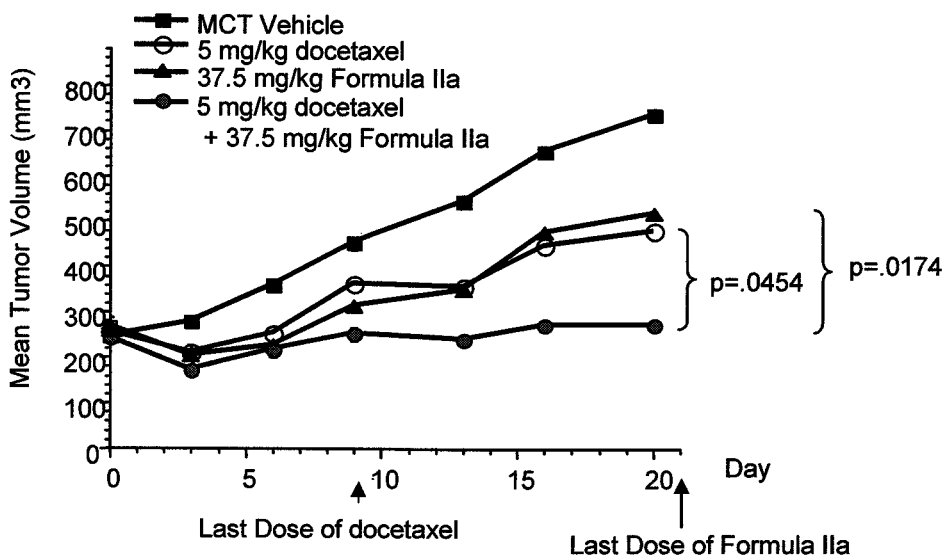
FIG. 23 shows the mean tumor volume change over time in CD-1 nude mice (Charles River Labs) with MDA-MB-361.1 breast tumor cell xenografts dosed on day 1 with: MCT Vehicle (0.5% methycellulose/0.2% Tween 80), 37.5 mg/kg Formula IIa , 5 mg/kg docetaxel and the combination of 37.5 mg/kg Formula IIa and 5 mg/kg. Mice were dosed with docetaxel on day 1, 5 and 9 (q4d×3) intravenously while Formula IIa was dosed daily for 21 days by oral gavage.

FIG. 23 shows the mean tumor volume change over time in CD-1 nude mice (Charles River Labs) with MDA-MB-361.1 breast tumor cell xenografts dosed on day 1 with: MCT Vehicle (0.5% methylcellulose/0.2% Tween 80), 37.5 mg/kg Formula IIa, 5 mg/kg docetaxel and the combination of 37.5 mg/kg Formula IIa and 5 mg/kg. Mice were dosed with docetaxel on day 1, 5 and 9 (q4d×3) intravenously while Formula IIa was dosed daily for 21 days by oral gavage. When administered on the same day, Formula IIa was dosed 1 hour after docetaxel. The group of 10 animals dosed with 37.5 mg/kg Formula IIa showed 30% inhibition and 2 partial regressions after 21 days. The group of 10 animals dosed with 5 mg/kg docetaxel showed 35% inhibition and 3 partial regressions after 21 days. The group of 10 animals dosed with the combination of Formula IIa 37.5 mg/kg and docetaxel 5 mg/kg showed 63% inhibition. The combination showed better efficacy in tumor inhibition and was statistically significant when compared to each single drug (p=0.0454 vs docetaxel and p=0.0174 vs Formula IIa).

Figure 24:
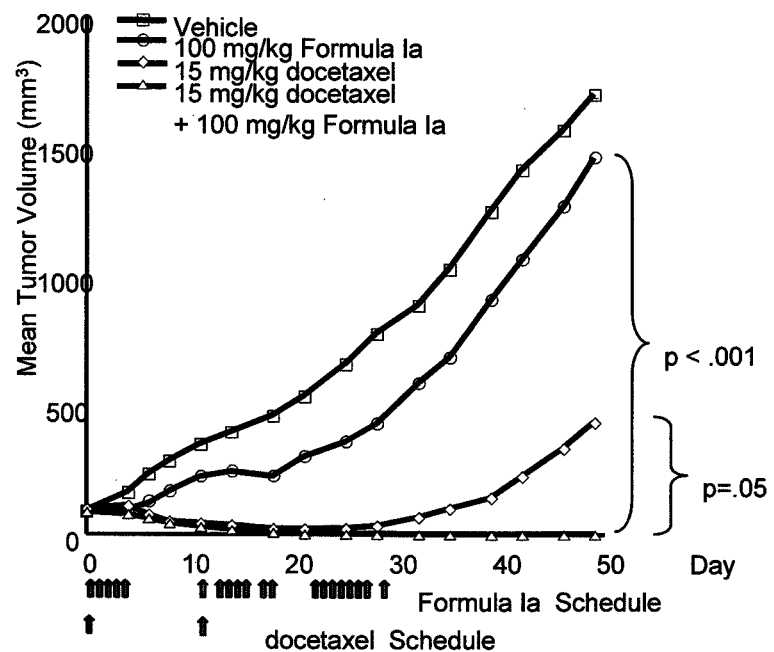
FIG. 24 shows the mean tumor volume change over time in NMRI female nu/nu (nude) mice with MAXF 401 primary breast tumor explant xenografts dosed on day 0 with: MCT Vehicle (0.5% methycellulose/0.2% Tween 80), 100 mg/kg Formula Ia (GDC-0941), 15 mg/kg docetaxel and the combination of 100 mg/kg Formula Ia and 15 mg/kg docetaxel. Mice were dosed intravenously with docetaxel on day 0 and day 11 while Formula Ia was dosed on day 0-4, 11-17 and 21-28 by oral gavage.

FIG. 24 shows the mean tumor volume change over time in NMRI female nu/nu (nude) mice with MAXF 401 (triple negative) primary breast tumor explant xenografts dosed on day 0 with: MCT Vehicle (0.5% methylcellulose/0.2% Tween 80), 100 mg/kg Formula Ia, 15 mg/kg docetaxel and the combination of 100 mg/kg Formula Ia and 15 mg/kg. MAXF 401 are primary breast tumors biopsied directly from a patient that responded to docetaxel and implanted subcutaneously into mice. This breast cancer group is a subpopulation of "triple negative" patients which are HER2 negative, ER (estrogen receptor) negative, and PR (progesterone receptor) negative. The sensitivity to docetaxel is retained in mice ex vivo. Mice were dosed intravenously with docetaxel on day 0 and day 11 while Formula Ia was dosed on day 0-4, 11-17 and 21-28 by oral gavage. Animals were monitored for an additional 22 days for tumor growth after the last dose of Formula Ia (total number of days animals were on-study was 50). When administered on the same day, Formula Ia was dosed 1 hour after docetaxel. The group of 10 animals dosed with 100 mg/kg Formula Ia showed 49% inhibition at day 28. The group of 10 animals dosed with 15 mg/kg docetaxel showed 95% inhibition at day 28. The group of 10 animals dosed with the combination of Formula Ia 150 mg/kg and docetaxel 15 mg/kg showed >90% inhibition after 28 days. At the end of the study (day 50), animals dosed with docetaxel and Formula Ia alone had regrowth of their tumors and tumor inhibition decreased from 95% to 68% and 49% to 10%, respectively. However, At the end of the study (day 50), the combination of docetaxel and Formula Ia resulted in all ten animals having sustained tumor regression (>90% inhibition) of MAXF 401 primary breast tumors and was statistically significant when compared to each single drug (p=0.05 vs docetaxel and p<0.001 vs Formula Ia). Given that MAXF 401 breast tumors are derived from a patient that responded to taxane therapy, the improved efficacy observed ex vivo suggests that the combination of Formula Ia may have clinical benefits in breast cancer when combined with docetaxel.

Figure 25:
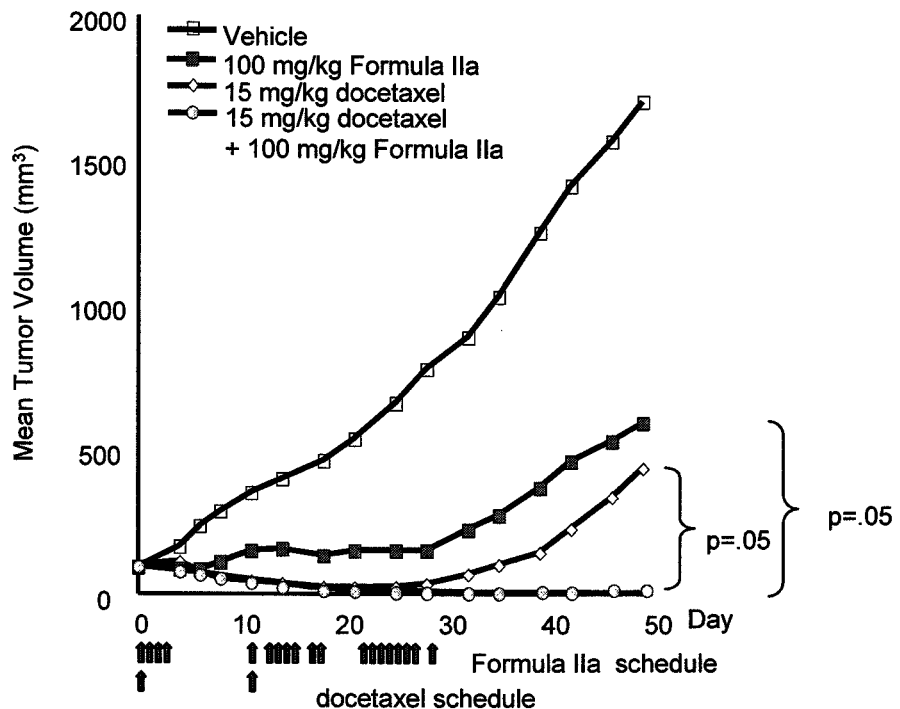
FIG. 25 shows the mean tumor volume change over time in NMRI female nu/nu nude mice with MAXF 401 primary breast tumor explant xenografts dosed on day 0 with: MCT Vehicle (0.5% methycellulose/0.2% Tween 80), 100 mg/kg Formula IIa , 15 mg/kg docetaxel and the combination of 100 mg/kg Formula IIa and 15 mg/kg docetaxel. Mice were dosed intravenously with docetaxel on day 0 and day 11 while Formula IIa was dosed on day 0-3, 11-17 and 21-28 by oral gavage.

FIG. 25 shows the mean tumor volume change over time in NMRI female nu/nu nude mice with MAXF 401 primary breast tumor explant xenografts dosed on day 0 with: MCT Vehicle (0.5% methylcellulose/0.2% Tween 80), 100 mg/kg Formula IIa, 15 mg/kg docetaxel and the combination of 100 mg/kg Formula IIa and 15 mg/kg docetaxel. MAXF 401 are primary breast tumors biopsied directly from a patient that responded to docetaxel and implanted subcutaneously into mice. The sensitivity to docetaxel is retained in mice ex vivo. Mice were dosed intravenously with docetaxel on day 0 and day 11 while Formula IIa was dosed on day 0-3, 11-17 and 21-28 by oral gavage. Animals were monitored for an additional 22 days for tumor growth after the last dose of Formula IIa (total number of days animals were on-study was 50). When administered on the same day, Formula IIa was dosed 1 hour after docetaxel. The group of 10 animals dosed with 100 mg/kg Formula IIa showed 82% tumor inhibition at day 28. The group of 10 animals dosed with 15 mg/kg docetaxel showed 95% tumor inhibition at day 28. The group of 10 animals dosed with the combination of Formula IIa 150 mg/kg and docetaxel 15 mg/kg showed 99% inhibition at day 28. At the end of the study (day 50), animals dosed with docetaxel and Formula IIa alone had regrowth of their tumors and tumor inhibition decreased to 68% and 51%, respectively. However, at the end of the study (day 50), the combination of 100 mg/kg Formula IIa and 15 mg/kg docetaxel resulted in sustained tumor regression (99% inhibition) of MAXF 401 primary breast tumors and was statistically significant when compared to each single drug (p=0.0118 vs docetaxel and p=0.0005 vs Formula IIa). Given that MAXF 401 breast tumors are derived from a patient that responded to taxane therapy, the improved efficacy observed ex vivo suggests that the combination of formula IIa may have clinical benefits in breast cancer when combined with docetaxel.

Figure 26:
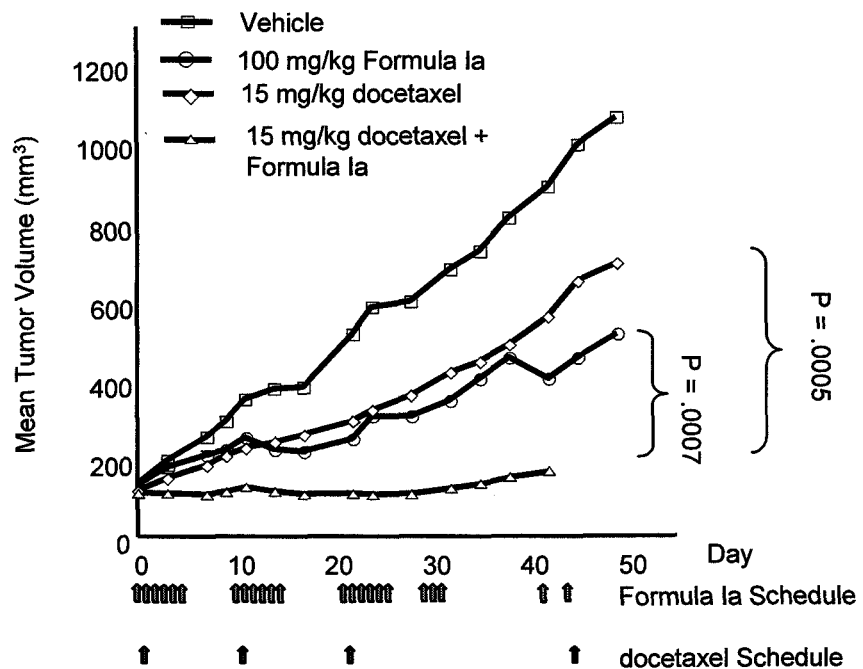
FIG. 26 shows the mean tumor volume change over time in NMRI female nu/nu nude mice with MAXF 1162 primary breast tumor explant xenografts dosed on day 0 with: MCT Vehicle (0.5% methycellulose/0.2% Tween 80), 100 mg/kg Formula Ia (GDC-0941), 15 mg/kg docetaxel and the combination of 100 mg/kg Formula Ia and 15 mg/kg docetaxel. Mice were dosed intravenously with docetaxel on day 0, 11, 22 and 44 and Formula Ia was dosed on day 0-5, 11-16, 22-27, 30-32, 42 and 44 by oral gavage.

FIG. 26 shows the mean tumor volume change over time in NMRI female nu/nu nude mice with MAXF 1162 primary breast tumor explant xenografts dosed on day 0 with: MCT Vehicle (0.5% methylcellulose/0.2% Tween 80), 100 mg/kg Formula Ia, 15 mg/kg docetaxel and the combination of 100 mg/kg Formula Ia and 15 mg/kg docetaxel. MAXF 1162 are primary breast tumors biopsied directly from a patient that failed docetaxel therapy and implanted subcutaneously into mice. The resistance to docetaxel is retained ex vivo in these mice. Mice were dosed intravenously with docetaxel on day 0, 11, 22 and 44 and Formula 1a was dosed on day 0-5, 11-16, 22-27, 30-32, 42 and 44 by oral gavage. Animals were monitored for an additional 6 days for tumor growth after the last dose of Formula Ia (total number of days animals were on-study was 50). When administered on the same day, Formula 1a was dosed 1 hour after docetaxel. The group of 10 animals dosed with 100 mg/kg Formula Ia showed 54% inhibition after 49 days. The group of 10 animals dosed with 15 mg/kg docetaxel showed 36% inhibition after 49 days. The group of 10 animals dosed with the combination of Formula Ia 100 mg/kg and docetaxel 15 mg/kg showed 87% inhibition after 49 days. At the end of the study (day 50), the combination resulted in sustained tumor regression (>87% inhibition) and was statistically significant when compared to each single drug (p=0.0005 vs docetaxel and p=0.0007 vs Formula Ia). Given that MAXF 1162 breast tumors are derived from a patient that failed taxane therapy, the improved efficacy observed ex vivo suggests that the combination of formula Ia with docetaxel may have clinical benefits in taxane-resistant breast cancer in humans.

Figure 27:
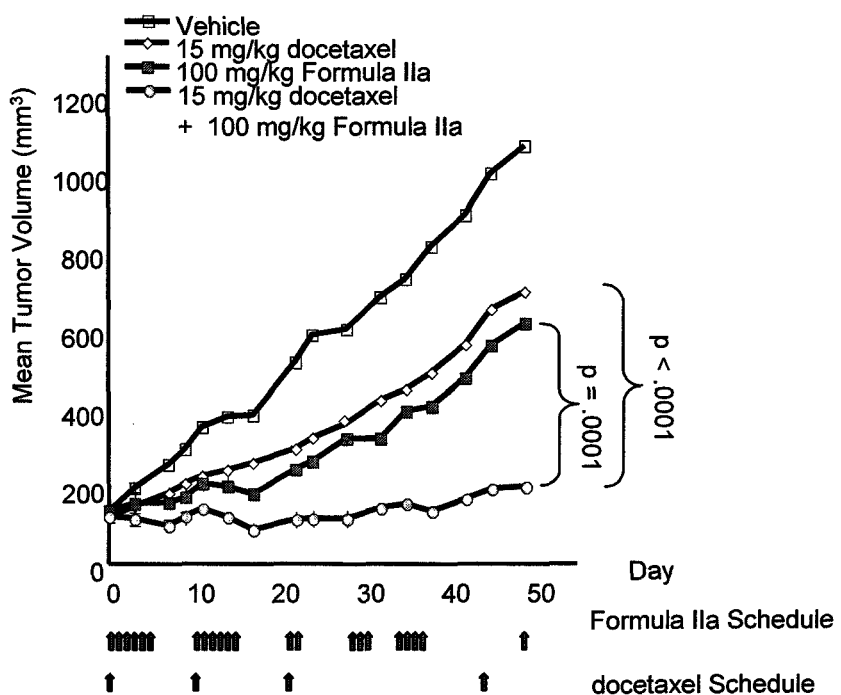
FIG. 27 shows the mean tumor volume change over time in NMRI female nu/nu nude mice with MAXF 1162 primary breast tumor xenografts dosed on day 0 with: MCT Vehicle (0.5% methycellulose/0.2% Tween 80), 100 mg/kg Formula IIa, 15 mg/kg docetaxel and the combination of 100 mg/kg Formula IIa and 15 mg/kg docetaxel. Mice were dosed intravenously with docetaxel on day 0, 11, 22 and 44 and Formula IIa was dosed on day 0-5, 11-16, 22-23, 29-31 and 35-38 by oral gavage.

FIG. 27 shows the mean tumor volume change over time in NMRI female nu/nu nude mice with MAXF 1162 primary breast tumor xenografts dosed on day 0 with: MCT Vehicle (0.5% methylcellulose/0.2% Tween 80), 100 mg/kg Formula IIa, 15 mg/kg docetaxel and the combination of 100 mg/kg Formula IIa and 15 mg/kg docetaxel. MAXF 1162 are primary breast tumors biopsied directly from a patient that failed docetaxel therapy and implanted subcutaneously into mice. The resistance to docetaxel is retained ex vivo in these mice. Mice were dosed intravenously with docetaxel on day 0, 11, 22 and 44 and Formula IIa was dosed on day 0-5, 11-16, 22-23, 29-31 and 35-38 by oral gavage. Animals were monitored for an additional 12 days for tumor growth after the last dose of Formula IIa (total number of days animals were on-study was 50). When administered on the same day, Formula IIa was dosed 1 hour after docetaxel. The group of 10 animals dosed with 100 mg/kg Formula IIa showed 32% inhibition after 49 days. The group of 10 animals dosed with 15 mg/kg docetaxel showed 36% inhibition after 49 days. The group of 10 animals dosed with the combination of Formula IIa 100 mg/kg and docetaxel 15 mg/kg showed 80% inhibition after 49 days. At the end of the study (day 50), the combination resulted in sustained tumor regression (>80% inhibition) of MAXF 1162 primary breast cancer tumors and was statistically significant when compared to each single drug (p<0.0001 vs docetaxel and p=0.0166 vs Formula IIa). Given that MAXF 1162 breast tumors are derived from a patient that failed taxane therapy, the improved efficacy observed ex vivo suggests that the combination of formula IIa with docetaxel may have clinical benefits in taxane-resistant human breast cancer.

Figure 28:
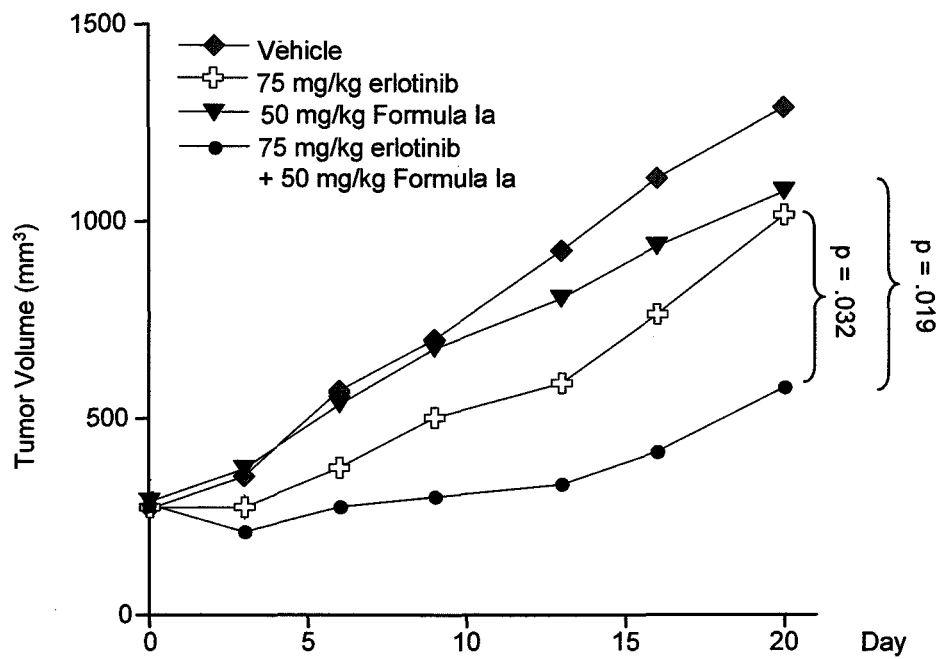
FIG. 28 shows the mean tumor volume change over time in CRL female nu/nu (nude) mice with NCI-H2122 non-small cell lung cancer (NSCLC) tumor xenografts dosed on day 0 with: MCT Vehicle (0.5% methylcellulose/0.2% Tween 80), 50 mg/kg Formula Ia (GDC-0941), 75 mg/kg erlotinib and the combination of 50 mg/kg Formula Ia and 75 mg/kg erlotinib. Mice were dosed daily with erlotinib and Formula Ia daily for 16 days by oral gavage.

FIG. 28 shows the mean tumor volume change over time in CRL female nu/nu (nude) mice with NCI-H2122 non-small cell lung cancer (NSCLC) tumor xenografts dosed on day 0 with: MCT Vehicle (0.5% methylcellulose/0.2% Tween 80), 50 mg/kg Formula Ia, 75 mg/kg erlotinib and the combination of 50 mg/kg Formula Ia and 75 mg/kg erlotinib. Mice were dosed daily with erlotinib and Formula Ia daily for 16 days by oral gavage. Animals were monitored for tumor growth for an additional 5 days (end of study was day 21). Both erlotinib and Formula Ia were administered simultaneously. The group of 8 animals dosed with 50 mg/kg Formula Ia showed 17% tumor inhibition after 20 days. The group of 8 animals dosed with 75 mg/kg erlotinib showed 21% inhibition after 20 days. The group of 8 animals dosed with the combination of Formula Ia 50 mg/kg and erlotinib 75 mg/kg showed 55% inhibition after 20 days. At the end of the study (day 21), the combination of 50 mg/kg Formula Ia and erlotinib was additive and resulted in significant tumor growth delay of NCI-H2122 NSCLC tumor xenografts when compared to each single drug (p=0.032 vs erlotinib and p=0.019 vs Formula Ia).

Figure 29:
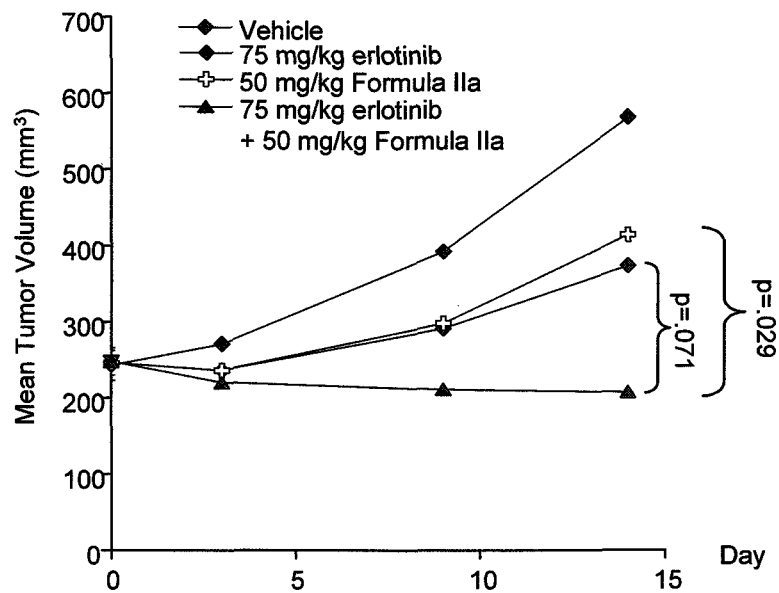
FIG. 29 shows the mean tumor volume change over time in CRL female nu/nu (nude) mice with NCI-H2122 non-small cell lung cancer (NSCLC) tumor xenografts dosed on day 0 with: MCT Vehicle (0.5% methylcellulose/0.2% Tween 80), 50 mg/kg Formula IIa, 75 mg/kg erlotinib and the combination of 50 mg/kg Formula IIa and 75 mg/kg erlotinib. Mice were dosed daily with erlotinib and Formula IIa for 14 days (end of study) by oral gavage.

FIG. 29 shows the mean tumor volume change over time in CRL female nu/nu (nude) mice with NCI-H2122 non-small cell lung cancer (NSCLC) tumor xenografts dosed on day 0 with: MCT Vehicle (0.5% methylcellulose/0.2% Tween 80), 50 mg/kg Formula IIa, 75 mg/kg erlotinib and the combination of 50 mg/kg Formula IIa and 75 mg/kg erlotinib. Mice were dosed daily with erlotinib and Formula IIa for 14 days (end of study) by oral gavage. Both erlotinib and Formula IIa were administered simultaneously. The group of 9 animals dosed with 50 mg/kg Formula IIa showed 27% tumor inhibition at the end of study. The group of 10 animals dosed with 75 mg/kg erlotinib showed 34% tumor inhibition at the end of study. The group of 9 animals dosed with the combination of Formula IIa 50 mg/kg and erlotinib 75 mg/kg showed 63% tumor inhibition at the end of study. At the end of the study (day 21), the combination of 50 mg/kg Formula IIa and 75 mg/kg erlotinib was additive and resulted in significant tumor growth delay of NSCLC tumor xenografts when compared to each single drug (p=0.032 vs erlotinib and p=0.029 vs Formula IIa).

Figure 30:
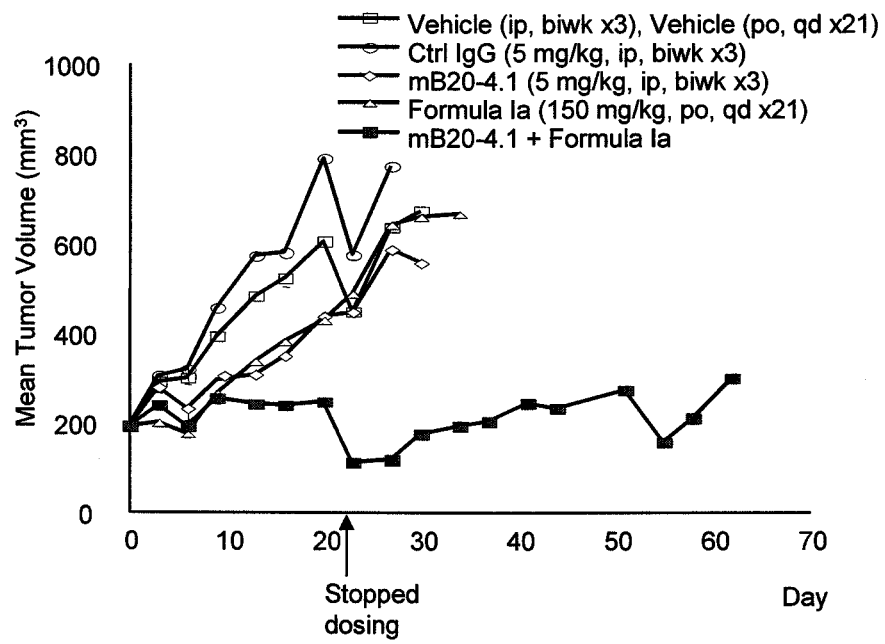
FIG. 30 shows the mean tumor volume change over time with HRLN female nu/nu mice with MCF-7 (PI3K mutant) breast tumor cell xenografts dosed on day 0 with: MCT and PBS vehicle (MCT; 0.5% methycellulose/0.2% Tween 80 and PBS; phosphate buffered saline), control IgG 5 mg/kg, mB20-4.1 murine anti-VEGF 5 mg/kg, Formula Ia (GDC-0941) 150 mg/kg, and the combination of Formula Ia 150 mg/kg and mB20-4.1 murine anti-VEGF 5 mg/kg. Animals were dosed with control IgG and mB20-4.1 intraperitonealy twice a week for 3 weeks and with Formula Ia daily for 21 days by oral gavage and tumor growth was monitored for an additional 41 days (total number of day on-study was 62). Formula Ia and mB20-4.1 were co-administered simultaneously.

FIG. 30 shows the mean tumor volume change over time in HRLN female nu/nu mice with MCF-7 (PI3K mutant) breast tumor cell xenografts dosed on day 1 with: MCT and PBS vehicle (MCT; 0.5% methylcellulose/0.2% Tween 80 and PBS; phosphate buffered saline), control IgG 5 mg/kg, mB20-4.1 murine anti-VEGF (anti-angiogenic) 5 mg/kg, Formula Ia 150 mg/kg, and the combination of Formula Ia 150 mg/kg and mB20-4.1 murine anti-VEGF 5 mg/kg. Animals were dosed with control IgG and mB20-4.1 intraperitonealy twice a week for 3 weeks and with Formula Ia daily for 21 days by oral gavage and tumor growth was monitored for an additional 41 days (total number of day on-study was 62). Formula Ia and mB20-4.1 were co-administered simultaneously. The group of 13 out of 15 animals dosed and on-study with control IgG showed 19% inhibition and 0 partial regressions after 21 days. The group of 10 out of 15 animals dosed and on-study with mB20-4.1 murine anti-VEGF showed 49% inhibition and 0 partial regressions after 21 days. The group of 13 animals dosed and on-study with 150 mg/kg Formula Ia compound showed 36% inhibition and 0 paritial regressions after 21 days. The group of 10 animals dosed and on-study with the combination of Formula Ia compound and mB20-4.1 murine anti-VEGF showed 66% inhibition and 4 complete regresssions after 21 days. Animals dosed with the combination of Formula Ia and mB20-4.1 murine anti-VEGF showed a significant inhibition and sustained regression of tumor growth 41 days after dosing was terminated (end of study) when compared to each single drug ($p<0.006$ vs Formula 1a and $<0.01$ vs mB20-4.1).

Figure 31:
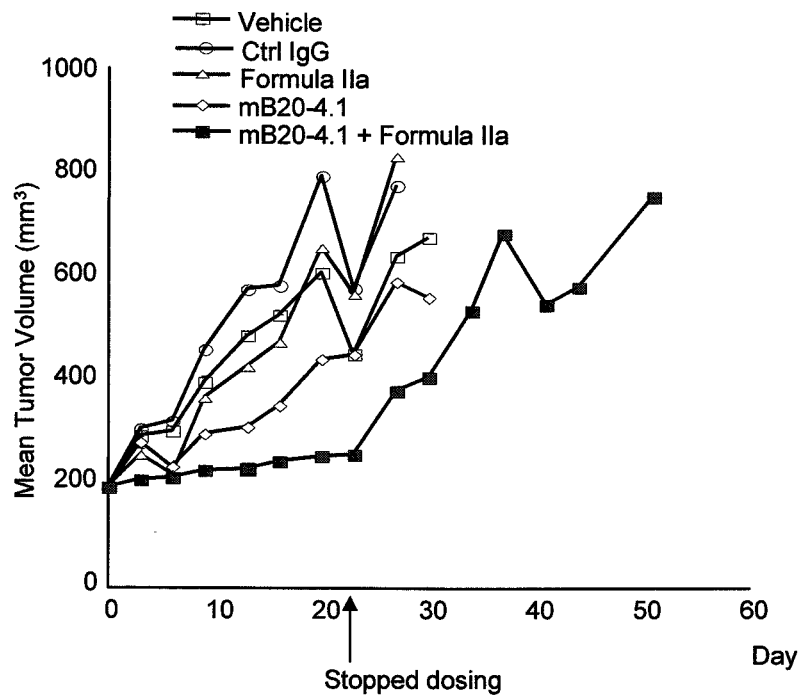
FIG. 31 shows the mean tumor volume change over time with HRLN female nu/nu mice with MCF-7 (PI3K mutant) breast tumor cell xenografts dosed on day 0 with: MCT and PBS vehicle (MCT; 0.5% methycellulose/0.2% Tween 80 and PBS; phosphate buffered saline), control IgG 5 mg/kg, mB20-4.1 murine anti-VEGF (anti-angiogenic) 5 mg/kg, Formula IIa 100 mg/kg, and the combination of Formula IIa 100 mg/kg and mB20-4.1 murine anti-VEGF 5 mg/kg. Animals were dosed with control IgG and mB20-4.1 intraperitonealy twice a week for 3 weeks and with Formula IIa orally daily for 21 days and tumor growth was monitored for an additional 41 days (total number of day on-study was 62). Formula IIa and mB20-4.1 were co-administered simultaneously.

FIG. 31 shows the mean tumor volume change over time in HRLN female nu/nu mice with MCF-7 (PI3K mutant) breast tumor cell xenografts dosed on day 1 with: MCT and PBS vehicle (MCT; 0.5% methycellulose/0.2% Tween 80 and PBS; phosphate buffered saline), control IgG 5 mg/kg, mB20-4.1 murine anti-VEGF (anti-angiogenic) 5 mg/kg, Formula IIa 100 mg/kg, and the combination of Formula IIa 100 mg/kg and mB20-4.1 murine anti-VEGF 5 mg/kg. Animals were dosed with control IgG and mB20-4.1 intraperitonealy twice a week for 3 weeks and with Formula IIa orally daily for 21 days and tumor growth was monitored for an additional 41 days (total number of day on-study was 62). Formula IIa and mB20-4.1 were co-administered simultaneously. The group of 12 out of 15 animals dosed and on-study with vehicle showed 10% inhibition and 0 partial regressions after 21 days. The group of 10 out of 15 animals dosed and on-study with mB20-4.1 murine anti-VEGF showed 49% inhibition and 0 partial regressions after 21 days. The group of 13 animals dosed and on-study with 100 mg/kg Formula IIa compound showed 5% inhibition and 0 partial regressions after 21 days. The group of 10 out of 15 animals dosed and on-study with the combination of Formula IIa compound and mB20-4.1 murine anti-VEGF showed 61% inhibition and 1 complete regression after 21 days . Animals dosed with the combination of Formula Ia and mB20-4.1 murine anti-VEGF showed a significant inhibition and delay in tumor growth 41 days after dosing was terminated when compared to each single drug ($p<0.001$ vs Formula IIa and $<0.01$ vs mB20-4.1).

Figure 32:
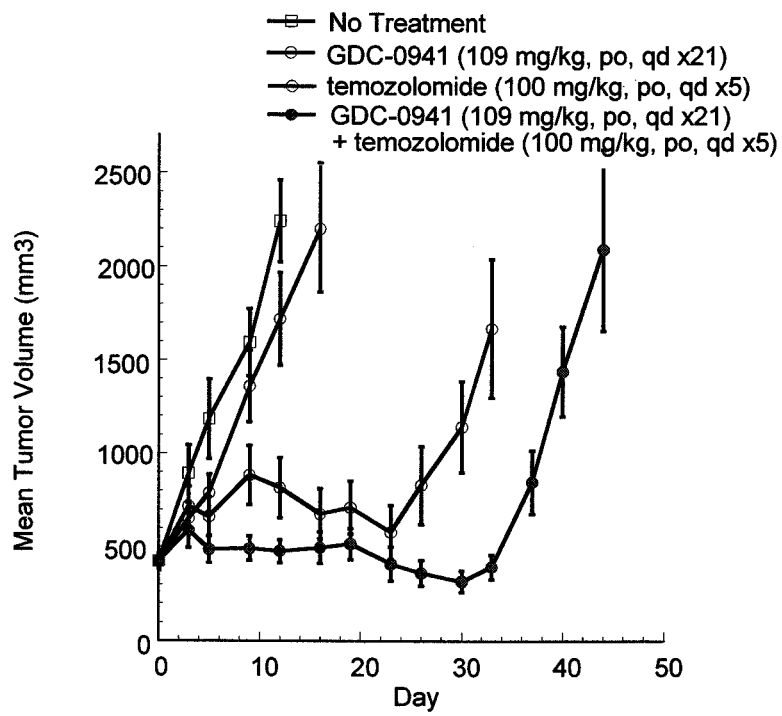
FIG. 32 shows the mean tumor volume change over time with Harlan female nu/nu with U87MG glioma tumor cell xenografts dosed on day 0 with: Formula Ia (GDC-0941) 109 mg/kg, temozolomide 100 mg/kg, and the combination of Formula Ia 109 mg/kg and temozolomide 100 mg/kg, along with mice receiving no drug (No Treatment group). Animals were dosed with Formula Ia orally daily for 21 days, and temozolomide orally daily for 5 days.

FIG. 32 shows the mean tumor volume change over time with Harlan female nu/nu mice with U87MG glioma tumor cell xenografts dosed on day 0 with: Formula Ia (GDC-0941) 109 mg/kg, temozolomide 100 mg/kg, and the combination of Formula Ia 109 mg/kg and temozolomide 100 mg/kg, along with mice receiving no drug (No Treatment group). Animals were dosed with Formula Ia orally daily for 21 days, and temozolomide orally daily for 5 days. The combination of 109 mg/kg of Formula Ia with 100 mg/kg of temozolomide synergized to inhibit U87MG glioma tumor growth in vivo greater than Formula Ia or temozolomide alone and resulted in tumor regression followed by tumor growth delay.

Figure 33:
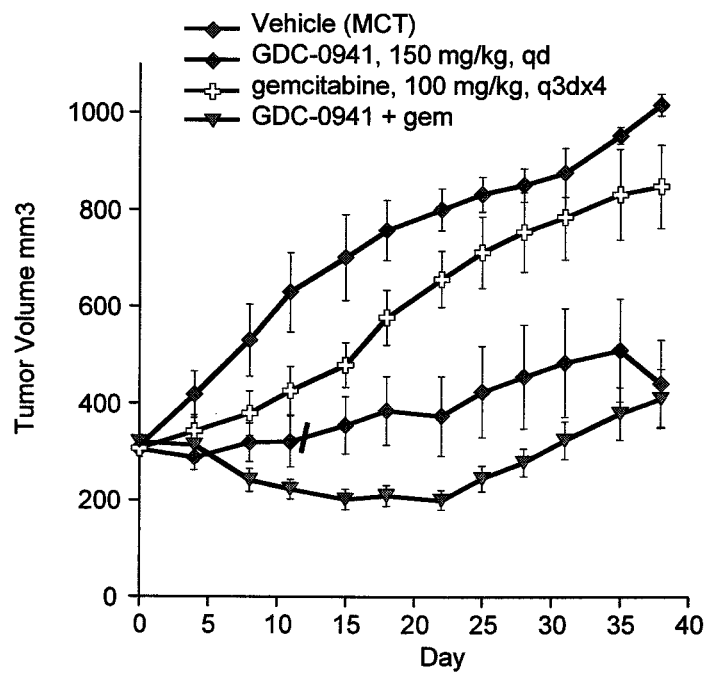
FIG. 33 shows the mean tumor volume change over time with CD-1 nude mice with MDA-MB-361.1 breast tumor cell xenografts dosed on day 0 with: Formula Ia (GDC-0941) 150 mg/kg, gemcitabine 100 mg/kg, and the combination of Formula Ia 150 mg/kg and gemcitabine 100 mg/kg, along with mice receiving no drug (Vehicle group). Animals were dosed with Formula Ia orally daily for 21 days, and gemcitabine intraperitoneal on days 1, 4, 7 and 10 (q3d×4).

FIG. 33 shows the mean tumor volume change over time with CD-1 nude CR/Hollister mice with MDA-MB-361.1 breast tumor cell xenografts dosed on day 0 with: Formula Ia (GDC-0941) 150 mg/kg, gemcitabine 100 mg/kg, and the combination of Formula Ia 150 mg/kg and gemcitabine 100 mg/kg, along with mice receiving no drug (Vehicle group). Animals were dosed with Formula Ia orally daily for 21 days, and gemcitabine intraperitonealy on days 1, 4, 7 and 10 (q3d× 4). The combination of 150 mg/kg of Formula Ia with 100 mg/kg of gemcitabine synergized to inhibit MDA-MB-361.1 breast tumor growth in vivo greater than Formula Ia or gemcitabine alone and resulted in tumor regression followed by tumor growth delay.

Figure 34:
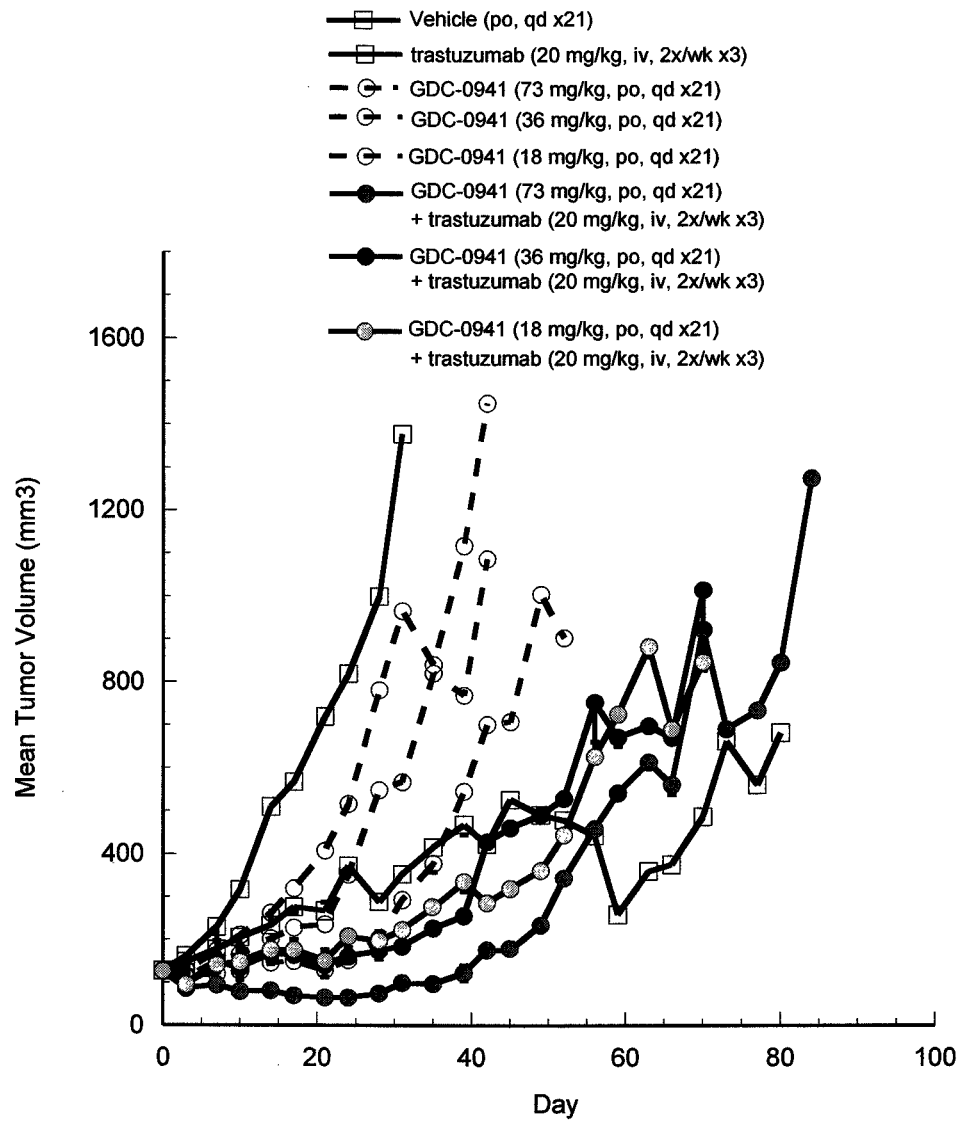
FIG. 34 shows the mean tumor volume change over time with Harlan female nu/nu mice with BT474 breast tumor cell xenografts dosed on day 0 with: Formula Ia (GDC-0941) at 18, 36, and 73 mg/kg, trastuzumab 20 mg/kg, and the combinations of Formula Ia at 18, 36, and 73 mg/kg and trastuzumab 20 mg/kg, along with mice receiving no drug (Vehicle group). Animals were dosed with Formula Ia orally daily for 21 days, and trastuzumab intravenously twice a week for 3 weeks.

FIG. 34 shows the mean tumor volume change over time with Harlan female nu/nu mice with BT474 breast tumor cell xenografts dosed on day 0 with: Formula Ia (GDC-0941) at 18, 36, and 73 mg/kg, trastuzumab 20 mg/kg, and the combinations of Formula Ia at 18, 36, and 73 mg/kg and trastuzumab 20 mg/kg, along with mice receiving no drug (Vehicle group). Animals were dosed with Formula Ia orally daily for 21 days, and trastuzumab intraperitonealy twice a week for 3 weeks. The combination of 73 mg/kg of Formula Ia with 20 mg/kg of trastuzumab synergized to inhibit BT474 breast tumor growth in vivo greater than Formula Ia or trastuzumab alone and resulted in tumor regression followed by tumor growth delay.

Treatment of BT474-M1 (in vivo passaged subclone of BT474) cells with trastuzumab caused a decrease in pAKT equal to the decrease achieved with Formula Ia compound (GDC-0941). Adding trastuzumab to 50 nM Formula Ia caused a dose dependent, enhanced, decrease in pAKT. At the maximal trastuzumab dose, the additional reduction was 29-38% of GDC-0941 treatment alone. The enhanced combinatorial effect on pAKT inhibition was not transient and could still be detected 48 h after treatment. The combinatorial effect seen in pAKT was also reflected in downstream AKT signaling components. BT474-M1 cells were treated for four hours with Formula Ia in the presence or absence of trastuzumab. The addition of trastuzumab further decreased the phosphorylation of direct AKT substrate PRAS40 (Thr246) and a distal substrate, phospho-S6 ribosomal protein (Ser235/236), suggesting that trastuzumab and Formula Ia have enhanced combinatorial effect on downstream AKT signaling. Enhanced PI3K/AKT pathway inhibition results in decreased cell proliferation/viability was demonstrated when BT474-M1 cells were treated for six days and cell viability was measured. Trastuzumab alone reduced proliferation/viability by 40%. In the absence of trastuzumab, the $IC_{50}$ value for Formula Ia was 296 nM. The addition of trastuzumab caused a dose-dependent, enhanced reduction in proliferation/viability. A maximal trastuzumab dose of 10 ug/ml resulted in a 64% decrease in the concentration of Formula Ia that is required to reach its IC50 of 106 nM, demonstrating an enhanced combinatorial effect in decreasing cell proliferation/viability as well. A similar combinatorial effect on pAKT and inhibition of proliferation was also observed when SKBR-3 cells were treated, but not when the trastuzumab non-responsive KPL-4 cells were treated. The combination of trastuzumab and Formula Ia inhibits proliferation synergistically in BT474 and SKBR-3 cells over most of the effective drug range as determined by CalcuSyn software, showing that the combination enhances the inhibitory effect on AKT and its downstream targets resulting in a synergistic effect on the proliferation of trastuzumab sensitive breast cancer cells.

The combination of trastuzumab and Formula Ia additively induces apoptosis of BT474-M1 cells breast cancer cells treated for 48 h. The combination of trastuzumab and Formula Ia increased the accumulation of cleaved caspase-3 fragments, indicative of activation of this key effector caspase. Combining trastuzumab and Formula Ia also resulted in an increase in cleaved PARP 89 kDa fragment, a known response to caspase-3 activation. The activity of caspases 3 and 7 was also increased when trastuzumab was added to Formula Ia treatment. Combining trastuzumab with 250 nM Formula Ia increased the activity of caspases 3 and 7 to a level similar to that detected with a four fold higher dose of (1000 nM) Formula Ia alone. Importantly, this increase in caspase activity was reflected on the apoptotic index of these cells. The addition of trastuzumab dramatically decreased the concentration of Formula Ia required to induce apoptosis. A near equivalent level of apoptosis was detected when cells were treated with 100 nM of Formula Ia and trastuzumab than when treated with 1000 nM of Formula Ia alone. As expected, the increase in apoptosis was reflected in a decrease in cell viability after 48 h. A similar increase in caspase activity and apoptosis was seen when SKBR-3 cells were treated with the inhibitor combination. The combination of Formula Ia with trastuzumab significantly lowers the Formula Ia concentration required for reaching the threshold of caspase activation and apoptosis in trastuzumab sensitive breast cancer cells. Therefore, trastuzumab treatment could be used to sensitize HER2 amplified cells to PI3K inhibition and thus provide an additional level of tumor specificity for the PI3K inhibitor Formula Ia.

Figure 35:
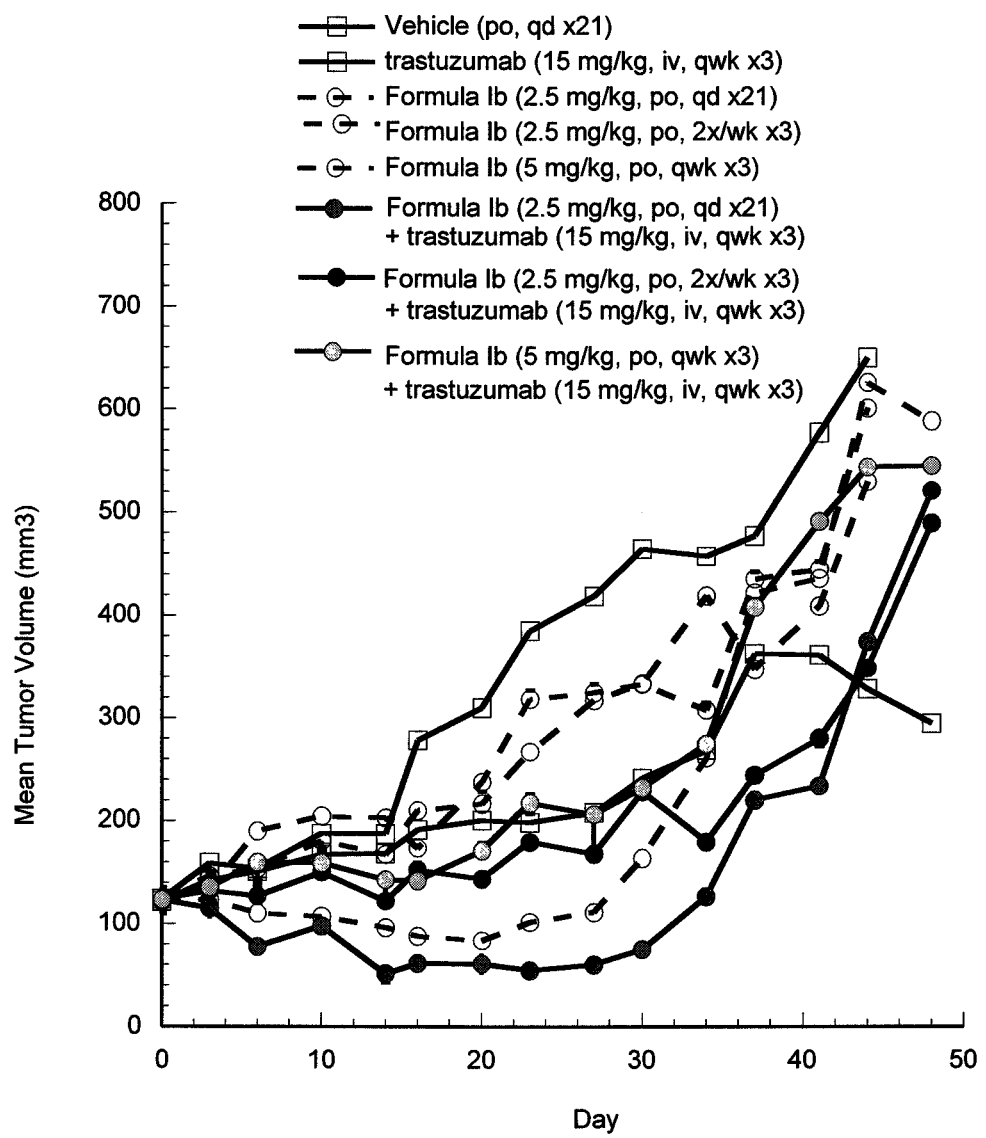
FIG. 35 shows the mean tumor volume change over time with Harlan female nu/nu mice with BT474 breast tumor cell xenografts dosed on day 0 with: Formula Ib at 2.5 mg/kg orally daily for 3 weeks, Formula Ib at 2.5 mg/kg orally twice a week for 3 weeks, Formula Ib at 5 mg/kg orally daily for 3 weeks, trastuzumab 15 mg/kg intravenously once a week for 3 weeks, and the combinations of Formula Ib at 2.5 mg/kg orally daily for 3 weeks and trastuzumab 15 mg/kg intravenously once a week for 3 weeks; Formula Ib at 2.5 mg/kg orally twice a week for 3 weeks and trastuzumab 15 mg/kg intravenously once a week for 3 weeks; and Formula Ib at 5 mg/kg orally daily for 3 weeks and trastuzumab 15 mg/kg intravenously once a week for 3 weeks, along with mice receiving no drug (Vehicle group).

FIG. 35 shows the mean tumor volume change over time with Harlan female nu/nu mice with BT474 breast tumor cell xenografts dosed on day 0 with: Formula Ib at 2.5 mg/kg orally daily for 3 weeks, Formula Ib at 2.5 mg/kg orally twice a week for 3 weeks, Formula Ib at 5 mg/kg orally daily for 3 weeks, trastuzumab 15 mg/kg intraperitonealy once a week for 3 weeks, and the combinations of: Formula Ib at 2.5 mg/kg orally daily for 3 weeks and trastuzumab 15 mg/kg intraperitonealy once a week for 3 weeks; Formula Ib at 2.5 mg/kg orally twice a week for 3 weeks and trastuzumab 15 mg/kg intraperitonealy once a week for 3 weeks; and Formula Ib at 5 mg/kg orally daily for 3 weeks and trastuzumab 15 mg/kg intraperitonealy once a week for 3 weeks, along with mice receiving no drug (Vehicle group). The combination of 2.5 mg/kg of Formula Ib dosed daily with 15 mg/kg of trastuzumab dosed once a week synergized to inhibit BT474 breast tumor growth in vivo greater than Formula Ia or trastuzumab alone and resulted in tumor growth delay.

Figure 36:
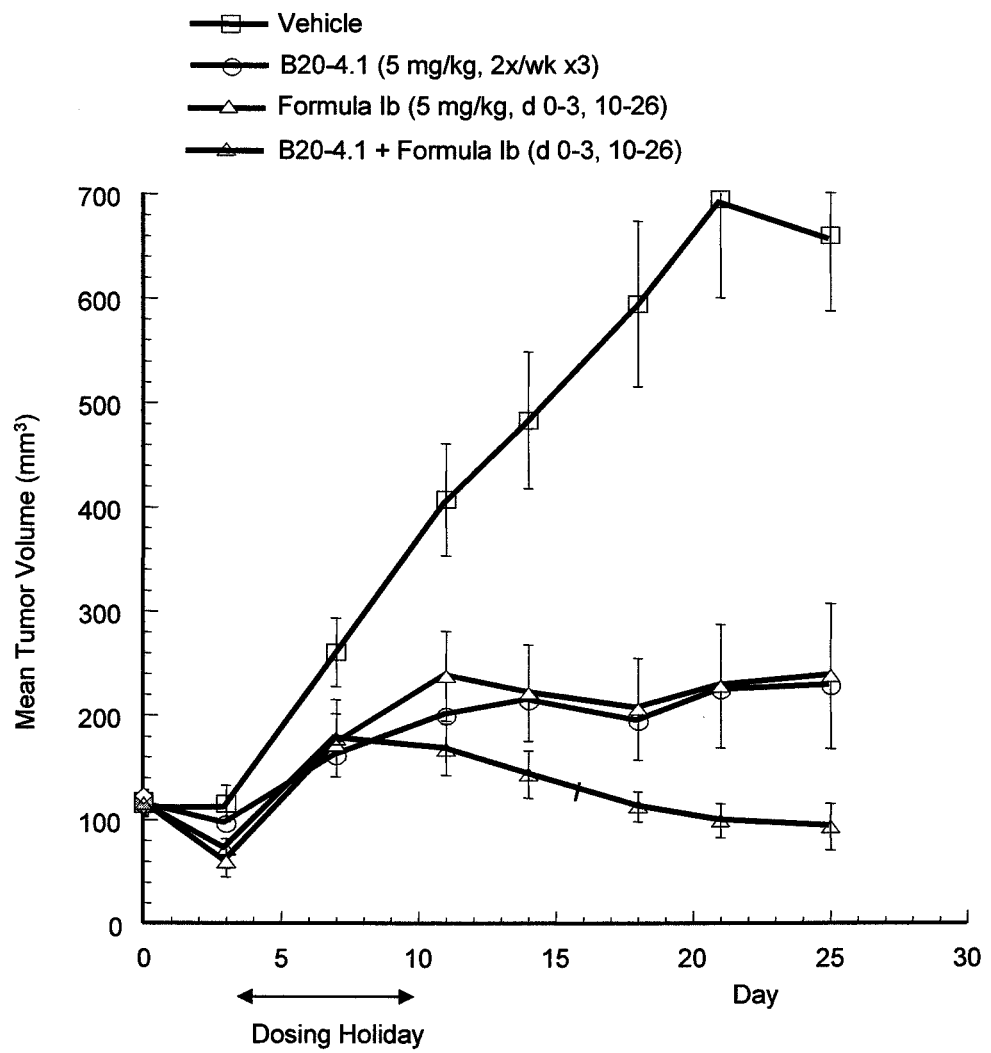
FIG. 36 shows the mean tumor volume change over time with Harlan female nu/nu mice with MCF-7 breast tumor cell xenografts dosed on day 0 with: murine anti-VEGF antibody B20-4.1 5 mg/kg intraperitoneal twice a week for 3 weeks, Formula Ib at 10 mg/kg orally daily for 4 days, Formula Ib at 5 mg/kg orally daily for days 0-3, 10-26, Formula Ib at 2 mg/kg orally daily for days 0-4, 10-25, and the combinations of: Formula Ib at 10 mg/kg orally daily for 4 days and B20-4.1 5 mg/kg intraperitoneal twice a week for 3 weeks; Formula Ib at 5 mg/kg orally daily for days 0-3, 10-26 and B20-4.1 5 mg/kg intraperitoneal twice a week for 3 weeks; and Formula Ib at 2 mg/kg orally daily for days 0-4, 10-25 and B20-4.1 5 mg/kg intraperitoneal twice a week for 3 weeks, along with mice receiving no drug (Vehicle group).

FIG. 36 shows the mean tumor volume change over time with Harlan female nu/nu mice with MCF-7 breast tumor cell xenografts dosed on day 0 with: murine anti-VEGF antibody B20-4.1 5 mg/kg intraperitonealy twice a week for 3 weeks, or Formula Ib at 5 mg/kg and the combinations of: Formula Ib at 5 mg/kg orally daily for days 0-3, 10-26 and B20-4.1 5 mg/kg intraperitonealy twice a week for 3 weeks along with mice receiving no drug (Vehicle group). The combination of 5.0 mg/kg of Formula Ib with 5 mg/kg B20-4.1 synergized to inhibit MCF-7 breast tumor growth in vivo greater than Formula Ib or B20-4.1 alone and resulted in tumor regression.

Figure 37:
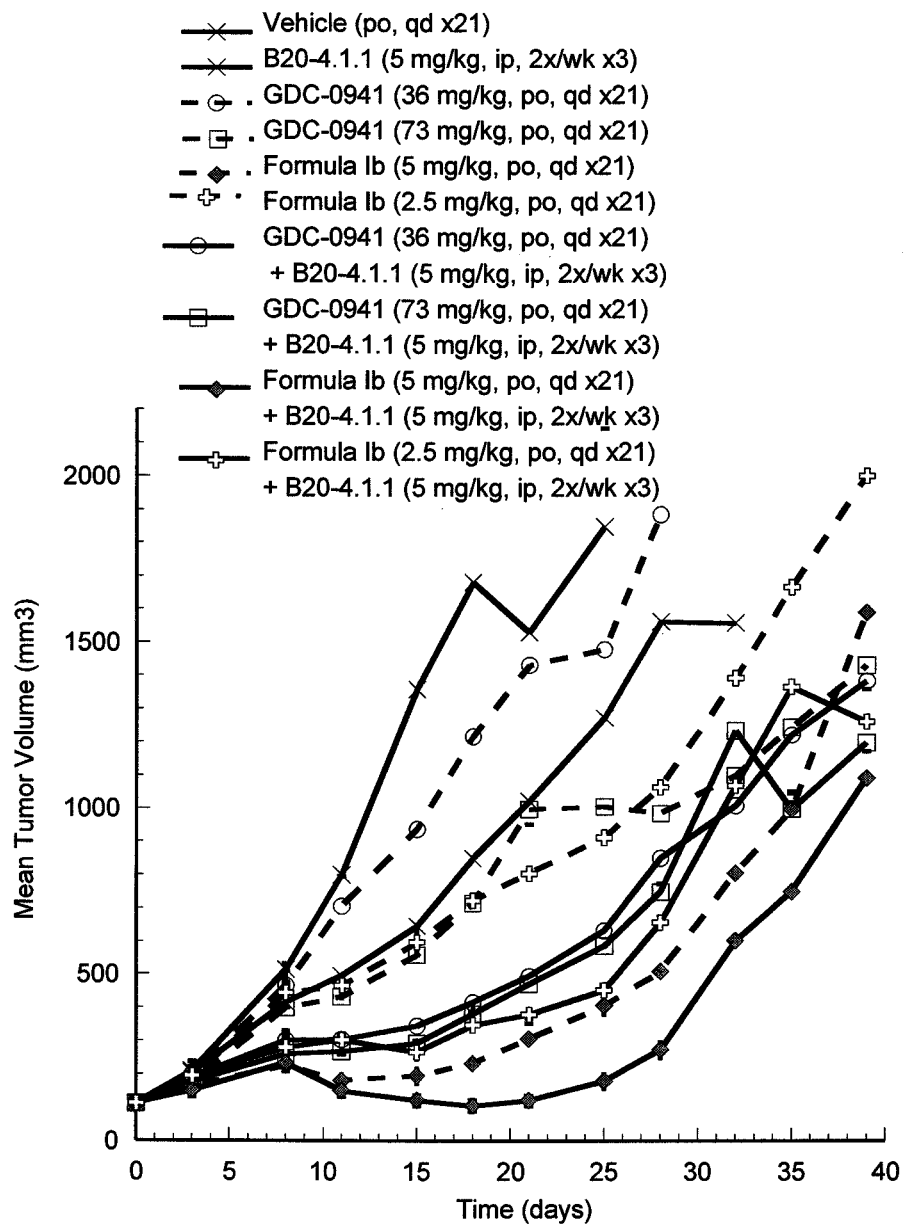
FIG. 37 shows the mean tumor volume change over time with Harlan female nu/nu mice with Fo5 breast tumor cell xenografts dosed on day 0 with: murine anti-VEGF antibody B20-4.1 5 mg/kg intraperitoneal twice a week for 3 weeks, Formula Ia (GDC-0941) at 36 and 73 mg/kg orally daily for 21 days, Formula Ib at 2.5 and 5 mg/kg orally daily for 21 days, and the combinations of: Formula Ia at 36 mg/kg orally daily for 21 days and B20-4.1 5 mg/kg intraperitoneal twice a week for 3 weeks; Formula Ia at 73 mg/kg orally daily for 21 days and B20-4.1 5 mg/kg intraperitoneal twice a week for 3 weeks; Formula Ib at 5 mg/kg orally daily for 21 days and B20-4.1 5 mg/kg intraperitoneal twice a week for 3 weeks, and Formula Ib at 2.5 mg/kg orally daily for 21 days and B20-4.1 5 mg/kg intraperitoneal twice a week for 3 weeks along with mice receiving no drug (Vehicle group).

FIG. 37 shows the mean tumor volume change over time with Harlan female nu/nu mice with Fo5 breast tumor cell xenografts dosed on day 0 with: murine anti-VEGF antibody B20-4.1 5 mg/kg intraperitonealy twice a week for 3 weeks, Formula Ia (GDC-0941) at 36 and 73 mg/kg orally daily for 21 days, Formula Ib at 2.5 and 5 mg/kg orally daily for 21 days, and the combinations of: Formula Ia at 36 mg/kg orally daily for 21 days and B20-4.1 5 mg/kg intraperitonealy twice a week for 3 weeks; Formula Ia at 73 mg/kg orally daily for 21 days and B20-4.1 5 mg/kg intraperitonealy twice a week for 3 weeks; Formula Ib at 5 mg/kg orally daily for 21 days and B20-4.1 5 mg/kg intraperitonealy twice a week for 3 weeks, and Formula Ib at 2.5 mg/kg orally daily for 21 days and B20-4.1 5 mg/kg intraperitonealy twice a week for 3 weeks along with mice receiving no drug (Vehicle group). The combination of 36 mg/kg of Formula Ia with 5 mg/kg B20-4.1 synergized to inhibit Fo5 breast tumor growth in vivo greater than Formula Ia or B20-4.1 alone and resulted in tumor growth delay. The combination of 73 mg/kg of Formula Ia with 5 mg/kg B20-4.1 also synergized to inhibit Fo5 breast tumor growth in vivo greater than Formula Ia or B20-4.1 alone and resulted in tumor growth delay. The combination of 2.5 mg/kg of Formula Ib with 5 mg/kg B20-4.1 synergized to inhibit Fo5 breast tumor growth in vivo greater than Formula Ib or B20-4.1 alone and resulted in tumor growth delay. The combination of 5.0 mg/kg of Formula Ib with 5.0 mg/kg B20-4.1 synergized to inhibit Fo5 breast tumor growth in vivo greater than Formula Ib or B20-4.1 alone and resulted in tumor growth regression.

Figure 38:
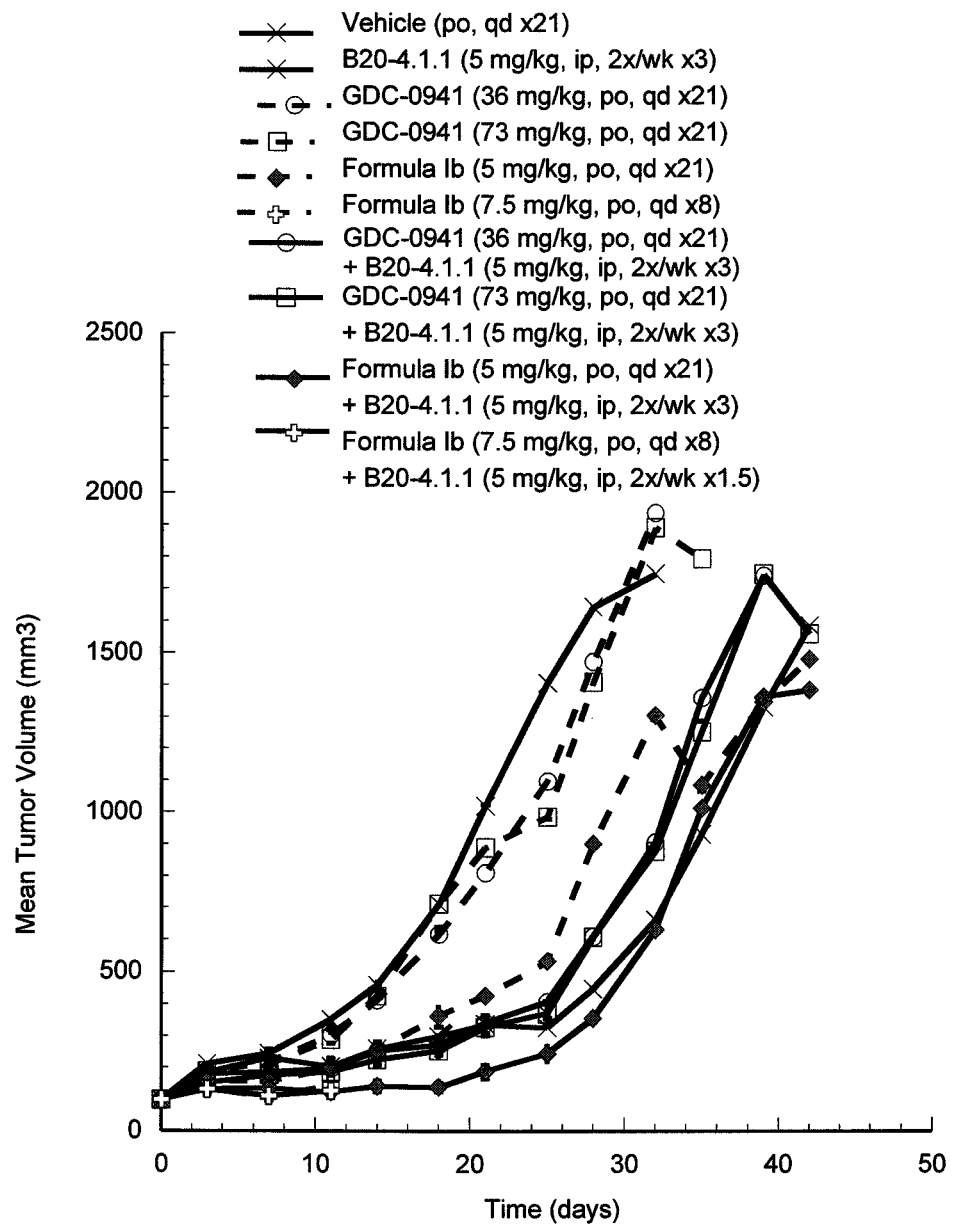
FIG. 38 shows the mean tumor volume change over time with Harlan female nu/nu mice with MDA-MB-231 breast tumor cell xenografts dosed on day 0 with: murine anti-VEGF antibody B20-4.1 5 mg/kg intraperitoneal twice a week for 3 weeks, Formula Ia (GDC-0941) at 36 and 73 mg/kg orally daily for 21 days, Formula Ib at 5 mg/kg orally daily for 21 days and Formula Ib at 7.5 mg/kg orally daily for 8 days, and the combinations of: Formula Ia at 36 mg/kg orally daily for 21 days and B20-4.1 5 mg/kg intraperitoneal twice a week for 3 weeks; Formula Ia at 73 mg/kg orally daily for 21 days and B20-4.1 5 mg/kg intraperitoneal twice a week for 3 weeks; Formula Ib at 5 mg/kg orally daily for 21 days and B20-4.1 5 mg/kg intraperitoneal twice a week for 3 weeks; and Formula Ib at 7.5 mg/kg orally daily for 8 days and B20-4.1 5 mg/kg intraperitoneal twice a week for 1.5 weeks, along with mice receiving no drug (Vehicle group).

FIG. 38 shows the mean tumor volume change over time with Harlan female nu/nu mice with MDA-MB-231 breast tumor cell xenografts dosed on day 0 with: murine anti-VEGF antibody B20-4.1 5 mg/kg intraperitonealy twice a week for 3 weeks, Formula Ia (GDC-0941) at 36 and 73 mg/kg orally daily for 21 days, Formula Ib at 5 mg/kg orally daily for 21 days and Formula Ib at 7.5 mg/kg orally daily for 8 days, and the combinations of: Formula Ia at 36 mg/kg orally daily for 21 days and B20-4.1 5 mg/kg intraperitonealy twice a week for 3 weeks; Formula Ia at 73 mg/kg orally daily for 21 days and B20-4.1 5 mg/kg intraperitonealy twice a week for 3 weeks; Formula Ib at 5 mg/kg orally daily for 21 days and B20-4.1 5 mg/kg intraperitonealy twice a week for 3 weeks; and Formula Ib at 7.5 mg/kg orally daily for 8 days and B20-4.1 5 mg/kg intraperitonealy twice a week for 1.5 weeks, along with mice receiving no drug (Vehicle group). The combination of 5.0 mg/kg of Formula Ib with 5.0 mg/kg B20-4.1 synergized to inhibit MDA-MB-231 breast tumor growth in vivo greater than Formula Ib or B20-4.1 alone and resulted in tumor growth delay.

Figure 39:
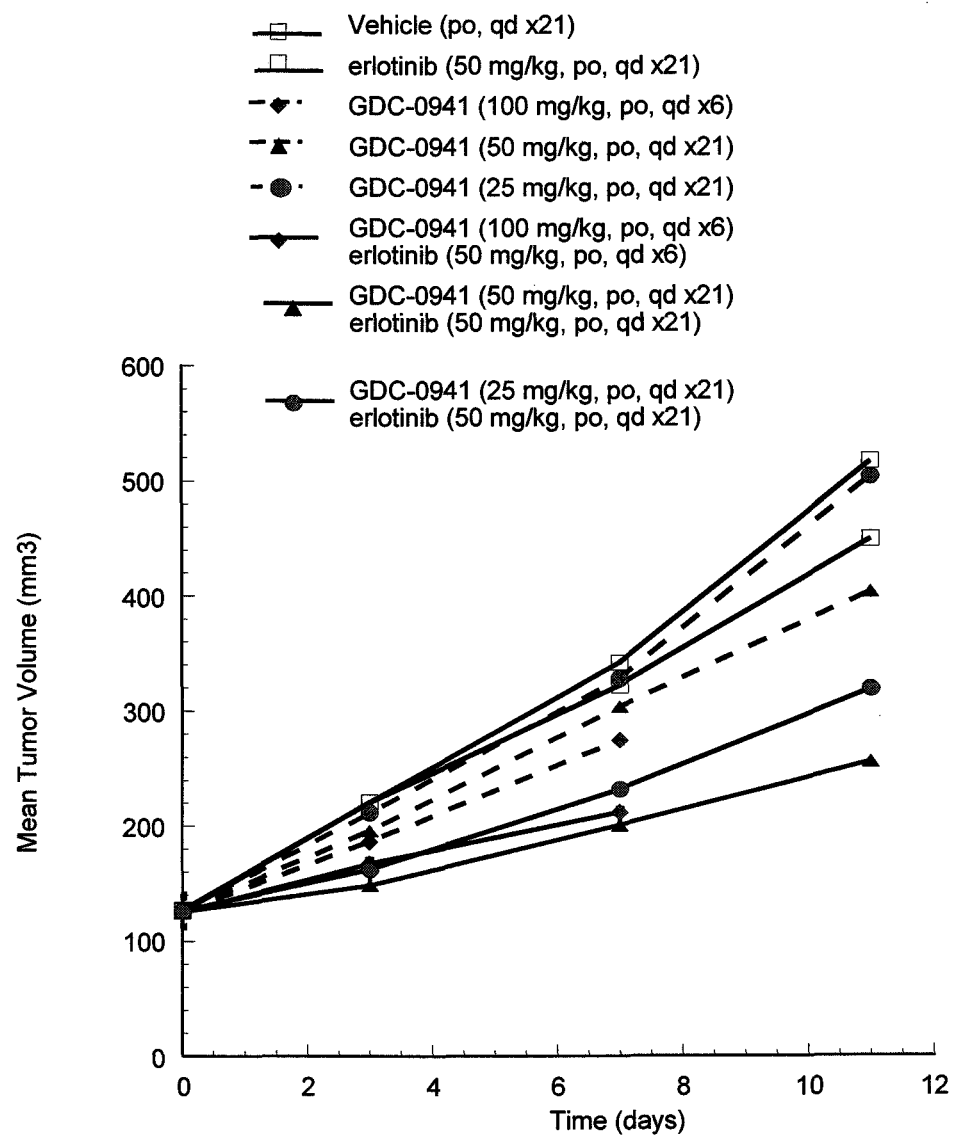
FIG. 39 shows the mean tumor volume change over time with Harlan female nu/nu mice with H1299 non-small cell lung cancer (NSCLC) tumor cell xenografts dosed on day 0 with: erlotinib 50 mg/kg orally daily for 21 days, Formula Ia (GDC-0941) at 100 mg/kg orally daily for 6 days, Formula Ia 50 mg/kg orally daily for 21 days, Formula Ia 25 mg/kg orally daily for 21 days, and the combinations of Formula Ia 100 mg/kg orally daily for 6 days and erlotinib 50 mg/kg orally daily for 6 days; Formula Ia 50 mg/kg orally daily for 21 days and erlotinib 50 mg/kg orally daily for 21 days; and Formula Ia 25 mg/kg orally daily for 21 days and erlotinib 50 mg/kg orally daily for 21 days, along with mice receiving no drug (Vehicle group).

FIG. 39 shows the mean tumor volume change over time with Harlan female nu/nu mice with H1299 non-small cell lung cancer (NSCLC) tumor cell xenografts dosed on day 0 with: erlotinib 50 mg/kg orally daily for 3 weeks, Formula Ia (GDC-0941) at 100 mg/kg orally daily for 6 days, Formula Ia at 50 mg/kg orally daily for 21 days, Formula Ia 25 mg/kg orally daily for 21 days, and the combinations of Formula Ia 100 mg/kg orally daily for 6 days and erlotinib 50 mg/kg orally daily for 6 days; Formula Ia 50 mg/kg orally daily for 21 days and erlotinib 50 mg/kg orally daily for 21 days; and Formula Ia 25 mg/kg orally daily for 21 days and erlotinib 50 mg/kg orally daily for 21 days, along with mice receiving no drug (Vehicle group). The combination of 25 mg/kg of Formula Ia with 50 mg/kg of erlotinib synergized to inhibit H1299 non-small cell lung cancer tumor growth in vivo greater than Formula Ia or erlotinib alone and resulted in tumor growth delay. The combination of 50 mg/kg of Formula Ia with 50 mg/kg of erlotinib also synergized to inhibit NCI-H1299 non-small cell lung cancer tumor growth in vivo greater than Formula Ia or erlotinib alone and resulted in tumor growth delay.

Figure 40:
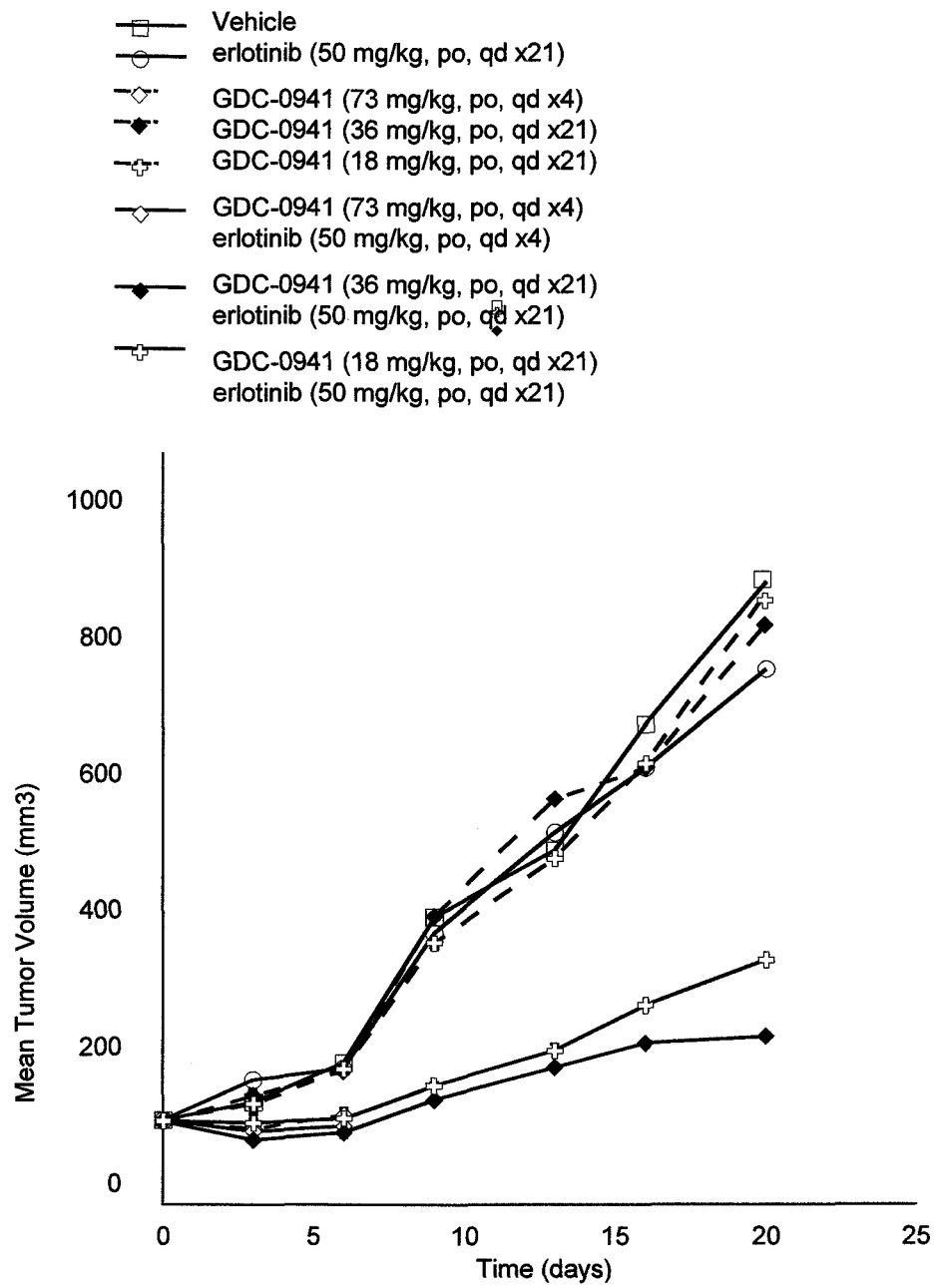
FIG. 40 shows the mean tumor volume change over time with Harlan female nu/nu mice with H520 non-small cell lung cancer (NSCLC) tumor cell xenografts dosed on day 0 with: erlotinib 50 mg/kg orally daily for 21 days, Formula Ia (GDC-0941) at 73 mg/kg orally daily for 4 days, Formula Ia at 36 mg/kg orally daily for 21 days, Formula Ia 18 mg/kg orally daily for 21 days, and the combinations of Formula Ia 73 mg/kg orally daily for 4 days and erlotinib 50 mg/kg orally daily for 4 days; Formula Ia 36 mg/kg orally daily for 21 days and erlotinib 50 mg/kg orally daily for 21 days; and Formula Ia 18 mg/kg orally daily for 21 days and erlotinib 50 mg/kg orally daily for 21 days, along with mice receiving no drug (Vehicle group).

FIG. 40 shows the mean tumor volume change over time with Harlan female nu/nu mice with H520 non-small cell lung cancer (NSCLC) tumor cell xenografts dosed on day 0 with: erlotinib 50 mg/kg orally daily for 3 weeks, Formula Ia (GDC-0941) at 73 mg/kg orally daily for 4 days, Formula Ia at 36 mg/kg orally daily for 21 days, Formula Ia 18 mg/kg orally daily for 21 days, and the combinations of Formula Ia 73 mg/kg orally daily for 4 days and erlotinib 50 mg/kg orally daily for 4 days; Formula Ia 36 mg/kg orally daily for 21 days and erlotinib 50 mg/kg orally daily for 21 days; and Formula Ia 18 mg/kg orally daily for 21 days and erlotinib 50 mg/kg orally daily for 21 days, along with mice receiving no drug (Vehicle group). The combination of 18 mg/kg of Formula Ia with 50 mg/kg of erlotinib synergized to inhibit H520 non-small cell lung cancer tumor growth in vivo greater than Formula Ia or erlotinib alone and resulted in tumor growth delay. The combination of 36 mg/kg of Formula Ia with 50 mg/kg of erlotinib also synergized to inhibit H520 non-small cell lung cancer tumor growth in vivo greater than Formula Ia or erlotinib alone and resulted in tumor growth delay.

Figure 41:
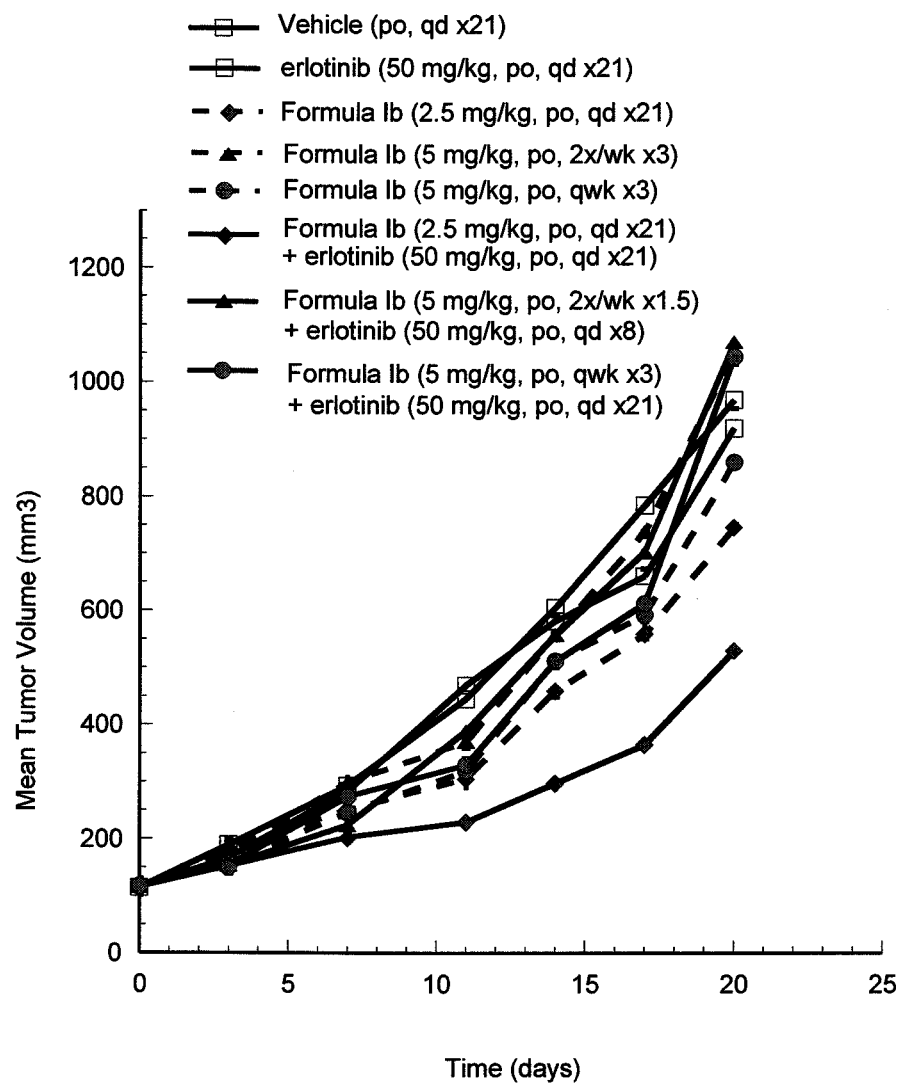
FIG. 41 shows the mean tumor volume change over time with Harlan female nu/nu mice with H1299 non-small cell lung cancer (NSCLC) tumor cell xenografts dosed on day 0 with: erlotinib 50 mg/kg orally daily for 3 weeks, Formula Ib at 2.5 mg/kg orally daily for 21 days, Formula Ib at 5 mg/kg orally twice per week for 3 weeks, Formula Ib at 5 mg/kg orally once per week for 3 weeks, and the combinations of: Formula Ib at 2.5 mg/kg orally daily for 21 days and erlotinib 50 mg/kg orally daily for 3 weeks; Formula Ib at 5 mg/kg orally twice per week for 3 weeks and erlotinib 50 mg/kg orally daily for 3 weeks; and Formula Ib at 5 mg/kg orally once per week for 3 weeks and erlotinib 50 mg/kg orally daily for 3 weeks, along with mice receiving no drug (Vehicle group).

FIG. 41 shows the mean tumor volume change over time with Harlan female nu/nu mice with H1299 non-small cell lung cancer (NSCLC) tumor cell xenografts dosed on day 0 with: erlotinib 50 mg/kg orally daily for 21 days, Formula Ib at 2.5 mg/kg orally daily for 21 days, Formula Ib at 5 mg/kg orally twice per week for 21 days, Formula Ib at 5 mg/kg orally once per week for 3 weeks, and the combinations of: Formula Ib at 2.5 mg/kg orally daily for 21 days and erlotinib 50 mg/kg orally daily for 21 days; Formula Ib at 5 mg/kg orally twice per week for 3 weeks and erlotinib 50 mg/kg orally daily for 21 days; and Formula Ib at 5 mg/kg orally once per week for 3 weeks and erlotinib 50 mg/kg orally daily for 21 days, along with mice receiving no drug (Vehicle group). The combination of 2.5 mg/kg of Formula Ib dosed orally daily with 50 mg/kg of erlotinib dosed orally daily for 21 days synergized to inhibit H520 non-small cell lung cancer tumor growth in vivo greater than Formula Ib or erlotinib alone and resulted in tumor growth delay.

Figure 42:
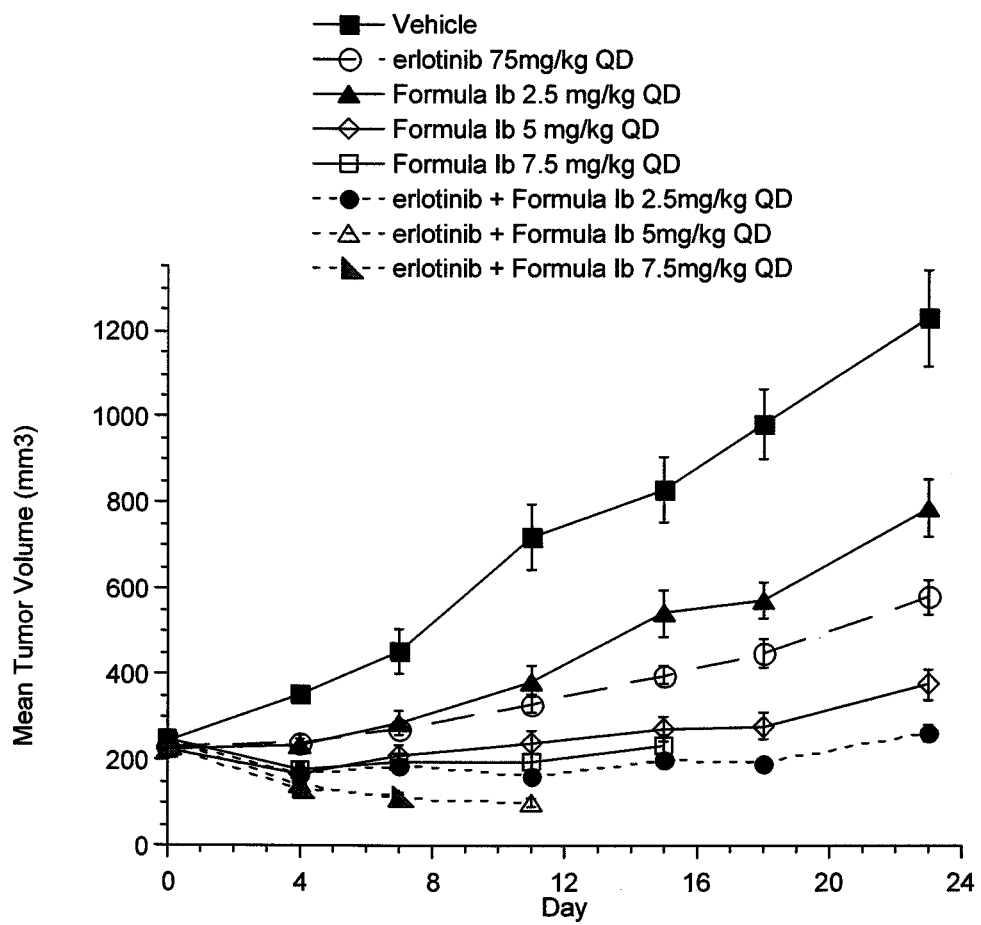
FIG. 42 shows the mean tumor volume change over time with Taconic NCR female nude mice with NCI-H2122 non-small cell lung cancer (NSCLC) tumor cell xenografts dosed on day 0 with: erlotinib 75 mg/kg orally daily for 16 days, Formula Ib at 2.5 mg/kg orally daily for 16 days, Formula Ib at 5 mg/kg orally daily for 16 days, Formula Ib at 7.5 mg/kg orally daily for 16 days, and the combinations of: Formula Ib at 2.5 mg/kg orally daily for 16 days and erlotinib 50 mg/kg orally daily for 3 weeks; Formula Ib at 5 mg/kg orally twice per week for 3 weeks and erlotinib 50 mg/kg orally daily for 16 days; and Formula Ib at 5 mg/kg orally daily for 16 days and erlotinib 50 mg/kg orally daily for 16 days, along with mice receiving no drug (Vehicle group).

FIG. 42 shows the mean tumor volume change over time with Taconic NCR female nude mice with NCI-H2122 non-small cell lung cancer (NSCLC) tumor cell xenografts dosed on day 0 with: erlotinib 75 mg/kg orally daily for 16 days, Formula Ib at 2.5 mg/kg orally daily for 16 days, Formula Ib at 5 mg/kg orally daily for 16 days, Formula Ib at 7.5 mg/kg orally daily for 16 days, and the combinations of: Formula Ib at 2.5 mg/kg orally daily for 16 days and erlotinib 50 mg/kg orally daily for 16 days; Formula Ib at 5 mg/kg orally daily for 16 days and erlotinib 50 mg/kg orally daily for 16 days; and Formula Ib at 7.5 mg/kg orally daily for 16 days and erlotinib 50 mg/kg orally daily for 16 days, along with mice receiving no drug (Vehicle group). The combination of 2.5 mg/kg of Formula Ib with 75 mg/kg of erlotinib synergized to inhibit NCI-H2122 non-small cell lung cancer tumor growth in vivo greater than Formula Ib or erlotinib alone and resulted in tumor stasis.

Figure 43:
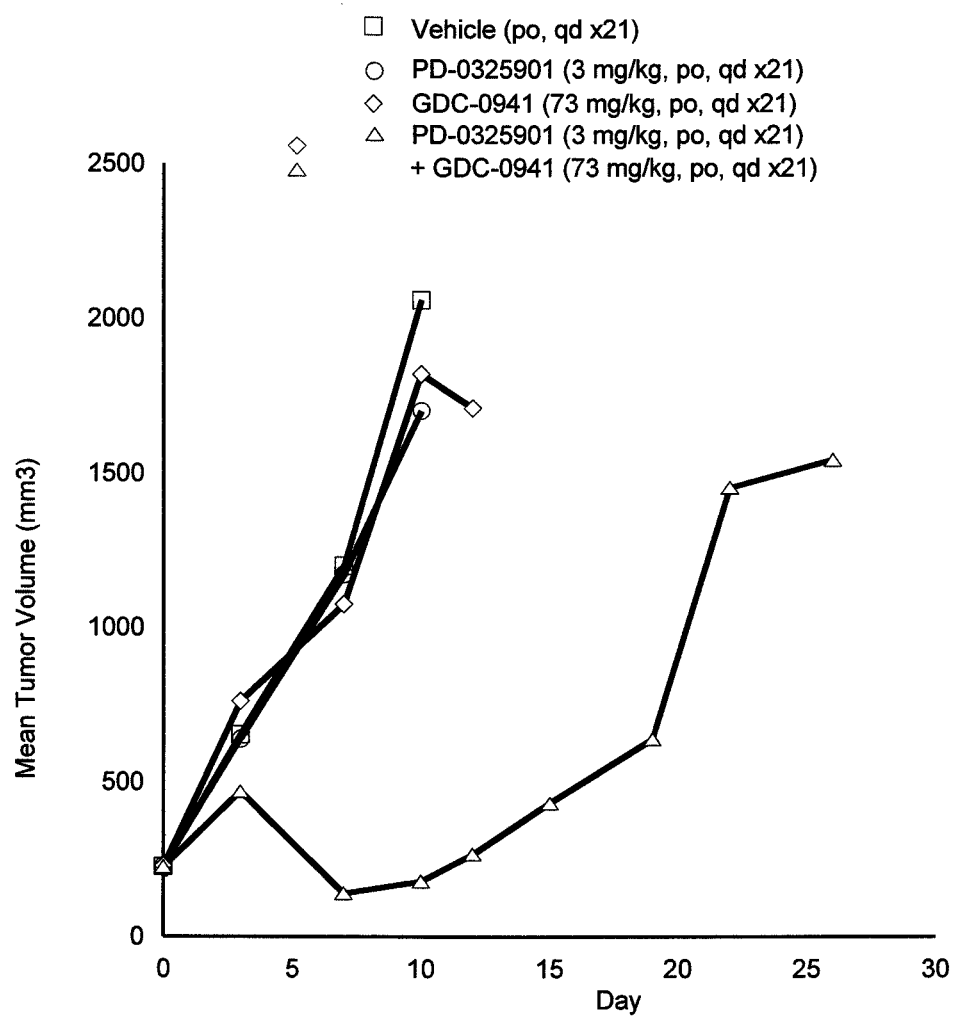
FIG. 43 shows the mean tumor volume change over time with Harlan female nu/nu mice with A375 human melanoma cancer tumor cell xenografts dosed on day 0 with: PD-0325901 3 mg/kg orally daily for 3 weeks, Formula Ia (GDC-0941) at 73 mg/kg orally daily for 3 weeks, and the combination of: PD-0325901 3 mg/kg orally daily for 3 weeks and Formula Ia 73 mg/kg orally daily for 3 weeks, along with mice receiving no drug (Vehicle group).

FIG. 43 shows the mean tumor volume change over time with Harlan female nu/nu mice with A375 human melanoma cancer cell xenografts dosed on day 0 with: PD-0325901 3 mg/kg orally daily for 3 weeks, Formula Ia (GDC-0941) at 73 mg/kg orally daily for 3 weeks, and the combination of: PD-0325901 3 mg/kg orally daily for 3 weeks and Formula Ia 73 mg/kg orally daily for 3 weeks, along with mice receiving no drug (Vehicle group). The combination of 73 mg/kg of Formula Ia with 3 mg/kg of PD-0325901 synergized to inhibit A375 human melanoma tumor growth in vivo greater than Formula Ia or PD-0325901 alone and resulted in tumor regression and tumor growth delay.

Figure 44:
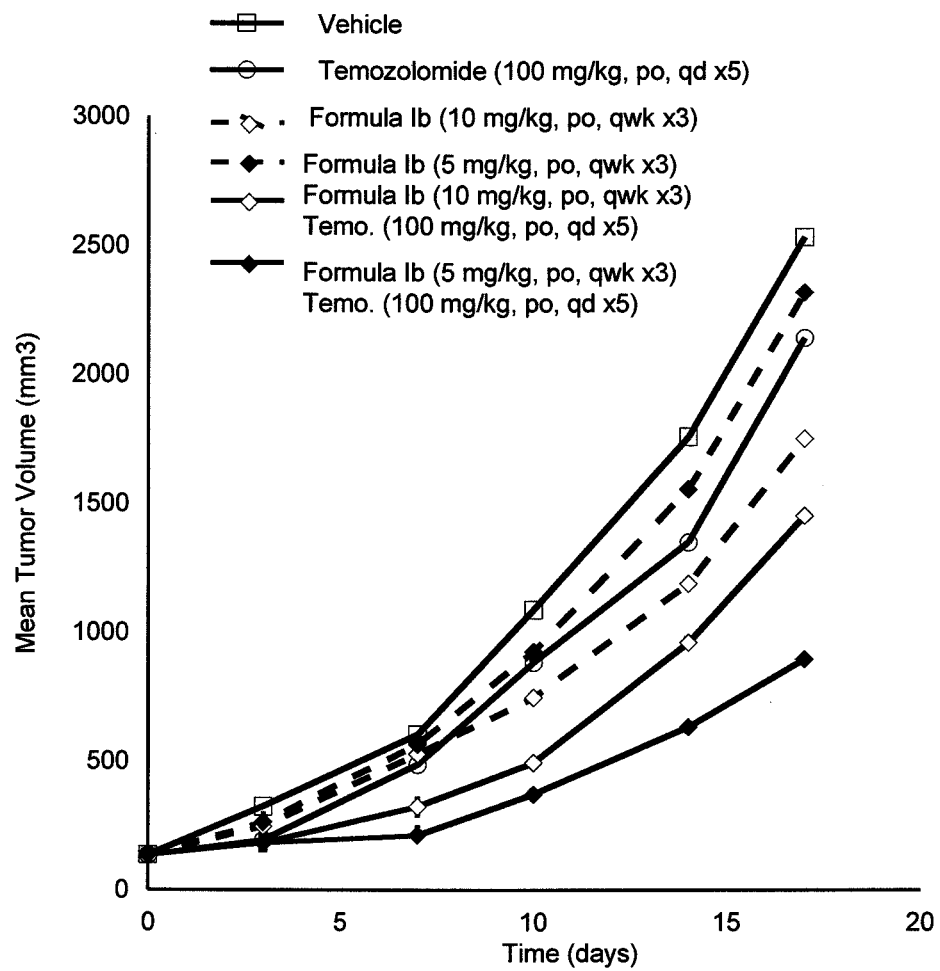
FIG. 44 shows the mean tumor volume change over time with Harlan female nu/nu mice with A375 human melanoma cancer tumor cell xenografts dosed on day 0 with: temozolomide 100 mg/kg orally daily for 5 days, Formula Ib at 10 mg/kg orally once weekly for 3 weeks, Formula Ib at 5 mg/kg orally weekly for 3 weeks, and the combinations of: Formula Ib at 10 mg/kg orally once weekly for 3 weeks and temozolomide 100 mg/kg orally daily for 5 days; and Formula Ib at 5 mg/kg orally once weekly for 3 weeks and temozolomide 100 mg/kg orally daily for 5 days, along with mice receiving no drug (Vehicle group).

FIG. 44 shows the mean tumor volume change over time with Harlan female nu/nu mice with A375 human melanoma cancer tumor cell xenografts dosed on day 0 with: temozolomide 100 mg/kg orally daily for 5 days, Formula Ib at 10 mg/kg orally once weekly for 3 weeks, Formula Ib at 5 mg/kg orally weekly for 3 weeks, and the combinations of: Formula Ib at 10 mg/kg orally once weekly for 3 weeks and temozolomide 100 mg/kg orally daily for 5 days; and Formula Ib at 5 mg/kg orally once weekly for 3 weeks and temozolomide 100 mg/kg orally daily for 5 days, along with mice receiving no drug (Vehicle group). The combination of 5 mg/kg of Formula Ib with 100 mg/kg of temozolomide synergized to inhibit A375 human melanoma tumor growth in vivo greater than Formula Ib or temozolomide alone and resulted in in tumor growth delay.

Figure 45:
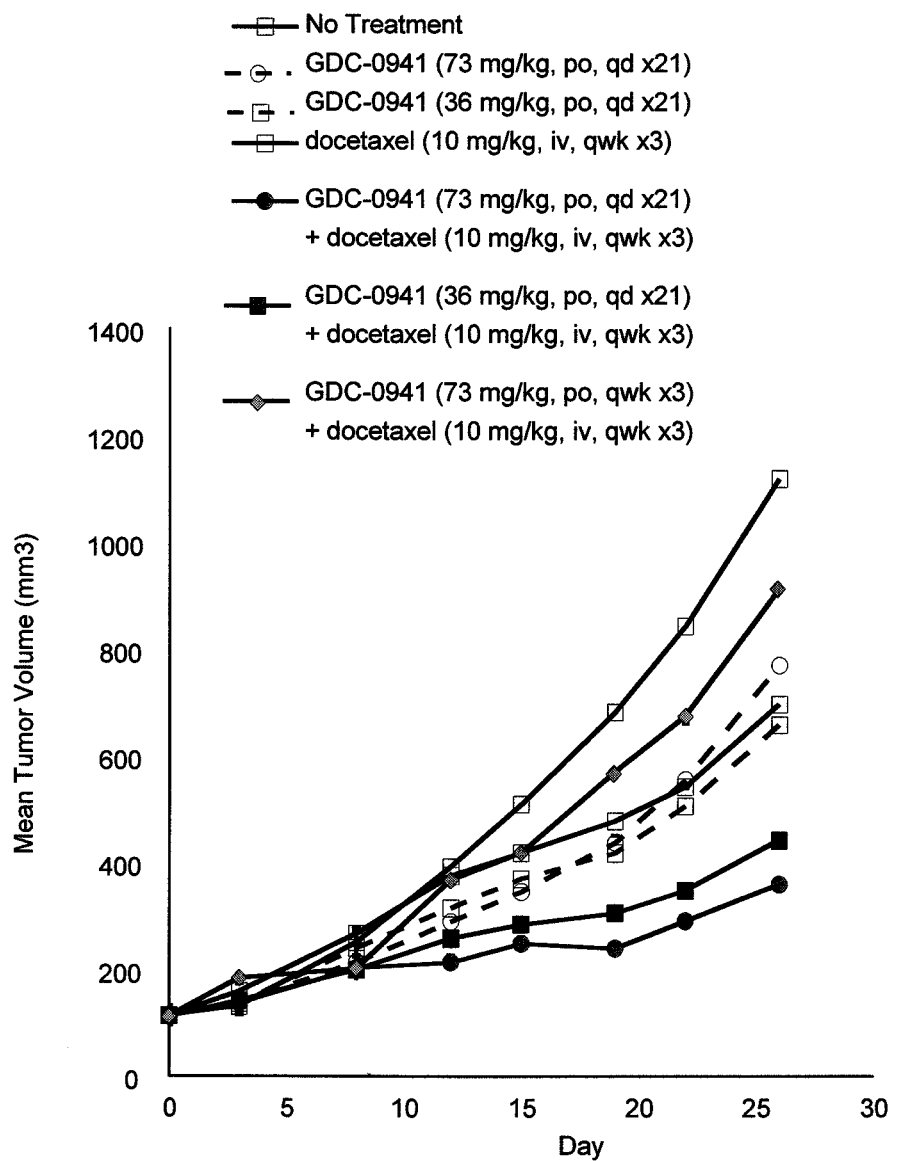
FIG. 45 shows the mean tumor volume change over time with Harlan female nu/nu mice with SKOV3 human ovarian cancer tumor cell xenografts dosed on day 0 with: Formula Ia (GDC-0941) 73 mg/kg orally daily for 3 weeks, Formula Ia 36 mg/kg orally daily for 3 weeks, docetaxel 10 mg/kg intraperitoneal weekly for 3 weeks, and the combinations of Formula Ia 73 mg/kg orally daily for 3 weeks and docetaxel 10 mg/kg intravenously weekly for 3 weeks; Formula Ia 36 mg/kg orally daily for 3 weeks and docetaxel 10 mg/kg intravenously weekly for 3 weeks; and Formula Ia 73 mg/kg orally weekly for 3 weeks and docetaxel 10 mg/kg intravenously weekly for 3 weeks, along with mice receiving no drug (Vehicle group).

FIG. 45 shows the mean tumor volume change over time with Harlan female nu/nu mice with SKOV3 human ovarian cancer cell xenografts dosed on day 0 with: Formula Ia (GDC-0941) 73 mg/kg orally daily for 3 weeks, Formula Ia 36 mg/kg orally daily for 3 weeks, docetaxel 10 mg/kg intravenously weekly for 3 weeks, and the combinations of: Formula Ia 73 mg/kg orally daily for 3 weeks and docetaxel 10 mg/kg intravenously weekly for 3 weeks; Formula Ia 36 mg/kg orally daily for 3 weeks and docetaxel 10 mg/kg intravenously weekly for 3 weeks; and Formula Ia 73 mg/kg orally weekly for 3 weeks and docetaxel 10 mg/kg intravenously weekly for 3 weeks, along with mice receiving no drug (Vehicle group). The combination of 36 mg/kg dosed daily of Formula Ia with 10 mg/kg of docetaxel synergized to inhibit SKOV3 human ovarian tumor growth in vivo greater than Formula Ib or docetaxel alone and resulted in tumor growth delay. The combination of 73 mg/kg of Formula Ia dosed daily with 10 mg/kg of docetaxel also synergized to inhibit SKOV3 human ovarian tumor growth in vivo greater than Formula Ib or docetaxel alone and resulted in tumor growth delay.

Figure 46:
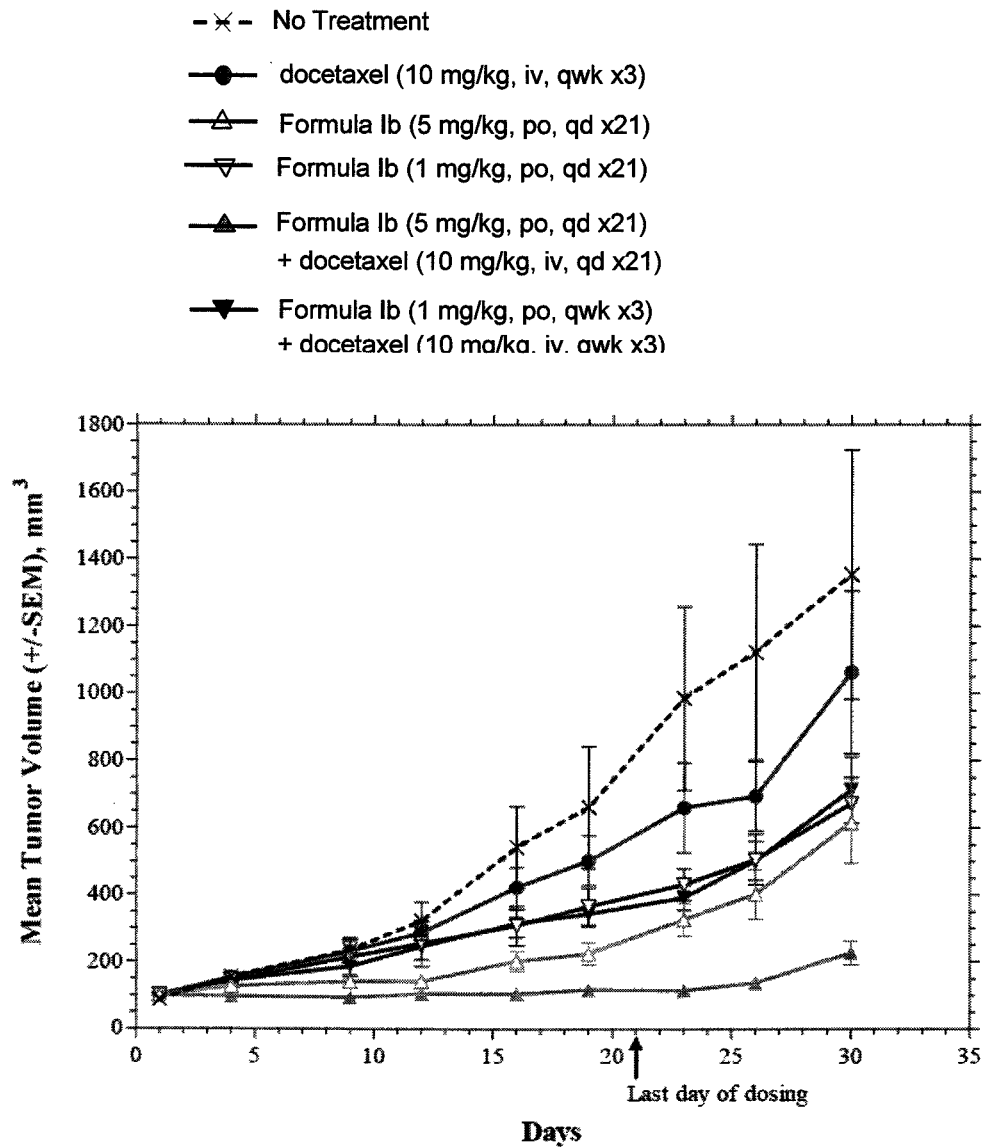
FIG. 46 shows the mean tumor volume change over time with Harlan female nu/nu mice with SKOV3 human ovarian cancer tumor cell xenografts dosed on day 0 with: Formula Ib 5 mg/kg orally daily for 3 weeks, Formula Ib 1 mg/kg orally daily for 3 weeks, docetaxel 10 mg/kg intravenously weekly for 3 weeks, and the combinations of: Formula Ib 5 mg/kg orally daily for 3 weeks and docetaxel 10 mg/kg intravenously weekly for 3 weeks; and Formula Ib 1 mg/kg orally daily for 3 weeks and docetaxel 10 mg/kg intravenously weekly for 3 weeks; along with mice receiving no drug (Vehicle group).

FIG. 46 shows the mean tumor volume change over time with Harlan female nu/nu mice with SKOV3 human ovarian cancer tumor cell xenografts dosed on day 0 with: Formula Ib 5 mg/kg orally daily for 3 weeks, Formula Ib 1 mg/kg orally daily for 3 weeks, docetaxel 10 mg/kg intravenously weekly for 3 weeks, and the combinations of: Formula Ib 5 mg/kg orally daily for 3 weeks and docetaxel 10 mg/kg intravenously weekly for 3 weeks; and Formula Ib 1 mg/kg orally daily for 3 weeks and docetaxel 10 mg/kg intravenoulsy weekly for 3 weeks; along with mice receiving no drug (Vehicle group). The combination of 5 mg/kg of Formula Ib with 10 mg/kg of docetaxel synergized to inhibit SKOV3 human ovarian tumor growth in vivo greater than Formula Ib or docetaxel alone and resulted in tumor stasis.

Figure 47:
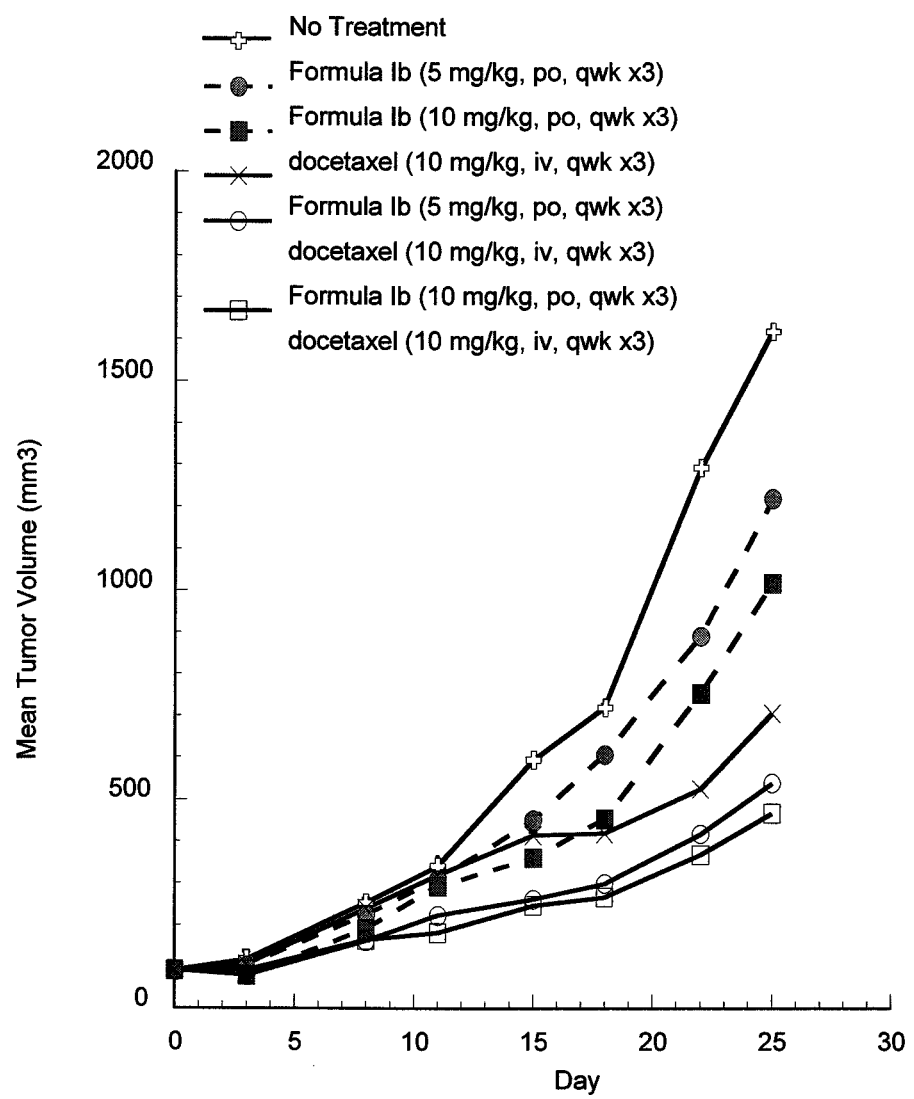
FIG. 47 shows the mean tumor volume change over time with Harlan female nu/nu mice with SKOV3 human ovarian cancer tumor cell xenografts dosed on day 0 with: Formula Ib 5 mg/kg orally weekly for 3 weeks, Formula Ib 10 mg/kg orally weekly for 3 weeks, docetaxel 10 mg/kg intravenously weekly for 3 weeks, and the combinations of: Formula Ib 5 mg/kg orally weekly for 3 weeks and docetaxel 10 mg/kg intravenously weekly for 3 weeks; and Formula Ib 10 mg/kg orally weekly for 3 weeks and docetaxel 10 mg/kg intravenously weekly for 3 weeks, along with mice receiving no drug (Vehicle group).

FIG. 47 shows the mean tumor volume change over time with Harlan female nu/nu mice with SKOV3 human ovarian cancer tumor cell xenografts dosed on day 0 with: Formula Ib 5 mg/kg orally weekly for 3 weeks, Formula Ib 10 mg/kg orally weekly for 3 weeks, docetaxel 10 mg/kg intravenously weekly for 3 weeks, and the combinations of: Formula Ib 5 mg/kg orally weekly for 3 weeks and docetaxel 10 mg/kg intravenously weekly for 3 weeks; and Formula Ib 10 mg/kg orally weekly for 3 weeks and docetaxel 10 mg/kg intravenously weekly for 3 weeks, along with mice receiving no drug (Vehicle group). The combination of 10 mg/kg of Formula Ib dosed orally weekly with 10 mg/kg of docetaxel synergized to inhibit SKOV3 human ovarian tumor growth in vivo greater than Formula Ib or docetaxel alone and resulted in tumor growth delay.

Figure 48:
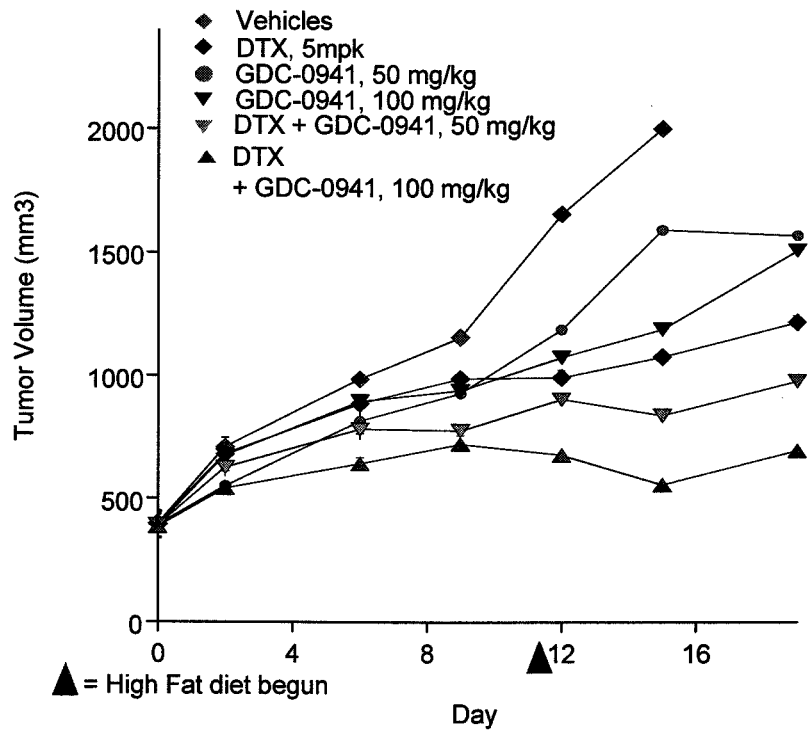
FIG. 48 shows the mean tumor volume change over time with female SCID Beige nude mice with LuCap 35V human primary prostate cancer tumor cell xenografts dosed on day 0 with: docetaxel 5 mg/kg intravenously on days 1, 5 and 9 (q4d×3), Formula Ia (GDC-0941) 50 mg/kg orally daily for 18 days, Formula Ia 100 mg/kg orally daily for 18 days, and the combinations of: docetaxel 5 mg/kg intravenously on days 1, 5 and 9 (q4d×3) and Formula Ia 50 mg/kg orally daily for 18 days and docetaxel 5 mg/kg intravenously on days 1, 5 and 9 (q4d×3) and Formula Ia 100 mg/kg orally daily for 18 days, along with mice receiving no drug (Vehicle group).

FIG. 48 shows the mean tumor volume change over time with female SCID Beige nude mice with LuCap 35V human primary prostate cancer tumor cell xenografts dosed on day 0 with: docetaxel 5 mg/kg intravenously on days 1, 5 and 9 (q4d×3) Formula Ia (GDC-0941) 50 mg/kg orally daily for 18 days Formula Ia 100 mg/kg orally daily for 18 days and the combinations of: docetaxel 5 mg/kg intravenously on days 1, 5 and 9 (q4d×3) and Formula Ia 50 mg/kg orally daily for 18 days and docetaxel 5 mg/kg intravenously on days 1, 5 and 9 (q4d×3) and Formula Ia 100 mg/kg orally daily for 18 days, along with mice receiving no drug (Vehicle group). The combination of 100 mg/kg of Formula Ia with 5 mg/kg of docetaxel synergized to inhibit LuCap 35 V human primary prostate tumor growth in vivo greater than Formula Ia or docetaxel alone and resulted in tumor regression.

Figure 49:
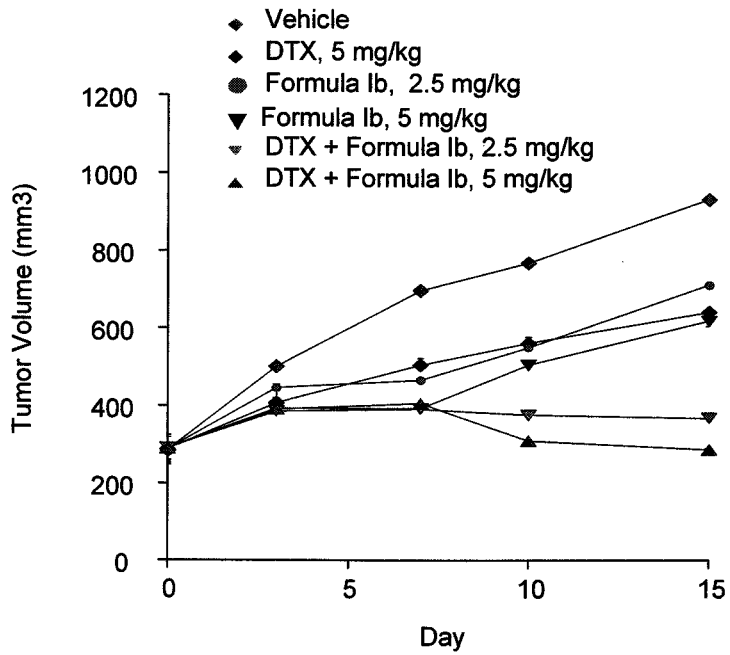
FIG. 49 shows the mean tumor volume change over time with female SCID Beige nude mice with LuCap 35V human primary prostate cancer tumor cell xenografts dosed on day 0 with: docetaxel 5 mg/kg intravenously on days 1, 5 and 9 (q4d×3), Formula Ib 2.5 mg/kg orally daily for 15 days, Formula Ib 5 mg/kg orally daily for 15 days, and the combinations of: docetaxel 5 mg/kg intravenously on days 1, 5 and 9 (q4d×3) and Formula Ib 2.5 mg/kg orally daily for 15 days and docetaxel 5 mg/kg intravenously on days 1, 5 and 9 (q4d×3) and Formula Ib 5 mg/kg orally daily for 15 days, along with mice receiving no drug (Vehicle group).

FIG. 49 shows the mean tumor volume change over time with female SCID Beige nude mice with LuCap 35V human primary prostate cancer tumor cell xenografts dosed on day 0 with: docetaxel 5 mg/kg intravenously on days 1, 5 and 9 (q4d×3) Formula Ib 2.5 mg/kg orally daily for 15 days, Formula Ib 5 mg/kg orally daily for 15 days and the combinations of: docetaxel 5 mg/kg intravenously on days 1, 5 and 9 (q4d×3) and Formula Ib 2.5 mg/kg orally daily for 15 days and docetaxel 5 mg/kg intravenously on days 1, 5 and 9 (q4d×3) and Formula Ib 5 mg/kg orally daily for 15 days along with mice receiving no drug (Vehicle group). The combination of 2.5 mg/kg of Formula Ib with 5 mg/kg of docetaxel synergized to inhibit LuCap 35 V human primary prostate tumor growth in vivo greater than Formula Ib or docetaxel alone and resulted in tumor regression. The combination of 5.0 mg/kg of Formula Ib with 5 mg/kg of docetaxel also synergized to inhibit LuCap 35 V human primary prostate tumor growth in vivo greater than Formula Ib or docetaxel alone and resulted in tumor regression.

Figure 50:
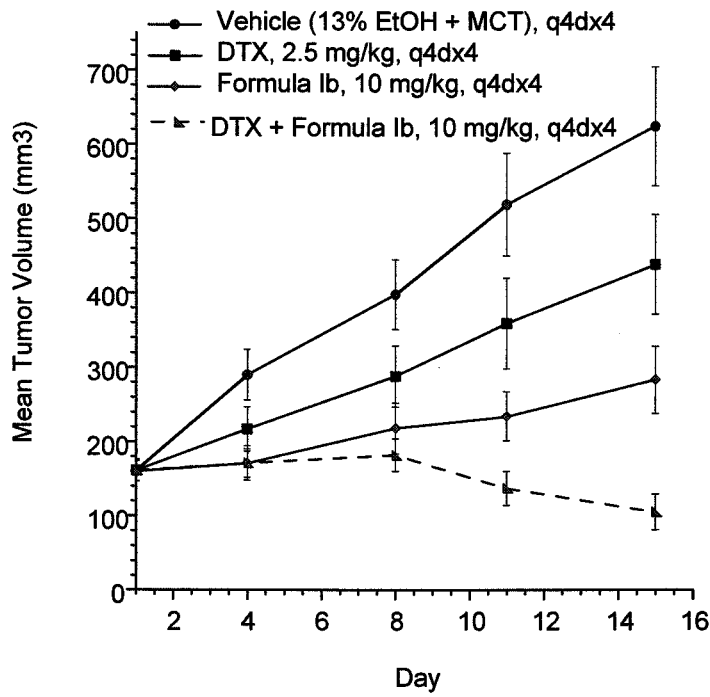
FIG. 50 shows the mean tumor volume change over time with CRL female nu/nu mice with PC3-NCI human primary prostate cancer tumor cell xenografts dosed on days 1, 5, 9, and 13 (q4d×4) with: docetaxel 2.5 mg/kg intravenously, Formula Ib 10 mg/kg orally on days 1, 5, 9 and 13 (q4d×4), and the combination of: docetaxel 2.5 mg/kg intravenously and Formula Ib 10 mg/kg orally on days 1, 5, 9 and 13 (q4d×4), along with mice receiving no drug (Vehicle group).

FIG. 50 shows the mean tumor volume change over time with CRL female nu/nu mice with PC3-NCI human primary prostate cancer tumor cell xenografts dosed on days 1, 5, 9, and 13 (q4d×4) with 2.5 mg/kg docetaxel intravenously, Formula 1b 2.5 mg/kg Formula 1b on days 1, 5, 9 and 13 (q4d×4), Formula Ib 10 mg/kg orally on days 1, 5, 9 and 13 (q4d×4), and the combination of: docetaxel 2.5 mg/kg intravenoulsy and Formula Ib 10 mg/kg orally, along with mice receiving no drug (Vehicle group). The combination of 10 mg/kg of Formula Ib dosed on days 1, 5, 9 and 13 with 5 mg/kg of docetaxel synergized to inhibit PC3-NCI human primary prostate tumor growth in vivo greater than Formula Ib or docetaxel alone and resulted in tumor regression.

Figure 51:
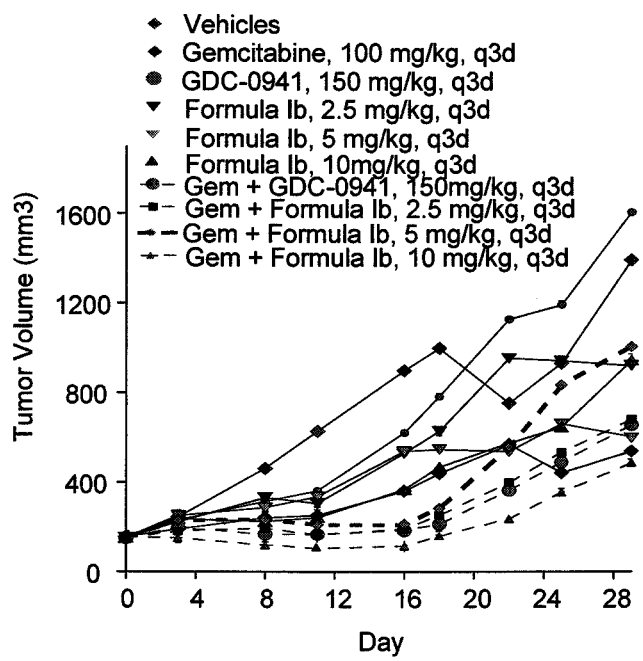
FIG. 51 shows the mean tumor volume change over time with CRL female nu/nu mice with PC3-NCI human primary prostate cancer tumor cell xenografts dosed on day 0 with: gemcitabine 100 mg/kg intraperitoneal every 3 days for 4 times, Formula Ia (GDC-0941) 150 mg/kg orally every 3 days (q3d) for 4 times, Formula Ib 2.5 mg/kg orally every 3 days (q3d) for 4 times, Formula Ib 5 mg/kg orally every 3 days for 4 times, and the combinations of: gemcitabine 100 mg/kg intraperitoneal every 3 days for 4 times and Formula Ia 150 mg/kg orally every 3 days for 4 times; gemcitabine 100 mg/kg intraperitoneal every 3 days for 4 times and Formula Ib 2.5 mg/kg orally every 3 days for 4 times, gemcitabine 100 mg/kg intraperitoneal every 3 days for 4 times and Formula Ib 5 mg/kg orally every 3 days for 4 times and Formula Ib 10 mg/kg orally every 3 days for 4 times, along with mice receiving no drug (Vehicle group).

FIG. 51 shows the mean tumor volume change over time with CRL female nu/nu mice with PC3-NCI human primary prostate cancer cell xenografts dosed on day 0 with: gemcitabine 100 mg/kg intraperitonealy every 3 days (q3d) for 4 times, Formula Ia (GDC-0941) 150 mg/kg orally every 3 days (q3d) for 4 times Formula Ib 2.5 mg/kg orally every 3 (q3d) days for 4 times, Formula Ib 5 mg/kg orally every 3 days for 4 times and the combinations of: gemcitabine 100 mg/kg intraperitonealy every 3 days for 4 times and Formula Ia 150 mg/kg orally every 3 days for 4 times; gemcitabine 100 mg/kg intraperitonealy every 3 days for 4 times and Formula Ib 2.5 mg/kg orally every 3 days for 4 times, gemcitabine 100 mg/kg intraperitonealy every 3 days for 4 times and Formula Ib 5 mg/kg orally every 3 days for 4 times, gemcitabine 100 mg/kg intraperitonealy every 3 days for 4 times and Formula Ib 10 mg/kg orally every 3 days for 4 times, along with mice receiving no drug (Vehicle group). The combination of 150 mg/kg of Formula Ia dosed orally every 3 days (q3d) for 4 times with 100 mg/kg of gemcitabine synergized to inhibit PC3-NCI human primary prostate tumor growth in vivo greater than Formula Ia or gemcitabine alone and resulted in tumor regression and tumor growth delay. The combination of 2.5 mg/kg of Formula Ib dosed orally every 3 days (q3d) for 4 times with 100 mg/kg of gemcitabine synergized to inhibit PC3-NCI human primary prostate tumor growth in vivo greater than Formula Ia or gemcitabine alone and resulted in tumor regression and tumor growth delay. The combination of 5.0 mg/kg of Formula Ib dosed orally every 3 days (q3d) for 4 times with 100 mg/kg of gemcitabine synergized to inhibit PC3-NCI human primary prostate tumor growth in vivo greater than Formula Ia or gemcitabine alone and resulted in tumor regression and tumor growth delay. The combination of 10 mg/kg of Formula Ib dosed orally every 3 days (q3d) for 4 times with 100 mg/kg of gemcitabine synergized to inhibit PC3-NCI human primary prostate tumor growth in vivo greater than Formula Ia or gemcitabine alone and resulted in tumor regression and tumor growth delay.

Figure 52:
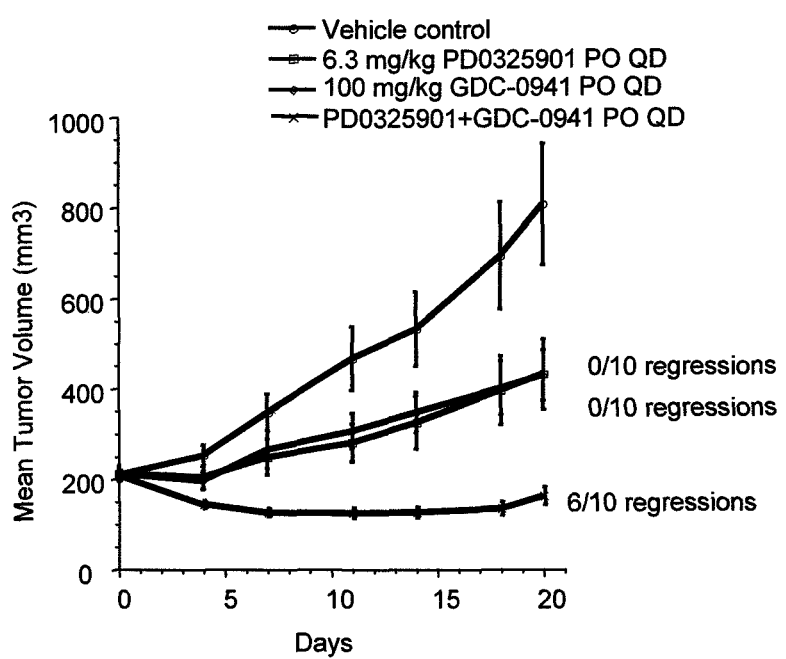

FIG. 52 shows the mean tumor volume change over time with Harlan female nude mice with NCI-H2122 (K-ras) non-small cell lung cancer (NSCLC) tumor cell xenografts dosed on day 0 with: PD-0325901 6.3 mg/kg orally daily for 21 days, Formula Ia (GDC-0941) at 100 mg/kg orally daily for 21 days, and the combination of: PD-0325901 6.3 mg/kg orally daily for 21 days and Formula Ia at 100 mg/kg orally daily for 21 days, along with mice receiving no drug (Vehicle group). The combination of 100 mg/kg of Formula Ia with 6.3 mg/kg of PD-0325901 synergized to inhibit NCI-H2122 (K-ras) NSCLC tumor growth in vivo greater than Formula Ia or PD-0325901 alone and resulted in tumor regression.

Genetically Engineered Mouse Model Tumor Efficacy

Combination therapy with Formula I compounds and chemotherapeutic agents was effective in treatment of small cell lung cancer (SCLC), non-small cell lung cancer (NSCLC), and pancreatic adenocarcinoma (PDAC) in genetically engineered mouse models (GEMM) which recapitulate human tumor progression in an endogenous tissue micro-environment (Singh, M. and Johnson, L. (2006) Clin. Cancer Res. 12(18):5312-5328; US 2007/0292948, both of which are incorporated by reference in their entirety). The surprising and unexpected results from these experiments may predict the clinical response of certain patient populations having select tumor types and mutations to such combination therapy with Formula I and II compounds and chemotherapeutic agents.

In a model for SCLC (Meuwissen et al (2003) Cancer Cell 4(3):181-189) bearing the mutations commonly found in the patient population, Formula Ia compound alone did not show effects on tumor growth as assessed by microCT imaging but did have an effect (significant hazard ratio) on survival as compared to controls. Animals dosed with the combination of Formula Ia compound and mB20-4.1.1 murine anti-VEGF-A showed a significant inhibition and regression of tumor growth by microCT imaging, when compared to controls and each single drug. The combination of Formula Ia compound and mB20-4.1 murine anti-VEGF-A also had a statistically significant impact on overall survival compared to controls. Animals dosed with the triple combination of Formula Ia compound, carboplatin, and mB20-4.1.1 murine anti-VEGF-A also showed a measurable and durable anti-tumor response as compared to single agents. The triple combination significantly increased survival as compared to single agents, and Formula Ia compound in this triple regimen enhanced the survival advantage compared to the carboplatin and mB20-4.1 murine anti-VEGF-A dual combination. In addition, these combinatorial regimens markedly decreased the incidence of metastases to regional lymph nodes and the liver when compared to controls and each single drug.

A GEMM for pancreatic cancer (Aguirre et al. (2003) Genes & Development 17:3112-3126) encompasses the mutations found in a majority of patients with this disease. These mice, when treated with Formula Ia compound, showed an initial decrease in tumor growth via ultrasound as compared to control-treated mice. However, this response was not durable and the single agent treatment had a modest (not statistically significant) effect on survival in these mice. In contrast, Formula Ia in combination with mB20-4.1.1 murine anti-VEGF-A showed significant decreases in tumor growth via ultrasound (as compared to untreated mice and single agents) as well as a significant impact on survival. Combination therapy with gemcitabine, either with or without mB20-4.1.1 murine anti-VEGF-A, did not show significant improvements in tumor growth inhibition (via ultrasound) or survival as compared to gemcitabine alone.

In a K-ras-driven NSCLC GEMM (Johnson et al (2001) Nature 410:1111-1116; Jackson et al (2001) Genes & Development 15:3243-3248), Formula Ia compound treatment alone minimally affected tumor growth as measured by microCT imaging, and had no effect on survival as compared to controls. Treatment with Formula Ia compound in combination with erlotinib showed modest tumor growth inhibition and survival advantage as compared to the single agent treatments. Treatment with Formula Ia compound in combination with mB20-4.1.1 murine anti-VEGF-A resulted in a notable decrease in tumor growth and increase in survival as compared to controls, albeit not significantly greater than the effects observed with mB20-4.1.1 murine anti-VEGF-A as a single agent. Animals dosed with the triple combination of Formula Ia compound, carboplatin, and mB20-4.1.1 murine anti-VEGF-A also showed a measurable and durable antitumor response as compared to controls and also markedly impacted survival in this model.

Pharmaceutical Compositions

Pharmaceutical compositions or formulations of the present invention include combinations of Formula I or II compounds, a chemotherapeutic agent, and one or more pharmaceutically acceptable carrier, glidant, diluent, or excipient.

The Formula I or II compounds, and chemotherapeutic agents of the present invention may exist in unsolvated as well as solvated forms with pharmaceutically acceptable solvents such as water, ethanol, and the like, and it is intended that the invention embrace both solvated and unsolvated forms.

The Formula I or II compounds, and chemotherapeutic agents of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents including a Formula I or II compound and a chemotherapeutic agent selected from the lists of the additional agents described herein, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

Pharmaceutical compositions also embrace isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^{3}$H and $^{14}$C) are useful in compound and/or substrate tissue distribution assays. Tritiated ($^{3}$H) and carbon-14 ($^{14}$C) isotopes are useful for their ease of preparation and detectability. Further, substitution with heavier isotopes such as deuterium ($^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Formula I or II compounds and chemotherapeutic agents are formulated in accordance with standard pharmaceutical practice for use in a therapeutic combination for therapeutic treatment (including prophylactic treatment) of hyperproliferative disorders in mammals including humans. The invention provides a pharmaceutical composition comprising a Formula I or II compound in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a Formula I or II compound having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations of the invention will be dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the Formula I or II compound administered orally or parenterally per dose will be in the range of about 0.01-1000 mg/kg, namely about 0.1 to 20 mg/kg of patient body weight per day, with the typical initial range of compound used being 0.3 to 15 mg/kg/day. The dose of the Formula I or II compound and the dose of the chemotherapeutic agent to be administered may range for each from about 1 mg to about 1000 mg per unit dosage form, or from about 10 mg to about 100 mg per unit dosage form. The doses of Formula I or II compound and the chemotherapeutic agent may administered in a ratio of about 1:50 to about 50:1 by weight, or in a ratio of about 1:10 to about 10:1 by weight.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate)microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

Sustained-release preparations of Formula I and II compounds may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D(-)3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I or II and/or chemotherapeutic agent suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of a compound of Formula I or II and/or a chemotherapeutic agent. The amount of compound of Formula I or II and the amount of chemotherapeutic agent may be formulated in a pill, capsule, solution or suspension as a combined formulation. Alternatively, the Formula I or II compound and the chemotherapeutic agent may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablet excipients of a pharmaceutical formulation of the invention may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the pharmaceutical formulations of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

Formula I and II compounds may be employed in combination with other chemotherapeutic agents for the treatment of a hyperproliferative disease or disorder, including tumors, cancers, and neoplastic tissue, along with pre-malignant and non-neoplastic or non-malignant hyperproliferative disorders. In certain embodiments, a compound of Formula I or II is combined in a pharmaceutical combination formulation, or dosing regimen as combination therapy, with a second compound that has anti-hyperproliferative properties or that is useful for treating the hyperproliferative disorder. The second compound of the pharmaceutical combination formulation or dosing regimen preferably has complementary activities to the compound of Formula I or II, and such that they do not adversely affect each other. Such compounds may be administered in amounts that are effective for the purpose intended. In one embodiment, a pharmaceutical formulation of this invention comprises a compound of Formula I or II, or a stereoisomer, geometric isomer, tautomer, solvate, metabolite, or pharmaceutically acceptable salt thereof, in combination with a chemotherapeutic agent such as described herein. In another embodiment, the therapeutic combination is administered by a dosing regimen wherein the therapeutically effective amount of a compound having Formula I or II is administered in a range from twice daily to once every three weeks (q3wk), and the therapeutically effective amount of the chemotherapeutic agent is administered in a range from twice daily to once every three weeks.

Therapeutic combinations of the invention include a product comprising a compound having Formula I or II, and a chemotherapeutic agent selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-1/2, HPPD, rapamycin, and lapatinib as a combined preparation for separate, simultaneous or sequential use in the treatment of a hyperproliferative disorder.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, a compound of Formula I or II, or a stereoisomer, geometric isomer, tautomer, solvate, metabolite, or pharmaceutically acceptable salt thereof, may be combined with a chemotherapeutic agent, including hormonal or antibody agents such as those described herein, as well as combined with surgical therapy and radiotherapy. Combination therapies according to the present invention thus comprise the administration of at least one compound of Formula I or II, or a stereoisomer, geometric isomer, tautomer, solvate, metabolite, or pharmaceutically acceptable salt thereof, and the use of at least one other cancer treatment method. The amounts of the compound(s) of Formula I or II and the other pharmaceutically active chemotherapeutic agent(s) and the relative timings of administration will be selected in order to achieve the desired combined therapeutic effect.

Administration of Pharmaceutical Compositions

The compounds of the invention may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices. Formulation of drugs is discussed in Remington's Pharmaceutical Sciences, 18$^{th}$ Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2$^{nd}$ Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 10 mg to about 1000 mg of Formula I or II compound. A typical dose may be about 100 mg to about 300 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

Methods of Treatment

Therapeutic combinations of: (1) a Formula I or II compound and (2) a chemotherapeutic agent are useful for treating diseases, conditions and/or disorders including, but not limited to, those characterized by activation of the PI3 kinase pathway. Accordingly, another aspect of this invention includes methods of treating diseases or conditions that can be treated by inhibiting lipid kinases, including PI3. In one embodiment, the method comprises administering to a mammal in need thereof a therapeutically effective amount of a compound of Formula I or II, or a stereoisomer, geometric isomer, tautomer, solvate, metabolite, or pharmaceutically acceptable salt thereof. Therapeutic combinations of (1) a Formula I or II compound and (2) a chemotherapeutic agent may be employed for the treatment of a hyperproliferative disease or disorder, including tumors, cancers, an dneoplastic tissue, along with pre-malignant and non-neoplastic or non-malignant hyperproliferative disorders. In one embodiment, a human patient is treated with a therapeutic combination and a pharmaceutically acceptable carrier, adjuvant, or vehicle, wherein the Formula I or II compound, or metabolite thereof, of said therapeutic combination is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Another aspect of this invention provides a pharmaceutical composition or therapeutic combination for use in the treatment of the diseases or conditions described herein in a mammal, for example, a human, suffering from such disease or condition. Also provided is the use of a pharmaceutical composition in the preparation of a medicament for the treatment of the diseases and conditions described herein in a warm-blooded animal, such as a mammal, for example a human, suffering from such disorder.

Metabolites of Compounds of Formula I and II

Also falling within the scope of this invention are the in vivo metabolic products of Formula I and II described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I and II, including compounds produced by a process comprising contacting a compound of this invention with a mammal for a period of time sufficient to yield a metabolic product thereof.

Metabolite products typically are identified by preparing a radiolabelled (e.g., $^{14}$C or $^{3}$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing Formula I and II compounds useful for the treatment of the diseases and disorders described above is provided. In one embodiment, the kit comprises a container comprising a compound of Formula I, or a stereoisomer, geometric isomer, tautomer, solvate, metabolite, or pharmaceutically acceptable salt thereof. The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II or a formulation thereof which is effective for treating the condition and may have a sterile access port (for example, the container may be an intravenous solution bag or a vial having a stopper pierceable by a hypodermic injection needle). At least one active agent in the composition is a compound of Formula I or II. The label or package insert indicates that the composition is used for treating the condition of choice, such as cancer. In one embodiment, the label or package inserts indicates that the composition comprising a compound of Formula I or II can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I or II and, if present, the second pharmaceutical formulation. For example, if the kit comprises a first composition comprising a compound of Formula I or II and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I or II, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I or II contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of Formula I or II and a second therapeutic agent, i.e. the chemotherapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

GENERAL PREPARATIVE PROCEDURES

General Procedure A-1

Suzuki Coupling

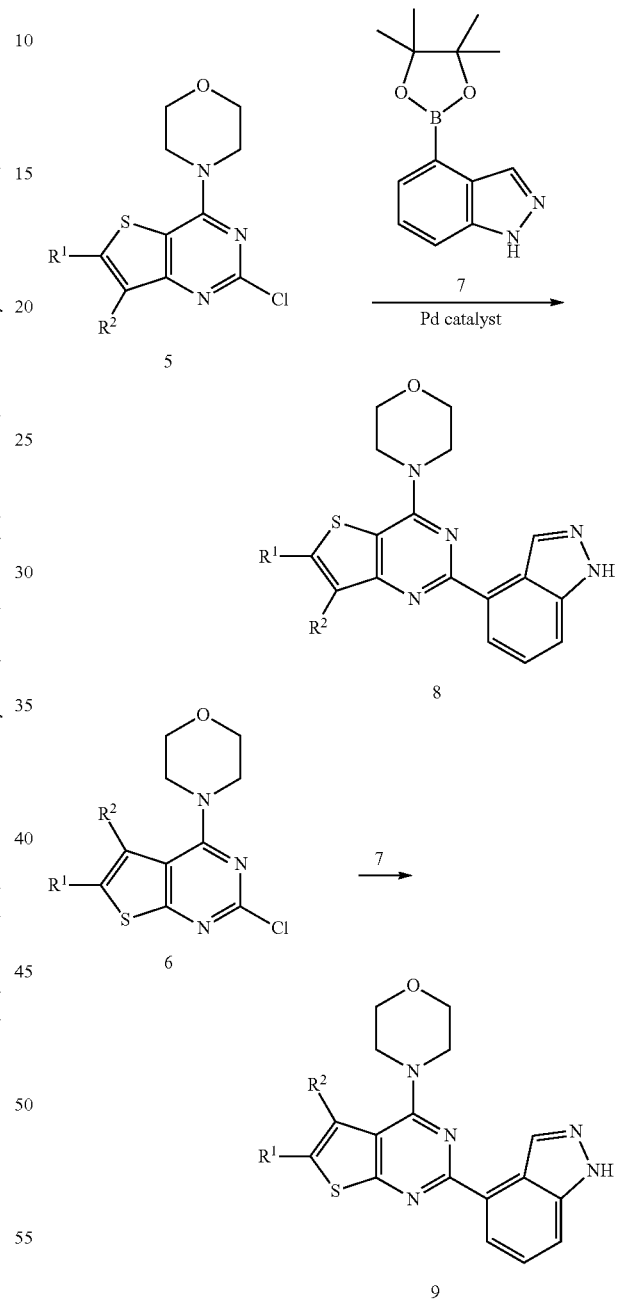

The Suzuki-type coupling reaction is useful to attach a fused bicyclic heterocycle or heteroaryl at the 2-position of the pyrimidine ring (see Scheme 4). Generally, substituted 2-chloro-4-morpholinothieno[3,2-d]pyrimidine 5 or substituted 2-chloro-4-morpholinothieno[2,3-d]pyrimidine 6 may be combined with 1.5 equivalents of 4-(4,4,5,5-tetramethyl-1,3,2-dioxaborolan-2-yl)1H-indazole 7, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example with a tetrahydropyranyl group. See compound 40. In some cases potassium acetate was used in place of sodium carbonate to adjust the pH of the aqueous layer. The reaction was then heated to about 140-150° C. under pressure in a Biotage Optimizer microwave reactor (Biotage, Inc.) for 10 to 30 minutes. The contents are extracted with ethyl acetate, or another organic solvent. After evaporation of the organic layer the product, 8 or 9, may be purified on silica or by reverse phase HPLC.

General Procedure A-2

Suzuki Coupling

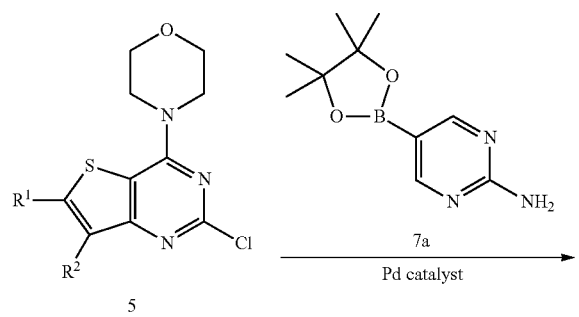

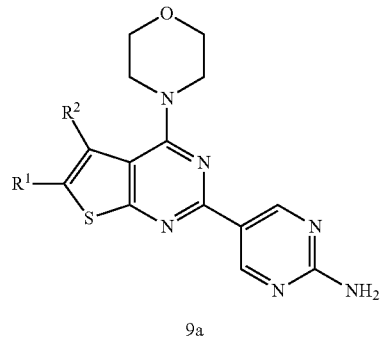

9a

The Suzuki-type coupling reaction is useful to attach a monocyclic heteroaryl at the 2-position of the pyrimidine ring (see Scheme 4). Generally, substituted 2-chloro-4-morpholinothieno[3,2-d]pyrimidine 5 or substituted 2-chloro-4-morpholinothieno[2,3-d]pyrimidine 6 may be combined with 1.5 equivalents of 5-(4,4,5,5-tetramethyl-1,3,2-dioxaborolan-2-yl)pyrimidin-2-amine 7a, and dissolved in 3 equivalents of sodium or potassium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the pinacol boronic ester indicated. Also alternatively, the nitrogen of the pyrimidin-2-amine may be protected, for example with a tetrahydropyranyl group. In some cases potassium acetate was used in place of sodium carbonate to adjust the pH of the aqueous layer. The reaction was then heated, for example to about 100-150° C. under pressure in a Biotage Optimizer microwave reactor (Biotage, Inc.) for 10 to 30 minutes. The contents are extracted with ethyl acetate, or another organic solvent. After evaporation of the organic layer the product, 8a or 9a, may be purified on silica or by reverse phase HPLC.

General Procedure B

Amide Coupling

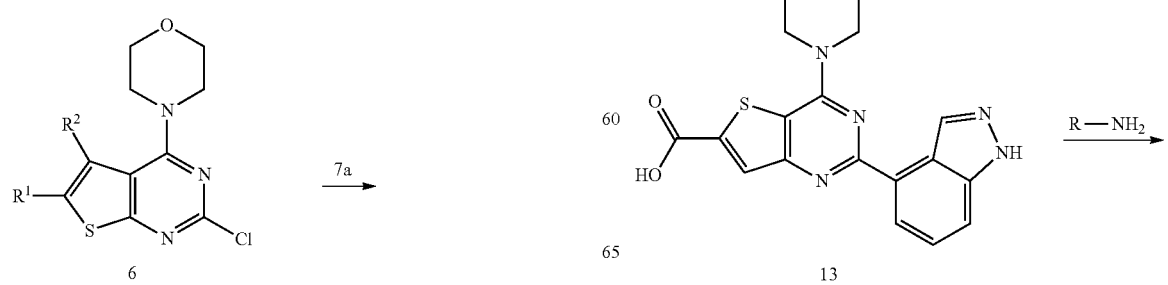

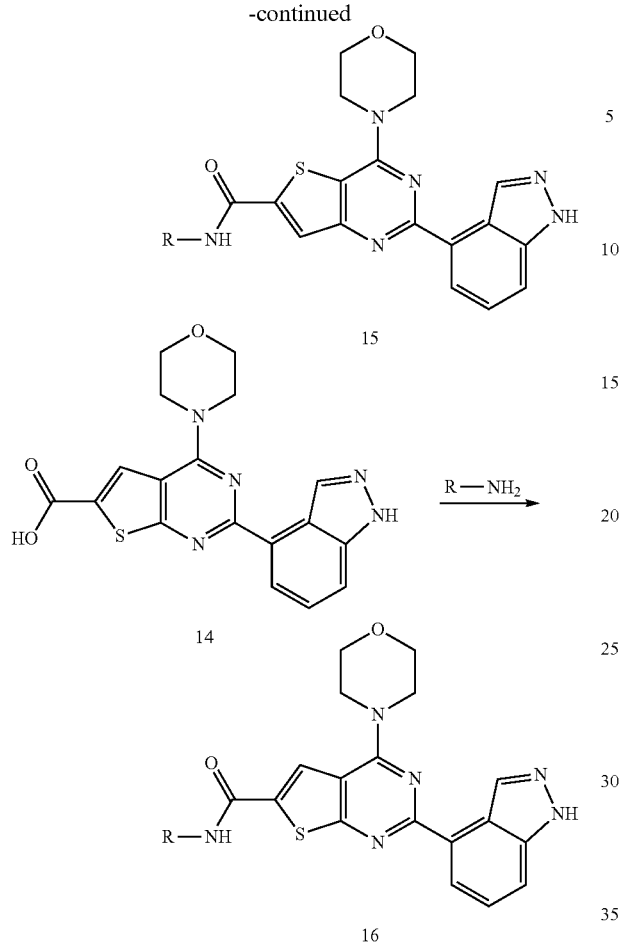

2-(1H-Indazol-4-yl)-4-morpholinothieno[3,2-d]pyrimidine-6-carboxylic acid 13 or 2-(1H-indazol-4-yl)-4-morpholinothieno[2,3-d]pyrimidine-6-carboxylic acid 14 is treated with 1.5 eq HATU, 3 eq of alkylamine and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15 or 16.

General Procedure B-1

Amide Coupling

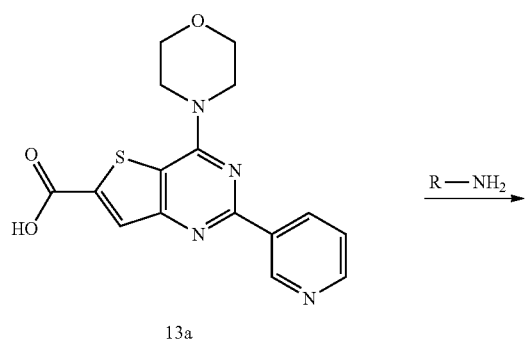

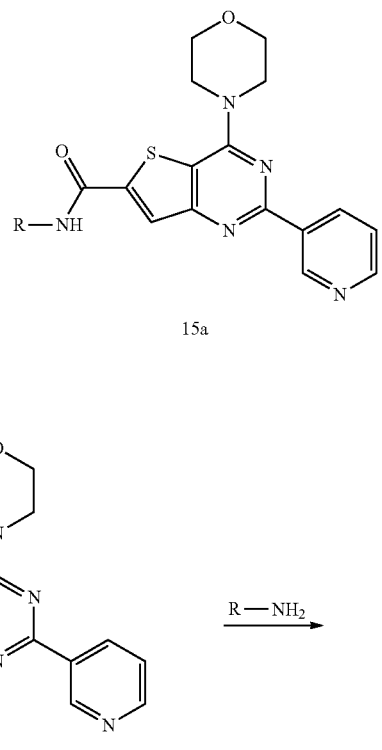

4-Morpholino-2-(pyridin-3-yl)thieno[3,2-d]pyrimidine-6-carboxylic acid 13a or 4-morpholino-2-(pyridin-3-yl)thieno[2,3-d]pyrimidine-6-carboxylic acid 14a is treated with 1.5 eq HATU, 3 eq of an alkylamine (R—NH$_2$) and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15a or 16a.

81

General Procedure B-2

Amide Coupling

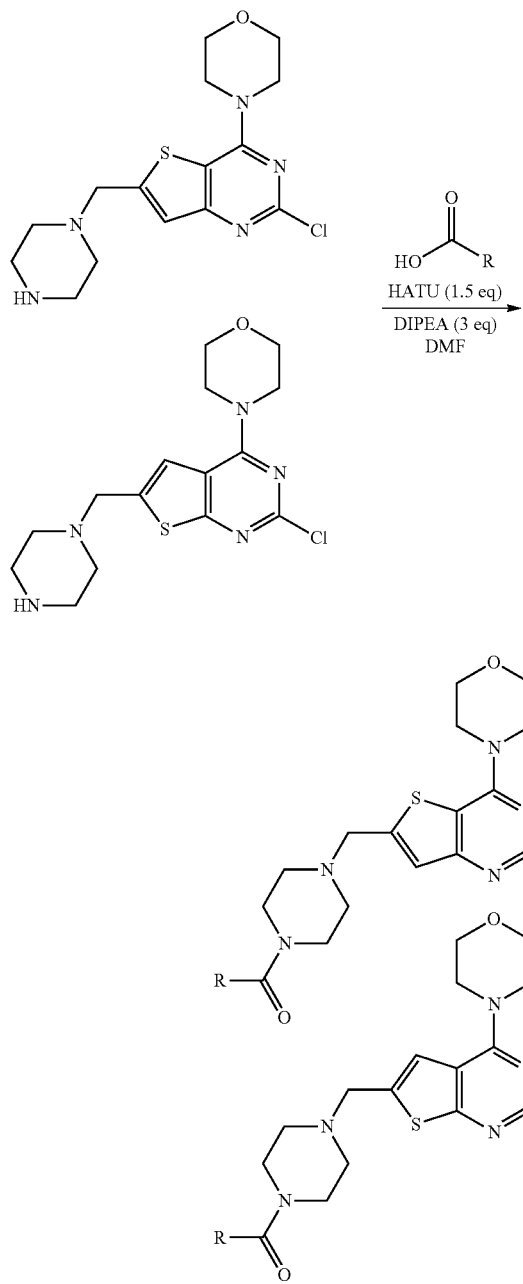

2-Chloro-4-morpholino-6-((piperazin-1-yl)methyl)thieno[3,2-d]pyrimidine or 2-chloro-4-morpholino-6-((piperazin-1-yl)methyl)thieno[2,3-d]pyrimidine is treated with 1.5 eq HATU, 3 eq of carboxylic acid (RCO$_2$H) and 3 eq of DIPEA in DMF to approximately 0.1 M concentration. The reaction is stirred until complete and extracted in ethyl acetate with saturated bicarbonate solution one time. The organic layer is dried, filtered and concentrated to yield the crude intermediate.

82

General Procedure B-3

Reductive Amination

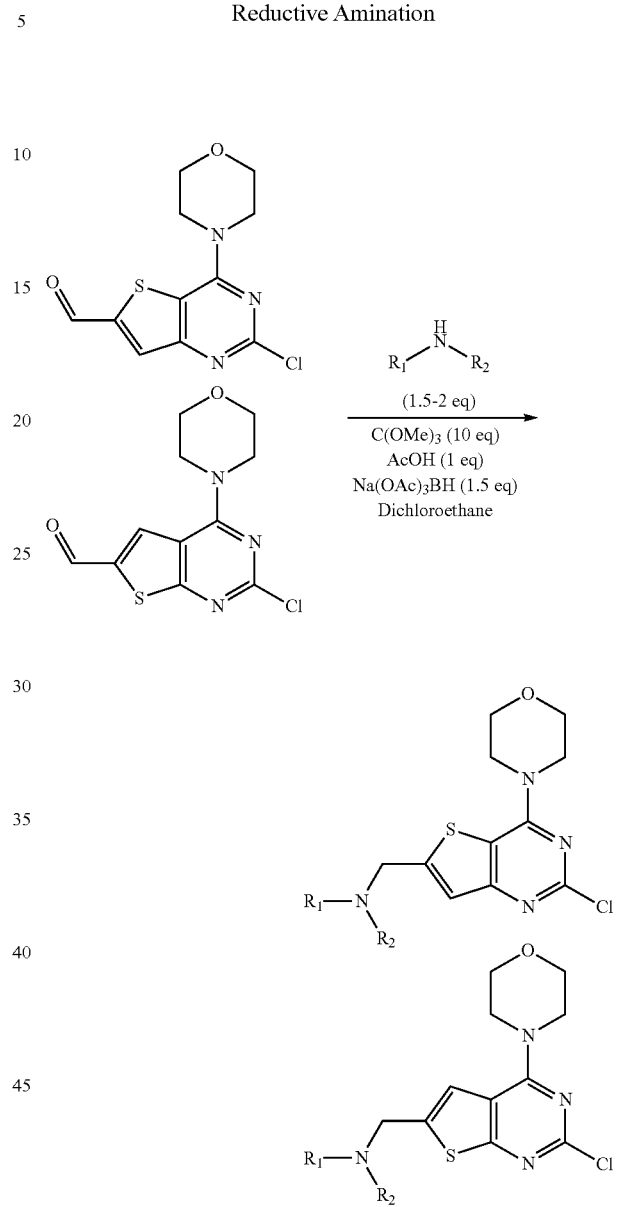

2-Chloro-4-morpholinothieno[3,2-d]pyrimidine-6-carbaldehyde 10 or 2-chloro-4-morpholinothieno[2,3-d]pyrimidine-6-carbaldehyde 33 was dissolved to a 0.2 M concentration in dichloroethane. To this solution was added 1.5 to 2.0 equivalents of an amine (R$^1$R$^2$NH), 10 equivalents of trimethylorthoformate, and 1 equivalent of acetic acid. The mixture was allowed to stir for 2-6 hours prior to adding 1.5 equivalents of sodium triacetoxyborohydride. Following 12 to 16 hours of stirring the reaction was poured into saturated sodium bicarbonate and extracted several times with ethyl acetate to give the reductive amination intermediate which was either purified on silica gel or used crude in the next reaction.

General Procedure C

Sulfonamide Formation

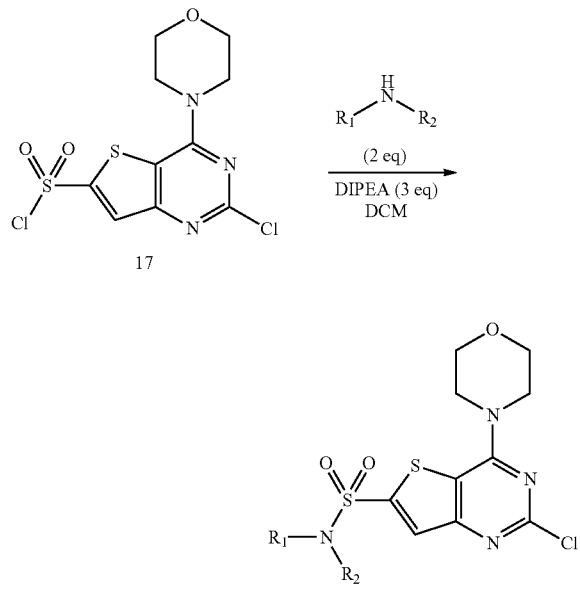

2-Chloro-4-morpholinothieno[3,2-d]pyrimidine-6-sulfonyl chloride 17 was suspended in 1 mL of DCM before addition of 2 eq of amine and 3 eq of DIPEA. The reactions were monitored by LCMS until complete. The crude reaction mixtures were diluted with ethyl acetate, extracted with saturated ammonium chloride and back-extracted once with ethyl acetate. The organic layers were combined and concentrated to dryness. The crude sulfonamide intermediates 18 were used directly in the subsequent Suzuki couplings.

General Procedure D

Alcohol Synthesis

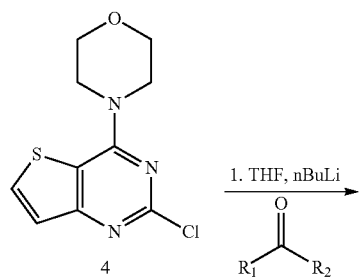

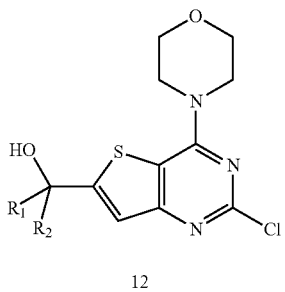

2-Chloro-4-morpholinothieno[3,2-d]pyrimidine 4 was suspended to a 0.2 molar concentration in THF and cooled to −50° C. in a dry ice/acetonitrile bath before adding 2 equivalents of 2.5 M nBuLi in hexanes. After 15 min 3.0 molar equivalents of a cyclic or acyclic ketone was added to the solution. The reaction continued to stir at −50° C. for 1 h and then in most cases was allowed to come to 0° C. When the reaction was complete by TLC or mass spec. it was quenched into a saturated ammonium chloride solution and extracted two times with EtOAc. The organic layer was concentrated and either used as a crude mixture, purified on silica, or the product 12 could be dissolved in a minimal amount of acetonitrile and filtered to remove remaining starting material 4.

General Procedure E

Removal of t-butoxylcarbonyl (BOC) Group

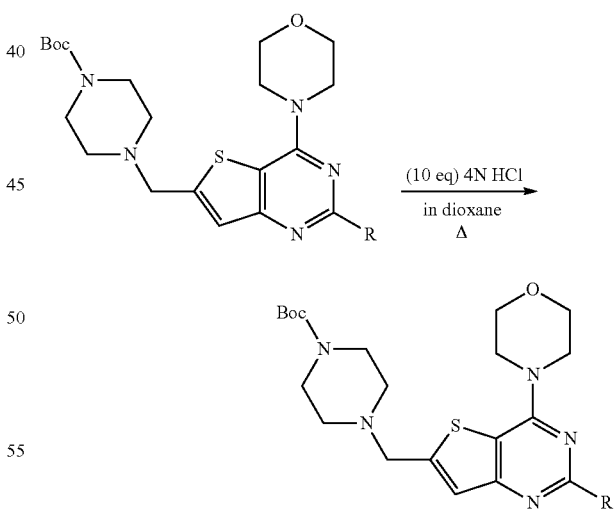

Ten or more equivalents of 4N HCl in dioxane, with or without dichloromethane as a co-solvent, are added to the starting material (general scheme shown above but similar scaffolds also used). Heating up to 40° C. for several hours is occasionally required to remove the Boc group. The reaction is concentrated to dryness and may be used crude in subsequent reactions.

General Procedure F Suzuki Coupling Reactions in One Pot

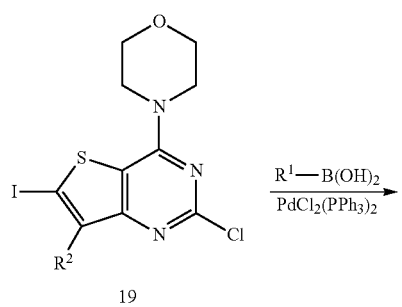

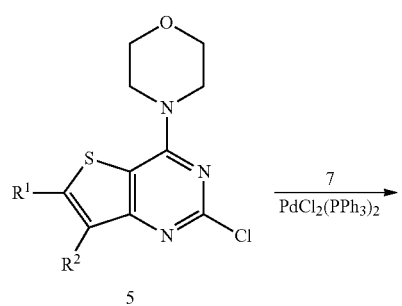

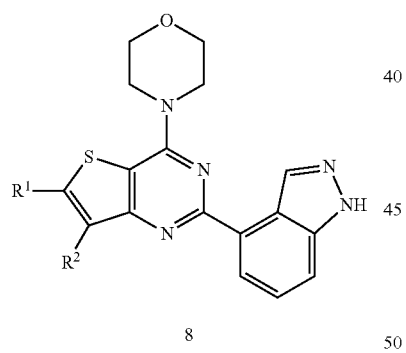

2-Chloro-6-iodo-4-morpholinothieno[3,2-d]pyrimidine 19 (1 eq), phenylboronic acid or heterocycleboronic acid ($R^1$—$B(OH)_2$, 1.1 eq) and bis(triphenylphosphine)palladium (II) dichloride (0.1 eq) in 1M $Na_2CO_3$ aqueous solution (3 eq) and acetonitrile (3 eq) was heated to 100° C. in a sealed microwave reactor for 10 to 40 min to give 5. Upon completion, 4-(4,4,5,5-tetramethyl-1,3,2-dioxaborolan-2-yl)-1H-indazole 7 (1.3 eq) and bis(triphenylphosphine)palladium(II) dichloride (0.1 eq) were added in the same pot. The reaction mixture was heated to 150° C. in a sealed microwave reactor for 10 to 15 min. The mixture was extracted with ethyl acetate (3×5 mL). The combined organic layers were concentrated to yield crude 8.

General Procedure G

Amide Coupling Reaction

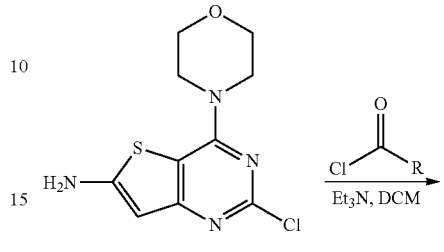

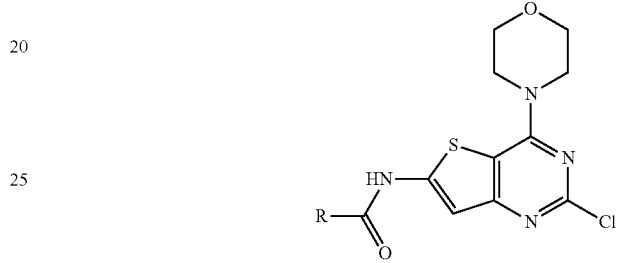

2-Chloro-4-morpholinothieno[3,2-d]pyrimidin-6-amine 22 (1 eq), Acid chloride (1.5~2 eq) and triethylamine (2 eq) in dichloromethane was stirred. The reaction was monitored by LC/MS until complete. The mixture was evaporated to give the crude amide 23, which was directly used for the next step reaction without purification.

General Procedure H

Preparation of Acetamide, Benzamidines, and Sulfonamides

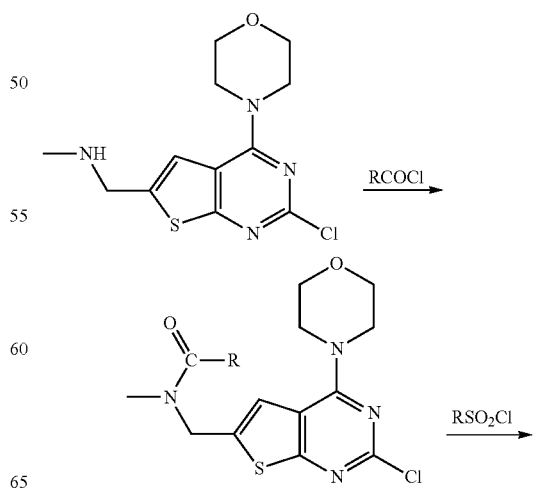

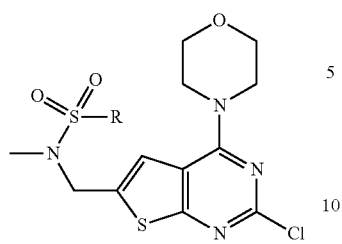

To a 0.25 to 0.40 M solution of 1-(2-chloro-4-morpholinothieno[2,3-d]pyrimidin-6-yl)-N-methylmethanamine in DCM cooled to 0° C. was added 1.5 eq. of TEA, followed by the drop-wise addition of 1.0 to 1.5 eq. of an alkyl or aryl-acid chloride or a sulfonylchloride, diluted in DCM. The reaction is stirred at ambient temperature and monitored for completeness by LCMS. After completion, the reaction volume is increased with DCM, and dilute aqueous sodium bicarbonate is added to the solution. The organic and aqueous layers are separated. Finally, the organic layer is washed with brine and dried (MgSO$_4$). The dried organic solution is concentrated in vacuo and the product is purified by silica chromatography if necessary.

General Procedure I

Amide Coupling Reaction for Benzenamine

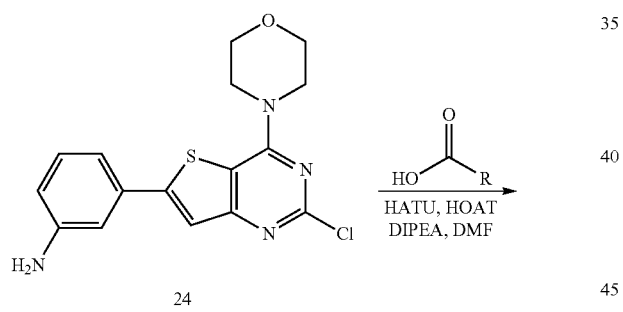

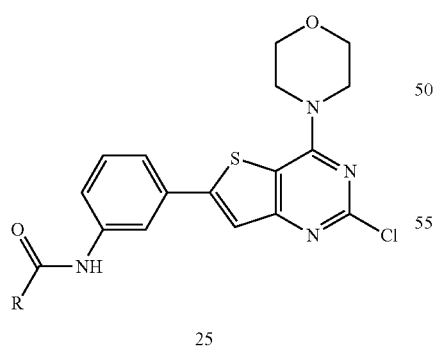

3-(2-Chloro-4-morpholinothieno[3,2-d]pyrimidin-6-yl)benzenamine 24 (1 eq), carboxylic acid (1.5 eq), 1-hydroxy-7-azabenzotriazole (0.2 eq), O-(7-azabenzotriazol-1-yl)-(N,N,N',N'-tetramethyluronium hexafluorophosphate (HATU, 1.5 eq), and N,N-diisopropylethylamine (2.5 eq) in DMF was stirred at room temperature. The reaction was monitored by LC/MS until complete. The reaction mixture was diluted with ethyl acetate, washed with saturated sodium bicarbonate and brine. The organic layer was dried over MgSO$_4$, filtered and evaporated to yield amide product 25.

General Procedure J

6-Iodo Displacement and 2-Suzuki Coupling

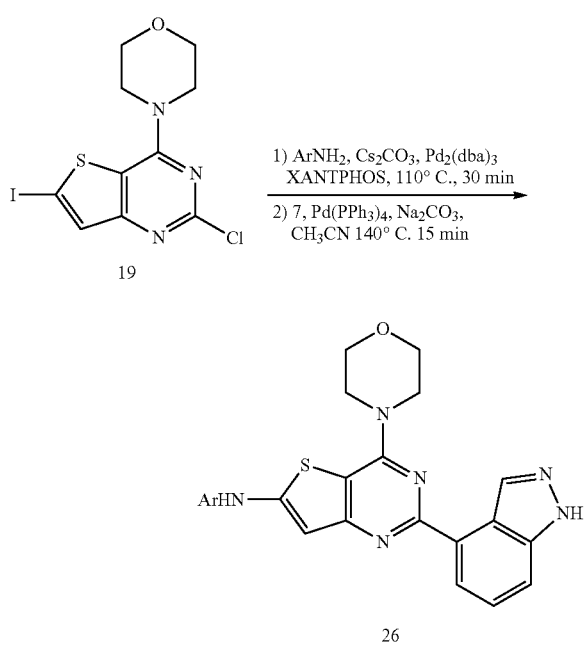

To a solution of 2-chloro-6-iodo-4-morpholinothieno[3,2-d]pyrimidine 19 (0.05 g, 0.13 mmol) in DMF (1.00 mL) was added the appropriate aniline (200 mol %), Cs—$_2$CO$_3$ (50 mol %), Pd$_2$(dba)$_3$ (5 mol %), and XANTPHOS (10 mol %). The reaction was heated to 110° C. under pressure in a Biotage optimizer microwave reactor for 30 min. The resulting solution was concentrated in vacuo to give 26, after following General Procedure A.

General Procedure K

6-Aminoalkyl Acylation and 2-Suzuki Coupling

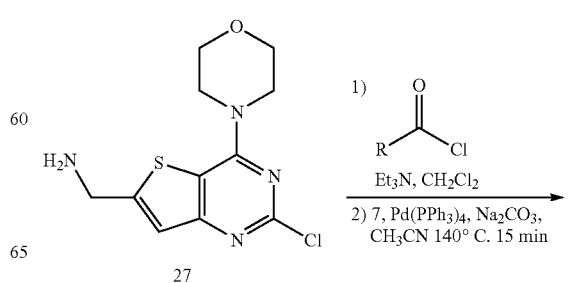

89

-continued

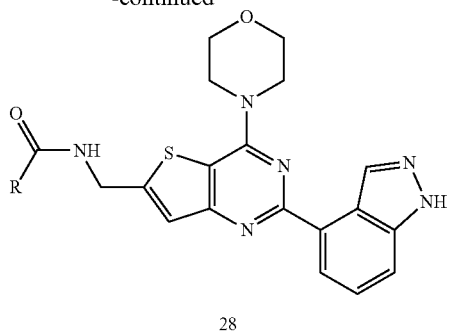

28

To a solution of (2-chloro-4-morpholinothieno[3,2-d]pyrimidin-6-yl)methanamine 27 (50 mg, 0.2 mmol) in $CH_2Cl_2$ (4 mL) was added $Et_3N$ (84 μL, 0.6 mmol) and the appropriate acid chloride or HCl salt thereof (0.3 mmol). The reaction stirred 18-48 hr at room temperature before being quenched with water. The aqueous layer was extracted with EtOAc. The combined organics were dried over $Na_2SO_4$ and concentrated in vacuo. The 2-chloro crude product was coupled with boronate reagent 7 and palladium catalyst according to General Procedure A to give 28 which was purified by reversed phase HPLC purification.

Alternatively, to a solution of (2-chloro-4-morpholinothieno[3,2-d]pyrimidin-6-yl)methanamine 27 (111 mg, 0.39 mmol) in DMF (5 mL) was added 2,6-lutidine (48.2 μL, 0.41 mmol) and the appropriate acid chloride or HCl salt thereof (0.39 mmol). The reaction stirred 18-72 hr at room temperature before being quenched with water. The aqueous layer was extracted with EtOAc. The combined organics were dried over $MgSO_4$ and concentrated in vacuo. The 2-chloro crude product was coupled with boronate reagent 7 and palladium catalyst according to General Procedure A to give 20 mg of 28 which was purified by reversed phase HPLC purification.

General Procedure L

Amine Substitution on Fluoropyridine

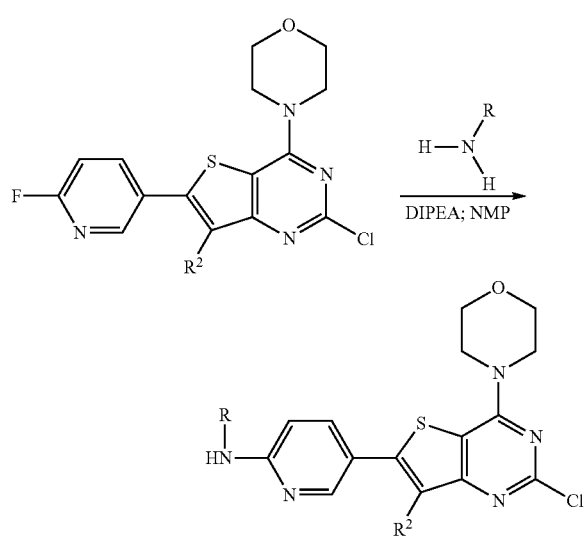

90

A mixture of 2-chloro-6-(6-fluoropyridin-3-yl)-4-morpholinothieno[3,2-d]pyrimidine or 2-chloro-6-(6-fluoropyridin-3-yl)-4-morpholinothieno[2,3-d]pyrimidine compound, about four equivalents of a primary or secondary amine (R=H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl), and about two eq. diisopropylethylamine in N-methylpyrrolidine (~0.1M) is heated to about 130-140° C. in a sealed microwave reactor for 10~40 min, followed by removal of volatiles under high vacuum. The crude mixture is purified by flash chromatography to give intermediate 2-chloro-6-(6-aminopyridin-3-yl)-4-morpholinothieno[3,2-d]pyrimidine or 2-chloro-6-(6-aminopyridin-3-yl)-4-morpholinothieno[2,3-d]pyrimidine compound, which may be Suzuki coupled with a monocyclic heteroaryl, fused bicyclic heterocycle or heteroaryl boronate reagent following General Procedure A.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Example 1

2,4-Dichloro-thieno[3,2-d]pyrimidine 3

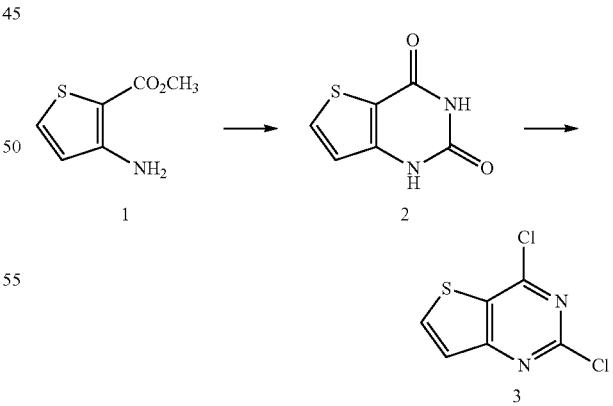

A mixture of methyl 3-amino-2-thiophenecarboxylate 1 (13.48 g, 85.85 mmol) and urea (29.75 g, 5 eq.) was heated at 190° C. for 2 hours. The hot reaction mixture was poured onto sodium hydroxide solution and any insoluble material was removed by filtration. The mixture was then acidified (HCl, 2N) to yield 1H-thieno[3,2-d]pyrimidine-2,4-dione 2 as a white precipitate, which was collected by filtration and air dried (9.49 g, 66%). $^1$H NMR 400 MHz, d$_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione 2 (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine 3 as a white solid (8.68 g, 75%). $^1$H NMR (400 MHz, CDCl$_3$) 7.56 (1H, d, J=5.5 Hz), 8.13 (1H, d, J=5.5 Hz).

Example 2

2-Chloro-4-morpholin-4-yl-thieno[3,2-d]pyrimidine 4

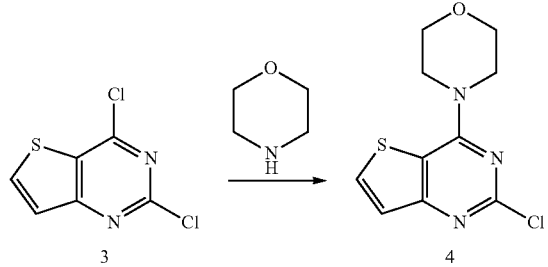 [SMILES: Clc1nc(Cl)c2sccc2n1 ; C1COCCN1 ; Clc1nc(N2CCOCC2)c2sccc2n1]

A mixture of 2,4-dichloro-thieno[3,2-d]pyrimidine 3, (8.68 g, 42.34 mmol), morpholine (8.11 mL, 2.2 eq.) and MeOH (150 mL) was stirred at room temperature for 1 h. The reaction mixture was then filtered, washed with water and MeOH, to yield 2-chloro-4-morpholin-4-yl-thieno[3,2-d]pyrimidine 4 as a white solid (11.04 g, 100%). $^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

Example 3

2-Chloro-4-morpholin-4-yl-thieno[3,2-d]pyrimidine-6-carbaldehyde 10

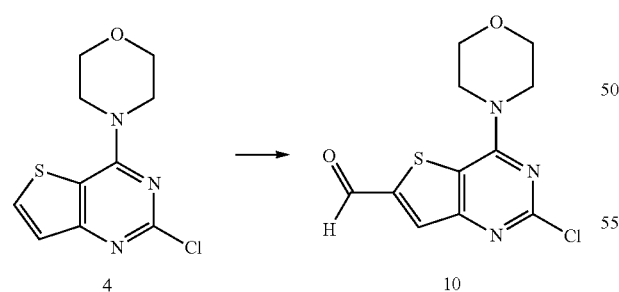

To a suspension of 2-chloro-4-morpholin-4-yl-thieno[3,2-d]pyrimidine 4 (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 µL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield 2-chloro-4-morpholin-4-yl-thieno[3,2-d]pyrimidine-6-carbaldehyde 10 (1.50 g, 77%). $^1$H NMR (400 MHz, d$_6$-DMSO) 3.76 (4H, t, J=4.9), 3.95 (4H, t, J=4.9), 8.28 (1H, s), 10.20 (1H, s).

Example 3a 2-chloro-4-morpholinothieno[2,3-d]pyrimidine-6-carbaldehyde 33

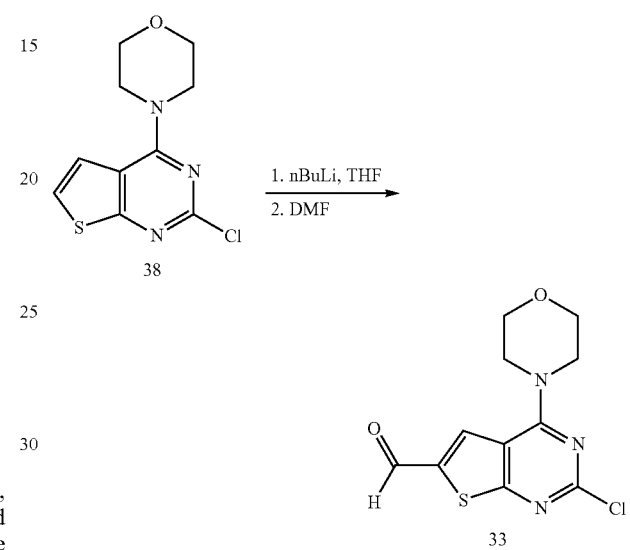

To a suspension of 2-chloro-4-morpholinothieno[2,3-d]pyrimidine 38 (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 µL, 1.5 eq.) was added. The reaction mixture was stirred for 1 h at −78° C. and then warmed slowly to room temperature. After a further 2 h at room temperature the reaction mixture was poured onto ice/water yielding a yellow precipitate which was collected by filtration and air-dried to yield 2-chloro-4-morpholinothieno[2,3-d]pyrimidine-6-carbaldehyde 33 (1.50 g) MS (Q1) 284 (M+).

Example 3b

2-Chloro-6-iodo-7-methyl-4-morpholinothieno[3,2-d]pyrimidine 41

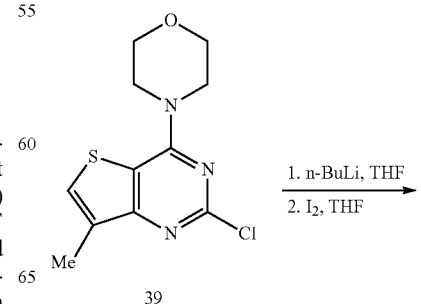

-continued

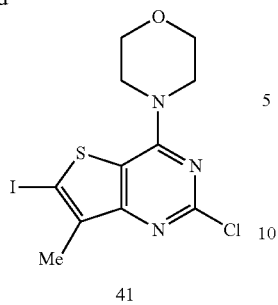

41

To a solution of 2-chloro-7-methyl-4-morpholinothieno[3,2-d]pyrimidine 39 (3.0 g, 11.1 mmol; prepared according to the procedure for the synthesis of 2-chloro-4-morpholin-4-yl-thieno[3,2-d]pyrimidine but commencing with 3-amino-4-methyl-thiophene-2-carboxylic acid ethyl ester) in THF (60 mL) at −78° C. was added n-BuLi (8.9 mL, 2.5 M in Et$_2$O). The resulting slurry was warmed to −40° C. and stirred 50 min. The reaction mixture was then cooled to −78° C. and a solution of I$_2$ (5.6 g, 22.2 mmol) in THF (30 mL) was added. The solution was warmed to room temperature and stirred 5 h. The reaction was quenched by the addition of water. The organic layer was separated and the aqueous layer was extracted with CH$_2$Cl$_2$. The combined organics were washed with saturated aqueous Na$_2$S$_2$O$_3$, dried over Na$_2$SO$_4$, filtered, and concentrated in vacuo to provide 2-chloro-6-iodo-7-methyl-4-morpholinothieno[3,2-d]pyrimidine 41 (3.8 g, 84% yield).

Example 3c 4-(2-Chloro-6-(piperazin-1-ylmethyl)thieno[3,2-d]pyrimidin-4-yl)morpholine 30

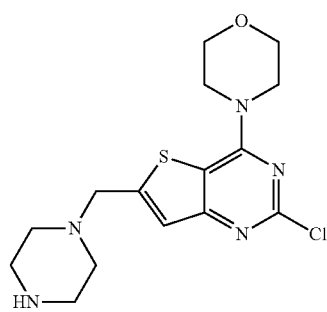

30

A mixture of 2-chloro-4-morpholin-4-yl-thieno[3,2-d]pyrimidine-6-carbaldehyde 10 (3.5 g), 1-BOC-piperazine (2.76 g) and trimethylorthoformate (4.05 mL) was stirred in 1,2-dichloroethane (300 mL) for 1 hr at room temperature. To this was added sodium triacetoxyborohydride (3.92 g) and the reaction mixture was stirred for 24 hours at room temperature. The mixture was then quenched with brine, extracted with dichloromethane, dried (MgSO$_4$) and the solvent removed in vacuo. The residue was purified using flash chromatography to yield 4-(2-chloro-4-morpholin-4-yl-thieno[3,2-d]pyrimidin-6-ylmethyl)-piperazine-1-carboxylic acid tert-butyl ester (3.4 g). Treatment with HCl in dichloromethane/methanol yielded 4-(2-chloro-6-(piperazin-1-ylmethyl)thieno[3,2-d]pyrimidin-4-yl)morpholine 30.

Example 3d (2-chloro-4-morpholinothieno[2,3-d]pyrimidin-6-yl)-N-methylmethanamine 34

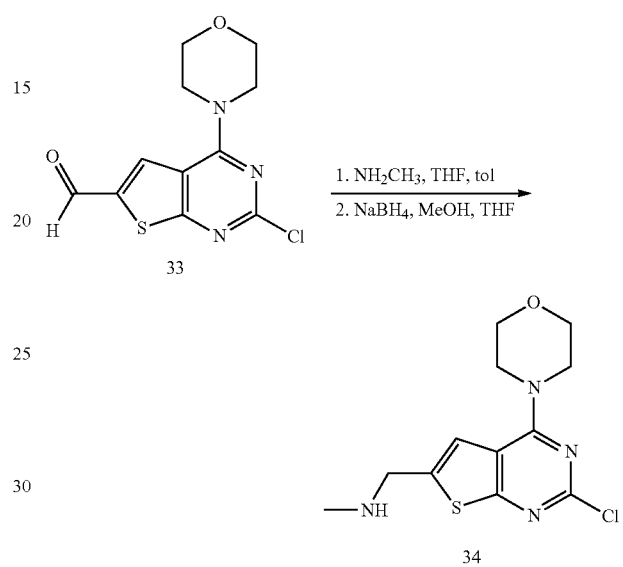

To 2-chloro-4-morpholinothieno[2,3-d]pyrimidine-6-carbaldehyde 33 (2.0 g) in 50 mL toluene and 50 mL THF was added 20 mL of 40% methylamine in H$_2$O. The reaction mixture was stirred at room temp under N$_2$ for 24 hours. The solvents were removed in vacuo and the residue was dissolved in 50 mL MeOH and 50 mL THF and the NaBH$_4$ added portion-wise. This reaction mixture was stirred at room temp under N$_2$ for 24 hours and complete reaction was confirmed by LCMS. The solvents were removed in vacuo and the crude product purified by flash chromatography (EtOAc/EtOH) to give 1.12 g 34 (53% yield). MS (Q1) 300 (M+).

Example 3e (2-chloro-4-morpholinothieno[3,2-d]pyrimidin-6-yl)-N-methylmethanamine 35

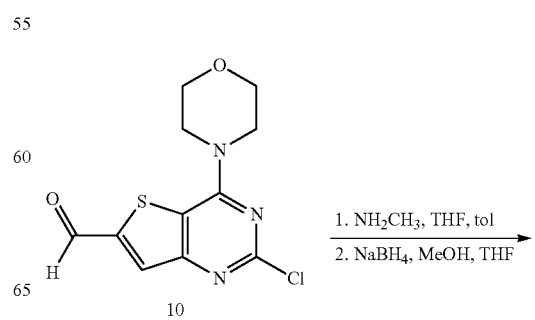

Example 3f (2-chloro-7-methyl-4-morpholinothieno[3,2-d]pyrimidin-6-yl)-N-methylmethanamine 37

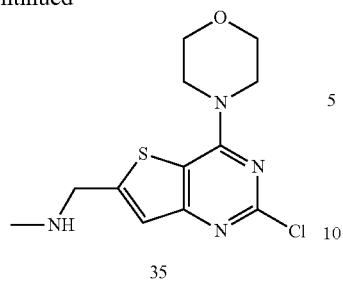

2-Chloro-4-morpholinothieno[3,2-d]pyrimidine-6-carbaldehyde 10 (2.0 g) was dissolved in 50 mL toluene and 50 mL THF followed by the addition of 20 mL of 40% methylamine in $H_2O$. The reaction mixture was stirred at room temp under $N_2$ for 24 hours. The solvents were removed in vacuo and the residue was dissolved in 50 mL methanol and 50 mL THF and the $NaBH_4$ added portion-wise. This reaction mixture was stirred at room temp under $N_2$ for 24 hours and complete reaction was confirmed by LCMS. The solvents were removed in vacuo and the crude product purified by flash chromatography (EtOAc/EtOH) to give 1.12 g 35 (53% yield). MS (Q1) 300 (M+).

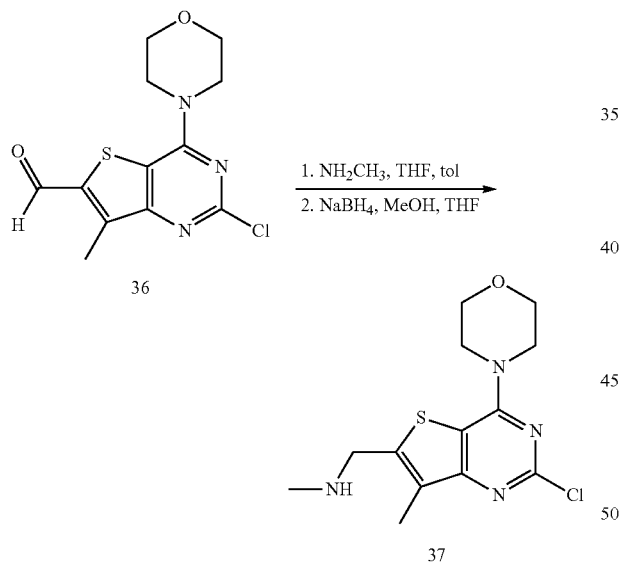

2-Chloro-7-methyl-4-morpholinothieno-[3,2-d]pyrimidine-6-carbaldehyde 36 was dissolved in 20 mL toluene and 20 mL THF followed by the addition of 15 mL 40% methylamine in $H_2O$ and the reaction was stirred for 24 hours. The reaction mixture was concentrated in vacuo and the residue dissolved in 30 mL methanol and 30 mL THF followed by the addition of $NaBH_4$. The reaction was stirred at room temp for at least 24 hours and product formation was confirmed by LCMS. The solvents were removed in vacuo and the crude product purified by flash chromatography to give 2.53 g (2-chloro-7-methyl-4-morpholinothieno[3,2-d]pyrimidin-6-yl)-N-methylmethanamine 37 (70% yield) MS (Q1) 314 (M)+

Example 4

4-(2-Chloro-6-((4-(methylsulfonyl)piperazin-1-ypmethyl)thieno[3,2-d]pyrimidin-4-yl)morpholine 31

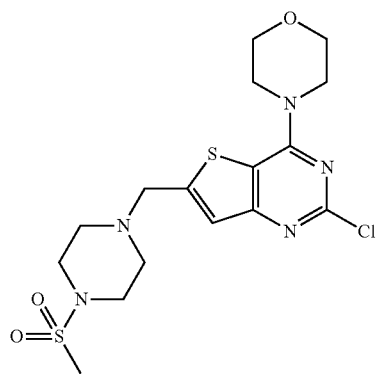

Reaction between N-BOC-piperazine and methane sulfonyl chloride in dichloromethane and triethylamine yielded 4-methanesulfonyl-piperazine-1-carboxylic acid tert-butyl ester. Cleavage of the BOC protecting group using HCl (2M) in dichloromethane yielded 1-methanesulfonyl-piperazine HCl salt.

A mixture of 2-chloro-4-morpholin-4-yl-thieno[3,2-d]pyrimidine-6-carbaldehyde 10 (1.00 g), 1-methanesulfonyl-piperazine (750 mg) and trimethylorthoformate (3.80 mL) was stirred in 1,2-dichloroethane (30 mL) for 6 hrs at room temperature. To this was added sodium triacetoxyborohydride (900 mg) and the reaction mixture was stirred for 24 hours at room temperature. The mixture was then quenched with brine, extracted with dichloromethane, dried ($MgSO_4$) and the solvent removed in vacuo. The residue was triturated with hot ethyl acetate to yield 4-(2-chloro-6-((4-(methylsulfonyl)piperazin-1-yl)methyl)thieno[3,2-d]pyrimidin-4-yl)morpholine 31 as a white solid (1.01 g).

Example 5

2-Chloro-6-(4-methanesulfonyl-piperazin-1-ylmethyl)-4-morpholin-4-yl-thieno[2,3-d]pyrimidine 32

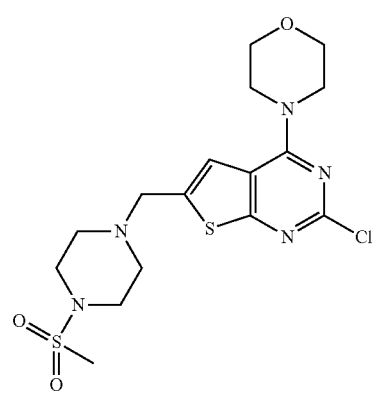

Reaction between 1-methanesulfonyl-piperazine HCL salt and 2-chloro-4-morpholin-4-yl-thieno[2,3-d]pyrimidine-6-carbaldehyde 33 using General Procedure C Yielded 2-chloro-6-(4-methanesulfonyl-piperazin-1-ylmethyl)-4-morpholin-4-yl-thieno[2,3-d]pyrimidine.

Example 6

4-(4,4,5,5-Tetramethyl-[1,3,2]dioxaborolan-2-yl)-1H-indazole 7-route 1

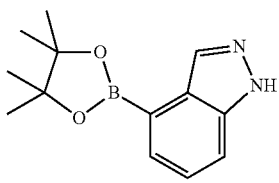

Intermediate 7 was prepared according to the methods of US 2008/0076768; US 2008/0076758; WO 2006/046031, incorporated by reference herein.

Example 8

1-(Tetrahydro-2H-pyran-2-yl)-4-(4,4,5,5-tetramethyl-1,3,2-dioxaborolan-2-yl)-1H-indazole 40

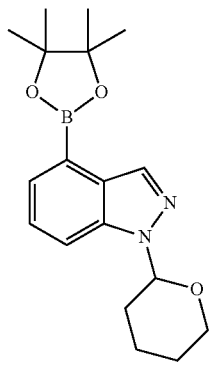

Intermediate 40 was prepared according to the methods of US 2008/0039459; US 2008/0076768; US 2008/0076758; WO 2006/046031, incorporated by reference herein.

Example 10

2-(1H-Indazol-4-yl)-4-morpholin-4-yl-thieno[3,2-d]pyrimidine-6-carbaldehyde 11

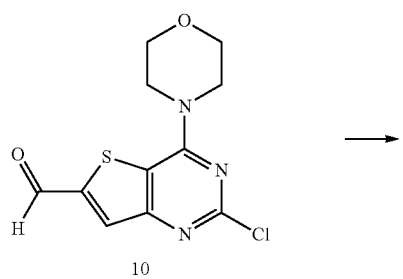

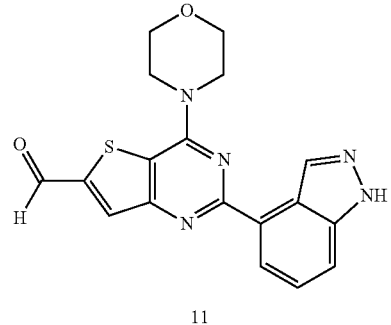

A mixture of 2-chloro-4-morpholin-4-yl-thieno[3,2-d]pyrimidine-6-carbaldehyde 10 (100 mg, 0.35 mmol), 4-(4,4,5,5-tetramethyl-[1,3,2]dioxaborolan-2-yl)-1H-indazole (70) (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 h and then partitioned between DCM and water, the organic layer was washed with brine, dried over magnesium sulfate, filtered and evaporated in vacuo. The resulting residue was purified using flash chromatography to yield 2-(1H-indazol-4-yl)-4-morpholin-4-yl-thieno[3,2-d]pyrimidine-6-carbaldehyde 11 (97 mg).

Example 11

4-(2-(1H-Indazol-4-yl)-6-((4-(methylsulfonyl)piperazin-1-yl)methyl)thieno[3,2-d]pyrimidin-4-yl)morpholine (Formula Ia, GDC-0941):

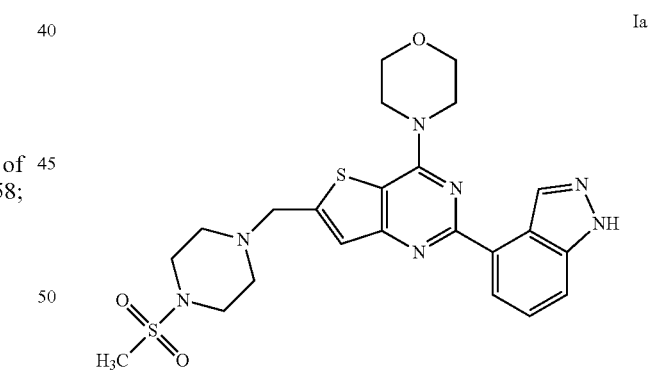

A mixture of 4-(2-chloro-6-((4-(methylsulfonyl)piperazin-1-yl)methyl)thieno[3,2-d]pyrimidin-4-yl)morpholine 31 from Example 4 (2.00 g), 4-(4,4,5,5-tetramethyl-[1,3,2]dioxaborolan-2-yl)-1H-indazole 7 (2.26 g), toluene (24 mL), ethanol (12 mL), water (6 mL), sodium carbonate (1.72 g) and PdCl$_2$(PPh$_3$)$_2$ (325 mg) was heated to 130° C. in the microwave for 90 minutes (US 2008/0076768; WO 2006/046031, incorporated by reference herein).

The reaction mixture was cooled, diluted with chloroform, washed with brine, dried (MgSO$_4$) and the solvent removed in vacuo. The residue was purified using flash chromatography (ethyl acetate then 5% ethyl acetate/methanol) and then trituration with ether yielded Formula Ia compound, GDC-0941

(1.4 g). MS data: (ESI+): MH+ 514. NMR data: (CDCl3): 2.67-2.71 (4H, m), 2.81 (3H, s), 3.29-3.33 (4H, m), 3.89 (2H, s), 3.89-3.93 (4H, m), 4.08-4.12 (4H, m),7.41 (1H, s), 7.51 (1H, t, J=7.2), 7.60 (1H, d, J=8.3), 8.28 (1H, d, J=7.5), 9.02 (1H, s), 10.10 (1H, br)

Example 12

4-(2-(1H-indazol-4-yl)-6-((4-(methylsulfonyl)piperazin-1-yl)methyl)thieno[2,3-d]pyrimidin-4-yl)morpholine (Formula IIa):

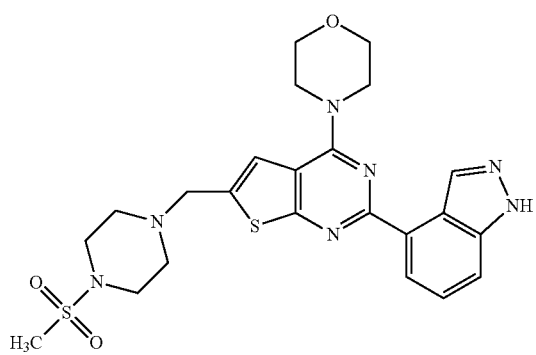

IIa

2-Chloro-6-(4-methanesulfonyl-piperazin-1-ylmethyl)-4-morpholin-4-yl-thieno[2,3-d]pyrimidine 32 from Example 5 was reacted with 4-(4,4,5,5-tetramethyl-[1,3,2]dioxaborolan-2-yl)-1H-indazole 7 and General Procedure A to give Formula IIa compound which was purified using flash chromatography (US 2008/0076758; WO 2006/046031, incorporated by reference herein). 400 MHz 1H NMR CDCl3: 2.67 (m, 4H, 2×CH2), 2.81 (s, 3H, CH3), 3.30 (m, 4H, 2×CH2), 3.83 (s, 2H, CH2), 3.92-3.94 (m, 4H, 2×CH2), 3.98-4.00 (m, 4H, 2×CH2), 7.17 (s, H, ArH), 7.50 (t, H, ArH, J=7.81 Hz), 7.59 (d, H, ArH, J=8.31 Hz), 8.31 (d, H, ArH, J=6.98 Hz), 10.12 (sbr, H, NH). MH+=514.10

Example 12a (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (Formula Ib):

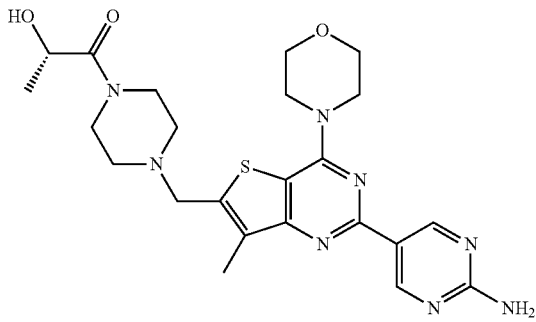

Ib

2-Chloro-7-methyl-4-morpholinothieno[3,2-d]pyrimidine-6-carbaldehyde 36 (495 mg) was reacted with Boc-piperazine via General Procedure B-3 to give tert-butyl 4-((2-chloro-7-methyl-4-morpholinothieno[3,2-d]pyrimidin-6-yl)methyl)piperazine-1-carboxylate.

Tert-butyl 44(2-chloro-7-methyl-4-morpholinothieno[3,2-d]pyrimidin-6-yl)methyl)piperazine-1-carboxylate (777 mg) was subjected to General Procedure E to give the HCl salt of 2-chloro-7-methyl-4-morpholino-6-((piperazin-1-yl)methyl)thieno[3,2-d]pyrimidine. The HCl salt of 2-chloro-7-methyl-4-morpholino-6-((piperazin-1-yl)methyl)thieno[3,2-d]pyrimidine (590 mg) was reacted with lactic acid via General Procedure B-2 to give (S)-1-(4-((2-chloro-7-methyl-4-morpholinothieno[3,2-d]pyrimidin-6-yl)methyl)piperazin-1-yl)-2-hydroxypropan-1-one.

(S)-1-(4-((2-Chloro-7-methyl-4-morpholinothieno[3,2-d]pyrimidin-6-yl)methyl)piperazin-1-yl)-2-hydroxypropan-1-one (60 mg) was reacted with 50 mg of 5-(4,4,5,5-tetramethyl-1,3,2-dioxaborolan-2-yl)pyrimidin-2-amine via General Procedure A-2 to give 10 mg of Formula Ib (WO 2008/070740, incorporated by reference). MS (Q1) 499.3 (M)+.

Example 13 p110α (alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM $MgCl_2$, 0.05% Chaps, and 1 mM DTT) to 10 mM $PIP_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume Proxiplates (PerkinElmer, Wellesley, Mass.) Fluorescence polarization values were plotted as a function of the protein concentration, and the $EC_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore (λex=530 nm; λem=590 nm) in 384-well black low volume proxi plates (PerkinElmer, Wellesley, Mass.) Fluorescence polarization values were plotted as a function of the antagonist concentration, and the $IC_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

Example 14

In Vitro Cell Proliferation Assay

Efficacy of Formula I or II compounds were measured by a cell proliferation assay employing the following protocol (Promega Corp. Technical Bulletin TB288; Mendoza et al (2002) Cancer Res. 62:5485-5488). The Cell-Titer Glo assay reagents and protocol are commercially available (Promega). The assay assesses the ability of compounds to get into cells and inhibit cell proliferation. The assay principle is the determination of the number of viable cells present by quantitating the ATP present. Cell-Titer Glo is the reagent used for this quantitation. It is a homogenous assay where addition of the Cell-Titer Glo results in cell lysis and generation of a luminescent signal through the luciferase reaction. The luminescent signal is proportional to the amount of ATP present.

Cells: see FIGS. 1A-C for cell lines and tumor type
DMSO and Media Plates: 96-well conical bottom polypropylene plates from Nunc (cat. #249946)
Cell Plates: 384-well black, clear bottom (microclear), TC plates with lid from Falcon (353962)
Cell Culture Medium: RPMI or DMEM high glucose, 10% Fetal Bovine Serum, 2 mM L-Glutamine, P/S
Cell Titer-Glo: Promega (cat. #G7572)
Procedure:
Day 1—Seed Cell Plates, Harvest cells, Seed PC3 cells at 1000 cells per 54 µl per well into 384 well Cell Plates for 3 days assay. Incubate O/N at 37 C, 5% CO2.
Day 2—Add Drug to Cells, Compound Dilution, DMSO Plates (serial 1:2 for 9 points), Add 20 ul compounds at 10 mM in the 2nd column of 96 well plate. Perform serial 1:2 across the plate (10 µl+10 µl 100% DMSO) for a total of 9 points using Precision. Media Plates (1:50 dilution) Add 147 µl of Media into all wells. Transfer 3 µl of DMSO+compound from each well in the DMSO Plate to each corresponding well on Media Plate using Rapidplate. For 2 drug combo studies, transfer one drug1.5 µl of DMSO+compound from each well in the DMSO Plate to each corresponding well on Media Plate using Rapidplate. Then, transfer another drug 1.5 ul to the medium plate.
Drug Addition to Cells, Cell Plate (1:10 dilution), Add 6 µl of media+compound directly to cells (54 µl of media on the cells already). Incubate 3 days at 37 C, 5% CO2 in an incubator that will not be opened often.
Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 µl Cell Titer Glo Reagent to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate robot (Zymark Corp., Hopkinton, Mass.). The diluted compounds were then added to quadruplicate wells in 384-well cell plates and incubated at 37 C and 5% CO2. After 4 days, relative numbers of viable cells were measured by luminescence using Cell-Titer Glo (Promega) according to the manufacturer's instructions and read on a Wallac Multilabel Reader (PerkinElmer, Foster City). EC50 values were calculated using Prism 4.0 software (GraphPad, San Diego). Drugs in combination assays were dosed starting at 4× EC50 concentrations. If cases where the EC50 of the drug was >2.5 µM, the highest concentration used was 10 µM. PI3K inhibitors and chemotherapeutic agents were added simultaneously or separated by 4 hours (one before the other) in all assays.

An additional exemplary in vitro cell proliferation assay includes the following steps:
1. An aliquot of 100 µl of cell culture containing about $10^4$ cells (see FIGS. 1A-C for cell lines and tumor type) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 15

FACS Annexin V/PI Assay

Cells ($2\times10^6$) were placed in a 10 cm tissue culture plate. After 16 hours, the cells were exposed to 0.1% DMSO (control) or Formula Ia (containing 0.1% DMSO) for 48 hours. Cells were then removed from the plate using trypsin and washed once with PBS. To detect apoptosis, cells (MB361, PC3) were resuspended in binding buffer (10 mM Hepes/NaOH [pH 7.4], 140 mM NaCl, and 2.5 mM $CaCl_2$) at $1\times10^6$ cells/mL and immediately stained with 5 µL annexin V-FITC (BD Pharmingen; Franklin Lakes, N.J.) and 500 µL propidium iodide (PI) solution containing 50 µg/mL PI (Sigma), 0.2 mg/mL RNase solution (Sigma), and 0.1% Triton-X (Sigma) in PBS. The mixture was incubated at room temperature for 30 minutes and cells were analyzed with a flow cytometer (BD Biosciences; San Jose, Calif.).

Example 16

Acinar Morphogenesis in 3D Culture of HER2+BT474M1 Cells

The biological activity of PI3K inhibitors and the most effective therapeutic combinations of PI3K and HER family inhibitors in HER2-amplified breast cancer cells were determined in 3D cell culture performed using the overlay method. Formula Ia compound was used as a suspension in dimethylsulfoxide at a concentration of 50 mM. Heregulin beta- $1_{177-244}$ (hereafter referred to as HRG) was provided at a storage concentration of 225.8 μM. BT474M1 cells were treated with 20 μg/ml trastuzumab, 25 μg/m1pertuzumab, 250 nM Formula Ia compound, or 250 nM Formula IIa compound in 3D culture. Cell viability was determined by measuring cellular ATP levels using the Cell Titer-Glo Luminescent Cell Viability Assay (Promega). Readings were based on the average of 3 replicates per assay condition. Morphogenesis was quantified by calculating the extent of bud-formation from phase-contrast images. 100 Acini in each assay condition, typically 9 days in duration, were scored for the number of buds formed on the acinar surface. Culture media is refreshed every 3 days.

In a titration curve, BT474M1 cells were treated with incremental doses of Formula Ia to determine an optimal concentration that effectively inhibited markers downstream of PI3K (AKT) and led to an overall decrease in cell viability (Cell Titer-Glo). BT474M1 cells were derived from a BT474 parental cell line purchased through the American Type Culture Collection. Cells were passaged through mice to obtain a viable estrogen-dependent cell line suitable for in vitro and in vivo studies.

All 3D assays were performed using the "overlay method" as described (Lee et al (2007) Nat Methods. 4:359-65). Forty-eight-well dishes were coated evenly with 100 ul of growth factor-reduced Matrigel (BD Biosciences) on ice. Plates were subsequently transferred to a 37° C. incubator for 20 minutes to allow for matrix polymerization. BT474M1 cells were harvested and 10,000 cells/well were seeded onto Matrigel-coated dishes. Cells were cultivated in growth medium supplemented with 5% Matrigel and corresponding drugs or ligand. Assays were typically 9-10 days in duration, and growth medium was replaced every 3 days. Phase-contrast images were recorded with a Sony Digital Camera (DXC-5500) adapted to a Leica DMIL microscope. Cell viability was determined by measuring cellular ATP levels using the Cell Titer-Glo Luminescent Cell Viability Assay (Promega). Readings were assessed by a luminometer and based on the average of 3 replicates per assay condition. Morphogenesis was quantified by calculating the extent of bud-formation from phase-contrast images. One hundred acini in each assay condition were scored for the number of buds formed on the acinar surface. Scores were totaled and grouped into categories of: 0-1, 2-3, or ≥4 buds per acini.

TABLE 1

PI3K inhibitor combinations evaluated in 3D cell culture

| | Combinations | Target(s) |
|---|---|---|
| 1 | 20 μg/ml trastuzumab | Her2 (extracellular subdomain IV) |
| | 250 nM Formula Ia | PI3K |
| 2 | 25 μg/ml pertuzumab | Her2 (extracellular subdomain II) |
| | 250 nM Formula Ia | PI3K |
| 3 | 20 μg/ml trastuzumab | Her2 (extracellular subdomain II) |
| | 25 μg/ml pertuzumab | Her2 (extracellular subdomain IV) |
| | 250 nM Formula Ia | PI3K |

Example 17

In Vivo Tumor Xenograft

Animals suitable for transgenic experiments can be obtained from standard commercial sources. Groups of female CD-1 nude mice (Charles River Laboratory) were implanted subcutaneously in the hind flank with 20 million MDA-MB-361.1 (PI3K mutant) breast cancer cells with matrigel and 0.36 mg of estrogen implants per mouse. Groups of female NMRI nu/nu mice (Janvier) were implanted with 150 mm3 fragments of MAXF 401 (Her2+/ER+/PR+) or MAXF 1162 (Her2+/ER+/PR+) primary breast tumors (biopsied directly from two individual breast cancer patients) with matrigel and 0.36 mg of estrogen pellets per mouse. Groups of female HRLN nu/nu (Harlan Labs) were implanted with 10 million MCF-7 (PI3K mutant) breast cancer cells with matrigel and 0.36 mg of estrogen pellets per mouse. Groups of female athymic nu/nu mice (Charles River Laboratory) were implanted with 15 million NCI-H2122 (K-Ras mutant) non-small cell lung cancer cells and matrigel per mouse. Mouse xenografts were dosed at day 1 with drug, drug combination, or vehicle according to the schedule specified for each tumor model. Docetaxel was administered intravenously, B20-1.4 was administered intraperitonealy and Formula Ia and IIa were delivered per os by oral gavage. Tumor sizes were recorded twice weekly over the course of the study. Mouse body weights were also recorded twice weekly, and the mice were observed regularly. Tumor volume was measured in two dimensions (length and width) using Ultra Cal-IV calipers (Model 54-10-111; Fred V. Fowler Co., Inc.; Newton, Mass.) and analyzed using Excel v.11.2 (Microsoft Corporation; Redmond, Wash.). Tumor inhibition graphs were plotted using KaleidaGraph, Version 3.6 (Synergy Software; Reading, Pa.). The tumor volume was calculated with formula: Tumor size (mm$^3$)=(longer measurement×shorter measurement$^2$)×0.5

Animal body weights were measured using an Adventurera Pro AV812 scale (Ohaus Corporation; Pine Brook, N.J.). Graphs were generated using KaleidaGraph Version 3.6. Percent weight change was calculated using formula: Group percent weight change=(1−(initial weight/new weight))× 100.

Mice whose tumor volume exceeded 2000 mm$^3$ or whose body weight loss was >20% of their starting weight were promptly euthanized according to regulatory guidance.

The percent tumor growth inhibition (% INH) at the end of study (EOS) was calculated using formula: % INH=100.∴. (EOS mean volume of tumors in animals given vehicle−EOS mean volume of tumors in animals given the drug)/EOS mean volume of tumors in animals given vehicle.

Tumor incidence (TI) was determined based on the number of measurable tumors remaining in each group at the end of the study. A partial response (PR) was defined as a >50% but <100% reduction in tumor volume, compared with the starting tumor volume, observed on any day of the study. A complete response (CR) was defined as a 100% reduction in tumor volume, compared with the initial tumor volume, observed on any day of the study. Data were analyzed and p-values were determined using the Dunnett's test with JMP statistical software, version 5.1.2 (SAS Institute; Cary, N.C.). Individual tumor volumes at end of study and mean tumor volume ±SEM values were calculated using JMP statistical software, version 5.1.2. Body weight data were graphed based on the mean percentage of change from initial body weights ±SEM.

Example 18

Phospho AKT Induction Assay

In a 6-well tissue culture plate cells were seeded at 5×10$^5$ cells per well overnight. Cells were treated with an EC$_{80}$ of the chemotherapeutic agent. Following treatment, cells were washed once with cold PBS and lysed in 1× Cell Extraction Buffer from Biosource (Carlsbad, Calif.) supplemented with protease inhibitors (Roche, Mannheim, Germany), 1 mM PMSF, and Phosphatase Inhibitor Cocktails 1 and 2 from Sigma (St. Louis, Mo.). Determination of protein concentration was performed using the Pierce BCA Protein Assay Kit (Rockford, Ill.). Levels of pAkt (Ser$^{473}$) and total Akt were assessed using bead kits from Biosource (Carlsbad, Calif.) and the Luminex Bio-Plex system (Bio-Rad, Hercules, Calif.).

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

We claim:

1. A method for determining compounds to be used in combination for the treatment of cancer comprising:
   a) administering a therapeutic combination of a compound having Formula I or II, and a chemotherapeutic agent to HER2-amplified breast cancer cells in laminin-rich, reconstituted basement membrane media, wherein the chemotherapeutic agent targets, binds to, or modulates a HER2 receptor, and
   b) measuring inhibition of cellular proliferation wherein nonmalignant and malignant mammary cells are discriminated by one or more phenotypic difference selected from cell viability and acinar morphogenesis;
   wherein the Formula I or II compound is selected from a compound of Formula Ia, Formula Ib and Formula IIa:

Ia

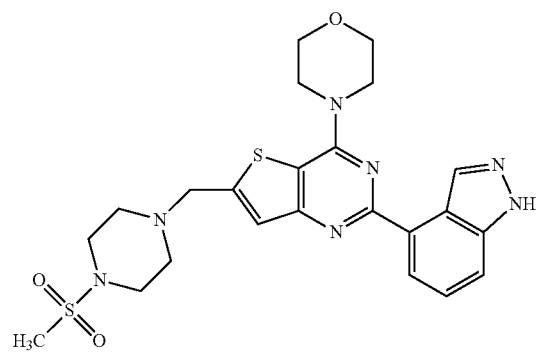

Ib

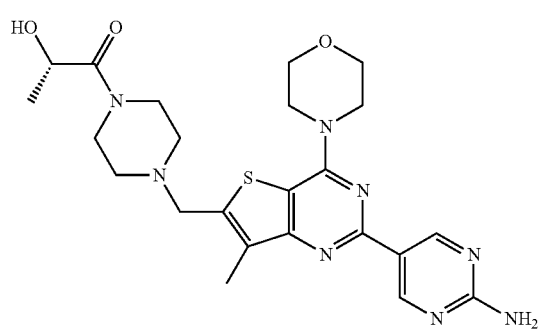

IIa

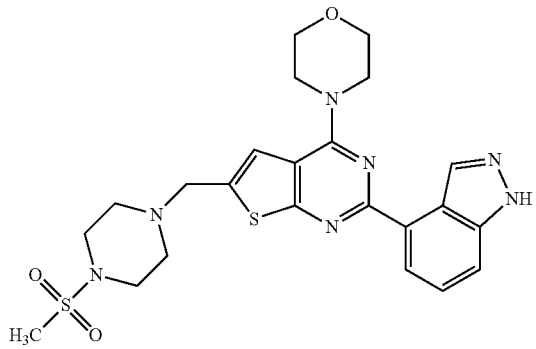

or stereoisomers, geometric isomers, tautomers, or pharmaceutically acceptable salts thereof.

2. The method of claim 1 wherein the Formula I or II compound is a compound of Formula Ia.

3. The method of claim 1 wherein the chemotherapeutic agent is an anti-HER2 antibody.

4. The method of claim 3 wherein the anti-HER2 antibody is selected from trastuzumab and pertuzumab.

5. The method of claim 1 wherein the chemotherapeutic agent is selected from erlotinib, docetaxel, 5-FU, gemcitabine, PD-0325901, cisplatin, carboplatin, paclitaxel, bevacizumab, trastuzumab, pertuzumab, temozolomide, tamoxifen, doxorubicin, Akti-½, HPPD, rapamycin, and lapatinib.

6. The method of claim 1 wherein the laminin-rich, reconstituted basement membrane media is Engelbreth-Holm-Swarm extracellular matrix extract.

7. The method of claim 1 wherein the Formula I or II compound is a compound of Formula Ib.

8. The method of claim 1 wherein the Formula I or II compound is a compound of Formula IIa.

9. The method of claim 1, wherein the therapeutic combination comprises a compound having Formula I or II, a first chemotherapeutic agent and second chemotherapeutic agent.

10. The method of claim 2, wherein the chemotherapeutic agent is trastuzumab.

11. The method of claim 2, wherein the chemotherapeutic agent is pertuzumab.

12. The method of claim 2, wherein the chemotherapeutic agent is lapatinib.

13. The method of claim 7, wherein the chemotherapeutic agent is trastuzumab.

14. The method of claim 7, wherein the chemotherapeutic agent is pertuzumab.

15. The method of claim 7, wherein the chemotherapeutic agent is lapatinib.

* * * * *